(12) United States Patent
Brinkmann et al.

(10) Patent No.: US 11,999,801 B2
(45) Date of Patent: Jun. 4, 2024

(54) MULTISPECIFIC ANTIBODIES

(71) Applicant: Hoffmann-La Roche Inc., Little Falls, NJ (US)

(72) Inventors: Ulrich Brinkmann, Weilheim (DE); Wolfgang Schaefer, Mannheim (DE); Klaus Mayer, Munich (DE)

(73) Assignee: Hoffman-La Roche Inc., Little Falls, NJ (US)

( * ) Notice: Subject to any disclaimer, the term of this patent is extended or adjusted under 35 U.S.C. 154(b) by 421 days.

(21) Appl. No.: 16/821,747

(22) Filed: Mar. 17, 2020

(65) Prior Publication Data

US 2020/0392254 A1    Dec. 17, 2020

Related U.S. Application Data

(60) Division of application No. 15/612,104, filed on Jun. 2, 2017, now Pat. No. 10,633,457, which is a continuation of application No. PCT/EP2015/078155, filed on Dec. 1, 2015.

(30) Foreign Application Priority Data

Dec. 3, 2014  (EP) ..................... 14196046

(51) Int. Cl.
| | |
|---|---|
| *C07K 16/46* | (2006.01) |
| *A61K 39/395* | (2006.01) |
| *C07K 16/28* | (2006.01) |
| *C07K 16/30* | (2006.01) |
| *C07K 16/32* | (2006.01) |
| *C07K 16/44* | (2006.01) |
| *G01N 33/53* | (2006.01) |
| *A61K 39/00* | (2006.01) |

(52) U.S. Cl.
CPC .......... *C07K 16/468* (2013.01); *A61K 39/395* (2013.01); *C07K 16/2803* (2013.01); *C07K 16/2878* (2013.01); *C07K 16/2896* (2013.01); *C07K 16/303* (2013.01); *C07K 16/32* (2013.01); *C07K 16/44* (2013.01); *G01N 33/53* (2013.01); *A61K 2039/505* (2013.01); *C07K 2317/35* (2013.01); *C07K 2317/524* (2013.01); *C07K 2317/55* (2013.01); *C07K 2317/56* (2013.01); *C07K 2317/60* (2013.01); *C07K 2317/622* (2013.01); *C07K 2317/64* (2013.01); *C07K 2317/73* (2013.01); *C07K 2319/70* (2013.01); *C07K 2319/72* (2013.01)

(58) Field of Classification Search
CPC ............. C07K 16/468; C07K 2317/60; C07K 2317/56; C07K 2317/66
USPC .......................................... 424/133.1, 136.1
See application file for complete search history.

(56) References Cited

U.S. PATENT DOCUMENTS

| | | |
|---|---|---|
| 3,773,919 A | 11/1973 | Bosswell et al. |
| 3,896,111 A | 7/1975 | Kupchan et al. |
| 4,120,649 A | 10/1978 | Schechter |
| 4,137,230 A | 1/1979 | Hashimoto et al. |
| 4,150,149 A | 4/1979 | Wolfsen et al. |
| 4,151,042 A | 4/1979 | Higahide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Davis et al. |
| 4,361,544 A | 11/1982 | Goldberg |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howely et al. |
| 4,424,219 A | 1/1984 | Hashimoto et al. |
| 4,444,744 A | 4/1984 | Goldberg |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,665,077 A | 5/1987 | Stringfellow et al. |

(Continued)

FOREIGN PATENT DOCUMENTS

| | | |
|---|---|---|
| CN | 1173878 A | 2/1998 |
| CN | 1176659 A | 3/1998 |

(Continued)

OTHER PUBLICATIONS

Dickopf et al (Computational and Structural Biotechnology Journal 18 (2020) 1221-1227).*

(Continued)

*Primary Examiner* — Lynn A Bristol

(74) *Attorney, Agent, or Firm* — Morrison & Foerster LLP

(57) ABSTRACT

The present invention relates to multispecific antibodies comprising at least three antigen binding sites wherein the third binding site is disulfide stabilized by introduction of cysteine, method for their production, pharmaceutical compositions containing said antibodies and uses thereof.

8 Claims, 17 Drawing Sheets

Specification includes a Sequence Listing.

(56) References Cited

U.S. PATENT DOCUMENTS

| | | |
|---|---|---|
| 4,737,456 A | 4/1988 | Weng et al. |
| 4,767,704 A | 8/1988 | Cleveland |
| 4,816,567 A | 3/1989 | Cabilly et al. |
| 4,927,762 A | 5/1990 | Darfler |
| 4,918,882 A | 8/1990 | Ruth |
| 4,965,199 A | 10/1990 | Capon |
| 4,975,278 A | 12/1990 | Senter et al. |
| 5,053,394 A | 10/1991 | Ellestad et al. |
| 5,114,721 A | 5/1992 | Cohen et al. |
| 5,122,469 A | 6/1992 | Mather et al. |
| 5,143,844 A | 9/1992 | Abrahmsen et al. |
| 5,202,238 A | 4/1993 | Fell, Jr. et al. |
| 5,204,244 A | 4/1993 | Fell et al. |
| 5,208,020 A | 5/1993 | Chari et al. |
| 5,264,365 A | 11/1993 | Georgiou et al. |
| 5,362,852 A | 11/1994 | Geoghegan |
| 5,416,064 A | 5/1995 | Chari et al. |
| 5,451,463 A | 9/1995 | Nelson et al. |
| 5,500,362 A | 3/1996 | Robinson et al. |
| 5,508,192 A | 4/1996 | Georgiou et al. |
| 5,519,142 A | 5/1996 | Hoess et al. |
| 5,541,313 A | 6/1996 | Ruth |
| 5,532,142 A | 7/1996 | Johnston et al. |
| 5,571,894 A | 11/1996 | Wels et al. |
| 5,574,141 A | 12/1996 | Seliger et al. |
| 5,585,481 A | 12/1996 | Arnold, Jr. et al. |
| 5,587,458 A | 12/1996 | King et al. |
| 5,591,828 A | 1/1997 | Bosslet et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter et al. |
| 5,648,260 A | 7/1997 | Winter et al. |
| 5,663,149 A | 9/1997 | Pettit et al. |
| 5,712,374 A | 1/1998 | Kuntsmann et al. |
| 5,714,586 A | 2/1998 | Kuntsmann et al. |
| 5,731,168 A | 3/1998 | Carter et al. |
| 5,739,113 A | 4/1998 | Lee |
| 5,739,116 A | 4/1998 | Hamann et al. |
| 5,747,654 A | 5/1998 | Pastan et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,798,229 A | 8/1998 | Strittmatter et al. |
| 5,817,786 A | 10/1998 | Ruth |
| 5,821,333 A | 10/1998 | Carter et al. |
| 5,821,337 A | 10/1998 | Carter et al. |
| 5,824,483 A | 10/1998 | Houston |
| 5,840,523 A | 11/1998 | Simmons et al. |
| 5,849,879 A | 12/1998 | Nguygen et al. |
| 5,869,046 A | 2/1999 | Presta et al. |
| 5,877,296 A | 3/1999 | Hamann et al. |
| 5,885,793 A | 3/1999 | Griffiths et al. |
| 5,932,448 A | 8/1999 | Tso et al. |
| 5,959,083 A | 9/1999 | Bosslet et al. |
| 5,959,177 A | 9/1999 | Hein et al. |
| 6,027,888 A | 2/2000 | Georgiou et al. |
| 6,040,498 A | 3/2000 | Stomp et al. |
| 6,083,715 A | 7/2000 | Georgiou et al. |
| 6,136,564 A | 10/2000 | Kopetzki |
| 6,153,190 A | 11/2000 | Young et al. |
| 6,166,185 A | 12/2000 | Davis et al. |
| 6,171,586 B1 | 1/2001 | Lam et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,350,860 B1 | 2/2002 | Buyse et al. |
| 6,417,429 B1 | 7/2002 | Hein et al. |
| 6,420,548 B1 | 7/2002 | Vezina et al. |
| 6,485,943 B2 | 11/2002 | Stevens et al. |
| 6,511,663 B1 | 1/2003 | King et al. |
| 6,531,581 B1 | 3/2003 | Nardone et al. |
| 6,534,628 B1 | 3/2003 | Nilsson et al. |
| 6,558,672 B1 | 5/2003 | Pastan et al. |
| 6,586,207 B2 | 7/2003 | Tirrell et al. |
| 6,602,684 B1 | 8/2003 | Umana et al. |
| 6,630,579 B2 | 10/2003 | Chari et al. |
| 6,660,843 B1 | 12/2003 | Feige et al. |
| 6,737,056 B1 | 5/2004 | Presta |
| 6,833,441 B2 | 12/2004 | Wang et al. |
| 6,835,809 B1 | 12/2004 | Liu et al. |
| 6,878,515 B1 | 1/2005 | Landegren |
| 6,897,044 B1 | 5/2005 | Braslawsky et al. |
| 6,919,426 B2 | 7/2005 | Boone et al. |
| 6,946,292 B2 | 9/2005 | Kanda et al. |
| 6,982,321 B2 | 1/2006 | Winter |
| 7,125,978 B1 | 10/2006 | Vezina et al. |
| 7,129,330 B1 | 10/2006 | Little et al. |
| 7,332,581 B2 | 2/2008 | Presta |
| 7,355,008 B2 | 4/2008 | Stavenhagen et al. |
| 7,371,826 B2 | 5/2008 | Presta |
| 7,381,408 B2 | 6/2008 | Mezo et al. |
| 7,498,298 B2 | 3/2009 | Doronina et al. |
| 7,504,256 B1 | 3/2009 | Ogawa et al. |
| 7,507,796 B2 | 3/2009 | Little et al. |
| 7,642,228 B2 | 1/2010 | Little et al. |
| 7,651,688 B2 | 1/2010 | Carter et al. |
| 7,666,622 B2 | 2/2010 | Hanai et al. |
| 7,695,936 B2 | 4/2010 | Sharma et al. |
| 7,919,257 B2 | 4/2011 | Carter et al. |
| 7,942,042 B2 | 5/2011 | Hoogenboom et al. |
| 8,216,805 B2 | 7/2012 | Kawakita et al. |
| 8,227,577 B2 | 7/2012 | Carter et al. |
| 8,242,247 B2 | 8/2012 | Klein et al. |
| 8,268,314 B2 | 9/2012 | Klein et al. |
| 8,304,713 B2 | 11/2012 | Baehner et al. |
| 8,309,300 B2 | 11/2012 | Pradel |
| 8,313,913 B2 | 11/2012 | Nakamura et al. |
| 8,796,424 B2 | 8/2014 | Jununtula et al. |
| 8,871,912 B2 | 10/2014 | Croasdale et al. |
| 9,308,259 B2 | 4/2016 | Epshtein et al. |
| 9,382,323 B2 | 7/2016 | Brinkmann et al. |
| 9,688,758 B2 | 6/2017 | Wranik et al. |
| 9,708,396 B2 | 7/2017 | Baehner et al. |
| 9,879,095 B2 | 1/2018 | Brinkmann et al. |
| 9,890,204 B2 | 2/2018 | Brinkmann et al. |
| 9,994,646 B2 | 6/2018 | Christensen et al. |
| 10,087,246 B2 | 10/2018 | Bedoucha et al. |
| 10,106,600 B2 | 10/2018 | Brinkmann et al. |
| 10,344,085 B2 | 7/2019 | Dengl et al. |
| 10,538,585 B2 | 1/2020 | Dengl et al. |
| 10,633,457 B2 | 4/2020 | Brinkman et al. |
| 10,730,938 B2 | 8/2020 | Bedoucha et al. |
| 11,286,300 B2 | 3/2022 | Ferrara Koller et al. |
| 11,486,882 B2 | 11/2022 | Molhoj et al. |
| 11,584,793 B2 | 2/2023 | Dengl et al. |
| 11,673,945 B2 | 6/2023 | Imhof-jung et al. |
| 2002/0051986 A1 | 5/2002 | Baez et al. |
| 2002/0155537 A1 | 10/2002 | Carter et al. |
| 2002/0164328 A1 | 11/2002 | Shinkawa et al. |
| 2003/0027751 A1 | 2/2003 | Kovesdi et al. |
| 2003/0115614 A1 | 6/2003 | Kanda et al. |
| 2003/0124129 A1 | 7/2003 | Oliner |
| 2003/0152987 A1 | 8/2003 | Cohen et al. |
| 2003/0157091 A1 | 8/2003 | Hoogenboom |
| 2003/0157108 A1 | 8/2003 | Presta |
| 2003/0170230 A1 | 9/2003 | Caterer et al. |
| 2003/0176352 A1 | 9/2003 | Min et al. |
| 2003/0195156 A1 | 10/2003 | Min et al. |
| 2003/0219817 A1 | 11/2003 | Zhu |
| 2003/0229023 A1 | 12/2003 | Oliner et al. |
| 2003/0236193 A1 | 12/2003 | Oliner et al. |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |

(56) References Cited

U.S. PATENT DOCUMENTS

| | | |
|---|---|---|
| 2004/0132140 A1 | 7/2004 | Satoh et al. |
| 2004/0214988 A1 | 10/2004 | Tirrell et al. |
| 2004/0220388 A1 | 11/2004 | Mertens et al. |
| 2004/0224372 A1 | 11/2004 | Li et al. |
| 2004/0259075 A1 | 12/2004 | Dimitrov et al. |
| 2005/0014934 A1 | 1/2005 | Hinton et al. |
| 2005/0031613 A1 | 2/2005 | Nakamura et al. |
| 2005/0054048 A1 | 3/2005 | Grasso et al. |
| 2005/0064509 A1 | 4/2005 | Bradbury et al. |
| 2005/0079170 A1 | 4/2005 | Le Gall et al. |
| 2005/0100543 A1 | 5/2005 | Hansen et al. |
| 2005/0123476 A1 | 6/2005 | Bugge et al. |
| 2005/0123546 A1 | 6/2005 | Umana et al. |
| 2005/0152894 A1 | 7/2005 | Krummen et al. |
| 2005/0163782 A1 | 7/2005 | Glaser et al. |
| 2005/0169933 A1 | 8/2005 | Steeves et al. |
| 2005/0186208 A1 | 8/2005 | Fyfe et al. |
| 2005/0214833 A1 | 9/2005 | Carter et al. |
| 2005/0238649 A1 | 10/2005 | Doronina et al. |
| 2005/0249722 A1 | 11/2005 | Beliard et al. |
| 2005/0260186 A1 | 11/2005 | Bookbinder et al. |
| 2006/0008845 A1 | 1/2006 | Kondejewski et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Mattheus Hoogenboom et al. |
| 2006/0280747 A1 | 12/2006 | Fuh Germaine et al. |
| 2007/0014794 A1 | 1/2007 | Carter et al. |
| 2007/0071675 A1 | 3/2007 | Wu et al. |
| 2007/0071742 A1 | 3/2007 | Fang et al. |
| 2007/0134759 A1 | 6/2007 | Nishiya et al. |
| 2007/0141065 A1 | 6/2007 | Fuh et al. |
| 2007/0178552 A1 | 8/2007 | Arathoon et al. |
| 2007/0196274 A1 | 8/2007 | Sun |
| 2007/0269369 A1 | 11/2007 | Gegg et al. |
| 2007/0274985 A1 | 11/2007 | Dubel et al. |
| 2007/0274998 A1 | 11/2007 | Uktu |
| 2007/0287170 A1 | 12/2007 | Davis et al. |
| 2008/0044834 A1 | 2/2008 | Heyduk |
| 2008/0063641 A1 | 3/2008 | Huang et al. |
| 2008/0187954 A1 | 8/2008 | Kallmeier et al. |
| 2008/0234183 A1 | 9/2008 | Hallbrink et al. |
| 2008/0241884 A1 | 10/2008 | Shitara et al. |
| 2008/0280778 A1 | 11/2008 | Urdea |
| 2009/0023811 A1 | 1/2009 | Biadatti et al. |
| 2009/0060910 A1 | 3/2009 | Johnson |
| 2009/0117105 A1 | 5/2009 | Hu et al. |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0194692 A1 | 9/2009 | Kobaru |
| 2009/0232811 A1 | 9/2009 | Klein et al. |
| 2010/0021943 A1 | 1/2010 | An et al. |
| 2010/0062436 A1 | 3/2010 | Jarosch et al. |
| 2010/0081796 A1 | 4/2010 | Brinkman et al. |
| 2010/0111967 A1 | 5/2010 | Baehner et al. |
| 2010/0254989 A1 | 10/2010 | Bossenmaier et al. |
| 2010/0256338 A1 | 10/2010 | Brinkmann et al. |
| 2010/0256339 A1 | 10/2010 | Bossenmaier et al. |
| 2010/0256340 A1 | 10/2010 | Brinkmann et al. |
| 2010/0266617 A1 | 10/2010 | Carven et al. |
| 2010/0286374 A1 | 11/2010 | Kannan |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2011/0243966 A1 | 10/2011 | Farrington et al. |
| 2012/0029481 A1 | 2/2012 | Pech et al. |
| 2012/0149879 A1 | 6/2012 | Brinkmann et al. |
| 2012/0164726 A1 | 6/2012 | Klein et al. |
| 2012/0184718 A1 | 7/2012 | Bruenker et al. |
| 2012/0225071 A1 | 9/2012 | Klein et al. |
| 2012/0237506 A1 | 9/2012 | Bossenmaier et al. |
| 2012/0237507 A1 | 9/2012 | Bossenmaier et al. |
| 2012/0302737 A1 | 11/2012 | Christensen et al. |
| 2012/0321627 A1 | 12/2012 | Baehner et al. |
| 2013/0022601 A1* | 1/2013 | Brinkmann ........ C07K 16/2863 536/23.4 |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2013/0288267 A1 | 10/2013 | Gerg et al. |
| 2013/0344094 A1 | 12/2013 | Gerg et al. |
| 2014/0249296 A1 | 9/2014 | Ploegh et al. |
| 2014/0294810 A1 | 10/2014 | Lowman et al. |
| 2014/0370019 A1 | 12/2014 | Bruenker et al. |
| 2014/0370020 A1 | 12/2014 | Kuramochi |
| 2015/0004166 A1 | 1/2015 | Baehner et al. |
| 2015/0030598 A1 | 1/2015 | Croasdale et al. |
| 2015/0133638 A1 | 5/2015 | Wranik et al. |
| 2015/0166670 A1 | 6/2015 | Castoldi et al. |
| 2015/0232541 A1 | 8/2015 | Fenn |
| 2015/0232560 A1 | 8/2015 | Heindl et al. |
| 2015/0232561 A1 | 8/2015 | Fenn et al. |
| 2015/0291704 A1 | 10/2015 | Beck |
| 2016/0002356 A1 | 1/2016 | Christensen et al. |
| 2017/0115304 A1 | 4/2017 | Molhoj et al. |
| 2017/0129962 A1 | 5/2017 | Regula et al. |
| 2017/0145116 A1 | 5/2017 | Regula et al. |
| 2017/0306018 A1 | 10/2017 | Vu et al. |
| 2017/0306036 A1 | 10/2017 | Vu et al. |
| 2017/0349669 A1 | 12/2017 | Imhof-Jung et al. |
| 2018/0237542 A1 | 8/2018 | Kannan |
| 2018/0282399 A1 | 10/2018 | Brinkmann et al. |
| 2020/0270347 A1* | 8/2020 | Freimoser-Grundschober ............ C07K 16/2863 |
| 2020/0369758 A1 | 11/2020 | Imhof-jung |
| 2021/0032349 A1 | 2/2021 | Dengl et al. |
| 2021/0122832 A1* | 4/2021 | Brinkmann ............ C07K 16/00 |
| 2021/0230278 A1* | 7/2021 | Weinzierl ............ C07K 16/2809 |
| 2022/0010014 A1* | 1/2022 | Freimoser-Grundschober ............ A61P 35/00 |
| 2022/0010015 A1* | 1/2022 | Carpy Gutierrez Cirlos ............ C07K 16/30 |
| 2022/0033525 A1* | 2/2022 | Brinkmann .......... C07K 16/468 |
| 2023/0129340 A1 | 4/2023 | Seeber et al. |

FOREIGN PATENT DOCUMENTS

| | | |
|---|---|---|
| CN | 1232039 A | 10/1999 |
| CN | 1603345 A | 4/2005 |
| CN | 101037671 A | 9/2007 |
| CN | 101052653 A | 10/2007 |
| CN | 101065151 A | 10/2007 |
| CN | 101205255 A | 6/2008 |
| CN | 101218251 A | 7/2008 |
| CN | 101355966 A | 1/2009 |
| CN | 101802197 A | 11/2010 |
| EP | 0 292 128 A1 | 11/1988 |
| EP | 0 307 434 B1 | 3/1989 |
| EP | 0 307 434 B2 | 3/1989 |
| EP | 0 313 219 A2 | 4/1989 |
| EP | 0 339 217 B1 | 11/1989 |
| EP | 0 340 109 A2 | 11/1989 |
| EP | 0 404 097 B1 | 12/1990 |
| EP | 0 423 839 A2 | 4/1991 |
| EP | 0 425 235 B1 | 5/1991 |
| EP | 0 523 978 A1 | 1/1993 |
| EP | 0 618 192 A1 | 10/1994 |
| EP | 0 637 593 A1 | 2/1995 |
| EP | 0 786 468 A2 | 7/1997 |
| EP | 1 074 563 A1 | 2/2001 |
| EP | 1 186 613 A1 | 3/2002 |
| EP | 1 391 213 A1 | 2/2004 |
| EP | 1 431 298 A1 | 6/2004 |
| EP | 1 538 221 A1 | 6/2005 |
| EP | 1 870 459 A1 | 12/2007 |

(56) References Cited

FOREIGN PATENT DOCUMENTS

| | | |
|---|---|---|
| EP | 2 050 764 A1 | 4/2009 |
| EP | 2 443 154 B1 | 4/2012 |
| EP | 2 647 707 A1 | 10/2013 |
| EP | 2 647 707 A4 | 10/2013 |
| EP | 3 227 332 A1 | 10/2017 |
| JP | 7-501698 A | 2/1995 |
| JP | 2008-518605 A | 6/2008 |
| JP | 2008-531049 A | 8/2008 |
| JP | 5766296 B2 | 8/2015 |
| RU | 2005/124281 A | 1/2006 |
| RU | 2295537 C2 | 3/2007 |
| WO | WO-1987/00195 A1 | 1/1987 |
| WO | WO-1989/02439 A1 | 3/1989 |
| WO | WO-1989/02931 A1 | 4/1989 |
| WO | WO-1989/12642 A1 | 12/1989 |
| WO | WO-1990/03430 A1 | 4/1990 |
| WO | WO-1990/08156 A1 | 7/1990 |
| WO | WO-1990/08187 A1 | 7/1990 |
| WO | WO-1990/11294 A1 | 10/1990 |
| WO | WO-1991/01133 A1 | 2/1991 |
| WO | WO-1991/06305 A1 | 5/1991 |
| WO | WO-1992/01047 A1 | 1/1992 |
| WO | WO-1992/04053 A1 | 3/1992 |
| WO | WO-1992/11388 A1 | 7/1992 |
| WO | WO-1993/01161 A1 | 1/1993 |
| WO | WO-1993/05060 A1 | 3/1993 |
| WO | WO-1993/06217 A1 | 4/1993 |
| WO | WO-1993/10819 A1 | 6/1993 |
| WO | WO-1993/11161 A1 | 6/1993 |
| WO | WO-1993/11162 A1 | 6/1993 |
| WO | WO-1993/16185 A2 | 8/1993 |
| WO | WO-1993/16185 A3 | 8/1993 |
| WO | WO-1993/21232 A1 | 10/1993 |
| WO | WO-1994/04550 A1 | 3/1994 |
| WO | WO-1994/09131 A1 | 4/1994 |
| WO | WO-1994/10202 A1 | 5/1994 |
| WO | WO-1994/10308 A1 | 5/1994 |
| WO | WO-1994/11026 A2 | 5/1994 |
| WO | WO-1994/11026 A3 | 5/1994 |
| WO | WO-1994/29350 A2 | 12/1994 |
| WO | WO-1994/29351 A2 | 12/1994 |
| WO | WO-1994/29351 A3 | 12/1994 |
| WO | WO-1995/05399 A1 | 2/1995 |
| WO | WO-1995/09917 A1 | 4/1995 |
| WO | WO-1995/17886 A1 | 7/1995 |
| WO | WO-1996/27011 A1 | 9/1996 |
| WO | WO-1996/27612 A1 | 9/1996 |
| WO | WO-1997/01580 A1 | 1/1997 |
| WO | WO-1997/05156 A1 | 2/1997 |
| WO | WO-1997/014719 A1 | 4/1997 |
| WO | WO-1997/028267 A1 | 8/1997 |
| WO | WO-1997/30087 A1 | 8/1997 |
| WO | WO-1997/43451 A1 | 11/1997 |
| WO | WO-1998/45331 A2 | 10/1998 |
| WO | WO-1998/45331 A3 | 10/1998 |
| WO | WO-1998/45332 A2 | 10/1998 |
| WO | WO-1998/45332 A3 | 10/1998 |
| WO | WO-1998/48032 A2 | 10/1998 |
| WO | WO-1998/48032 A3 | 10/1998 |
| WO | WO-1998/050431 A2 | 11/1998 |
| WO | WO-1998/050431 A3 | 11/1998 |
| WO | WO-1998/58964 A1 | 12/1998 |
| WO | WO-1999/06587 A2 | 2/1999 |
| WO | WO-1999/06587 A3 | 2/1999 |
| WO | WO-1999/22764 A1 | 5/1999 |
| WO | WO-1999/37791 A1 | 7/1999 |
| WO | WO-1999/51642 A1 | 10/1999 |
| WO | WO-1999/54342 A1 | 10/1999 |
| WO | WO-1999/66951 A2 | 12/1999 |
| WO | WO-1999/66951 A3 | 12/1999 |
| WO | WO-2000/24770 A2 | 5/2000 |
| WO | WO-2000/24770 A3 | 5/2000 |
| WO | WO-2000/29004 A1 | 5/2000 |
| WO | WO-2000/35956 A1 | 6/2000 |
| WO | WO-2000/61739 A1 | 10/2000 |
| WO | WO-2001/29246 A1 | 4/2001 |
| WO | WO-2001/42505 A2 | 6/2001 |
| WO | WO-2001/42505 A3 | 6/2001 |
| WO | WO-2001/77342 A1 | 10/2001 |
| WO | WO-2001/085795 A1 | 11/2001 |
| WO | WO-2001/90192 A2 | 11/2001 |
| WO | WO-2001/90192 A3 | 11/2001 |
| WO | WO-2002/02781 A1 | 1/2002 |
| WO | WO-2002/031140 A1 | 4/2002 |
| WO | WO-2002/051870 A2 | 7/2002 |
| WO | WO-2002/051870 A3 | 7/2002 |
| WO | WO 2002/072141 A2 | 9/2002 |
| WO | WO 2002/072141 A8 | 9/2002 |
| WO | WO-2002/088172 A2 | 11/2002 |
| WO | WO-2002/088172 A3 | 11/2002 |
| WO | WO-2002/092620 A2 | 11/2002 |
| WO | WO-2002/092620 A3 | 11/2002 |
| WO | WO-2002/096948 A2 | 12/2002 |
| WO | WO-2002/096948 A3 | 12/2002 |
| WO | WO 2003/011878 A2 | 2/2003 |
| WO | WO 2003/011878 A3 | 2/2003 |
| WO | WO-2003/012069 A2 | 2/2003 |
| WO | WO-2003/012069 A3 | 2/2003 |
| WO | WO-2003/019145 A2 | 3/2003 |
| WO | WO-2003/019145 A3 | 3/2003 |
| WO | WO-2003/030833 A2 | 4/2003 |
| WO | WO-2003/030833 A3 | 4/2003 |
| WO | WO-2003/031589 A2 | 4/2003 |
| WO | WO-2003/031589 A8 | 4/2003 |
| WO | WO-2003/035694 A2 | 5/2003 |
| WO | WO-2003/035694 A3 | 5/2003 |
| WO | WO-2003/035835 A2 | 5/2003 |
| WO | WO-2003/035835 A3 | 5/2003 |
| WO | WO-2003/055993 A1 | 7/2003 |
| WO | WO-2003/057134 A2 | 7/2003 |
| WO | WO-2003/057134 A3 | 7/2003 |
| WO | WO-2003/066660 A2 | 8/2003 |
| WO | WO-2003/066660 A3 | 8/2003 |
| WO | WO-2003/073238 A2 | 9/2003 |
| WO | WO-2003/073238 A3 | 9/2003 |
| WO | WO-2003/084570 A1 | 10/2003 |
| WO | WO-2003/085107 A1 | 10/2003 |
| WO | WO-2003/085119 A1 | 10/2003 |
| WO | WO-2003/097105 A1 | 11/2003 |
| WO | WO 2003/104249 A1 | 12/2003 |
| WO | WO-2003/106501 A1 | 12/2003 |
| WO | WO-2004/032961 A1 | 4/2004 |
| WO | WO-2004/056312 A2 | 7/2004 |
| WO | WO-2004/056312 A3 | 7/2004 |
| WO | WO-2004/058298 A1 | 7/2004 |
| WO | WO 2004/062602 A2 | 7/2004 |
| WO | WO 2004/062602 A3 | 7/2004 |
| WO | WO-2004/065417 A2 | 8/2004 |
| WO | WO-2004/065417 A3 | 8/2004 |
| WO | WO-2004/065540 A2 | 8/2004 |
| WO | WO-2004/065540 A3 | 8/2004 |
| WO | WO-2004/072117 A2 | 8/2004 |
| WO | WO-2004/072117 A3 | 8/2004 |
| WO | WO 2004/081051 A1 | 9/2004 |
| WO | WO-2004/092215 A2 | 10/2004 |
| WO | WO-2004/092215 A3 | 10/2004 |
| WO | WO-2005/000900 A1 | 1/2005 |
| WO | WO-2005/001025 A2 | 1/2005 |
| WO | WO-2005/001025 A3 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/035572 A2 | 4/2005 |
| WO | WO-2005/035572 A3 | 4/2005 |
| WO | WO-2005/035586 A1 | 4/2005 |
| WO | WO-2005/035727 A2 | 4/2005 |
| WO | WO-2005/035727 A3 | 4/2005 |
| WO | WO-2005/035778 A1 | 4/2005 |

(56) References Cited

FOREIGN PATENT DOCUMENTS

| | | |
|---|---|---|
| WO | WO-2005/044853 A2 | 5/2005 |
| WO | WO-2005/044853 A3 | 5/2005 |
| WO | WO-2005/044859 A2 | 5/2005 |
| WO | WO-2005/044859 A3 | 5/2005 |
| WO | WO-2005/051976 A2 | 6/2005 |
| WO | WO-2005/051976 A3 | 6/2005 |
| WO | WO-2005/053742 A1 | 6/2005 |
| WO | WO-2005/063816 A2 | 7/2005 |
| WO | WO-2005/063816 A3 | 7/2005 |
| WO | WO 2005/074417 A2 | 8/2005 |
| WO | WO 2005/074417 A3 | 8/2005 |
| WO | WO-2005/074524 A2 | 8/2005 |
| WO | WO-2005/074524 A3 | 8/2005 |
| WO | WO-2005/075514 A2 | 8/2005 |
| WO | WO-2005/075514 A3 | 8/2005 |
| WO | WO-2005/100402 A1 | 10/2005 |
| WO | WO-2006/020258 A2 | 2/2006 |
| WO | WO-2006/020258 A3 | 2/2006 |
| WO | WO-2006/028956 A2 | 3/2006 |
| WO | WO-2006/028956 A3 | 3/2006 |
| WO | WO-2006/029879 A2 | 3/2006 |
| WO | WO-2006/029879 A3 | 3/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | WO-2006/082515 A2 | 8/2006 |
| WO | WO-2006/082515 A3 | 8/2006 |
| WO | WO-2006/089364 A1 | 8/2006 |
| WO | WO-2006/091209 A2 | 8/2006 |
| WO | WO-2006/091209 A3 | 8/2006 |
| WO | WO-2006/093794 A1 | 8/2006 |
| WO | WO-2006/103100 A2 | 10/2006 |
| WO | WO-2006/103100 A3 | 10/2006 |
| WO | WO-2006/113665 A2 | 10/2006 |
| WO | WO-2006/113665 A3 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO 2006/137932 A2 | 12/2006 |
| WO | WO 2006/137932 A3 | 12/2006 |
| WO | WO-2007/024715 A2 | 3/2007 |
| WO | WO-2007/024715 A3 | 3/2007 |
| WO | WO-2007/031875 A2 | 3/2007 |
| WO | WO-2007/031875 A3 | 3/2007 |
| WO | WO 2007/038658 A2 | 4/2007 |
| WO | WO 2007/038658 A3 | 4/2007 |
| WO | WO-2007/044323 A2 | 4/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO 2007/059816 A1 | 5/2007 |
| WO | WO-2007/068895 A1 | 6/2007 |
| WO | WO-2007/069092 A2 | 6/2007 |
| WO | WO-2007/069092 A3 | 6/2007 |
| WO | WO-2007/084181 A2 | 7/2007 |
| WO | WO-2007/084181 A3 | 7/2007 |
| WO | WO-2007/085837 A1 | 8/2007 |
| WO | WO-2007/089445 A2 | 8/2007 |
| WO | WO-2007/089445 A3 | 8/2007 |
| WO | WO-2007/095338 A2 | 8/2007 |
| WO | WO-2007/095338 A3 | 8/2007 |
| WO | WO-2007/108013 A2 | 9/2007 |
| WO | WO-2007/108013 A3 | 9/2007 |
| WO | WO-2007/109254 A2 | 9/2007 |
| WO | WO-2007/109254 A3 | 9/2007 |
| WO | WO-2007/110205 A2 | 10/2007 |
| WO | WO-2007/110205 A3 | 10/2007 |
| WO | WO-2007/147901 A1 | 12/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/022349 A2 | 2/2008 |
| WO | WO-2008/077077 A2 | 6/2008 |
| WO | WO-2008/077077 A3 | 6/2008 |
| WO | WO-2008/077546 A1 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2008/143954 A2 | 11/2008 |
| WO | WO-2008/143954 A3 | 11/2008 |
| WO | WO-2009/007124 A1 | 1/2009 |
| WO | WO-2009/018386 A1 | 2/2009 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/030780 A2 | 3/2009 |
| WO | WO-2009/030780 A3 | 3/2009 |
| WO | WO-2009/032782 A2 | 3/2009 |
| WO | WO-2009/032782 A3 | 3/2009 |
| WO | WO-2009/037659 A2 | 3/2009 |
| WO | WO-2009/037659 A3 | 3/2009 |
| WO | WO-2009/059278 A1 | 5/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO 2009/105671 A2 | 8/2009 |
| WO | WO 2009/105671 A3 | 8/2009 |
| WO | WO-2009/126944 A1 | 10/2009 |
| WO | WO-2010/034441 A1 | 4/2010 |
| WO | WO-2010/035012 A1 | 4/2010 |
| WO | WO-2010/040508 A1 | 4/2010 |
| WO | WO-2010/040508 A8 | 4/2010 |
| WO | WO-2010/045193 A1 | 4/2010 |
| WO | WO-2010/065882 A1 | 6/2010 |
| WO | WO-2010/069532 A1 | 6/2010 |
| WO | WO-2010/087994 A2 | 8/2010 |
| WO | WO-2010/087994 A3 | 8/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/115598 A1 | 10/2010 |
| WO | WO 2010/118169 A2 | 10/2010 |
| WO | WO 2010/118169 A3 | 10/2010 |
| WO | WO-2010/129304 A2 | 11/2010 |
| WO | WO-2010/129304 A3 | 11/2010 |
| WO | WO-2010/136172 A1 | 12/2010 |
| WO | WO-2010/145792 A1 | 12/2010 |
| WO | WO-2010/145792 A8 | 12/2010 |
| WO | WO-2010/145793 A1 | 12/2010 |
| WO | WO-2011/003557 A1 | 1/2011 |
| WO | WO-2011/028952 A1 | 3/2011 |
| WO | WO-2011/034605 A2 | 3/2011 |
| WO | WO-2011/034605 A3 | 3/2011 |
| WO | WO-2011/090754 A1 | 7/2011 |
| WO | WO-2011/090762 A1 | 7/2011 |
| WO | WO-2011/133886 A2 | 10/2011 |
| WO | WO-2011/133886 A3 | 10/2011 |
| WO | WO-2011/143545 A1 | 11/2011 |
| WO | WO-2012/006633 A1 | 1/2012 |
| WO | WO-2012/025525 A1 | 3/2012 |
| WO | WO-2012/025530 A1 | 3/2012 |
| WO | WO-2012/058768 A1 | 5/2012 |
| WO | WO-2012/075037 A1 | 6/2012 |
| WO | WO-2012/085069 A2 | 6/2012 |
| WO | WO-2012/085069 A3 | 6/2012 |
| WO | WO-2012/085111 A1 | 6/2012 |
| WO | WO-2012/085113 A1 | 6/2012 |
| WO | WO-2012/116927 A1 | 9/2012 |
| WO | 2012131555 A2 | 10/2012 |

(56) References Cited

FOREIGN PATENT DOCUMENTS

| WO | WO-2012/131555 A2 | 10/2012 |
|----|-------------------|---------|
| WO | WO-2012/131555 A3 | 10/2012 |
| WO | WO-2012/143379 A1 | 10/2012 |
| WO | 2012131555 A3 | 12/2012 |
| WO | WO-2013/003555 A1 | 1/2013 |
| WO | WO-2013/006544 A1 | 1/2013 |
| WO | WO-2013/006544 A8 | 1/2013 |
| WO | WO-2013/012733 A1 | 1/2013 |
| WO | WO-2013/026833 A1 | 2/2013 |
| WO | WO-2013/092716 A1 | 6/2013 |
| WO | WO-2013/096291 A2 | 6/2013 |
| WO | WO-2013/096291 A3 | 6/2013 |
| WO | WO-2013/119966 A2 | 8/2013 |
| WO | WO-2013/119966 A3 | 8/2013 |
| WO | 2013150043 A1 | 10/2013 |
| WO | WO-2013/157953 A1 | 10/2013 |
| WO | WO-2013/157954 A1 | 10/2013 |
| WO | WO-2013/174873 A1 | 11/2013 |
| WO | WO-2014/001326 A1 | 1/2014 |
| WO | WO-2014/012085 A2 | 1/2014 |
| WO | WO-2014/012085 A3 | 1/2014 |
| WO | WO-2014/049003 A1 | 4/2014 |
| WO | WO-2014/144357 A1 | 9/2014 |
| WO | WO-2015/101588 A1 | 7/2015 |
| WO | WO-2016/055432 A2 | 4/2016 |
| WO | WO-2016/055432 A3 | 4/2016 |
| WO | WO-2016/087416 A1 | 6/2016 |

OTHER PUBLICATIONS

Dickopf et al (Biological Chemistry (2019), 400(3), 343-350).*

Lloyd et al. Protein Engineering, Design & Selection 22:159-168, 2009).*

Edwards et al., (J Mol Biol. 334(1): 103-118, Nov. 14, 2003).*

Adams et al. (Sep. 1, 1993). "Highly Specific In Vivo Tumor Targeting By Monovalent and Divalent Forms of 741F8 Anti-c-erbB-2 Single-Chain Fv," *Cancer Res.* 53:4026-4034.

Agata et al. "Expression Of The PD-1 Antigen On The Surface Of Stimulated Mouse T and B Lymphoctes," Int. Immunology 8(5):765-772, (1996).

Aggarwal et al. "Fibroblast Activation Protein Peptide Substrates Identified from Human Collagen I Derived Gelatin Cleavage Sites," *Biochemistry* 47(3):1076-1086, (Jan. 22, 2008, e-pub. Dec. 21, 2007).

Alt et al. "Novel Tetravalent and Bispecific IgG-Like Antibody Molecules Combining Single-Chain Diabodies With the Immunoglobulin γ1 Fc or CH3 Region," *FEBS Lett.* 454(1-2):90-94, (Jul. 2, 1999).

An et al. "Targeted Drug Delivery to Mesothelioma Cells Using Functionally Selected Internalizing Human Single-Chain Antibodies," *Mol. Cancer Ther.* 7(3):569-578, (Mar. 2008), 17 pages.

Anonymous. "Production in Reasts of Stable Antibody Fragments," *Expert Opinion on Therapeutic Patents* 7(2):179-183, (1997).

Anthony, R.M. et al. "A Recombinant IgG Fc That Recapitulates the Antiinflammatory Activity of IVIG", *Science* 320(5874):373-376, (Apr. 18, 2008), 12 pages.

Arié et al. "Chaperone Function of FkpA, a Heat Shock Prolyl Isomerase, in the Periplasm of *Escherichia coli*," *Mol. Microbiol.* 39(1):199-210, (2001).

Armour, K.L. et al. "Recombinant Human IgG Molecules Lacking Fcγ Receptor I Binding and Monocyte Triggering Activities," *Eur. J. Immunol.* 29:2613-2624, (1999).

Arndt, K.M. et al. "Helix-Stabilized Fv (hsFv) Antibody Fragments: Substituting the Constant Domains of a Fab Fragment for a Heterodimeric Coiled-Coil Domain," *J. Mol. Biology* 312(1):221-228, (Sep. 7, 2001).

Arndt et al. "Factors Influencing the Dimer to Monomer Transition of An Antibody Single-Chain Fv Fragment," *Biochemistry* 15:37(37):12918-12926, (1998).

Atwell et al. "Stable Heterodimers From Remodeling the Domain Interface of A Homodimer Using A Phage Display Library," *J. Mol. Biol.* 270 (1):26-35 (1997).

Ausubel et al. *Short Protocols in Molecular Biology*, Greene Publishing and Wiley Interscience, New York, New York, (Table of Contents), (1995).

Avgeris et al. "Kallikrein-Related Peptidase Genes As Promising Biomarkers for Prognosis and Monitoring of Human Malignancies," *Biol. Chem* 391(5):505-511, (May 2010).

Bachman. "Derivations and Genotypes of Some Mutant Derivatives of *Escherichia coli* K-12," Chapter 72 in *Escherichia Coli and Samonella Typimurium Cellular and Molecular Biology*, vol. 2, American Society for Microbiology, Washington D.C., pp. 1190-1219, (1987).

Backer et al. "Molecular Vehicles for Targeted Drug Delivery," *Bioconjugate Chem.* 13:462-467, (2002, e-pub. Apr. 12, 2002).

Baldwin et al. "Monoclonal Antibodies in Cancer Treatment," *Lancet* 60:603-606, (1986).

Bao et al. "HER2-Mediated Upregulation of MMP-1 Is Involved in Gastric Cancer Cell Invasion," *Arch Biochem Biophys* 499(1-2):49-55, (Jul. 2010, e-pub. May 10, 2010).

Barbin et al. "Influence of Variable N-Glycosylation on the Cytolytic Potential of Chimeric CD19 Antibodies, "*J. Immunother.* 29(2):122-133, (Mar.-Apr. 2006).

Barnes et al. "Methods for Growth of Cultured Cells in Serum-free Medium," *Anal. Biochem.* 102:255-270, (Mar. 1, 1980).

Barnes et al. "Advances in Animal Cell Recombinant Protein Production: GS-NS0 Expression System," *Cytotechnology* 32 (2):109-123 (Feb. 2000).

Barnes et al. "Characterization of the Stability of Recombinant Protein Production in the GS-NS0 Expression System," *Biotechnol Bioeng.* 73(4):261-270 (May 2001).

Bass et al. "Hormone Phage: An Enrichment Method for Variant Proteins With Altered Binding Properties," *Proteins* 8:309-314, (1990).

Behrens. "Synthesis of Achiral Linker Reagents for Direct Labelling of Oligonucleotides on Solid Supports," *Nucleosides & Nucleotides* 18:291-305, (1999, e-pub. Oct. 4, 2006).

Bendig. "Humanization of Rodent Monoclonal Antibodies by CDR Grafting," *Methods: A companion to Methods in Enzymology* 8:83-93 (1995).

Bera et al., "A Bivalent Disulfide-Stabilized Fv With Improved Antigen Binding to ErbB2," *J. Mol. Biol.* 281(3):475-483, (Aug. 21, 1998).

Berkman, R.A. et al. "Expression Of The Vascular Permeability Factor/Vascular Endothelial Growth Factor Gene In Central Nervous System Neoplasms," J. Clin. Invest. 91:153-159, (Jan. 1993).

Bird et al. "Single-Chain Antigen-Binding Proteins," *Science* 242(4877):423-426. (Oct. 21, 1988).

Bird et al. "Single-Chain Antigen-Binding Proteins," *Science* 244(4903):409, Erratum. (Apr. 28, 1989).

Boado, R.J. et al. "Engineering And Expression Of a Chimeric Transferrin Receptor Monoclonal Antibody For Blood-Brain Barrier Delivery In The Mouse," Biotechnology And Bioengineering 102(4):1251-1258, Mar. 1, 2009.

Boado, R.J. et al. "Selective Targeting Of a TNFR Decoy Receptor Pharmaceutical To The Primate Brain As a Receptor-Specific IgG Fusion Protein," J. Of Biotechnology 146(1-2):84-91, (Mar. 1, 2010).

Boado, R.J. et al. "Drug Targeting Of Erythropoietin Across The Primate Blood-Brain Barrier With An IgG Molecular Trojan Horse," J. Pharmacology and Experimental Therapeutics 333(3):961-969, (Jun. 1, 2010).

Boado et al., "IgG-Single Chain Fv Fusion Protein Therapeutic for Alzheimer's Disease: Expression in CHO Cells and Pharmacokinetics and Brain Delivery in the Rhesus Monkey," *Biotechnology and Bioengineering* 105(3):627-635, (Feb. 15, 2010, e-pub. Oct. 8, 2009).

Boerner et al., "Production of Antigen—Specific Human Monoclonal Antibodies From In Vitro-Primed Human Splenocytes," *J. Immunol.* 147(1):86-95, (Jul. 1, 1991).

(56) References Cited

OTHER PUBLICATIONS

Booy et al. "Monoclonal and Bispecific Antibodies as Novel Therapeutics," *Arch. Immunol. Ther. Exp.* 54:85-101, (Mar.-Apr. 2006, e-pub. Mar. 24, 2006).

Bordusa, F. "Protease-Catalyzed Formation of C-N Bonds," in *Highlights in Bioorganic Chemistry* Schmuck, C. and Wennemers, H. (eds.), Wiley VCH, Weinheim, pp. 389-403, (2004).

Borgström et al. "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," *Cancer Research* 56:4032-4039, (Sep. 1, 1996).

Bothmann et al. "The Periplasmic *Escherichia coli* Peptidylprolyl cis,trans-Isomerase FkpA. I. Increased Functional Expression of Antibody Fragments With and Without cis-Prolines," *J. Biol. Chem.* 275(22):17100-17105, (Jun. 2, 2000).

Brennan et al. "Preparation of Bispecific Antibodies By Chemical Recombination of Monoclonal Immunoglobulin G1 Fragments," *Science* 229:81-83, (1985).

Briggs et al., "Cystatin E/M Suppresses Legumain Activity and invasion of Human Melanoma," *BMC Cancer* 10(17):1-13, (Jan. 2010).

Brinkmann et al. "A Recombinant Immunotoxin Containing A Disulfide-Stabilized Fv Fragment," *Proc. Nat'l. Acad. Sci. USA* 90(16):7538-7542, (1993).

Brinkmann. "Disulfide-Stabilized Fv Fragments," Chapter 14 in 2 in *Antibody Engineering*, Kontermaan et al. eds., vol. 2, Springer-Verlag, Berlin Heidelberg, Germany, pp. 181-189, (Apr. 30, 2010).

Brorson et al. "Mutational Analysis of Avidity and Fine Specificity of Anti-Levan Antibodies," *J. Immunol.* 163:6694-6701, (1994).

Brown, L.F., et al. "Expression Of Vascular Permeability Factor (Vascular Endothelial Growth Factor) and Its Receptors In Adenocarcinomas Of The Gastrointestinal Tract," *Cancer Res.* 53:4727-4735, (Oct. 1, 1993).

Brown, L.F. et al. "Expression Of Vascular Permeability Factor (Vascular Endothelial Growth Factor) and Its Receptors In Breast Cancer," *Human Pathol.* 26:86-91, (1995).

Brüggemann et al. "Comparison of the effector functions of human immunoglobulins using a matched set of chimeric antibodies," *J Exp Med.* 166(5):1351-61, (Nov. 1987).

Brüggemann et al. "Designer Mice: The Production of Human Antibody Repertoires in Transgenic Animals," *Year in Immuno.* 7:33-40, (1993).

Brummell et al., "Probing the Combining Site of an Anti-Carbohydrate Antibody By Saturation-Mutagenesis: Role of the Heavy-Chain CDR3 Residues," *Biochemistry* 32(4):1180-1187, (1993).

Brunhouse et al. "Isotypes of IgG: Comparison of the Primary Structures of Three Pairs of Isotypes Which Differ in their Ability To Activate Complement," *Mol Immunol.* 16(11): 907-917 (Nov. 1979).

Budtschanow et al. "System of Humoral Immunity Antibodies (Theme 2)," *Guidance Manual for General Immunology*, Twer (2008), both English Equivalent and Russian Reference, 5 pages.

Burgess et al. "Possible Dissociation Of The Heparin-Binding and Mitogenic Activities of Heparin-Binding (Acidic Fibroblast) Growth Factor-1 From Its Receptor-Binding Activities By Site-Directed Mutagenesis of A Single Lysine Residue," *Journal of Cell Biology* 111:2129-2138, (Nov. 1990).

Burks et al., "In Vitro Scanning Saturation Mutagenesis of An Antibody Binding Pocket," *PNAS* 94(2):412-417, (Jan. 1997).

Burton et al., "The C1q Receptor Site on Immunoglobulin G," *Nature* 288(5789):338-344, (Nov. 27, 1980).

Burton. "Immunoglobulin G: Functional Sites," *Molec. Immunol.* 22(3):161-206, (1985).

Cao et al. "Bispecific Antibody Conjugates in Therapeutics," *Advanced Drug Delivery Reviews* 55:171-197, (2003).

Capel et al. "Heterogenity of Human IgG Fc Receptors," *Immunomethods* 4:25-34, (1994).

Carlsson et al. "Protein Thiolation and Reversible Protein-Protein Conjugation. N-Succinimidyl 3-(2-Pyridyldithio)Propionate, a New Heterobifunctional Reagent," *Biochem. J.* 173:723-737, (Sep. 1, 1978).

Carmichael et al. "Evaluation of a Tetrazolium-Based Semiautomated Colorimetric Assay: Assessment of Chemosensitivity Testing," *Cancer Res.* 47:936-942, (Feb. 15, 1987).

Caron et al. "Engineered Humanized Dimeric Forms of IgG Are More Effective Antibodies," *J. Exp. Med.* 176(4):1191-1195, (Oct. 1, 1992).

Carro et al. "Serum Insulin-Like Growth Factor I Regulates Brain Amyloid-$\beta$ Levels," *Nature Medicine* 8(12):1390-1397, (2002, e-pub. Nov. 4, 2002).

Carter et al. "High Level *Escherichia Coli* Expression and Production of A Bivalent Humanized Antibody Fragment," *Bio/Technology* 10:163-167, (1992).

Carter et al. "Humanization of an Anti-P185$^{HER2}$ Antibody for Human Cancer Therapy," *Proc. Natl. Acad. Sci. USA.* 89(10): 4285-4289, (May 1992).

Carter. "Bispecific Human IgG By Design," *Immunol. Methods* 248:7-15, (2001).

Carter, P.J. "Potent Antibody Therapeutics By Design," *Nature Reviews Immunology* 6:343-357, (May 2006, e-pub. Apr. 18, 2006).

Castoldi et al. "TetraMabs: Simultaneous Targeting Of Four Oncogenic Receptor Tyrosine Kinases For Tumor Growth Inhibition In Heterogeneous Tumor Cell Populations," Protein Engineering, Design & Selection 29(10):467-475, (2016, e-pub Aug. 29, 2016).

Chames P. et al. "Bispecific Antibodies for Cancer Therapy," *Current Opinion in Drug Discovery & Development*, 12(2):276-283, (2009).

Chan, L.A. et al. "Variable Region Domain Exchange in Human IgGs Promotes Antibody Complex Formulation with Accompanying Structural Changes and Altered Effector Functions," *Molecular Immunology* 41(5):527-538, (2004).

Chan et al. "Therapeutic Antibodies for Autoimmunity and Inflammation," *Nature Reviews* 10(5):301-316, (May 2010).

Chang et al. "A General Method for Facilitating Heterodimeric Pairing Between Two Proteins: Application to Expression of $\alpha$ and $\beta$ T-cell Receptor Extracellular Segments," *Proc. Natl. Acad. Sci. U.S.A.* 91:11408-11412, (Nov. 1994).

Chari et al. "Immunoconjugates Containing Novel Maytansinoids: Promising Anticancer Drugs," *Cancer Research* 52:127-131, (Jan. 1, 1992).

Charlton, K.A., "Expression and Isolation of Recombinant Antibody Fragments in *E. Coli*," In *Methods in Molecular Biology, vol. 248*, Lo, B.K.C. (ed.), Humana Press, Totowa, NJ (2003), pp. 245-254.

Chen et al. "Selection and Analysis of an Optimized Anti-VEGF Antibody: Crystal Structure of an Affinity-Matured Fab in Complex With Antigen," *J. Mol. Biol.* 293(4):865-681, (Nov. 5, 1999).

Chen et al. "Chaperone Activity of DsbC," *J. Biol. Chem* 274(28):19601-19605, (Jul. 9, 1999).

Chen et al. "Improved Variants of SrtA for Site-Specific Conjugation on Antibodies and Proteins With High Efficiency," *Scientific Reports* 6(31899):1-12, (Aug. 18, 2016), 12 pages.

Cheong et al. "Affinity Enhancement of Bispecific Antibody Against Two Different Epitopes in the Same Antigen," *Biochem. Biophys. Res. Commun.* 173(3):795-800, (Dec. 31, 1990).

Chernaia, "Cathepsin L From Human Brain Tumor. Purification and Contents," *Ukr Biokhim Zh.* 70(5):97-103, (Sep.-Oct. 1998). (English Translation of Abstract) (Article in Russian).

Cheung, A.H. et al. "Endothelial Tie2/Tek Ligands Angiopoietin-1 (ANGPT1) and Angiopoietin-2 (ANGPT2): Regional Localization Of The Human Genes To 8q22.3-q23 and 8p23," *Genomics* 48:389-391, (1998).

Chin, J.W. et al. "In Vivo Photocrosslinking With Unnatural Amino Acid Mutagenesis," *ChemBioChem*, 3(11):1135-1137, (2002).

Chin, J.W. et al. "Addition of p-Azido-L-Phenylalanine To The Genetic Code of *Escherichia Coli*", *J. Am. Chem. Soc.* 124(31):9026-9027, (2002).

Chin, J.W., et al. "Addition of a Photocrosslinking Amino Acid To The Genetic Code of *Escherichia coli*," *Proc. Natl. Acad. Sci. U.S.A.* 99(17):11020-11024, (Aug. 20, 2002).

(56) References Cited

OTHER PUBLICATIONS

Chinai et al. "New Immunotherapies Targeting The PD-1 Pathway," *Trends in Pharmacological Sciences* 36(9):587-595, (Sep. 2015), 21 pages.
Chitnis et al. "The Type 1 Insulin-Like Growth Factor Receptor Pathway," *Clin. Cancer Res.* 14(20):6364-6370, (Oct. 15, 2008, e-pub. Oct. 16, 2008).
Chothia et al. "Canonical Structures for the Hypervariable Regions of Immunoglobulins," *J. Mol. Biol.* 196:901-917, (1987).
Chow et al. "Studies on the Subsite Specificity of Rat Nardilysin (N-Arginine Dibasic Convertase)," *J. Biol. Chem.* 275(26):19545-19551, (Jun. 30, 2000).
Chung et al. "Development of A Novel Albumin-Binding Prodrug That Is Cleaved By Urokinase-Type-Plasminogen Activator (uPA)," *Bioorg Med Chem Lett.* 16(19):5157- 5163, (Oct. 1, 2006, e-pub. Jul. 27, 2006).
Clackson et al. "Making Antibody Fragments Using Phage Display Libraries," *Nature* 352:624-628, (Aug. 15, 1991).
Clancy, K.W., et al. "Sortase Transpeptidases: Insights Into Mechanism, Substrate Specificity, and Inhibition", *Biopolymers*, 94(4):385-396, (2010).
Clynes et al. "Fe Receptors are Required in Passive and Active Immunity to Melanoma," *Proc. Natl. Acad. Sci. USA* 95:652-656, (Jan. 1998).
Cocuzza "A Phosphoramidite Reagent for Automated Solid Phase Synthesis of 5'-Biotinylated Oligonucleotides," *Tetrahedron Letters* 30:6287-6290, (1989).
Cohen et al. "Nonchromosomal Antibiotic Resistance in Bacteria: Genetic Transformation of *Escherichia Coli* By R-Factor DNA," *Proc. Natl. Acad. Sci. USA* 69(8):2110-2114 (Aug. 1972).
Cole et al. "The EBV-Hybridoma Technique and Its Application to Human Lung Cancer," in *Monoclonal Antibodies and Cancer Therapy*, New York: Alan R. Liss, Inc. pp. 77-96 (1985).
Coleman. "Effects of Amino Acid Sequence Changes on Antibody-Antigen Interactions," *Research in Immunol.* 145(1):33-38, (1994).
Coloma et al. "Design and Production of Novel Tetravalent Bispecific Antibodies," Nature Biotechnology 15(2):159-163 (Feb. 1997).
Connolly, D.T. et al. "Human Vascular Permeability Factor," J. Biol. Chem. 264(33):20017-20024, (Nov. 25, 1989).
Cordingley et al. "Substrate Requirements of Human Rhinovirus 3C Protease for Peptide Cleavage In Vitro," *J. Biol. Chem.* 265(16):9062-9065, (Jun. 5, 1990).
Cortesio et al. "Calpain 2 and PTP1B Function in A Novel Pathway With Src to regulate Invadopodia Dynamics and Breast Cancer Cell Invasion," *J. Cell Biol.* 180(5):957-971, (Mar. 10, 2008).
Coxon et al. "Combined Treatment of Angiopoietin and VEGF Pathway Antagonists Enhances Antitumor Activity in Preclinical Models of Colon Carcinoma," *99th AACR Annual Meeting*, Abstract #1113, (Apr. 2008), 2 pages.
Cragg, M.S. et al. "Complement-Mediated Lysis By Anti-CD20 mAb Correlates With Segregation Into Lipid Rafts," Blood 101(3):1045-1052, (Feb. 1, 2003, e-pub. Sep. 19, 2002).
Cragg, M.S. et al. "Antibody Specificity Controls In Vivo Effector Mechanisms Of Anti-CD20 Reagents," Blood 103(7):2738-2743, (Apr. 1, 2004, e-pub. Oct. 9, 2003).
Crawford et al. "Matrix Metalloproteinase-7 Is Expressed By Pancreatic Cancer Precursors and Regulates Acinar-To-Ductal Metaplasia in Exocrine Pancreas," *J. Clin. Invest.* 109(11):1437-1444, (Jun. 2002).
Cruse, J.M. et al. *Illustrated Dictionary of Immunology* 2nd ed., CRC Press (2003) p. 37, 316-317.
Cudic et al. "Extracellular Proteases As Targets for Drug Development," *Curr. Protein Pept Sci* 10(4):297-307, (Aug. 2009).
Cullen et al. "Granzymes in Cancer and Immunity," *Cell Death Differ* 17(4):616-623, (Apr. 2010).
Daëron. "Fe Receptor Biology," *Annu. Rev. Immunol.* 15:203-234, (1997).
Dall'Acqua, W. et al. "Contribution of Domain Interface Residues to the Stability of Antibody $C_H3$ Domain Homodimers", *Biochemistry*, 37:9266-9273, (1998, e-pub. Jul. 6, 1998).

Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering, Design & Selection* 23(4):195-202, (2010, e-pub. Feb. 4, 2010).
Davies et al. "'Camelising' Human Antibody Fragments: NMR Studies on VH Domains," *Febs Letter* 339:285-290, (1994).
Davies et al. "Expression of GnTIII in a Recombinant Anti-CD20 CHO Production Cell Line: Expression of Antibodies With Altered Glycoforms Leads to An Increase in ADCC Through Higher Affinity for FcγRIII," *Biotechnol. Bioeng.* 74:288-294, (2001).
De Graaf et al. "Nonnatural Amino Acids for Site Specific Protein Conjugation," *Bioconjug. Chem.* 20(7):1281-1295, (2009, e-pub. Feb. 3, 2009).
De Haas et al. "Fcy Receptors of Phagocytes," *J. Lab. Clin. Med.* 126(4):330-341, (Oct. 1995).
Dervan, P.B. "Molecular Recognition of DNA By Small Molecules," *Bioorg. Med. Chem.* 9:2215-2235, (2001).
Deyev. "Multivalency: The Hallmark of Antibodies Used for Optimization of tumor Targeting By Design," *Bioessays* 30(9):904-918, (2008).
Deyev et al. "Modern Technologies for Creating synthetic Antibodies for Clinical Application," *Acta Naturae* 1:32-50, (2009).
Dickopf, S. et al. "Highly Flexible, IgG-Shaped, Trivalent Antibodies Effectively Target Tumor Cells and Induce T Cell-Mediated Killing," *Biol. Chem.* Abstract (Jan. 9, 2019). Abstract Only.
Dillman, R.O. (1989). "Monoclonal Antibodies for Treating Cancer" Annals of Internal Medicine 111:592-603.
Dimmock, N.J. et al. "Valency of Antibody Binding to Virions and Its Determination By Surface Plasmon Resonance," *Rev. Med. Virol.* 14:123-135, (2004).
Ding, H., et al., "Gold Nanorods Coated with Multilayer Polyelectrolyte as Contrast Agents for Multimodal Imaging," *J. Phys. Chem. C* 111:12552-12557, (2007, e-pub. Aug. 9, 2007).
Donaldson et al., "Design and Development of Masked Therapeutic Antibodies to Limit Off-Target Effects: Application to Anti-EGFR Antibodies," *Cancer Biology & Therapy* 8(22):2145-2150, (Nov. 15, 2009).
Dooley et al. "Antibody Repertoire Development in Cartilaginous Fish," *Dev. Comp. Immunol.* 30(1-2):43-56, (2006, e-pub. Jul. 22, 2005).
Doronina et al. "Development of Potent Monoclonal Antibody Auristatin Conjugates for Cancer Therapy," *Nat. Biotechnol.* 21(7):778-784, (Jul. 2, 2003, e-pub. Jun. 1, 2003).
Dubowchik et al. "Doxorubicin Immunoconjugates Containing Bivalent, Lysosomally-Cleavable Dipeptide Linkages," *Bioorg. & Med. Chem. Letters* 12:1529-1532, (2002).
Dufner et al. "Harnessing Phage and Ribosome Display for Antibody Optimization," *Trends Biotechol.* 24(11):523-29, (2006, e-pub. Sep. 26, 2006).
Duncan, A.R. et al. "The Binding Site For Clq On IgG," Nature 322:738-740,(1988).
Durocher et al. "High-Level and High-Throughput Recombinant Protein Production By Transient Transfection of Suspension-Growing Human 293-EBNA1 Cells," *Nucleic Acids Research* 30(2 e9):9 pages, (2002).
Dvorak, H. et al. "Vascular Permeability Factor/Vascular Endothelial Growth Factor, Microvascular Hyperpermeability, and Angiogenesis," Am. J. Pathol. 146(5):1029-1039, (May 1995).
Eaton et al. "Construction and Characterization of an Active Factor VIII Variant Lacking the Central One-Third of the Molecule," *Biochemistry* 25(26):8343-8347, (Dec. 30, 1986).
Edelman et al. "The Covalent Structure of an Entire γG Immunoglobulin Molecule," *Proc. Natl. Acad. Sci. USA* 63:78-85, (1969).
Ellman, J. et al. "Biosynthetic Method for Introducing Unnatural Amino Acids Site—Specifically into Proteins," *Meth. Enzym.* 202:301-336, (1991).
Els Conrath et al. "Camel Single-Domain Antibodies as Modular Building Units in Bispecific and Bivalent Antibody Constructs," *Journal of Biological Chemistry* 276(10):7346-7350, (Mar. 9, 2001, e-pub. Oct. 25, 2000).
Extended European Search Report dated Aug. 5, 2013, for European Patent Application No. 10817575.3, 11 pages.

(56) References Cited

OTHER PUBLICATIONS

Ferrara, N. et al. "The Biology of Vascular Endothelial Growth Factor," Endocr. Rev. 18(1):4-25(1997).
Fischer et al. "Bispecific Antibodies: Molecules That Enable Novel Therapeutic Strategies," Pathobiology 74:3-14, (2007).
Flatman et al. "Process Analytics for Purification of Monoclonal Antibodies," J. Chromatography B 848:79-87, (2007, e-pub. Dec. 11, 2006).
Fraker et al. "Protein and Cell Membrane Iodinations With a Sparingly Soluble Chloroamide, 1,3,4,6-Tetrachloro-3a,6a-Diphenylglycoluril," Biochem. Biophys. Res. Commun. 80(4):49-57, (Feb. 28, 1978).
Frese "Formylglycine Aldehyde Tag—Protein Engineering Through A Novel Post-Translational Modification," ChemBioChem 10:425-427, (2009).
Friend, P.J. et al. "Phase I Study of an Engineered Aglycosylated Humanized CD3 Antibody in Renal Transplant Rejection," Transplantation, 68(11):1632-1637, (1999), 10 pages.
Gadgil et al. "Identification of Cysteinylation of a Free Cysteine in the Fab Region of a Recombinant Monoclonal IgG1 Antibody Using Lys-C Limited Proteolysis Coupled With LC/MS Analysis," Analytical Biochem. 355:185-174, (2006, e-pub. Jun. 15, 2006).
Galamb et al. "Inflammation, Adenoma and Cancer: Objective Classification of Colon Biopsy Specimens With Gene Expression Signature," Dis Markers 25(1):1-16, (2008).
Gautier, A. et al. "An Engineered Protein tag for Multiprotein Labeling in Living Cells," Chem. Biol. 15:128-136, (Feb. 2008).
Gazzano-Santoro et al. "A Non-Radiative Complement-Dependent Cytotoxicity Assay for Anti-CD20 Monoclonal Antibody," J. Immunol. Methods 202:163-171, (1997).
Geisse et al. "Eukaryotic Expression Systems: A Comparison," Protein Expression and Purification 8:271-282 (1996).
Geoghegan et al. "Site-Directed Conjugation of Nonpeptide Groups to Peptides and Proteins via Periodate Oxidation of a 2-Amino Alcohol. Application Modification at N Terminator Serine," Bioconjugate Chem. 3(2):138-146, (1992).
Gerngross, T.U. "Advances in the Production of Human Therapeutic Proteins in Yeasts and filamentous Fungi," Nat. Biotech. 22(11):1409-1414, (Nov. 2004).
Gerspach et al. "Target-Selective Activation of a TNF Prodrug By Urokinase-Type Plasminogen Activator (uPA) Mediated Proteolytic Processing At the Cell Surface," Cancer Immunol. Immunother 55:1590-1600, (2006).
Gold et al. "A Novel Bispecific, Trivalent Antibody Construct for targeting Pancreatic Carcinoma," Cancer Res. 68(12):4819-4826, (Jun. 15, 2008).
Goldenberg et al. "Multifunctional Antibodies By the Dock-and-Lock Method for Improved Cancer Imaging and Therapy By Pretargeting," J. Nuc. Med. 49:158-163, (Jan. 2008).
Goldenberg et al. "Bi-Specific Antibodies that Bind Specific Target Tissue and Targeted Conjugates," Derwent Information Ltd. (2012), 12 pages.
Goodman et al. "Immunoglobulin Proteins," Chapter 6: Basic and Clinical Immunology, 8$^{th}$ edition, Appleton & Lange, Norwalk, CT, pp. 66-79, (1994).
Graham et al., "A New Technique for the Assay of Infectivity of Human Adenovirus 5 DNA," Virology 52 (2):456-467, (1973).
Graham et al. "Characteristics of a Human Cell Line Transformed by DNA From Human Adenovirus Type 5," J. Gen Virol. 36:59-72, (1977).
Greenwood et al. "Structural Motifs Involved in Human IgG Antibody Effector Functions,". Eur. J. Immunology 23(5):1098-1104, (May 1993).
Grönwall C. et al. "Generation of Affibody Ligands Binding Interleukin-2 Receptor Alpha/CD25," Biotechnol. Appl. Biochem. 50(Pt. 2):97-112, (Jun. 2008).
Grote et al. "Bispecific Antibody Derivatives Based on Full-Length IgG Formats," Chapter 16 in Methods in Molecular Biology 901:247-263, (2012).

Gruber et al. "Efficient Tumor Cell Lysis Mediated By A Bispecific Single Chain Antibody Expressed in Escherichia Coli," J. Immunol. 152:5368-5374, (1994).
Gunasekaran et al., "Enhancing Antibody Fc Heterodimer Formation Through Electrostatic Steering Effects: Applications to Bispecific Molecules And Monovalent IgG," The Journal of Biological Chemistry 285(25):19637-19646, (Jun. 18, 2010, e-pub. Apr. 16, 2010).
Guss et al. "Structure of the IgG-Binding Regions of Streptococcal Protein G," EMBO J. 5(7):1567-1575, (1986).
Guyer et al. "Immunoglobulin Binding by Mouse Intestinal Epithelial Cell Receptors," J. Immunol. 117(2):587-593, (Aug. 1976).
Hackenberger "Chemoselective ligation and modification strategies for peptides and proteins," Angew. Chem. Int. Ed. 47:10030-10074, (2008).
Ham et al. "Media and Growth Requirements," Meth. Enz. 58:44-93,(1979).
Hamers-Casterman et al. "Naturally Occurring Antibodies Devoid of Light Chains," Nature 363:446-448, (Jun. 3, 1993).
Hara et al. "Overproduction of Penicillin-Binding Protein 7 Suppresses Thermosensitive Growth Defect at Low Osmolarity Due to an spr Mutation of Escherichia coli," Microbial Drug Resistance 2(1):63-72, (1996).
Hartog et al. "The Insulin-Like Growth Factor 1 Receptor in Cancer: Old Focus, New Future," European Journal of Cancer 43(13):1895-1904, (Aug. 23, 2007, e-pub. Jul. 10, 2007).
Hatfield, K.J. et al. "Antiangiogenic Therapy in Acute Myelogenous Leukemia: Targeting of Vascular Endothelial Growth Factor and Interleukin 8 As Possible Antileukemic Strategies," Curr. Cancer Drug Targets, 5(4):229-248, (2005).
Hayashi et al. "Application of L-DNA as a Molecular Tag," Nucl. Acids Symp. Ser. 49:261-262, (2005).
Hellstrom, I. et al. "Strong Antitumor Activities Of IgG3 Antibodies To A Human Melanoma-Associated Ganglioside," Proc. Natl. Acad. Sci. USA 82:1499-1502, (Mar. 1985).
Hellstrom, I. et al. "Antitumor Effects Of L6, An IgG2a Antibody That Reacts With Most Human Carcinomas," Proc. Natl. Acad. Sci. USA 83:7059-7063, (Sep. 1986).
Henry et al. "Clinical Implications of Fibroblast Activation Protein in Patients With Colon Cancer," Clin Cancer Res. 13(6):1736-1741, (Mar. 15, 2007).
Herberman. "Immunodiagnosis of Cancer", in Fleisher (ed.), The Clinical Biochemistry of Cancer, p. 347-374, (1979).
Hey et al. "Artificial, Non-Antibody Binding Proteins for Pharmaceutical and Industrial Applications," Trends Biotechnol. 23(10):514-522, (Oct. 2005, e-pub. Jul. 28, 2005).
Hezareh et al. "Effector Function Activities of a Panel of Mutants of a Broadly Neutralizing Antibody against Human Immunodeficiency Virus Type 1," Journal of Virology 75(24):12161-12168, (Dec. 2001).
Hinman et al. "Preparation and Characterization of Monoclonal Antibody Conjugates of the Calicheamicins: A Novel and Potent Family of Antitumor Antibiotics," Cancer Res. 53:3336-3342, (Jul. 15, 1993).
Hollander. "Bispecific Antibodies for Cancer Therapy," Immunotherapy 1(2):211-222, (Mar. 2009).
Holliger et al. "'Diabodies': Small Bivalent and Bispecific Antibody Fragments," Proc. Natl. Acad. Sci. USA 90-6444-6448, (Jul. 1993).
Holliger et al. "Engineered Antibody Fragments and the Rise of Single Domains," Nat. Biotechnol. 23(9):1126-1136, (Sep. 2005, e-pub. Sep. 7, 2005).
Holt et al. "Domain Antibodies: Proteins for Therapy," Trends Biotechnol. 21(11):484-490, (Nov. 2003).
Hoogenboom et al. "By-Passing Immunisation. Human Antibodies From Synthetic Repertoires of Germline $V_H$ Gene Segments Rearranged in vitro," J. Mol. Biol. 227(2):381-388, (Sep. 20, 1992).
Hoppe et al. "A Parallel Three Stranded α-Helical Bundle At the Nucleation Site of Collagen Triple-Helix Formation," FEBS Lett. 344:191-195, (1994).
Huber, R. et al. "Crystallographic Structure Studies of an IgG Molecule and an Fc Fragment," Nature, 264:415-420, (Dec. 2, 1976).
Hudson et al. "Engineered Sntibodies," Nat. Med. 9:129-134, (Jan. 2003).

(56) References Cited

OTHER PUBLICATIONS

Hust et al. "Single Chain Fab (scFab) Fragment," *BMC Biotechnology* 7(14):1-15, (Mar. 8, 2007).
Huston et al. "Protein Engineering Of Antibody Binding Sites: Recovery Of Specific Activity in an Anti-Digoxin Single-Chain Fv Analogue Produced In *Escherichia Coli*," *Proc. Natl. Acad. Sci. U.S.A.* 85(16):5879-5883, (Aug. 1988).
Huston, J.S. et al. "Medical Applications of Single-Chain Antibodies," *Intern. Rev. Immunol.* 10(2-3):195-217, (1993).
Huynh et al. "Synthesis of Cholesteryl Supports and Phosphoramidites Containing A Novel Peptidyl Linker for Automated Synthesis of Triple-Helix Forming Oligonucleotides (TFOs)," *Nucleic Acids Symposium Series 29* (Second International Symposium on Nucleic Acids Chemistry), pp. 19-20, (1993).
Ibragimova et al. "Stability of the β-Sheet of the WW domain: A molecular dynamics simulation study," *Biophysical Journal* 77:2191-2198, (Oct. 1999).
Idusogie et al. "Mapping of the C1q Binding Site on Rituxan, A Chimeric Antibody with A Human IgG1Fc," *The Journal of Immunology* 164:4178-4184, (2000).
Ilangovan, U. et al. "Structure of Sortase, the Transpeptidase That Anchors Proteins to the Cell Wall of *Staphylococcus aureus*," *Proc. Natl. Acad. Sci. U.S.A.* 98(11):6056-6061, (2001).
International Preliminary Report on Patentability for PCT/EP2011/054505, dated Oct. 2, 2012, filed on Mar. 24, 2011, 8 pages.
International Preliminary Report on Patentability dated Aug. 21, 2014, for PCT Patent Application No. PCT/US2013/025365, filed on Feb. 8, 2013, 11 pages.
International Preliminary Report On Patentability for PCT Application No. PCT/EP2014/079353, dated Jul. 12, 2016, filed Dec. 29, 2014, 9 pages.
International Search Report for PCT Application No. PCT/EP2014/079353, dated Apr. 20, 2015, filed Dec. 29, 2014, 6 pages.
International Search Report dated Jun. 15, 2011 for PCT Patent Application No. PCT/US2010/002546 filed on Sep. 16, 2010, 5 pages.
International Search Report for PCT/EP2011/054505 dated Jun. 28, 2011, filed on Mar. 24, 2011, 7 pages.
International Search Report and Written Opinion, dated Feb. 11, 2016, for PCT Patent Application No. PCT/EP2015/078155 filed on Dec. 1, 2015, seven pages.
International Search Report dated Aug. 5, 2014, for PCT Patent Application No. PCT/EP2013/063258, filed on Jun. 25, 2013, 7 pages.
International Search Report dated Dec. 6, 2011, for PCT Patent Application No. PCT/EP2011/064476 filed on Aug. 23, 2011, 7 pages.
International Search Report dated Dec. 6, 2011, for PCT Patent Application No. PCT/EP2011/064468 filed on Aug. 23, 2011, seven pages.
International Search Report dated Aug. 6, 2013, PCT Patent Application No. PCT/EP2013/063260, filed on Jun. 25, 2013, seven pages.
International Search Report dated Aug. 6, 2013, for PCT Application No. PCT/US2013/025365, filed Feb. 8, 2013, 6 pages.
International Search Report and Written Opinion, dated Feb. 11, 2016, for PCT Patent Application No. PCT/EP2015/078155 filed on Dec. 1, 2015, twelve pages.
Ishida et al. "Induced Expression Of PD-1, A Novel Member Of The immunoglobulin Gene Superfamily, Upon Programmed Cell Death," *EMBO J.* 11(11):3887-3895, (1992).
Iyer, R.P. "Abasic Oligodeoxyribonucleoside Phosphorothioates: Synthesis and Evaluation As Anti-HIV-1 Agents," *Nucleic Acids Research* 18(10):2855-2859, (1990).
Jackman et al. "Development of a Two-part Strategy to Identify a Therapeutic Human Bispedfic Antibody That Inhibits IgE Receptor Signaling," *The Journal of Biological Chemistry* 285(27):20850-20859, (Jul. 2, 2010).
Jakobovits et al. "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90(6):2551-2555, (Mar. 15, 1993).
Jakobovits et al. "Germ-line Transmission and Expression of a Human-derived Yeast Artificial Chromosome," *Nature* 362:255-258, (Mar. 1993).
Janeway. "Immunotherapy By Peptdes?" *Nature* 341:482-483, (Oct. 12, 1989).
Jang et al. "The Structural Basis for DNA Binding By An Anti-DNA Autoantibody," *Mol. Immunol.* 35(18):1207-1217 (1998).
Jefferis, R. et al. "Interaction Sites on Human IgG-Fc for FcγR: Current Models," *Immunol. Lett.* 82:57-65, (2002).
Jefferis et al. "IgG-Fc-Mediated Effector Functions: Molecular Definition of interaction Sites for Effector Ligands and the Role of Glycosylation," *Immunol Rev.* 163:59-76, (1998).
Jeffrey, S.C., et al. "Dipeptide-Based Highly Potent Doxorubicin Antibody Conjugates," Bioorg. Med. Chem. Lett. 16:358-362, (2006, e-pub. Nov. 3, 2005).
Jendreyko et al. "Simultaneous, Phenotypic Knockout of VEGF-R2 and Tie-2 With an Intradiabody Enhances Antiangiogenic Effects In Vivo," Therapieoptimierung and Risikostratifizierung, *Scripps Research Institute* 218:143-151, (2006).
Jia et al. "A Novel Trifunctional IgG-like Bispecific Antibody to Inhibit HIV-1 Infection and Enhance Lysis of HIV By Targeting Activation of Complement," *Virology Journal* 7(142):1-4, (Jun. 29, 2010).
Jian, R.K. (Jul. 1994). "Barriers to Drug Delivery in Solid Tumors," *Sci. Am.* 27(1):58-65.
Jiang et al. (Feb. 11, 2005). "A Novel Peptide Isolated from a Phage Display Peptide Library with Trastuzumab Can Mimic Antigen Epitope of HER-2," *J. Biol. Chem.* 280(6):4656-4662.
Jiang, X.R. et al. "Advances in the assessment and control of the effector functions of therapeutic antibodies", *Nat. Rev. Drug Discov.* 10(2):101-111, (Feb. 2011).
Johnson et al. "Kabat Database and its applications: 30 years after the first variability plot," *Nucleic Acids Research* 28(1):214-218, (2000).
Johnson et al. "Construction of Single-Chain Fv Derivatives Monoclonal Antibodies and Their Production in *Escherichia coli*," *Methods Enzymol.* 203:88-98, (1991).
Johnson et al. "The Kabat Database and a Bioinformatics Example," Chapter 2 in *Methods in Molecular Biology*, Lo, B.K.C, Humana Press, Totawa, N.J., 248:11-25, (2003).
Joly et al. "Overexpression of *Escherichia coli* Oxidoreductases Increases Recombinant Insulin-like Growth Factor-I Accumulation," *Proc. Natl. Acad. Sci. USA* 95-2773-2777, (Mar. 1998).
Jones et al. "Replacing the Complementarity-Determining Regions in a Human Antibody With Those From a Mouse," *Nature* 321:522-525, (May 29, 1986).
Kabat et al. "Evolutionary and Structural Influences on Light Chain Constant ($C_L$) Region of Human and Mouse Immunoglobulins," *Proc. Natl. Acad. Sci. USA* 72(7):2785-2788, (Jul. 1975).
Kabat et al. *Sequences of Proteins of Immunological Interest* (Table of Contents and Introduction), 5th edition, Bethesda, MD: Public Health Service, NIH, vol. 1, (1991).
Kam, N.W. et al. "Carbon Nanotubes As Multifunctional Biological Transporters And Near-Infrared Agents For Selective Cancer Cell Destruction," *Proc. Natl. Acad. Sci. USA* 102(33):11600-11605, (Aug. 16, 2005).
Kanda, Y. et al. "Comparison of Cell Lines for Stable Production of Fucose-Negative Antibodies With Enhanced ADCC," Biotechnol. Bioeng. 94:680-688, (2006, e-pub. Apr. 11, 2006).
Karadag et al. "ADAM-9 (MDC-9/meltrin-γ), A Member of the a Disintegrin and Metalloproteinase Family, Regulates Myeloma-Cell-Induced Interleukin-6 Production in Osteoblasts By Direct Interaction With the αvβ5 Integrin," *Blood* 107(8):3271-3278, (Apr. 2006, e-pub. Dec. 22, 2005).
Kaufman. "Overview of Vector Design for Mammalian Gene Expression," *Molecular Biotechnology* 16:151-160, (2000).
Kazama et al. "Hepsin, A Putative Membrane-Associated Serine Protease, Activates Human Factor VII and Initiates a Pathway of Blood Coagulation on the Cell Surface Leading to Thrombin Formation," *J. Bio. Chem.* 270(1):66-72, (Jan. 1995).

(56) References Cited

OTHER PUBLICATIONS

Keck, P.J. et al. "Vascular Permeability Factor, An Endothelial Cell Mitogen Related To PDGF," Science 246:1309-1312., (Dec. 8, 1989).
Kim et al. "Inhibition of Vascular Endothelial Growth Factor-Induced Angiogenesis Suppresses Tumour Growth In Vivo," Nature 362:841-844, (Apr. 29, 1993).
Kim et al. "Localization of the Site of the Murine IgG1 Molecule that is Involved in Binding to the Murine Intestinal Fc Receptor," Eur J Immunol. 24:2429-2434, (1994).
Kim, I., et al. "Molecular Cloning and Characterization Of a Novel Angiopoietin Family Protein, Angiopoietin-3," FEBS Lett. 443:353-356; (1999).
Kim, I., et al. "Molecular Cloning, Expression, and Characterization of Angiopoietin-related Protein," J. Biol. Chem. 274(37):26523-26528, (Sep. 10, 1999).
Kindt, T.J. et al. Kuby Immunology, 6th ed., W.H. Freeman and Co., N.Y. p. 91, (2007).
King, H.D. et al. "Monoclonal Antibody Conjugates of Doxorubicin Prepared With Branched Peptide Linkers: Inhibition of Aggregation By Methoxytriethyleneglycol Chains," J. Med. Chem. 45(19):4336-4343, (2002, e-pub. Aug. 14, 2002).
Klein et al. "Progress in Overcoming the Chain Association Issue in Bispecific Heterodimeric IgG Antibodies" mAbs 4(6):653-663, (Nov./Dec. 2012).
Klein et al. "The Use Of CrossMAb Technology For The Generation Of Bi-and Multispecific Antibodies," MABS 8(6):1010-1020, (2016).
Kleinschmidt et al. "Design of a Modular Immunotoxin Connected By Polyionic Adapter Peptides," J. Mol. Biol. 327(2):445-452, (Mar. 21, 2003).
Kobayshi et al. "Similarities in the Biodistribution of Iodine-Labeled Anti-Tac Single-Chain Disulfide-Stabilized Fv Fragment and Anti-Tac Disulfide-Stabilized Fv Fragment," Nuclear Medicine & Biology 25:387-393, (1998).
Kobayshi et al. "Tryptophan H33 Plays an Important Role in Pyrimidine (6-4) Pyrimidone Photoproduct Binding By a High-Affinity Antibody," Protein Engineering 12(10):879-844 (1999).
Kodukula et al. "Biosynthesis of Phosphatidylinositol Glycan-Anchored Membrane Proteins. Design of a Simple Protein Substrate To Characterize the Enzyme That Cleaves the COOH-Terminal Signal Peptide," The Journal of Biological Chemistry 266(7):4464-4470 (Mar. 5, 1991).
Koerber et al. "An Improved Single-Chain Fab Platform for Efficient Display and Recombinant Expression," J. Mol. Biol. 427 (2): 576-586, (Jan. 30, 2015), 21 pages.
Kontermann, R.E. (Apr. 20, 2010). "Alternative Antibody Formats," Curr. Op. in. Mol. Ther. 12(2):176-183.
Kostelny, S.A., et al. "Formation of a Bispecific Antibody By the Use of Leucine Zippers," J. Immunol. 148(5):1547-1553, (Mar. 1, 1992).
Kratz, F. et al. "Prodrugs of anthracyclines in cancer chemotherapy," Current Med. Chem. 13:477-523, (2006).
Krugmann et al. "Structural Requirements for Assembly of Dimeric IgA Probed by Site-Directed Mutagenesis of J Chain and a Cysteine Residue of the α-chain CH2 Domain," The Journal of Immunology 159:244-249, (1997).
Kumar et al." Molecular Cloning and Expression of the Fabs of Human Autoantibodies in Escherichia coli," J. Biol. Chem. 275(45):35129-35136, (Nov. 10, 2000).
Labrijn et al. "Species-Specific Determinants in the IgG CH3 Domain Enable Fab-Arm Exchange by Affecting the Noncovalent CH3—CH3 Interaction Strength," The Journal of Immunology 187:3238-3246, (2011, e-pub. Aug. 12, 2011).
Lamkanfi et al. "Inflammasomes: Guardians of Cytosolic Sanctity," Immunol. Rev. 227(1):95-105, (Jan. 2009).
Landschulz et al. "The Leucine Zipper: A Hypothetical Structure Common to a New Class of DNA Binding Proteins," Science 240:1759-1764, (Jun. 24, 1988).

Lazar et al., "Transforming growth factor α: Mutation of aspartic acid 47 and leucine 48 results in different biological activities," Molecular and Cellular Biology 8(3):1247-1252, (Mar. 1988).
Lee et al. "Generation And Characterization of A Novel Single-Gene-Encoded Single-Chain Immunoglobulin Molecule With Antigen Binding Activity and Effector Functions" Mol. Immunol. 36(1):61-71, (1999).
Lee et al. "Using Substrate Specificity of Antiplasmin-Cleaving Enzyme For Fibroblast Activation Protein Inhibitor Design," Biochemistry 48(23):5149-5158, (Jun. 16, 2009, e- pub. Apr. 29, 2009).
Leeman et al., "The Structure, Regulation, and Function of Human Matrix Metalloproteinase-13," Crit. Rev Biochem Mol. Biol. 37(3):149-166, (2002).
Levary et al. "Protein-Protein Fusion Catalyzed By Sortase A," PLOS One 6(4):e18342.1-e18342.6, (Apr. 6, 2011).
Leung, D.W. et al. "Vascular Endothelial Growth Factor Is a Secreted Angiogenic Mitogen," Science 246:1306-1309, (1989).
Li, H., et al. "Optimization of Humanized IgGs in Glycoengineered Pichia Pastoris," Nat. Biotech. 24(2):210-215, (Feb. 2006, e-pub. Jan. 22, 2006).
Liang et al., "Cross-Species Vascular Endothelial Growth Factor (VEGF)-Blocking Antibodies Completely Inhibit the Growth of Human Tumor Xenografts and Measure the Contribution of Stromal VEGF," Journal of Biological Chemistry 281(2):951-961, (Jan. 13, 2006).
Lifely et al., "Glycosylation and Biological Activity of CAMPATH-1H Expressed in Different Cell Lines and Grown Under Different Culture Conditions," Glycobiology 5(8):813-822, (Dec. 1995).
Lin et al. "Structure-Function Relationships in Glucagon: Properties of Highly Purified Des-His-, Monoiodo-, and [Des-Asn$^{28}$, Thr$^{29}$](Homoserine Lactone$^{27}$)-Glucagon," Biochemistry USA 14(8):1559-1563, (1975).
Lindmark et al. "Binding of Immunoglobulins to Protein A and Immunoglobulin Levels in Mammalian Sera," J. Immunol. Meth. 62:1-13, (1983).
Liotta et al. "Metastatic potential correlates with enzymatic degradation of basement membrane collagen," Nature 284(5751) 67-68, (Mar. 6, 1980).
Liu et al. "Eradication of Large Colon Tumor Xenografts by Targeted Delivery of Maytansinoids," Proc. Natl. Acad. Sci. USA 93:8618-8623. (Aug. 6, 1996).
Liu, B., et al. "Mapping Tumor Epitope Space By Direct Selection of Single-Chain Fv Antibody Libraries On Prostate Cancer Cells," Cancer Res. 64:704-710, (Jan. 15, 2004).
Liu et al. "Clinical and imaging diagnosis of primary hepatic lymphoma," J First Mil Med. Univ, 25(10):1290-1292, three pages, (2005). (Translation of the Abstract Only.).
Liu et al. "Heterogeneity of Monoclonal Antibodies," Journal of Pharmaceutical Sciences 97(7):2426-2447, (Jul. 2008).
Lode et al. "Targeted Therapy With a Novel Enediyene Antibiotic Calicheamicin $\theta^I_1$ Effectively Suppresses Growth and Dissemination of Liver Metastases in a Syngeneic Model of Murine Neuroblastoma," Cancer Res. 58:2925-2928, (Jul. 15, 1998).
Lopez-Otin et al. "The Regulatory Crosstalk Between Kinases and Proteases in Cancer," Nat. Rev. Cancer 10(4):278-292, (Apr. 2010, e-pub. Mar. 19, 2010).
Love et al. "Recombinant Antibodies Possessing Novel Effector Functions," Methods in Enzymology 178:515-527, (1989).
Lu et al. "Fab-scFv Fusion Protein: an Efficient Approach to Production of Bispecific Antibody Fragments," J. Immunol Methods 267(2):213-226, (2002).
Lu et al. "Simultaneous Blockage of Both the Epidermal Growth Factor Receptor And the Insulin-Like Growth Factor Receptor Signaling Pathways in Cancer Cells With a Fully Human Recombinant Bispecific Antibody," J. Biol. Chem. 279(4):2856-2865, (Jan. 23, 2004).
Lu et al. "The Effect Of Variable Domain Orientation And Arrangement on the Antigen-Binding Activity of a Recombinant Human Bispecific Diabody," Biochem. Biophys. Res. Commun. 318(2):507-513, (2004. E-pub. Apr. 22, 2004).
Lu et al. "A Fully Human Recombinant IgG-Like Bispecific Antibody to Both the Epidermal growth Factor Receptor and the

(56) References Cited

OTHER PUBLICATIONS

Insulin-Like Growth Factor Receptor for Enhanced Antitumor Activity," *The Journal of Biological Chemistry* 280(20):19665-19672, (May 20, 2005).
Lu et al. "ADAMTS1 and MMP1 Proteolytically Engage EGF-Like Ligands in an Osteolytic Signaling Cascade for Bone Metastasis," *Genes Dev.* 23(16):1882-1894, (Aug. 2009).
Lukas et al. "Inhibition of C1-Mediated Immune Hemolysis by Monomeric and Dimeric Peptides from the Second Constant Domain of Human Immunoglobulin G," *The Journal of Immunolgy* 127(6):2555-2560, (Dec. 1981).
Lund et al. "Oligosaccharide-Protein Interactions in IgG Can Modulate Recognition by Fcγ Receptors," *FASEB Journal* 9:115-119, (1995).
Mabry, R. et al. (Mar. 2010, e-pub. Dec. 18, 2009). "Engineering of Stable Bispecific Antibodies Targeting II-17A and IL-23," Protein Eng. Des. Sel. 23 (3):115-127.
MacCallum et al. "Antibody-Antigen Interactions: Contact Analysis and Binding Site Topography," *J. Mol. Biol.* 262:732-745, (1996).
Madej, M.P. et al. "Engineering of An Anti-Epidermal Growth Factor Receptor Antibody to Single Chain Format and Labeling by Sortase A-Mediated Protein Ligation," *Biotechnology and Bioengineering* 109(6):1461-1470, (Jun. 2012, e-pub. Dec. 26, 2011).
Maisonpierre, P.C. et al. "Angiopoietin-2, A Natural Antagonist for Tie2 That Disrupts in vivo Angiogenesis," Science 277:55-60, (Jul. 4, 1997).
Makrides, S.C. "Components of Vectors for Gene Transfer and Expression in Mammalian Cells," *Protein Expression and Purification* 17:183-202, (1999).
Mallender et al. "Comparative Properties of the Single Chain Antibody and Fv Derivatives of mAb Apr. 4, 2020. Relationship Between Interdomain Interactions and the High Affinity for Fluorescein Ligand," *Journal of Biological Chemistry* 271(10):5338-5346, (Mar. 8, 1996).
Malmborg et al. "BIAcore as a Tool in Antibody Engineering," *J. Immunol. Methods* 183:7-13, (1995).
Mamoune et al. "Calpain-2 as a Target for Limiting Prostate Cancer Invasion," *Cancer Res.* 63(15):4632-4640, (Aug. 1, 2003).
Mandler et al. "Synthesis and Evaluation of Antiproliferative Activity of a Geldanamycin-Herceptin™ Immunoconjugate," *Biorganic & Med. Chem. Letters* 10:1025-1028, (May 15, 2000).
Mandler et al. "Immunoconjugates of Geldanamycin and Anti-HER2 Monoclonal Antibodies: Antiproliferative Activity on Human Breast Carcinoma Cell Lines," *J. of the Nat. Cancer Inst.* 92(19):1573-1581, (Oct. 4, 2000).
Mandler et al. "Modifications in Synthesis Strategy Improve the Yield and Efficacy of Geldanamycin-herceptin Immunoconjugates," *Bioconjugate Chem.* 13(4):786-791, (Jul.-Aug. 2002, e-pub. Jun. 19, 2002).
Mann "Proteomic Analysis of Post-Translational Modifications," *Biochemistry* 21:255-261, (Mar. 2003).
Marks et al. "By-Passing Immunization: Human Antibodies From V-gene Libraries Displayed On Phage," *J. Mol. Biol.* 222(3):581-597, (Dec. 5, 1991).
Marvin et al., "Recombinant Approaches to IgG-Like Bispecific Antibodies," *Acta Pharmacol. Sin.* 26:649-658, (Jun. 2005).
Marvin et al. "Bispecific Antibodies for Dual-Modality Cancer Therapy: Killing Two Signaling Cascades With One Stone," *Curr. Opin. Drug Discov. Devl.* 9(2):184-193, (2006).
Mason et al. "Coiled Coil Domains: Stability, Specificity, and Biological Implications," *ChemBioChem* 5:170-176, (2004).
Mather "Establishment and Characterization of Two Distinct Mouse Testicular Epithelial Cell Lines," *Biol. Reprod.* 23:243-251, (1980).
Mather et al. "Culture of Testicular Cells in Hormone-supplemented Serum-Free Medium," *Annals N.Y. Aca. Sci.* 383:44-68, (1982).
Matrisian. "Cancer Biology: Extracellular Proteinases in Malignancy," *Curr. Biol.* 9(20):R776-R778, (Oct. 1999).

Mattern, J. et al. "Association Of Vascular Endothelial Growth Factor Expression With Intratumoral Microvessel Density and Tumour Cell Proliferation In Human Epidermoid Lung Carcinoma," Brit. J. Cancer 73:931-934, (1996).
Mayer, K. et al. "TriFabs-Trivalent IgG-Shaped Bispecific Antibody Derivatives: Design, Generation, Characterization and Application for Targeted Payload Delivery," *International Journal of Molecular Sciences* 16:27497-27507, (2015).
McCarron et al. "Antibody Conjugates and Therapeutic Strategies," *Mol. Interventions* 5(6):368-380, (2005).
McKeen, C.M., et al. "Synthesis of Fluorophore and Quencher Monomers For Use in Scorpion Primers and Nucleic Acid Structural Probes," *Organic & Biomol. Chem.* 1:2267-2275, (2003, e-pub. May 28, 2003).
Mclean, G.R. et al. "A Point Mutation in the CH3 Domain of Human IgG3 Inhibits Antibody Secretion Without Affecting Antigen Specificity," *Molecular Immunology*, 42:1111-1119, (2005, e-pub. Jan. 4, 2005).
Meissner et al. "Transient Gene Expression: Recombinant Protein Production with Suspension-Adapted HEK293-EBNA Cells," *Biotechnology and Bioengineering* 75:197-203, (2001).
Melnyk et al. "Vascular Endothelial Growth Factor Promotes Tumor Dissemination by a Mechanism Distinct from Its Effect on Primary Tumor Growth," *Cancer Research* 56:921-924, (Feb. 15, 1996).
Merchant et al. "An Efficient Route To Human Bispecific IgG," *Nature Biotechnology* 16:677-681, (Jul. 1998).
Metz, S. et al. "Bispecific Digoxigenin-Binding Antibodies for Targeted Payload Delivery," *Proc. Natl. Acad. Sci. U.S.A.* 108 (20):8194-8199, (May 17, 2011).
Metz, S. et al. "Bispecific Antibody Derivatives with Restricted Binding Functionalities that are Activated by Proteolytic Processing," *Protein Engineering Design and Selection* 25(10):571-580, (2012, e-pub. Sep. 13, 2012).
Meyer, A. et al. "Oligonucleotide Sequential Bis-Conjugation Via Click-Oxime and Click-Huisgen Procedures," *Journal of Organic Chemistry* 75:3927-3930, (2010, e-pub. May 5, 2010).
Michaelson et al., "Anti-Tumor Activity of Stability-Engineered IgG-like Bispecific Antibodies Targeting TRAIL-R2 and LTβR," *MAbs* 1(2):128-141, (Mar. 2009, e-pub. Mar. 11, 2009).
Miller et al. "Design, Construction, and In Vitro Analyses of Multivalent Antibodies," *J. Immunol.* 170:4854-4861, (2003).
Milstein et al. "Hybrid Hybridomas and Their Use in Immunohistochemistry," *Nature* 305: 537-540, (Oct. 6, 1983).
Mimura et al. "Role of Oligosaccharide Residues of IgG1-Fc in FcγRIIb Binding," *The Journal of Biological Chemistry* 276(49): 45539-45547, (Dec. 7, 2001, e-pub. Sep. 20, 2001).
Minn et al. "Genes that Mediate Breast Cancer Metastasis to Lung," *Nature* 436(7050):518-524, (Jul. 2005), 15 pages.
Mirny, L. et al. "Protein Folding Theory: From Lattice to All-Atom Models," *Annu. Rev. Biophys. Biomol. Struct.* 30:361-396, (2001).
Mizukami, Y. et al. "Induction of Interleukin-8 Preserves the Angiogenic Response in HIF-1alpha-Deficient Colon Cancer Cells," *Nat. Med.* 11(9):992-997, (Sep. 2005, e- pub. Aug. 28, 2005).
Möhlmann S. et al. "In Vitro Sortagging of an antibody Fab Fragment: Overcoming Unproductive Reactions of Sortase With Water and Lysine Side Chains," *Chembiochem: A European Journal of Chemical Biology* 12(11):1774-1780, (2011).
Morgan et al. "The N-Terminal End of the $C_H2$ Domain of Chimeric Human IgG1 anti-HLA-DR is Necessary for C1q, FcγRI and FcγRIII Binding," *Immunology* 86:319-324, (1995).
Morimoto et al. "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *J. Biochem. Biophys. Meth.* 24:107-117, (1992).
Morocho, A.M., et al., "Novel Biotin Phosphoramidites With Super-Long Tethering Arms," *Nucleosides, Nucleotides & Nucleic Acids* 22(5-8):1439-1441, (2003, e-pub. Aug. 31, 2006).
Morrison et al. "Chimeric Human Antibody Molecules: Mouse Antigen-Binding Domains with Human Constant Region Domains," *Proc. Natl. Acad. Sci. USA* 81(21):6851-6855, (Nov. 1984).

(56) References Cited

OTHER PUBLICATIONS

Morrison et al. "Variable Region Domain Exchange Influences The Functional Properties of IgG," *Journal of Immunology, American Association of Immunologists* 160:2802-2808, (Jan. 1, 1998).
Morrison. "Two Heads are Better than One," *Nature Biotechnology* 25(11):1233-1234, (Nov. 2007).
Morrison. "Success in Specification," *Nature* 368:812-813, (Apr. 28, 1994).
Mukhopadhyay et al. "Matrix Metalloproteinase-12 is a Therapeutic Target For Asthma in Children and Young Adults," *J. Allergy Clin Immunol.* 126:70-76, (2010, e-pub. May 24, 2010).
Müller et al. "The First Constant Domain ($C_H1$ and $C_L$) of an Antibody Used As Heterodimerization Domain for Bispecific Miniantibodies," *FEBS Letters* 422:259-264, (1998).
Muller et al. "A Dimeric Bispecific Miniantibody Combines Two Specificities With Avidity," *FEBS Lett.* 432:45-49, (1998).
Muller et al. "Processing and Sorting of the Prohormone Convertase 2 Propeptide," *J. Biol. Chem.* 275(50):39213-39222, (Dec. 15, 2000).
Müller et al. "Recombinant Bispecific Antibodies for Cellular Cancer Immunotherapy," *Current Opinion in Molecular Therapeutics* 9(4):319-326, (2007).
Müller et al. "Bispecific Antibodies," Chapter 2 in *Handbook of Therapeutic Antibodies*, Dübel, S. ed., Wiley-VCH Verlag GmbH & Company KGaA, Weinheim, pp. 345-378, (2007).
Murakami et al. "Cell Cycle Regulation, Oncogenes, and Antineoplastic Drugs" Chapter 1 in *The Molecular Basis of Cancer*, Mendelsohn and Israel, Philadelphia, W.B. Saunders, Philadelphia pp. 3-17, (1995).
Muyldermas et al. "Recognition of Antigens by Single-domain Antibody Fragments: the Superfluous Luxury of Paired Domains," *Trend Biochem. Sci.* 26(4):230-235, (Apr. 2001).
Nagy, A., et al. "Stability of Cytotoxic Luteinizing Hormone-Releasing Hormone Conjugate (AN-152) Containing Doxorubicin 14-O-Hemiglutarate in Mouse and Human Serum In Vitro: Implications for the Design of Preclinical Studies," *Proc. Natl. Acad. Sci. USA* 97:829-834, (2000).
Natsume et al. "Fucose Removal From Complex-type Oligosaccharide Enhances the Antibody-dependent Cellular Cytotoxicity of Single-gene-encoded Bispecific Antibody Comprising of Two Single-Chain Antibodies Linked to the Antibody Constant Region," *Journal of Biochemistry* 140(3):359-368, (Sep. 1, 2006).
Nelson, P.S., et al., "Oligonucleotide Labeling Methods. 3. Direct Labeling of Oligonucleotides Employing a Novel, Non-Nucleosidic, 2-Aminobutyl-1,3-Propanediol Backbone," *Nucleic Acids Research* 20(23):6253-6259, (1992).
Neri et al. "High-Affinity Antigen Binding by Chelating Recombinant Antibodies (CRAbs)," *J. Mol. Biol.* 246:367-373, (1995).
Netzel-Arnett et al. "Sequence Specificities of Human Fibroblast and Neutrophil Collagenases," *J. Biol. Chem.* 266(11):6747-6755, (Apr. 15, 1991).
Netzel-Arnett et al. "Comparative Sequence Specificities of Human 72-and 92-kDa Gelatinases (Type IV Collagenases) and PUMP (Matrilysin)," *Biochemistry* 32(25):6427-6432, (Jun. 29, 1993).
Neuberger et al. "A Hapten-Specific Chimaeric IgE Antibody With Human Physiological Effector Function," *Nature* 314:268-270, (Mar. 21, 1985).
Nicolaou et al. Calicheamicin $\theta^I_1$: A Rationally Designed Molecule with Extremely Potent and Selective DNA Cleaving Properties and Apoptosis Inducing Activity, *Agnew Chem. Intl. Ed. Engl.* 33(2):183-186, (1994).
Niculescu-Duvaz et al. "Antibody-Directed Enzyme Prodrug Therapy (ADEPT): A Review," *Adv. Drg. Del. Rev.* 26:151-172, (1997).
Nielsen et al. "Therapeutic Efficacy of Anti-ErbB2 immunoliposomes Targeted By A Phage Antibody Selected For Cellular Endocytosis," *Biochim. Biophys. Acta* 1591:109-118, (2002).
Nieri et al. "Antibodies for Therapeutic Uses and the Evolution of Biotechniques," *Current Med. Chem.* 16(6):753-779. (Feb. 1, 2009).
Nilsson et al. "A Synthetic IgG-Binding Domain Based on *Staphylococcal* Protein A," *Prot. Eng.* 1:107-133, (1987).

Niwa et al., "IgG Subclass-Independent Improvement of Antibody-Dependent Cellular Cytotoxicity By Fucose Removal From $Asn^{297}$-Linked Oligosaccharides," *J. Immunol. Methods* 306:151-160, (2005, e-pub. Sep. 22, 2005).
Nord et al. "A Combinatorial Library of an α-Helical Bacterial Receptor Domain, "*Prot. Eng.* 8(6):601-608, (1995).
Nord et al. "Binding Proteins Selected From Combinatorial Libraries of An α-Helical Bacterial Receptor Domain," *Nat. Biotech.* 15:772-777, (Aug. 1997).
Norderhaug et al., "Versatile Vectors for Transient and Stable Expression of Recombinant Antibody Molecules in Mammalian Cells," *Journal of Immunological Methods* 204:77-87, (1997).
Noren, C.J. et al. "A General Method for Site-Specific Incorporation of Unnatural Amino Acids into Proteins", *Science*, 244:182-188, (1989).
Novellino, L. et al. "A Listing of Human Tumor Antigens Recognized by T Vells: Mar. 2004 update", *Cancer Immunol. Immunother.* 54(3):187-207, (2005).
Novotný, J. et al. "Structural Invariants of Antigen Binding: Comparison of Immunoglobulin $V_L$-$V_H$ and $V_L$-$V_L$ Domain Dimmers," *Proc. Natl. Acad. Sci. USA*, 82:4592-4596, (Jul. 1985).
Offner et al. "T Cell Receptor Peptide Therapy Triggers Autoregulation of Experimental Encephalomyelitis," *Science* 251:430-432, (Jan. 25, 1991).
Ohno et al. "Antigen-Binding Specificities of Antibodies Are Primarily Determined By Seven Residues of $V_H$," *Proc. Natl. Acad. Sci. USA* 82(9):2945-2949, (May 1985).
Okazaki, A et al. "Fucose Depletion From Human IgG1 Oligosaccharide Enhances Binding Enthalpy and Association Rate Between IgG1 and RcγRIIIa," *J. Mol. Biol.* 336:1239-1249, (2004).
Oliner et al., "Suppression of Angiogenesis and Tumor Growth by Selective Inhibition of Angiopoietin-2," *Cancer Cell* 6:507-516, (Nov. 2004).
Orcutt, et al. "A Modular IgG-scFv Bispecific Antibody Topology," *Protein Engineering, Design & Selection* 23(4):221-228, (Apr. 2010, e-pub. Dec. 17, 2009).
Orlandi et al. "Cloning Immunoglobulin Variable Domains for Expression by the Polymerase Chain Reaction," *Proc. Natl. Acad. Sci. USA* 86:3833-3837, (May 1989).
O'Shea et al. "Peptide 'Velcro': Design of a Heterodimeric Coiled Coil," *Current Biology* 3(10):658-667, (1993).
Pace et al., "How to Measure and Predict the Molar Absorption Coefficient of a Protein," *Protein Science* 4(11): 2411-2423, (Nov. 1995).
Pack et al. "Miniantibodies: Use of Amphipathic Helices to Produce Functional, Flexibly Linked Dimeric FV Fragments With High Avidity in *Escherichia Coli*," *Biochem.* 31(6):1579-1584, (Feb. 18, 1992).
Pakula et al., "Genetic Analysis of Protein Stability and Function," *Annu. Rev. Genet.* 23:289-310, (1989).
Pan, Q. et al. "Blocking Neuropilin-1 Function Has an Additive Effect with Anti-VEGF to Inhibit Tumor Growth," *Cancer Cell* 11:53-67, (Jan. 2007).
Pardridge, W.M. "Drug Transport Across The Blood-Brain Barrier," J. Of Cerebral Blood Flow & Metabolism 32(11):1959-1972, (Aug. 29, 2012).
Parmiani, G. et al. "Unique Human Tumor Antigens: Immunobiology and Use in Clinical Trials," *J. Immunol*, 178(4):1975-1979, (2007).
Paul. "Structure and Function of Immunoglobulins," Chapter 9 in *Fundamental Immunology*, Third Edition, Raven Press, New York, New York, pp. 292-295, (1993).
Petkova, S.B. et al. "Enhanced Half-Life Of Genetically Engineered Human IgG1 Antibodies In a Humanized FcRn Mouse Model: Potential Application in Humorally Mediated Autoimmune Disease," *Int. Immunol.* 18(12):1759-1769, (2006).
Pettit et al. "Marine Animal Biosynthetic Constituents for Cancer Chemotherapy," *J. Nat. Prod.* 44:482-485, (Jul.-Aug. 1981).
Pettit et al. "The Dolastatins," *Fortschr. Chem. Org. Naturst.* 70:1-79, (1997).
Pettit et al. "Antineoplastic Agents 360. Synthesis and Cancer Cell Growth Inhibitory Studies of Dolastatin 15 Structural Modifications," *Anti-Cancer Drug Design* 13:47-66, (1998).

(56) References Cited

OTHER PUBLICATIONS

Pettit et al. "Specific Activities of Dolastatin 10 and Peptide Derivatives Against Cryptococcus neoformans," *Antimirob. Agents Chemother.* 42(11):2961-2965, (Nov. 1998).

Pleass et al. "Identification of Residues in the CH2/CH3 Domain Interface of IgA Essential for Interaction With the Human Fcα Receptor (Fcα R) CD89," *The Journal of Biology Chemistry* 274(33):23508-23514, (Aug. 13, 1999).

Plückthun. "Antibodies from *Escherichia coli*," Chapter 11 in *The Pharmacology of Monoclonal Antibodies: Handbook of Pharmacology*, Rosenberg and Moore, eds., Berlin: Springer-Verlag, vol. 113, pp. 269-315, (1994).

Plückthun et al., "New Protein Engineering Approaches to Multivalent and Bispecific Antibody Fragments," *Immunotechnology* 3:83-105, (1997).

Pon, R.T., "A Long Chain Biotin Phosphoramidite Reagent For The Automated Synthesis of 5'-Biotinylated Oligonucleotides," *Tetrahedron Letters* 32(14):1715-1718, (1991).

Poncet "The Dolastatins, A Family of Promising Antineoplastic Agents," *Curr. Pharm. Des.* 5:139-162, (1999).

Popp M.W. et al. "Making and Breaking Peptide Bonds: Protein Engineering Using Sortase," *Angewandte Chemie*, 50(22):5024-5032, (2011).

Portolano et al. "Lack of Promiscuity in Autoantigen-Specific H and L Chain Combinations As Revealed By Human H and L Chain Roulette," *J. Immunol.* 150(3):880- 887, (Feb. 1, 1993).

PreScission Protease, GE Healthcare Catalogue No. 27-0843-01, located at http://www.gelifesciences.com/webapp/wcs/stores/servlet/productById/en/GELifeScience, last visited on Jul. 10, 2013, 1 page.

Presta "Antibody Engineering," *Curr. Op. Struct. Biol.* 2:593-596, (1992).

Presta et al. "Humanization of an Antibody Directed Against IgE," *J. Immunol.* 151(5):2623-2632, (Sep. 1, 1993).

Presta et al. "Humanization of An Anti-Vascular Endothelial Growth Factor Monoclonal Antibody for the Therapy of Solid Tumors and Other Disorders," *Cancer Res.* 57:4593-4599, (Oct. 15, 1997).

Presta, L.G. "Molecular Engineering and Design of Therapeutic Antibodies," *Current Opinion in Immunology* 20:460-470, (2008).

Proba et al. (Jul. 4, 1995). "Functional Antibody Single-Chain Fragments From The Cytoplasm of *Escherichia coli*: Influence Of Thioredoxin Reductase (TrxB)," *Gene* 159:203-207.

Prokhorenko, I.A., et al. "Incorporation of a Pyrene Nucleoside Analogue Into Synthetic Oligodeoxynucleotides Using a Nucleoside-Like Synthon," *Bioorganic & Medicinal Chemistry Letters* 5(18):2081-2084, (1995).

Putnam et al. "Synthesis and Evaluation of RNA Transesterification Efficiency Using Stereospecific Serinol-Terpyridine Conjugates," *Nucleosides, Nucleotides & Nucleic Acids* 24:1309-1323, (2005, e-pub. Aug. 31, 2006).

Raag et al. "Single-Chain Fvs," *The FASEB Journal* 9:73-80, (Jan. 1995).

Radaev et al. "Recognition of IgG by Fcγ Receptor," *The Journal of Biological Chemistry* 276(19): 16478-16483, (May 11, 2001).

Rajagopal et al. "A Form of Anti-Tac(Fv) Which is Both Single-chain and Disulfide Stabilized: Comparison with its single-chain and Disulfide-stabilized Homologs," *Protein Engineering* 10(12):1453-1459, (1997).

Raju. "Glycosylation Variations with Expression Systems and Their Impact on Biological Activity of Therapeutic Immunoglobulins," *BioProcess International* 1(4): 44-53, (Apr. 2003).

Ramm et al. "The Periplasmic *Escherichia coli* Peptidylprolyl cis,trans-Isomerase FkpA," *J. Biol. Chem.* 275(22):17106-17113, (Jun. 2, 2001, e-pub. Mar. 22, 2000).

Ramzaeva et al. Oligonucleotides Functionalized by Fluorescein and Rhodamine Dyes: Michael Addition of Methyl Acrylate to 2'-Deoxypseudouridine, *Helv. Chim. Acta* 83:1108-1126, (2000).

Ravetch et al. "Fc Receptors," *Annu. Rev. Immunol.* 9:457-492, (1991).

Rawlings. "A Large and Accurate Collection of Peptidase Cleavages in the MEROPS Database," *Database* (Oxford), pp. 1-14, (2009, e-pub. Nov. 2, 2009).

Reiter et al. "Stabilization of the Fv Fragments in Recombinant Immunotoxins by Disulfide Bonds Engineered into Conserved Framework Regions," *Biochemistry* 33(18):5451-5449, (1994).

Reiter et al. "Improved Binding And Antitumor Activity Of A Recombinant Anti-erbB2 Immunotoxin by Disulfide Stabilization of the Fv Fragment," *J. Biol. Chem.* 269(28):18327-18331, (Jul. 15, 1994).

Reiter et al. "Engineering Interchain Disulfide Bonds Into Conserved Framework Regions Of Fv Fragments: Improved Biochemical Characteristics Of Recombinant Immunotoxins Containing Disulfide-Stabilized Fv," *Protein Eng.* 7(5):697-704, (May 1994).

Reiter et al., "Cytotoxic and Antitumor Activity of a Recombinant Immunotoxin Composed of Disulfide-Stabilized Anti-Tac Fv Fragment and Truncated," Pseudomonas Exotoxin, *International Journal of Cancer* 58:142-149, (1994).

Reiter et al., "Antitumor Activity and Pharmacokinetics in Mice of a Recombinant Immunotoxin Containing a Disulfide-Stabilized Fv Fragment," *Cancer Research* 54:2714-2718, (May 15, 1994).

Reiter et al. Antibody Engineering of Recombinant Fv Immunotoxins for Improved Targeting of Cancer: Disulfide-Stabilized Fv Immunotoxins,"*Clin. Cancer Res.* 2(2):245-252, (Feb. 1996, e-pub. Feb. 1, 1996). ".

Reiter et al. "Disulfide Stabilization of Antibody Fv: Computer Predictions and Experimental Evaluation," *Protein Engineering* 8(12):1323-1331(1995).

Reiter et al. "Construction of a Functional Disulfide-Stabilized TCR Fv Indicates That Antibody and TCR Fv Frameworks Are Very Similar in Structure," *Immunity* 2:281-287 (Mar. 1995).

Reiter et al. "Engineering Antibody Fv Fragments for Cancer Detection and Therapy: Disulfide-Stabilized Fv Fragments," *Nature Biotechnology* 14:1239-1245, (Oct. 1996).

Remacle et al. "Substrate Cleavage Analysis of Furin and Related Proprotein Convertases," *Journal of Biological Chemistry* 283(30):20897-20906, (Jul. 25, 2008).

Remington's Pharmaceutical Sciences, Table Of Contents (1980).

Ren, Y. et al. "Macrophage Migration Inhibitory Factor Stimulates Angiogenic Factor Expression and Correlates With Differentiation and Lymph Node Status in Patients With Esophageal Squamous Cell Carcinoma," *Ann. Surg.* 242(1):55-63, (Jul. 2005).

Ren et al. "A Biocompatible Condensation Reaction for the Labeling of terminal Cysteine Residues on Proteins," *Angew. Chem. Int. Ed.* 48:9658-9662, (2009).

Ridgway et al. "Knobs-into-holes' Engineering of antibody $C_H3$ domains for heavy chain heterodimerization," *Protein Engineering* 9(7):617-621, (1996).

Riechmann et al. "Reshaping Human Antibodies for Therapy," *Nature* 332:323-327, (Mar. 24, 1988).

Ripka, J. et al. "Two Chinese Hamster Ovary Glycosylation Mutants Affected In The Conversion of GDP-Fucose," Arch. Biochem. Biophys. 249:533-545, (1986).

Roget et al. "Synthesis and Use of Labelled Nucleoside Phosphoramidite Building Blocks Bearing a Reporter Group: Biotinyl, Dinitrophenyl, Pyrenyl and Dansyl," *Nucleic Acids Research* 17(19):7643-7651, (1989).

Roitt et al. "Immunology," *Moscow, Mir.* pp. 110-111 (English Translation), (2000), 8 pages.

Roitt A. et al. "Multispecific Antibodies Comprising Full Length Antibodies and Single Chain Fab Fragments," *Immunology*, English Translation, Moscow:Mir, pp. 388-389, (2000), 2 pages.

Rose et al. "Quantitative Analysis of the Interaction Strength and Dynamics of Human IgG4 Half Molecules by Native Mass Spectrometry," *Structure* 19:1274-1282, (Sep. 7, 2011).

Rossi, E.A. et al. "Multivalent Anti-CD20/Anti-CD22 Bispecific Antibody Fusion Proteins Made by the DNL Method Show Potent Lymphoma Cytotoxicity," Abstract 2495 *Blood, American Society of Hematology* 801: Abstract 2495, (2006), 3 pages.

Routier et al. "The Glycosylation Pattern of a Humanized IgGl Antibody (D1.3) Expressed in CHO Cells," *Glycoconjugate Journal* 14:201-207, (1997).

(56) References Cited

OTHER PUBLICATIONS

Routledge, E.G. et al. "The Effect of Aglycosylation on the Immunogenicity of a Humanized Therapeutic CD3 Monoclonal Antibody," *Transplantation* 60(8):847-853, (Oct. 27, 1995).
Roux, K.H. et al. "Comparisons of the Ability of human IgG3 Hinge Mutants, IgM, IgE, and IgA2, to Form Small Immune Complexes: A Role for Flexibility and Geometry," *J. Immunol.* 161(8):4083-4090, (1998).
Rowland et al. "Drug Localisation and Growth Inhibition Studies of Vindesine-Monoclonal Anti-CEA Conjugates in a Human Tumour Xenograft," *Cancer Immunol. Immunother.* 21:183-187, (1986).
Rudikoff, S. et al. "Single Amino Acid Substitution Altering Antigen-Binding Specificity," *Proc. Natl. Acad. Sci. USA* 79:1979-1983, (Mar. 1982).
Ruppert et al. "Cloning and Expression of Human $TAF_{II}250$: a TBP-Associated Factor Implicated in Cell-Cycle Regulation," *Nature* 362:175-179, (Mar. 11, 1993).
Ruppert et al. "Protease Levels in Breast, Ovary and Other Gynecological Tumor Tissues: Prognostic Importance in Breast Cancer," *Cancer Detect. Prev.* 21(5):452-459 (1997).
Sakamoto et al. "Enzyme-Mediated Site-Specific Antibody-Protein Modification Using a ZZ Domain as a Linker," *BioConjugate Chem.* 21:2227-2233, (2010, e-pub. Nov. 11, 2010).
Salfeld, J.G. "Isotype Selection in Antibody Engineering," *Nat. Biotechnol.* 25(12):1369-1372, (Dec. 2007).
Sambrook et al. *Molecular Cloning: A Laboratory Manual* "The Table of Contents" Cold Spring Harbor, New York: Cold Spring Harbor Laboratory Press, (1989).
Santos et al. "Generation and Characterization of a Single Gene-Encoded Single-Chain-tetravalent Antitumor Antibody" *Clinical Cancer Research* 5(10 Suppl):3118s-3123s, (Oct. 1999).
Schaefer et al. "Immunoglobulin Domain Crossover as a Generic Approach for the Production of Bispecific IgG Antibodies," *Proc. Natl. Acad. Sci. U.S.A.* 108(27):11187-11192, (Jul. 5, 2011, e-pub. Jun. 20, 2011).
Schanzer, J.M. et al. (Jul. 4, 2014). "A Novel Glycoengineered Bispecific Antibody Format for Targeted Inhibition of Epidermal Growth Factor Receptor (EGFR) and Insulin-like Growth Factor Receptor Type I (IGF-1R) Demonstrating Unique ," J. Biol. Chem. 289(27):18693-18706.
Scher, H.I. (Dec. 6, 2000). "EDIORIALS. HER2 in Prostate Cancer—A Viable Target or Innocent Bystander?," Journal of the National Cancer Institute 92(23):1866-1868.
Scheuer et al. "Anti-Tumoral, Anti-Angiogenic and Anti-Metastatic Efficacy Of A Tetravalent Bispecific Antibody (TAvi6) Targeting VEGF-A and Angiopoietin-2," *MABS* 8(3):562-573, (2016).
Schirrmann et al. "Oligomeric Forms of Single Chain Immunoglobulin (sclgG)," *Landes Bioscience* 2(1):73-76, (Jan./Feb. 2010).
Schlaeger. "The Protein Hydrolysate, Primatone RL, is a Cost Effective Multiple Growth Promoter of Mammalian Cell Culture in Serum-containing and Serum-free Media and Displays Anti-apoptosis Properties," *Journal of Immunological Methods* 194:191-199, (1996).
Schlaeger et al. "Transient Gene Expression in Mammalian Cells Grown in Serum-free Suspension Culture," *Cytotechnology* 30:71-83, (1999).
Schmidt et al., "Suppression of Metastasis Formation by a Recombinant Single Chain Antibody-Toxin Targeted to Full-length and Oncogenic Variant EGF Receptors," *Oncogene* 18:1711-1721, (1999).
Schmiedl et al. "Expression of a Bispecific dsFv-dsFv' Antibody Fragment in *Escherichia coli*," *Protein Engineering* 13(10):725-734, (Oct. 2000).
Schoonjans et al. "Efficient Heterodimerization of Recombinant Bi-and Trispecific Antibodies" *Bioseparation* 9(3):179-183, (2000).
Schoonjans, et al. "Fab Chains As An Efficient Heterodimerization Scaffold For The Production of Recombinant Bispecific and Trispecific Antibody Derivatives," *Journal of Immunology* 165:7050-7057, (2000).

Schröder et al. "III. Formation of the Peptide Bond," in *The Peptides*, vol. 1, Academic Press, New York, New York, pp. 76-136, (1965).
Schwartz et al. "A Superactive Insulin: [B10-aspartic Acid]Insulin(Human)," *Proc. Natl. Acad. Sci. USA* 84:6408-6411, (Sep. 1987).
Scott et al. "Biologic Protease Inhibitors As Novel Therapeutic Agents," *Biochimie* 92(11):1681-1688, (Nov. 2010, e-pub. Mar. 24, 2010.).
Seela, F. "Oligodeoxyribonucleotides Containing 1,3-Propanediol As Nucleoside Substitute," *Nucleic Acids Research* 15(7):3113-3129, (1987).
Sensi, M. et al. "Unique Tumor Antigens: Evidence for Immune Control of Genome Integrity and Immunogenic Targets for T Cell-Mediated Patient-Specific Immunotherapy," *Clin. Cancer Res.* 12(17):5023-5032, (Sep. 1, 2006).
Senter, P.D. "Potent Antibody Drug Conjugates For Cancer Therapy," *Curr. Opin. Chem. Biol.* 13:235-244, (2009, e-pub. May 4, 2009).
Seo et al. "Post-Translational Modifications and Their Biological Functions: Proteomic Analysis and Systematic Approaches," *Biochemistry and Molecular Biology* 37(1):35-44, (Jan. 2004).
Shechter et al. "Selective Chemical Cleavage of Tryptophanyl Peptide Bonds by Oxidative Chlorination With N-Chlorosuccinimide," *Biochemistry* 15(23):5071-5075, (1976).
Shen et al. "Single Variable Domain Antibody as a Versatile Building Block for the Construction of IgG-Like Bispecific Antibodies," *Journal of Immunological Methods* 318:65-74, (2007).
Shen et al. "Single Variable Domain-IgG Fusion: A Novel Recombinant Approach to Fc Domain-Containing Bispecific Antibodies," *J. of Biological Chemistry* 281(16):10706-10714, (Apr. 21, 2006, e-pub. Feb. 15, 2006).
Sheriff et al. "Redefining the Minimal Antigen-Binding Fragment," *Nature Struct. Biol.* 3(9):733-736, (Sep. 1996).
Shi et al. "A Stereospecific Synthesis of L-Deoxyribose, L-Ribose and L-Ribosides," *Tetrahed.* 58:3287-3296, (2002).
Shields et al. "High Resolution Mapping of the Binding Site on Human IgG1 for FcγRI, FcγRII, FcγRIII and FcRn and Design of IgG1 Variants with Improved Binding to the FcγR," *Journal of Biological Chemistry* 276(9):6591-6604, (2001).
Shields et al. "Lack of Fucose on Human IgG1 N-Linked Oligosaccharide Improves Binding to Human FcγRIII and Antibody-dependent Cellular Toxicity," *J. Biol. Chem.* 277(30):26733-26740, (Jul. 26, 2002).
Shinkawa et al. "The Absence of Fucose but Not the Presence of Galactose or Bisecting N-Acetylglucosamine of Human IgG1 Complex-Type Oligosaccharides Shows the Critical Role of Enhancing Antibody-Dependent Cellular Cytotoxicity," *J. Biol. Chem.* 278(5):3466-3473, (Jan. 31, 2003).
Siebenlist et al. "*E. coli* RNA Polymerase Interacts Homologously with Two Different Promoters," *Cell* 20:269-281, (Jun. 1980).
Silva et al. Synthesis of a New Phosphoramidite Nucleoside Biotinylated For The Preparation Oligonucleotide Multibiotinilados (English Abstract Only) *Biotecnologia Aplicada* 15:154-158, (1998).
Simmons et al. "Expression of Full-Length Immunoglobulins in *Escherichia coli*: Rapid and Efficient production of Aglycosylated Antibodies," *Journal of Immunological Methods* 263:133-147, (2002).
Simon et al. "Antibody Domain Mutants Demonstrate Autonomy of the Antigen Binding Site," *The EMBO Journal* 9(4):1051-1056, (1990).
Sims et al. "A Humanized CD18 Antibody Can Block Function Without Cell Destruction," *J. Immunol.* 151(4):2296-2308, (Aug. 15, 1993).
Singer, M. et al. "Genes and genomes," Moscoer, MIR 1:63-64 (With English Translation). (1998).
Smith-Gill et al. "Contributions of Immunoglobulin Heavy and Light Chain to Antibody Specificity for Lysozyme and Two Haptens," *J. Immunol.* 139(12):4135-4144, (Dec. 15, 1987).
Sondermann, P. et al. "The 3.2-Å Crystal Structure of the Human IgG1 Fc Fragment-FcγRIII Complex," *Nature*, 406:267-273, (Jul. 20, 2000).
Song et al. "Light Chain of Natural Antibody Plays a Dominant Role in Protein Antigen Binding," *Biochem. Biophys. Res. Comm.* 268(2):390-394, (2000).

(56) References Cited

OTHER PUBLICATIONS

Stancovski, I. et al. (Oct. 1991). "Mechanistic Aspect of the Opposing Effects of Monoclonal Antibodies to the ERBB2 Receptor on Tumor Growth," Proc. Natl. Acad. Sci. USA 88:8691-8695.
Steiner. "The Biosynthesis of Biologically Active Peptides: A Perspective," Chapter 1 in *Peptide Biosynthesis and Processing*, Fricker ed., CRC Press, Boca Raton, FL pp. 1-15, (1991).
Stella et al. "Prodrugs: A Chemical Approach to Target Drug Delivery" *Directed Drug Delivery*, Borchardt et al (ed.), Human Press, pp. 247-267, (1985).
Stetler-Stevenson et al. "Progelatinase A Activation During Tumor Cell Invasion," *Invasion Metastasis* 14(1-6):259-268, (1994-1995).
Stevenson et al., "A chimeric antibody with dual Fc regions (bisFabFc) prepared by manipulations at the IgG hinge," *Anti-cancer Drug Des.* 3(4):219-230, (Mar. 1989).
Stites et al. (1994). "Immunoglobulin Protiens," Chapter 6 in *Basic Clinical Immunology*, 8th Edition, Appleton & Lange, Norwalk, CT, pp. 66-79.
Stork et al. "A Novel Tri-Functional Antibody Fusion Protein with Improved Pharmacokinetic Properties Generated By Fusing a Bispecific Single-Chain Diabody With an Albumin-Binding Domain From Streptococcal Protein G," *Protein Eng. Des. Sel.* 20(11):569-576, (Nov. 2007, e-pub. Nov. 3, 2007).
Strop, P. et al. "Generating Bispecific Human IgG1 and IgG2 Antibodies from Any Antibody Pair," *Journal of Molecular Biology*, 420(3):204-219, (2012, e-pub. Apr. 25, 2012).
Su et al. "Novel Non-Nucleosidic Phosphoramidites for Oligonucleotide Modification And Labeling," *Bioorganic & Medicinal Chemistry Letters* 7(13):1639-1644, (1997).
Sunbul "Site Specific Protein Labeling By Enzymatic Post-translational Modification," *Org. Biomol. Chem.* 7:3361-3371, (2009).
Syrigos et al. "Antibody Directed Enzyme Prodrug Therapy (ADEPT): A Review of the Experimental and Clinical Considerations," *Anticancer Research* 19:605-614, (1999).
Ta, H.T. et al. "Enzymatic Single-Chain Antibody Tagging: A Universal Approach to Targeted Molecular Imaging and Cell Homing in Cardiovascular Disease", *Circulation Research*, 109(4):365-373, (2011).
Taki, M., et al. "Transglutaminase-Mediated N-and C-Terminal Fluorescein Labeling of a Protein Can Support the Native Activity of the Modified Protein," *Prot. Eng. Des. Sel.* 17(2):119-126, (2004, e-pub. Jan. 12, 2004).
Tao et al. "The Differential Ability of Human IgG1 and IgG4 to Activate Complement is Determined by the COOH-terminal Sequence of the $C_H2$ Domain," *J. Exp. Med* 173:1025-1028, (Apr. 1991).
Taylor, E. et al. "Native Chemical Ligation: Semisynthesis of Post-Translationally Modified Proteins and Biological Probes," *Nucl. Acids Mol. Biol.* 22:65-96, (2009).
Theisen, P., et al. "Fluorescent Dye Phosphoramidite Labelling of Oligonucleotides," *Nucleic Acids Symposium Series 27 (Nineteenth Symposium on Nucleic Acids Chemistry)*, pp. 99-100, (1992).
Thie et al. "Multimerization Domains for Antibody Phage Display and Antibody Production," *New Biotech.* 26(6):314-321, (Jul. 22, 2009).
Thies, M.J. et al. "Folding and Association of the Antibody Domain CH3: Prolyl Isomerization Preceeds Dimerization," *J. Mol. Biol.*, 293:67-79, (1999).
Thommesen et al. "Lysine 322 in the Human IgG3 $C_H2$ Domain is Vrucial for Antibody Dependent Complement Activation," *Molecular Immunology* 37:995-1004, (2000).
Thorpe. "Antibody Carriers of Cyotoxic Agents in Cancer Therapy: A Review," in *A Monoclonal Antibodies 84: Biological and Clinical Applications*, A. Pinchera et al (eds) pp. 475-506, (1985).
Ton-That, H. et al. "Purification and Vharacterization of Sortase, The Transpeptidase That Cleaves Surface Proteins of *Staphylococcus aureus* at the LPXTG Motif," *Proc. Natl. Acad. Sci. U.S.A.*, 96(22):12424-12429, (Oct. 26, 1999).
Torgov, M.Y. et al. "Generation of an Intensely Potent Anthracycline By a Monoclonal Antibody-β-Galactosidase Conjugate," *Bioconjug. Chem.* 16:717-721, (2005, e-pub. Apr. 27, 2005).

Torres, M. et al. "Variable-Region-Identical Antibodies Differing in Isotype Demonstrate Differences in Fine Specificity and Idiotype," *The Journal of Immunology*, 174:2132-2142, (2005).
Tripathi et al. "Laminin-332 is a Substrate for Hepsin, a Protease Associated with Prostate Cancer Progression," *J. Biol. Chem.* 283(45):30576-30584, (Nov. 7, 2008, e-pub. Sep. 9, 2008).
Tso et al. "Preparation of a Bispecific F(ab')₂ Targeted to the Human II-2 Receptor," *J. Hematotherapy* 4:389-394, (1995).
Tsukiji S. et al. "Sortase-Mediated Ligation: A Gift from Gram-Positive Bacteria to Protein Engineering", *Chembiochem*, 10(5):787-798, (2009).
Umaña et al. "Engineered Glycoforms of an Antineuroblastoma IgG1 with Optimized Antibody-Dependent Cellular Cytotoxic Activity," *Nature Biotechnology* 17(2):176-180, (Feb. 1999).
Urata, H. et al. "Synthesis and Properties of Mirror-Image DNA," *Nucl. Acids Res.* 20(13):3325-3332, (1992).
Urlaub et al. "Isolation of Chinese Hamster Cell Mutants Deficient in Dihydrofolate Reductase Activity," *Proc. Natl. Acad Sci USA* 77(7):4216-4220, (Jul. 1980).
Vallböhmer, D. et al. "Molecular Determinants of Cetuximab Efficacy," *J. Clin. Oncol.*, 23(15):3536-3544, (May 20, 2005).
Van Dijk et al. "Human Antibodies as Next Generation Therapeutics," *Curr. Opin. Chem. Biol.* 5(4):368-374, (Aug. 2001).
Van Spriel et al. "Immunotherapeutic Perspective for Bispecific Antibodies," *Immunology Today* 21(8):391-397, (Aug. 2000).
Van't Veer et al. "Gene Expression Profiling Predicts Clinical Outcome of Breast Cancer," *Nature* 415(6871):530-536, (Jan. 31, 2002).
Vazquez-Ortiz et al. "Overexpression of Cathepsin F, Matrix Metalloproteinases 11 and 12 in Cervical Cancer," *BMC Cancer* 5:68, (Jun. 30, 2005), 11 pages.
Velasco et al. "Human Cathepsin O.: Molecular Cloning from a Breast Carcinoma, Production of the Active Enzyme in *Escherichia coli*, and Expression Analysis in Human Tissues," *J. Biol Chem* 269(43):27136-27142, (Oct. 28, 1994).
Verhoeyen et al. "Reshaping Human Antibodies: Grafting an Antilysozyme Activity," *Science* 239:1534-1536, (Mar. 25, 1988).
Veveris-Lowe et al. "Seminal Fluid Characterization for Male Fertility and Prostate Cancer: Kallikrein-Related Serine Proteases and whole Proteome Approaches," *Semin Thromb Hemost.* 33(1):87-99, (2007).
Vijayalakshmi. "Antibody Purification Methods," *Applied Biochemistry and Biotechnology* 75:93-102, (1998).
Vitetta et al. "Redesigning Nature's Poisons to Create Anti-tumor Reagents," *Science* 238:1098-1104, (Nov. 20, 1987).
Wagner et al. "Bispecific Antibody Generated With Sortase and Click Chemistry Has Broad Antiinfluenza Virus Activity," *Proc. Natl. Acad. Sci. USA* 111:16820-16825, (Nov. 25, 2014).
Walker et al. "Efficient Recovery of High-Affinity Antibodies From a Single-Chain Fab Yeast Display Library," *J. Mol. Biol.* 389(2):365-375, (Jun. 5, 2009, e-pub. Apr. 16, 2009).
Walker et al. "Efficient and Rapid Affinity Purification of Proteins Using Recombinant Fusion Proteases," *Bio/Technology* 12:601-605, (1994).
Wang, L. et al. "Expanding the Genetic Code," *Chem. Commun (Camb.)* 7:1-11, (2002).
Wang et al. "Site-Specific Fluorescent Labeling of DNA Using Staudinger Ligation," *Bioconjugate Chemistry* 14:697-701, (2003, e-pub. Apr. 2, 2003).
Ward et al. "Binding Activities of a Repertoire of Single Immunoglobulin Variable Domains Secreted From *Escherichia coli*," *Nature* 341:544-546, (Oct. 12, 1989).
Ward, E.S. et al. "The Effector Functions of Immunoglobulins: Implications for Therapy," *Ther. Immunol.* 2:77-94, (1995).
Warren et al. "Regulation by Vascular Endothelial Growth Factor of Human Colon Cancer Tumorigenesis in a Mouse Model of Experimental Liver Metastasis," *J. Clin. Invest.* 95:1789-1797, (1995).
Webber et al. "Preparation and Characterization of a Disulfide-Stabilized Fv Fragment of the Anti-Tac Antibody: Comparison With Its Single-Chain Analog," *Molecular Immunology* 32(4):249-258, (1995).
Weiner, L.M. (Aug. 1999). "An Overview of Monoclonal Antibody Therapy of Cancer," Seminars in Oncology 26(4)(Supp. 12):41-50.

(56) References Cited

OTHER PUBLICATIONS

Werner et al. "Appropriate Mammalian Expression Systems for Biopharmaceuticals," *Drug Research* 48(8):870-880, (1998).
Wielockx et al. "Matrilysin (Matrix Metalloproteinase-7): A New Promising Drug Target in Cancer And Inflammation?" *Cytokine Growth Factor Rev.* 15(2-3):111-115, (Apr.-Jun. 2004).
Willems et al. "Optimizing Expression and Purification From Cell Culture Medium of Trispecific Recombinant Antibody Derivatives," *Journal of Chromatography B* 786:161-176, (2003).
Wilman. "Prodrugs in Cancer Chemotherapy," *Biochemical Society Transactions* 615th Meeting Belfast, 14:376-382, (1986), 8 pages.
Witte M.D. et al. "Preparation of Unnatural N-to-N and C-to-C Protein Fusions," *Proceedings of the National Academy of Sciences of the United States of America*, 109(30):11993-11998, (Jul. 24, 2012).
Wojczewski et al. "Fluorescent Oligonucleotides—Versatile Tools as Probes and Primers for DNA and RNA Analysis," *Synlett* 10:1667-1678, (1999).
Woof et al. "Human Antibody-FC Receptor Interactions Illuminated By Crystal Structures," *Nat. Rev. Immunol.* 4:1-11, (Feb. 2004).
Wörn et al. "Stability Engineering of Antibody Single-Chain Fv Fragments," *J. Mol. Biol.* 305:989-1010, (2001).
Woyke et al. "In Vitro Activities and Postantifungal Effects of the Potent Dolastatin10 Derivative Auristatin PHE," *Antimicrob. Agents and Chemother.* 45(12):3580-3584, (Dec. 2001).
Wranik et al. "LUZ-Y: A Novel Platform for the Mammalian Cell Production of Full-length IgG Bispecific Antibodies," *Journal of Biological Chemistry* 287(52):43331-43339, Dec. 21, 2012).
Wright et al. "Effect of Glycosylation on Antibody Function: Implications for Genetic Engineering," *Trends in Biotechnology* 15:26-32, (Jan. 1997).
Wright et al. "ADAM28: A Potential Oncogene Involved in Asbestos-Related Lung Adenocarcinomas," *Genes Chromosomes Cancer* 49(8):688-698, (Aug. 2010, e-pub. Apr. 29, 2010).
Wright et al. "Phage Display of Chelating Recombinant Antibody Libraries," *Molecular Immunology* 44:2860-2869, (2007).
Written Opinion of the International Searching Authority dated Oct. 2, 2012, for PCT Patent Application No. PCT/EP2011/054505 filed on Mar. 24, 2011, 7 pages.
Written Opinion of the International Searching Authority dated Dec. 6, 2011, for PCT Patent Application No. PCT/EP2011/064476 filed on Aug. 23, 2011, 4 pages.
Written Opinion International for PCT Application No. PCT/EP2014/079353, dated Apr. 20, 2015, filed Dec. 29, 2014, 8 pages.
Written Opinion of the International Searching Authority dated Dec. 6, 2011, for PCT Patent Application No. PCT/EP2011/064468 filed on Aug. 23, 2011, 4 pages.
Written Opinion of the International Searching Authority dated Aug. 5, 2014, for PCT Patent Application No. PCT/EP2013/063258, filed on Jun. 25, 2013, 7 pages.
Written Opinion of the International Searching Authority dated Aug. 6, 2013, PCT Patent Application No. PCT/EP2013/063260, filed on Jun. 25, 2013, eight pages.
Written Opinion dated Aug. 6, 2013, for PCT Application No. PCT/US2013/025365, filed Feb. 8, 2013, 9 pages.
Written Opinion of the International Searching Authority dated Jun. 15, 2011 for PCT Patent Application No. PCT/US2010/002546 filed on Sep. 16, 2010, 7 pages.
Written Opinion International for PCT Application No. PCT/EP2014/079353, dated Apr. 4, 2015, filed Dec. 29, 2014, 8 pages.
Wu et al. "Simultaneous Targeting of Multiple Disease Mediators by a Dual-Variable-Domain Immunoglobulin," *Nature Biotechnology* 25(11):1290-1297, (Nov. 2007, e- pub. Oct. 14, 2007).
Xie et al. "A New Format of Bispecific Antibody: Highly Efficient Heterodimerization, Expression and Tumor Cell Lysis," *J. of Immunol. Methods* 296:95-101, (2005, e-pub. Nov. 19, 2004).
Xu et al. "Diversity in the CDR3 Region of V(H) is Sufficient for Most Antibody Specificities," *Immunity* 13:37-45, (Jul. 2000).
Yamaguchi et al. "Proteolytic Fragmentation With High Specificity of Mouse Immunoglobulin G," *Journal of Immunological Methods* 181:259-267, (1995).
Yamane-Ohnuki, N. et al. "Establishment of FUT8 Knockout Chinese Hamster Ovary Cells: An Ideal Host Cell Line For Producing Completely Defucosylated Antibodies With Enhanced Antibody-Dependent Cellular Cytotoxicity," *Biotech. Bioeng.* 87:614-622, (2004, e-pub. Aug. 6, 2004).
Yancopoulos, G.D. et al. "Vascular-Specific Growth Factors and Blood Vessel Formation," *Nature* 407:242-248, (Sep. 14, 2000).
Yaniv. "Enhancing Elements for Activation of Eukaryotic Promoters," *Nature* 297:17-18, (May 6, 1982).
Yazaki, P.J. et al. *Methods in Molecular Biology*, vol. 248, Lo, B.K.C. (ed.), Humana Press, Totowa, NJ pp. 255-268, (2004).
Yu, Y.J. et al. "Developing Therapeutic Antibodies For Neurodegenerative Disease," Neurotherapeutics 10(3):459-472, (Apr. 3, 2013).
Zahn et al. "Alternative Heterocycles for DNA Recognition: A 3-Pyrazole/Pyrrole Pair Specifies for G.C Base Pairs," *Bioorg. Med. Chem.* 8:2467-2474, (2000).
Zapata et al. "Engineering Linear F(ab')₂ Fragments for Efficient Production in *Escherichia coli* and Enhanced Antiproliferative Activity," *Protein Eng.* 8(10):1057-1062, (1995).
Zeidler et al. "Simultaneous activation of T cells and Accessory Cells by a New Class of Intact Bispecific Antibody Results In Efficient Tumor Cell Killing," *Journal of Immunology* 163:1246-1252, (1999).
Zhu et al. "Remodeling Domain Interfaces to Enhance Heterodimer Formation," *Protein Science* 6:781-788, (1997).
Zuo et al. "An Efficient Route to the Production of an IgG-Like Bispecific Antibody," *Protein Engineering* 13(5):361-367, (2000).
Fenn, S. et al . . . (Apr. 1, 2013). "Crystal Structure of an Anti-Ang2 CrossFab Demonstrates Complete Structural and Functional Integrity of the Variable Domain," PLOS ONE 8(4):e61953, 7 pages.
Klein, C. et al. (2012). "Progress in Overcoming the Chain Association Issue in Bispecific Heterodimeric IgG Antibodies," mAbs 4(6):653-663.

\* cited by examiner

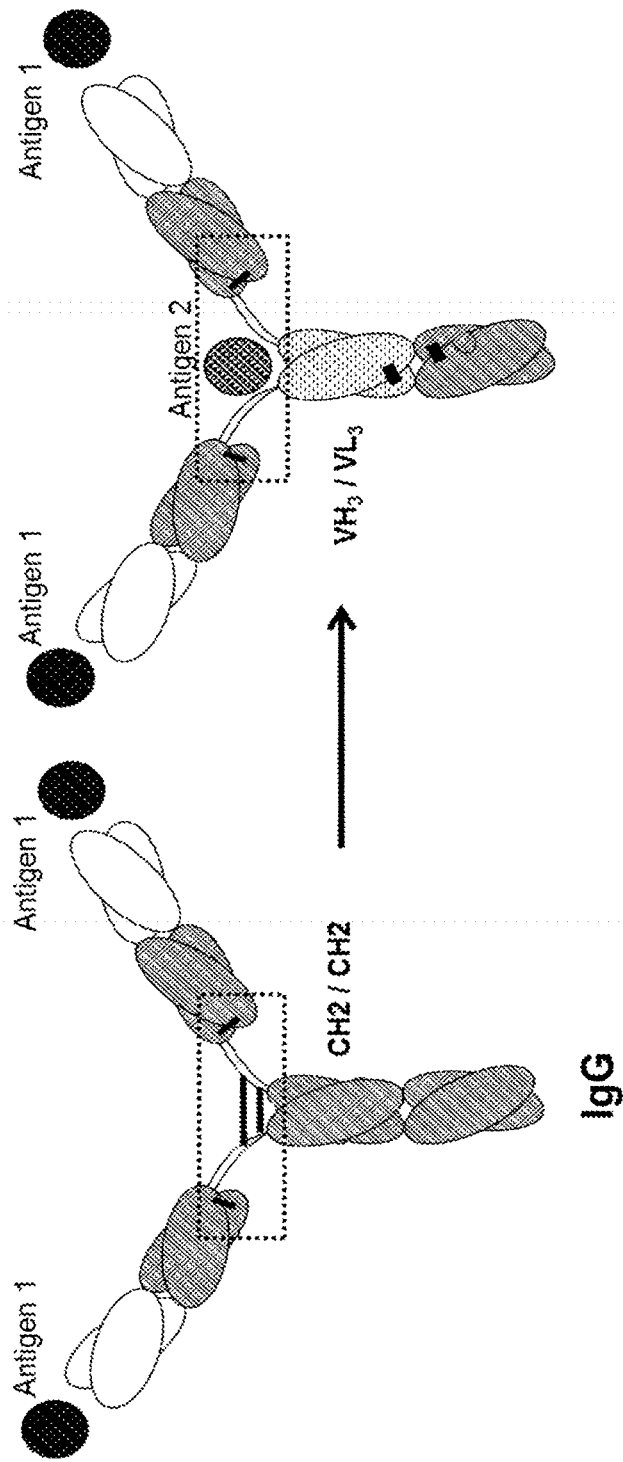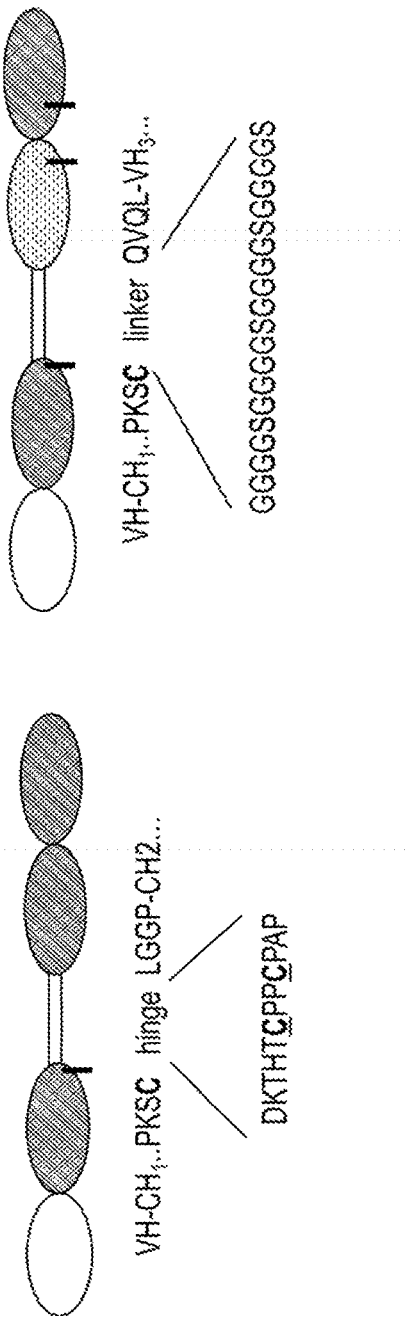
Fig. 4A
Fig. 4B

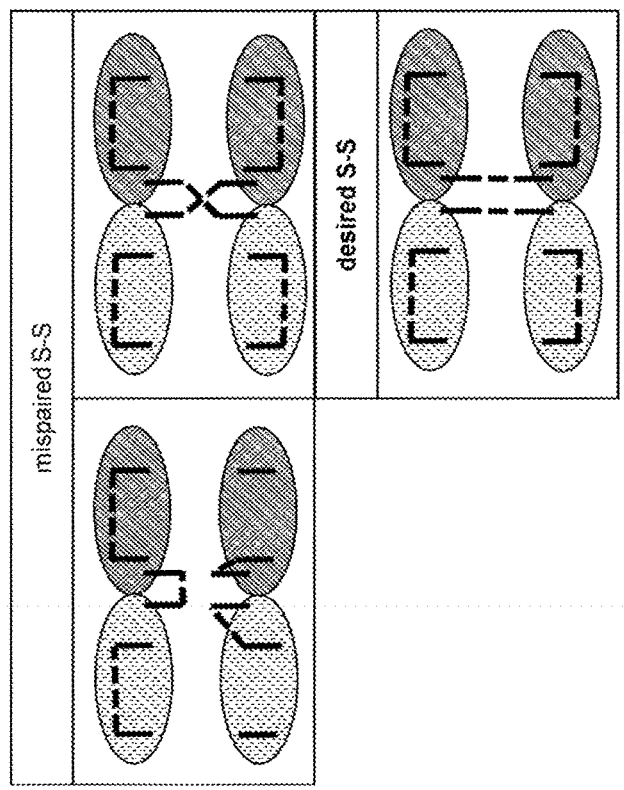
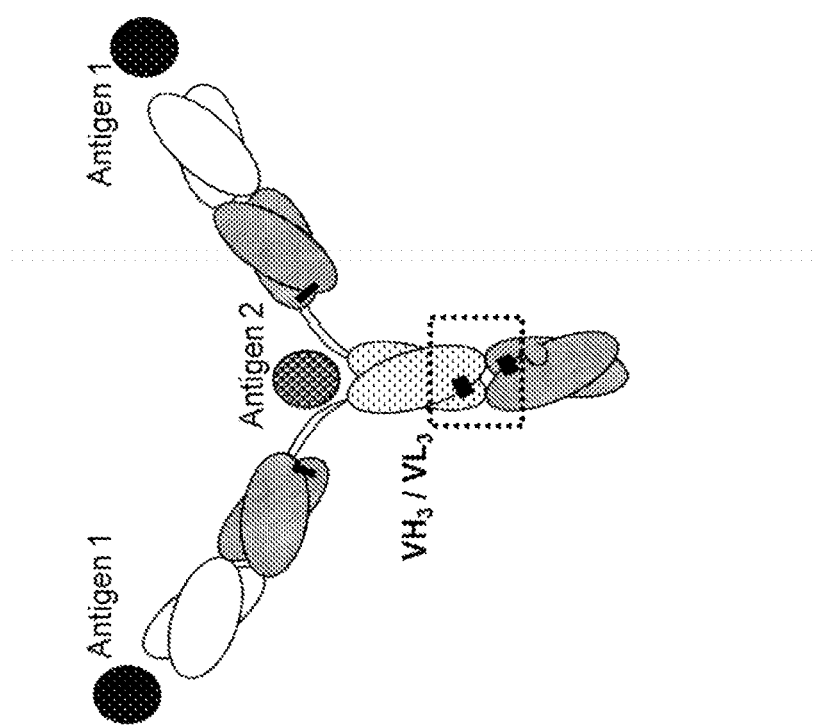
Fig. 5A

SEQUENCE LISTING

<160> NUMBER OF SEQ ID NOS: 47

<210> SEQ ID NO 1
<211> LENGTH: 52
<212> TYPE: PRT
<213> ORGANISM: Artificial Sequence
<220> FEATURE:
<223> OTHER INFORMATION: exemplary fusion site of <anti-DIG>VL3-CH3
      fusion site of an antibody according to example 1

<400> SEQUENCE: 1

Thr Tyr Tyr Cys Gln Gln Ser Ile Thr Leu Pro Pro Thr Phe Gly Cys
1               5                   10                  15

Gly Thr Lys Val Glu Ile Lys Gly Gln Pro Arg Glu Pro Gln Val Cys
                20                  25                  30

Thr Leu Pro Pro Ser Arg Asp Glu Leu Thr Lys Asn Gln Val Ser Leu
            35                  40                  45

Ser Cys Ala Val
    50

<210> SEQ ID NO 2
<211> LENGTH: 5
<212> TYPE: PRT
<213> ORGANISM: Artificial Sequence
<220> FEATURE:
<223> OTHER INFORMATION: N-terminus of CH3 domains (alternative 1)

```
<400> SEQUENCE: 2

Gly Gln Pro Arg Glu
1               5

<210> SEQ ID NO 3
<211> LENGTH: 5
<212> TYPE: PRT
<213> ORGANISM: Artificial Sequence
<220> FEATURE:
<223> OTHER INFORMATION: N-terminus of CH3 domains (alternative 2)

<400> SEQUENCE: 3

Ala Ser Thr Arg Glu
1               5

<210> SEQ ID NO 4
<211> LENGTH: 5
<212> TYPE: PRT
<213> ORGANISM: Artificial Sequence
<220> FEATURE:
<223> OTHER INFORMATION: N-terminus of CH3 domains (alternative 3)

<400> SEQUENCE: 4

Arg Thr Val Ala Ala
1               5

<210> SEQ ID NO 5
<211> LENGTH: 214
<212> TYPE: PRT
<213> ORGANISM: Artificial Sequence
<220> FEATURE:
<223> OTHER INFORMATION: light chain polypeptide with digoxigenin
      binding site

<400> SEQUENCE: 5

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 474
<212> TYPE: PRT
<213> ORGANISM: Artificial Sequence
<220> FEATURE:
<223> OTHER INFORMATION: polypeptide VH-CH1-linker-VH3-CH3 of BsAb
      Dig-LeY-Dig

<400> SEQUENCE: 6

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Gly Gly Gly Ser Gly Gly Gly Ser Gly
225                 230                 235                 240

Gly Gly Ser Gly Gly Gly Ser Asp Val Lys Leu Val Glu Ser Gly
                245                 250                 255

Gly Gly Leu Val Gln Pro Gly Gly Ser Leu Lys Leu Ser Cys Ala Thr
            260                 265                 270

Ser Gly Phe Thr Phe Ser Asp Tyr Tyr Met Tyr Trp Val Arg Gln Thr
        275                 280                 285

Pro Glu Lys Arg Leu Glu Trp Val Ala Tyr Ile Ser Asn Asp Asp Ser
    290                 295                 300

Ser Ala Ala Tyr Ser Asp Thr Val Lys Gly Arg Phe Thr Ile Ser Arg
305                 310                 315                 320

Asp Asn Ala Arg Asn Thr Leu Tyr Leu Gln Met Ser Arg Leu Lys Ser
                325                 330                 335
```

Glu Asp Thr Ala Ile Tyr Tyr Cys Ala Arg Gly Leu Ala Trp Gly Ala
                340                 345                 350

Trp Phe Ala Tyr Trp Gly Gln Gly Thr Leu Val Thr Val Ser Ser Gly
            355                 360                 365

Gln Pro Arg Glu Pro Gln Val Tyr Thr Leu Pro Pro Cys Arg Asp Glu
        370                 375                 380

Leu Thr Lys Asn Gln Val Ser Leu Trp Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 7
<211> LENGTH: 467
<212> TYPE: PRT
<213> ORGANISM: Artificial Sequence
<220> FEATURE:
<223> OTHER INFORMATION: polypeptide VH-CH1-linker-VL3-CH3 of BsAb
      Dig-LeY-Dig

<400> SEQUENCE: 7

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu

Pro Lys Ser Cys Gly Gly Gly Ser Gly Gly Gly Ser Gly Gly
225                 230                 235                 240

Gly Gly Ser Gly Gly Gly Ser Asp Val Leu Met Thr Gln Ser Pro
            245                 250                 255

Leu Ser Leu Pro Val Ser Leu Gly Asp Gln Ala Ser Ile Ser Cys Arg
        260                 265                 270

Ser Ser Gln Ile Ile Val His Ser Asn Gly Asn Thr Tyr Leu Glu Trp
            275                 280                 285

Tyr Leu Gln Lys Pro Gly Gln Ser Pro Lys Leu Leu Ile Tyr Lys Val
    290                 295                 300

Ser Asn Arg Phe Ser Gly Val Pro Asp Arg Phe Ser Gly Ser Gly Ser
305                 310                 315                 320

Gly Thr Asp Phe Thr Leu Lys Ile Ser Arg Val Glu Ala Glu Asp Leu
            325                 330                 335

Gly Val Tyr Tyr Cys Phe Gln Gly Ser His Val Pro Phe Thr Phe Gly
            340                 345                 350

Ser Gly Thr Lys Leu Glu Ile Lys Gly Gln Pro Arg Glu Pro Gln Val
        355                 360                 365

Cys Thr Leu Pro Pro Ser Arg Asp Glu Leu Thr Lys Asn Gln Val Ser
370                 375                 380

Leu Ser Cys Ala Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Val Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 8
<211> LENGTH: 219
<212> TYPE: PRT
<213> ORGANISM: Artificial Sequence
<220> FEATURE:
<223> OTHER INFORMATION: light chain polypeptide with Lewis Y binding
      site

<400> SEQUENCE: 8

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ile Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

```
Ser His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 474
<212> TYPE: PRT
<213> ORGANISM: Artificial Sequence
<220> FEATURE:
<223> OTHER INFORMATION: polypeptide VH-CH1-linker-VH3-CH3 of BsAb
      LeY-Dig(SS)-LeY

<400> SEQUENCE: 9

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Asp Ser Ser Ala Ala Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
                85                  90                  95

Ala Arg Gly Leu Ala Trp Gly Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Gly Gly Gly Gly Ser Gly Gly Gly
225                 230                 235                 240
```

Gly Ser Gln Val Gln Leu Val Glu Ser Gly Gly Leu Val Lys Pro
            245                 250                 255

Gly Gly Ser Leu Arg Leu Ser Cys Ala Ala Ser Gly Phe Thr Phe Ser
        260                 265                 270

Asp Tyr Ala Met Ser Trp Ile Arg Gln Ala Pro Gly Lys Cys Leu Glu
            275                 280                 285

Trp Val Ser Ser Ile Asn Ile Gly Ala Thr Tyr Ile Tyr Tyr Ala Asp
        290                 295                 300

Ser Val Lys Gly Arg Phe Thr Ile Ser Arg Asp Asn Ala Lys Asn Ser
305                 310                 315                 320

Leu Tyr Leu Gln Met Asn Ser Leu Arg Ala Glu Asp Thr Ala Val Tyr
            325                 330                 335

Tyr Cys Ala Arg Pro Gly Ser Pro Tyr Glu Tyr Asp Lys Ala Tyr Tyr
            340                 345                 350

Ser Met Ala Tyr Trp Gly Gln Gly Thr Thr Val Thr Val Ser Ser Gly
            355                 360                 365

Gln Pro Arg Glu Pro Gln Val Tyr Thr Leu Pro Pro Cys Arg Asp Glu
            370                 375                 380

Leu Thr Lys Asn Gln Val Ser Leu Trp Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
        450                 455                 460

Gln Lys Ser Leu Ser Leu Ser Pro Gly Lys
465                 470

<210> SEQ ID NO 10
<211> LENGTH: 456
<212> TYPE: PRT
<213> ORGANISM: Artificial Sequence
<220> FEATURE:
<223> OTHER INFORMATION: polypeptide VH-CH1-linker-VL3-CH3 of BsAb
      LeY-Dig(SS)-LeY

<400> SEQUENCE: 10

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Asp Ser Ser Ala Ala Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
            85                  90                  95

Ala Arg Gly Leu Ala Trp Gly Ala Trp Phe Ala Tyr Trp Gly Gln Gly
        100                 105                 110

Thr Leu Val Thr Val Ser Ser Ala Ser Thr Lys Gly Pro Ser Val Phe

-continued

```
            115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Gly
        210                 215                 220

Gly Gly Ser Gly Gly Gly Gly Ser Gly Gly Gly Gly Ser Gly Gly Gly
225                 230                 235                 240

Gly Ser Asp Ile Gln Met Thr Gln Ser Pro Ser Ser Leu Ser Ala Ser
                245                 250                 255

Val Gly Asp Arg Val Thr Ile Thr Cys Arg Ala Ser Gln Asp Ile Lys
            260                 265                 270

Asn Tyr Leu Asn Trp Tyr Gln Gln Lys Pro Gly Lys Ala Pro Lys Leu
        275                 280                 285

Leu Ile Tyr Tyr Ser Ser Thr Leu Leu Ser Gly Val Pro Ser Arg Phe
    290                 295                 300

Ser Gly Ser Gly Ser Gly Thr Asp Phe Thr Leu Thr Ile Ser Ser Leu
305                 310                 315                 320

Gln Pro Glu Asp Phe Ala Thr Tyr Tyr Cys Gln Gln Ser Ile Thr Leu
                325                 330                 335

Pro Pro Thr Phe Gly Cys Gly Thr Lys Val Glu Ile Lys Gly Gln Pro
            340                 345                 350

Arg Glu Pro Gln Val Cys Thr Leu Pro Pro Ser Arg Asp Glu Leu Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 11
<211> LENGTH: 471
<212> TYPE: PRT
<213> ORGANISM: Artificial Sequence
<220> FEATURE:
<223> OTHER INFORMATION: polypeptide VH-CH1-linker-VH3-CH3 of BsAb
      Dig-CD33-Dig

<400> SEQUENCE: 11

Gln Val Gln Leu Val Glu Ser Gly Gly Gly Leu Val Lys Pro Gly Gly
1               5                   10                  15
```

-continued

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Gly Gly Gly Ser Gly Gly Gly Ser Gly
225                 230                 235                 240

Gly Gly Ser Gly Gly Gly Ser Glu Val Gln Leu Val Gln Ser Gly
                245                 250                 255

Ala Glu Val Lys Lys Pro Gly Ser Ser Val Lys Val Ser Cys Lys Ala
            260                 265                 270

Ser Gly Tyr Thr Ile Thr Asp Ser Asn Ile His Trp Val Arg Gln Ala
        275                 280                 285

Pro Gly Gln Ser Leu Glu Trp Ile Gly Tyr Ile Tyr Pro Tyr Asn Gly
    290                 295                 300

Gly Thr Asp Tyr Asn Gln Lys Phe Lys Asn Arg Ala Thr Leu Thr Val
305                 310                 315                 320

Asp Asn Pro Thr Asn Thr Ala Tyr Met Glu Leu Ser Ser Leu Arg Ser
                325                 330                 335

Glu Asp Thr Ala Phe Tyr Tyr Cys Val Asn Gly Asn Pro Trp Leu Ala
            340                 345                 350

Tyr Trp Gly Gln Gly Thr Leu Val Thr Val Ser Ser Gly Gln Pro Arg
        355                 360                 365

Glu Pro Gln Val Tyr Thr Leu Pro Pro Cys Arg Asp Glu Leu Thr Lys
    370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser

```
                 435                 440                 445
Cys Ser Val Met His Glu Ala Leu His Asn His Tyr Thr Gln Lys Ser
        450                 455                 460

Leu Ser Leu Ser Pro Gly Lys
465             470

<210> SEQ ID NO 12
<211> LENGTH: 466
<212> TYPE: PRT
<213> ORGANISM: Artificial Sequence
<220> FEATURE:
<223> OTHER INFORMATION: polypeptide VH-CH1-linker-VL3-CH3 of BsAb
      Dig-CD33-Dig

<400> SEQUENCE: 12

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Gly Gly Gly Ser Gly Gly Gly Ser Gly
225                 230                 235                 240

Gly Gly Ser Gly Gly Gly Ser Asp Ile Gln Leu Thr Gln Ser Pro
                245                 250                 255

Ser Thr Leu Ser Ala Ser Val Gly Asp Arg Val Thr Ile Thr Cys Arg
            260                 265                 270

Ala Ser Glu Ser Leu Asp Asn Tyr Gly Ile Arg Phe Leu Thr Trp Phe
        275                 280                 285

Gln Gln Lys Pro Gly Lys Ala Pro Lys Leu Leu Met Tyr Ala Ala Ser
    290                 295                 300

Asn Gln Gly Ser Gly Val Pro Ser Arg Phe Ser Gly Ser Gly Ser Gly
305                 310                 315                 320
```

```
Thr Glu Phe Thr Leu Thr Ile Ser Ser Leu Gln Pro Asp Asp Phe Ala
                325                 330                 335

Thr Tyr Tyr Cys Gln Gln Thr Lys Glu Val Pro Trp Ser Phe Gly Gln
            340                 345                 350

Gly Thr Lys Val Glu Val Lys Gly Gln Pro Arg Glu Pro Gln Val Cys
        355                 360                 365

Thr Leu Pro Pro Ser Arg Asp Glu Leu Thr Lys Asn Gln Val Ser Leu
    370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 13
<211> LENGTH: 218
<212> TYPE: PRT
<213> ORGANISM: Artificial Sequence
<220> FEATURE:
<223> OTHER INFORMATION: light chain polypeptide with CD33 binding site

<400> SEQUENCE: 13

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys
                85                  90                  95

Glu Val Pro Trp Ser Phe Gly Gln Gly Thr Lys Val Glu Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

```
Val Thr Lys Ser Phe Asn Arg Gly Glu Cys
    210                 215
```

<210> SEQ ID NO 14
<211> LENGTH: 471
<212> TYPE: PRT
<213> ORGANISM: Artificial Sequence
<220> FEATURE:
<223> OTHER INFORMATION: polypeptide VH-CH1-linker-VH3-CH3 of BsAb
      CD33-Dig(SS)-CD33

<400> SEQUENCE: 14

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Gly Gly Gly Ser
    210                 215                 220

Gly Gly Gly Gly Ser Gly Gly Gly Ser Gly Gly Gly Gly Ser Gln
225                 230                 235                 240

Val Gln Leu Val Glu Ser Gly Gly Gly Leu Val Lys Pro Gly Gly Ser
                245                 250                 255

Leu Arg Leu Ser Cys Ala Ala Ser Gly Phe Thr Phe Ser Asp Tyr Ala
            260                 265                 270

Met Ser Trp Ile Arg Gln Ala Pro Gly Lys Cys Leu Glu Trp Val Ser
        275                 280                 285

Ser Ile Asn Ile Gly Ala Thr Tyr Ile Tyr Tyr Ala Asp Ser Val Lys
    290                 295                 300

Gly Arg Phe Thr Ile Ser Arg Asp Asn Ala Lys Asn Ser Leu Tyr Leu
305                 310                 315                 320

Gln Met Asn Ser Leu Arg Ala Glu Asp Thr Ala Val Tyr Tyr Cys Ala
                325                 330                 335

Arg Pro Gly Ser Pro Tyr Glu Tyr Asp Lys Ala Tyr Tyr Ser Met Ala
            340                 345                 350
```

```
Tyr Trp Gly Gln Gly Thr Thr Val Thr Val Ser Ser Gly Gln Pro Arg
            355                 360                 365

Glu Pro Gln Val Tyr Thr Leu Pro Pro Cys Arg Asp Glu Leu Thr Lys
370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 15
<211> LENGTH: 453
<212> TYPE: PRT
<213> ORGANISM: Artificial Sequence
<220> FEATURE:
<223> OTHER INFORMATION: polypeptide VH-CH1-linker-VL3-CH3 of BsAb
      CD33-Dig(SS)-CD33

<400> SEQUENCE: 15

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Gly Gly Gly Ser
    210                 215                 220

Gly Gly Gly Gly Ser Gly Gly Gly Ser Gly Gly Gly Gly Ser Asp
```

Ile Gln Met Thr Gln Ser Pro Ser Leu Ser Ala Ser Val Gly Asp
225                 230                 235                 240

Arg Val Thr Ile Thr Cys Arg Ala Ser Gln Asp Ile Lys Asn Tyr Leu
            245                 250                 255

Asn Trp Tyr Gln Gln Lys Pro Gly Lys Ala Pro Lys Leu Leu Ile Tyr
                275                 280                 285

Tyr Ser Ser Thr Leu Leu Ser Gly Val Pro Ser Arg Phe Ser Gly Ser
        290                 295                 300

Gly Ser Gly Thr Asp Phe Thr Leu Thr Ile Ser Ser Leu Gln Pro Glu
305                 310                 315                 320

Asp Phe Ala Thr Tyr Tyr Cys Gln Gln Ser Ile Thr Leu Pro Pro Thr
            325                 330                 335

Phe Gly Cys Gly Thr Lys Val Glu Ile Lys Gly Gln Pro Arg Glu Pro
                340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
            405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 16
<211> LENGTH: 470
<212> TYPE: PRT
<213> ORGANISM: Artificial Sequence
<220> FEATURE:
<223> OTHER INFORMATION: polypeptide VH-CH1-linker-VH3-CH3 of BsAb
      Dig-GPC3-Dig

<400> SEQUENCE: 16

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Pro Gly Ser Pro Tyr Glu Tyr Asp Lys Ala Tyr Tyr Ser Met
        100                 105                 110

Ala Tyr Trp Gly Gln Gly Thr Thr Val Thr Val Ser Ser Ala Ser Thr
    115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Gly Gly Gly Ser Gly Gly Gly Ser Gly Gly
225                 230                 235                 240

Gly Gly Ser Gly Gly Gly Ser Gln Val Gln Leu Val Gln Ser Gly
                245                 250                 255

Ala Glu Val Lys Lys Pro Gly Ala Ser Val Lys Val Ser Cys Lys Ala
            260                 265                 270

Ser Gly Tyr Thr Phe Thr Asp Tyr Glu Met His Trp Val Arg Gln Ala
        275                 280                 285

Pro Gly Gln Gly Leu Glu Trp Met Gly Ala Leu Asp Pro Lys Thr Gly
    290                 295                 300

Asp Thr Ala Tyr Ser Gln Lys Phe Lys Gly Arg Val Thr Leu Thr Ala
305                 310                 315                 320

Asp Lys Ser Thr Ser Thr Ala Tyr Met Glu Leu Ser Ser Leu Thr Ser
                325                 330                 335

Glu Asp Thr Ala Val Tyr Tyr Cys Thr Arg Phe Tyr Ser Tyr Thr Tyr
            340                 345                 350

Trp Gly Gln Gly Thr Leu Val Thr Val Ser Ser Gly Gln Pro Arg Glu
        355                 360                 365

Pro Gln Val Tyr Thr Leu Pro Pro Cys Arg Asp Glu Leu Thr Lys Asn
    370                 375                 380

Gln Val Ser Leu Trp Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 17
<211> LENGTH: 467
<212> TYPE: PRT
<213> ORGANISM: Artificial Sequence
<220> FEATURE:
<223> OTHER INFORMATION: polypeptide VH-CH1-linker-VL3-CH3 of BsAb
      Dig-GPC3-Dig

<400> SEQUENCE: 17

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
            35                  40                  45

Ser Ser Ile Asn Ile Gly Ala Thr Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Gly Gly Gly Ser Gly Gly Gly Ser Gly Gly Gly Gly
225                 230                 235                 240

Gly Gly Ser Gly Gly Gly Gly Ser Asp Val Val Met Thr Gln Ser Pro
                245                 250                 255

Leu Ser Leu Pro Val Thr Pro Gly Glu Pro Ala Ser Ile Ser Cys Arg
            260                 265                 270

Ser Ser Gln Ser Leu Val His Ser Asn Arg Asn Thr Tyr Leu His Trp
            275                 280                 285

Tyr Leu Gln Lys Pro Gly Gln Ser Pro Gln Leu Leu Ile Tyr Lys Val
290                 295                 300

Ser Asn Arg Phe Ser Gly Val Pro Asp Arg Phe Ser Gly Ser Gly Ser
305                 310                 315                 320

Gly Thr Asp Phe Thr Leu Lys Ile Ser Arg Val Glu Ala Glu Asp Val
                325                 330                 335

Gly Val Tyr Tyr Cys Ser Gln Asn Thr His Val Pro Pro Thr Phe Gly
            340                 345                 350

Gln Gly Thr Lys Leu Glu Ile Lys Gly Gln Pro Arg Glu Pro Gln Val
            355                 360                 365

Cys Thr Leu Pro Pro Ser Arg Asp Glu Leu Thr Lys Asn Gln Val Ser
            370                 375                 380

Leu Ser Cys Ala Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Val Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 18
<211> LENGTH: 219
<212> TYPE: PRT
<213> ORGANISM: Artificial Sequence
<220> FEATURE:
<223> OTHER INFORMATION: light chain polypeptide with Glypican 3 binding
      site

<400> SEQUENCE: 18

Asp Val Val Met Thr Gln Ser Pro Leu Ser Leu Pro Val Thr Pro Gly
1               5                   10                  15

Glu Pro Ala Ser Ile Ser Cys Arg Ser Gln Ser Leu Val His Ser
            20                  25                  30

Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 19
<211> LENGTH: 470
<212> TYPE: PRT
<213> ORGANISM: Artificial Sequence
<220> FEATURE:
<223> OTHER INFORMATION: polypeptide VH-CH1-linker-VH3-CH3 of BsAb
      GPC3-Dig(SS)-GPC3

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

```
Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Gly Gly Gly Ser Gly
    210                 215                 220

Gly Gly Gly Ser Gly Gly Gly Ser Gly Gly Gly Ser Gln Val
225                 230                 235                 240

Gln Leu Val Glu Ser Gly Gly Leu Val Lys Pro Gly Gly Ser Leu
            245                 250                 255

Arg Leu Ser Cys Ala Ala Ser Gly Phe Thr Phe Ser Asp Tyr Ala Met
                260                 265                 270

Ser Trp Ile Arg Gln Ala Pro Gly Lys Cys Leu Glu Trp Val Ser Ser
            275                 280                 285

Ile Asn Ile Gly Ala Thr Tyr Ile Tyr Tyr Ala Asp Ser Val Lys Gly
    290                 295                 300

Arg Phe Thr Ile Ser Arg Asp Asn Ala Lys Asn Ser Leu Tyr Leu Gln
305                 310                 315                 320

Met Asn Ser Leu Arg Ala Glu Asp Thr Ala Val Tyr Tyr Cys Ala Arg
                325                 330                 335

Pro Gly Ser Pro Tyr Glu Tyr Asp Lys Ala Tyr Tyr Ser Met Ala Tyr
                340                 345                 350

Trp Gly Gln Gly Thr Thr Val Thr Val Ser Ser Gly Gln Pro Arg Glu
            355                 360                 365

Pro Gln Val Tyr Thr Leu Pro Pro Cys Arg Asp Glu Leu Thr Lys Asn
370                 375                 380

Gln Val Ser Leu Trp Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
```

Ser Leu Ser Pro Gly Lys
465              470

<210> SEQ ID NO 20
<211> LENGTH: 452
<212> TYPE: PRT
<213> ORGANISM: Artificial Sequence
<220> FEATURE:
<223> OTHER INFORMATION: polypeptide VH-CH1-linker-VL3-CH3 of BsAb
      GPC3-Dig(SS)-GPC3

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Gly Gly Gly Gly Ser Gly
    210                 215                 220

Gly Gly Gly Ser Gly Gly Gly Gly Ser Gly Gly Gly Gly Ser Asp Ile
225                 230                 235                 240

Gln Met Thr Gln Ser Pro Ser Ser Leu Ser Ala Ser Val Gly Asp Arg
                245                 250                 255

Val Thr Ile Thr Cys Arg Ala Ser Gln Asp Ile Lys Asn Tyr Leu Asn
            260                 265                 270

Trp Tyr Gln Gln Lys Pro Gly Lys Ala Pro Lys Leu Leu Ile Tyr Tyr
        275                 280                 285

Ser Ser Thr Leu Leu Ser Gly Val Pro Ser Arg Phe Ser Gly Ser Gly
    290                 295                 300

Ser Gly Thr Asp Phe Thr Leu Thr Ile Ser Ser Leu Gln Pro Glu Asp
305                 310                 315                 320

Phe Ala Thr Tyr Tyr Cys Gln Gln Ser Ile Thr Leu Pro Pro Thr Phe
                325                 330                 335

```
Gly Cys Gly Thr Lys Val Glu Ile Lys Gly Gln Pro Arg Glu Pro Gln
                340                 345                 350

Val Cys Thr Leu Pro Pro Ser Arg Asp Glu Leu Thr Lys Asn Gln Val
            355                 360                 365

Ser Leu Ser Cys Ala Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 21
<211> LENGTH: 469
<212> TYPE: PRT
<213> ORGANISM: Artificial Sequence
<220> FEATURE:
<223> OTHER INFORMATION: polypeptide VH-CH1-linker-VH3-CH3 of BsAb
      LeY-Bio(SS)-LeY

<400> SEQUENCE: 21

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Asp Ser Ser Ala Ala Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
                85                  90                  95

Ala Arg Gly Leu Ala Trp Gly Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Gly Gly Gly Gly Ser Gly Gly Gly
225                 230                 235                 240
```

```
Gly Ser Gln Val Gln Leu Val Gln Ser Gly Ala Glu Val Lys Lys Pro
            245                 250                 255

Gly Ser Ser Val Lys Val Ser Cys Lys Ser Ser Gly Phe Asn Asn Lys
            260                 265                 270

Asp Thr Phe Phe Gln Trp Val Arg Gln Ala Pro Gly Gln Cys Leu Glu
            275                 280                 285

Trp Met Gly Arg Ile Asp Pro Ala Asn Gly Phe Thr Lys Tyr Ala Gln
            290                 295                 300

Lys Phe Gln Gly Arg Val Thr Ile Thr Ala Asp Thr Ser Thr Ser Thr
305                 310                 315                 320

Ala Tyr Met Glu Leu Ser Ser Leu Arg Ser Glu Asp Thr Ala Val Tyr
            325                 330                 335

Tyr Cys Ala Arg Trp Asp Thr Tyr Gly Ala Ala Trp Phe Ala Tyr Trp
            340                 345                 350

Gly Gln Gly Thr Leu Val Thr Val Ser Ser Gly Gln Pro Arg Glu Pro
            355                 360                 365

Gln Val Tyr Thr Leu Pro Pro Cys Arg Asp Glu Leu Thr Lys Asn Gln
            370                 375                 380

Val Ser Leu Trp Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 22
<211> LENGTH: 456
<212> TYPE: PRT
<213> ORGANISM: Artificial Sequence
<220> FEATURE:
<223> OTHER INFORMATION: polypeptide VH-CH1-linker-VL3-CH3 of BsAb
      LeY-Bio(SS)-LeY

<400> SEQUENCE: 22

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
            35                  40                  45

Ala Tyr Ile Ser Asn Asp Ser Ser Ala Ala Tyr Ser Asp Thr Val
            50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
            85                  90                  95

Ala Arg Gly Leu Ala Trp Gly Ala Trp Phe Ala Tyr Trp Gly Gln Gly
            100                 105                 110

Thr Leu Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Gly Gly Gly Gly Ser Gly Gly Gly
225                 230                 235                 240

Gly Ser Asp Ile Gln Met Thr Gln Ser Pro Ser Ser Leu Ser Ala Ser
                245                 250                 255

Val Gly Asp Arg Val Thr Ile Thr Cys Arg Ala Ser Gly Asn Ile His
            260                 265                 270

Asn Tyr Leu Ser Trp Tyr Gln Gln Lys Pro Gly Lys Val Pro Lys Leu
        275                 280                 285

Leu Ile Tyr Ser Ala Lys Thr Leu Ala Asp Gly Val Pro Ser Arg Phe
    290                 295                 300

Ser Gly Ser Gly Ser Gly Thr Asp Phe Thr Leu Thr Ile Ser Ser Leu
305                 310                 315                 320

Gln Pro Glu Asp Val Ala Thr Tyr Tyr Cys Gln His Phe Trp Ser Ser
                325                 330                 335

Ile Tyr Thr Phe Gly Cys Gly Thr Lys Leu Glu Ile Lys Gly Gln Pro
            340                 345                 350

Arg Glu Pro Gln Val Cys Thr Leu Pro Pro Ser Arg Asp Glu Leu Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 23
<211> LENGTH: 466
<212> TYPE: PRT
<213> ORGANISM: Artificial Sequence
<220> FEATURE:
<223> OTHER INFORMATION: polypeptide VH-CH1-linker-VH3-CH3 of BsAb
      CD33-Bio(SS)-CD33

<400> SEQUENCE: 23

Glu Val Gln Leu Val Gln Ser Gly Ala Glu Val Lys Lys Pro Gly Ser
1               5                   10                  15
```

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
            35                  40                  45

Gly Tyr Ile Tyr Pro Tyr Asn Gly Gly Thr Asp Tyr Asn Gln Lys Phe
            50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
            85                  90                  95

Val Asn Gly Asn Pro Trp Leu Ala Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Gly Gly Gly Gly Ser
210                 215                 220

Gly Gly Gly Gly Ser Gly Gly Gly Ser Gly Gly Gly Gly Ser Gln
225                 230                 235                 240

Val Gln Leu Val Gln Ser Gly Ala Glu Val Lys Lys Pro Gly Ser Ser
            245                 250                 255

Val Lys Val Ser Cys Lys Ser Ser Gly Phe Asn Asn Lys Asp Thr Phe
            260                 265                 270

Phe Gln Trp Val Arg Gln Ala Pro Gly Gln Cys Leu Glu Trp Met Gly
            275                 280                 285

Arg Ile Asp Pro Ala Asn Gly Phe Thr Lys Tyr Ala Gln Lys Phe Gln
            290                 295                 300

Gly Arg Val Thr Ile Thr Ala Asp Thr Ser Thr Ser Thr Ala Tyr Met
305                 310                 315                 320

Glu Leu Ser Ser Leu Arg Ser Glu Asp Thr Ala Val Tyr Tyr Cys Ala
            325                 330                 335

Arg Trp Asp Thr Tyr Gly Ala Ala Trp Phe Ala Tyr Trp Gly Gln Gly
            340                 345                 350

Thr Leu Val Thr Val Ser Ser Gly Gln Pro Arg Glu Pro Gln Val Tyr
            355                 360                 365

Thr Leu Pro Pro Cys Arg Asp Glu Leu Thr Lys Asn Gln Val Ser Leu
            370                 375                 380

Trp Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His

```
                435             440             445
Glu Ala Leu His Asn His Tyr Thr Gln Lys Ser Leu Ser Leu Ser Pro
    450                 455                 460

Gly Lys
465

<210> SEQ ID NO 24
<211> LENGTH: 453
<212> TYPE: PRT
<213> ORGANISM: Artificial Sequence
<220> FEATURE:
<223> OTHER INFORMATION: polypeptide VH-CH1-linker-VL3-CH3 of BsAb
      CD33-Bio(SS)-CD33

<400> SEQUENCE: 24

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Gly Gly Gly Ser
    210                 215                 220

Gly Gly Gly Gly Ser Gly Gly Gly Ser Gly Gly Gly Gly Ser Asp
225                 230                 235                 240

Ile Gln Met Thr Gln Ser Pro Ser Ser Leu Ser Ala Ser Val Gly Asp
                245                 250                 255

Arg Val Thr Ile Thr Cys Arg Ala Ser Gly Asn Ile His Asn Tyr Leu
            260                 265                 270

Ser Trp Tyr Gln Gln Lys Pro Gly Lys Val Pro Lys Leu Leu Ile Tyr
        275                 280                 285

Ser Ala Lys Thr Leu Ala Asp Gly Val Pro Ser Arg Phe Ser Gly Ser
    290                 295                 300

Gly Ser Gly Thr Asp Phe Thr Leu Thr Ile Ser Ser Leu Gln Pro Glu
305                 310                 315                 320
```

Asp Val Ala Thr Tyr Tyr Cys Gln His Phe Trp Ser Ile Tyr Thr
            325                 330                 335

Phe Gly Cys Gly Thr Lys Leu Glu Ile Lys Gly Gln Pro Arg Glu Pro
        340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 25
<211> LENGTH: 465
<212> TYPE: PRT
<213> ORGANISM: Artificial Sequence
<220> FEATURE:
<223> OTHER INFORMATION: polypeptide VH-CH1-linker-VH3-CH3 of BsAb
      GPC3-Bio(SS)-GPC3

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Gly Gly Gly Gly Ser Gly
    210                 215                 220

Gly Gly Gly Ser Gly Gly Gly Ser Gly Gly Gly Ser Gln Val
225                 230                 235                 240

Gln Leu Val Gln Ser Gly Ala Glu Val Lys Lys Pro Gly Ser Ser Val
            245                 250                 255

Lys Val Ser Cys Lys Ser Gly Phe Asn Asn Lys Asp Thr Phe Phe
        260                 265                 270

Gln Trp Val Arg Gln Ala Pro Gly Gln Cys Leu Glu Trp Met Gly Arg
            275                 280                 285

Ile Asp Pro Ala Asn Gly Phe Thr Lys Tyr Ala Gln Lys Phe Gln Gly
        290                 295                 300

Arg Val Thr Ile Thr Ala Asp Thr Ser Thr Ser Thr Ala Tyr Met Glu
305                 310                 315                 320

Leu Ser Ser Leu Arg Ser Glu Asp Thr Ala Val Tyr Tyr Cys Ala Arg
                325                 330                 335

Trp Asp Thr Tyr Gly Ala Ala Trp Phe Ala Tyr Trp Gly Gln Gly Thr
            340                 345                 350

Leu Val Thr Val Ser Ser Gly Gln Pro Arg Glu Pro Gln Val Tyr Thr
                355                 360                 365

Leu Pro Pro Cys Arg Asp Glu Leu Thr Lys Asn Gln Val Ser Leu Trp
            370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
        450                 455                 460

Lys
465

<210> SEQ ID NO 26
<211> LENGTH: 452
<212> TYPE: PRT
<213> ORGANISM: Artificial Sequence
<220> FEATURE:
<223> OTHER INFORMATION: polypeptide VH-CH1-linker-VL3-CH3 of BsAb
      GPC3-Bio(SS)-GPC3

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr

```
                100                 105                 110
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Gly Gly Gly Gly Ser Gly
210                 215                 220

Gly Gly Ser Gly Gly Gly Ser Gly Gly Gly Ser Asp Ile
225                 230                 235                 240

Gln Met Thr Gln Ser Pro Ser Ser Leu Ser Ala Ser Val Gly Asp Arg
                245                 250                 255

Val Thr Ile Thr Cys Arg Ala Ser Gly Asn Ile His Asn Tyr Leu Ser
            260                 265                 270

Trp Tyr Gln Gln Lys Pro Gly Lys Val Pro Lys Leu Leu Ile Tyr Ser
        275                 280                 285

Ala Lys Thr Leu Ala Asp Gly Val Pro Ser Arg Phe Ser Gly Ser Gly
    290                 295                 300

Ser Gly Thr Asp Phe Thr Leu Thr Ile Ser Ser Leu Gln Pro Glu Asp
305                 310                 315                 320

Val Ala Thr Tyr Tyr Cys Gln His Phe Trp Ser Ile Tyr Thr Phe
                325                 330                 335

Gly Cys Gly Thr Lys Leu Glu Ile Lys Gly Gln Pro Arg Glu Pro Gln
            340                 345                 350

Val Cys Thr Leu Pro Pro Ser Arg Asp Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 27
<211> LENGTH: 214
<212> TYPE: PRT
<213> ORGANISM: Artificial Sequence
<220> FEATURE:
<223> OTHER INFORMATION: light chain polypeptide with Biotin binding
      site

<400> SEQUENCE: 27
```

-continued

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ser Trp Tyr Gln Gln Lys Pro Gly Lys Val Pro Lys Leu Leu Ile
            35                  40                  45

Tyr Ser Ala Lys Thr Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 28
<211> LENGTH: 469
<212> TYPE: PRT
<213> ORGANISM: Artificial Sequence
<220> FEATURE:
<223> OTHER INFORMATION: polypeptide VH-CH1-linker-VH3-CH3 of BsAb
      Bio-LeY(SS)-Bio

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
            35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Gly Gly Gly Ser Gly Gly Gly Ser Gly Gly Gly Ser Gly
225                 230                 235                 240

Gly Gly Ser Asp Val Lys Leu Val Glu Ser Gly Gly Gly Leu Val Gln
            245                 250                 255

Pro Gly Gly Ser Leu Lys Leu Ser Cys Ala Thr Ser Gly Phe Thr Phe
            260                 265                 270

Ser Asp Tyr Tyr Met Tyr Trp Val Arg Gln Thr Pro Glu Lys Cys Leu
        275                 280                 285

Glu Trp Val Ala Tyr Ile Ser Asn Asp Asp Ser Ser Ala Ala Tyr Ser
290                 295                 300

Asp Thr Val Lys Gly Arg Phe Thr Ile Ser Arg Asp Asn Ala Arg Asn
305                 310                 315                 320

Thr Leu Tyr Leu Gln Met Ser Arg Leu Lys Ser Glu Asp Thr Ala Ile
                325                 330                 335

Tyr Tyr Cys Ala Arg Gly Leu Ala Trp Gly Ala Trp Phe Ala Tyr Trp
            340                 345                 350

Gly Gln Gly Thr Leu Val Thr Val Ser Ser Gly Gln Pro Arg Glu Pro
        355                 360                 365

Gln Val Tyr Thr Leu Pro Pro Cys Arg Asp Glu Leu Thr Lys Asn Gln
    370                 375                 380

Val Ser Leu Trp Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 29
<211> LENGTH: 462
<212> TYPE: PRT
<213> ORGANISM: Artificial Sequence
<220> FEATURE:
<223> OTHER INFORMATION: polypeptide VH-CH1-linker-VL3-CH3 of BsAb
      Bio-LeY(SS)-Bio

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr

```
                20                  25                  30
Phe Phe Gln Trp Val Arg Gln Ala Pro Gly Gln Gly Leu Glu Trp Met
            35                  40                  45
Gly Arg Ile Asp Pro Ala Asn Gly Phe Thr Lys Tyr Ala Gln Lys Phe
 50                  55                  60
Gln Gly Arg Val Thr Ile Thr Ala Asp Thr Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Trp Asp Thr Tyr Gly Ala Ala Trp Phe Ala Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Gly
            210                 215                 220
Gly Gly Gly Ser Gly Gly Gly Gly Ser Gly Gly Gly Gly Ser Gly Gly
225                 230                 235                 240
Gly Gly Ser Asp Val Leu Met Thr Gln Ser Pro Leu Ser Leu Pro Val
                245                 250                 255
Ser Leu Gly Asp Gln Ala Ser Ile Ser Cys Arg Ser Ser Gln Ile Ile
            260                 265                 270
Val His Ser Asn Gly Asn Thr Tyr Leu Glu Trp Tyr Leu Gln Lys Pro
            275                 280                 285
Gly Gln Ser Pro Lys Leu Leu Ile Tyr Lys Val Ser Asn Arg Phe Ser
            290                 295                 300
Gly Val Pro Asp Arg Phe Ser Gly Ser Gly Ser Gly Thr Asp Phe Thr
305                 310                 315                 320
Leu Lys Ile Ser Arg Val Glu Ala Glu Asp Leu Gly Val Tyr Tyr Cys
                325                 330                 335
Phe Gln Gly Ser His Val Pro Phe Thr Phe Gly Cys Gly Thr Lys Leu
            340                 345                 350
Glu Ile Lys Gly Gln Pro Arg Glu Pro Gln Val Cys Thr Leu Pro Pro
            355                 360                 365
Ser Arg Asp Glu Leu Thr Lys Asn Gln Val Ser Leu Ser Cys Ala Val
            370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Val Ser Lys Leu Thr Val Asp Lys Ser Arg Trp
            420                 425                 430
Gln Gln Gly Asn Val Phe Ser Cys Ser Val Met His Glu Ala Leu His
            435                 440                 445
```

```
Asn His Tyr Thr Gln Lys Ser Leu Ser Leu Ser Pro Gly Lys
        450                 455                 460

<210> SEQ ID NO 30
<211> LENGTH: 466
<212> TYPE: PRT
<213> ORGANISM: Artificial Sequence
<220> FEATURE:
<223> OTHER INFORMATION: polypeptide VH-CH1-linker-VH3-CH3 of BsAb
      Bio-CD33(SS)-Bio

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Gly Gly Gly Ser Gly Gly Gly Gly Ser Gly Gly Gly Gly Ser Gly Gly
225                 230                 235                 240

Gly Gly Ser Glu Val Gln Leu Val Gln Ser Gly Ala Glu Val Lys Lys
                245                 250                 255

Pro Gly Ser Ser Val Lys Val Ser Cys Lys Ala Ser Gly Tyr Thr Ile
            260                 265                 270

Thr Asp Ser Asn Ile His Trp Val Arg Gln Ala Pro Gly Gln Cys Leu
        275                 280                 285

Glu Trp Ile Gly Tyr Ile Tyr Pro Tyr Asn Gly Gly Thr Asp Tyr Asn
    290                 295                 300

Gln Lys Phe Lys Asn Arg Ala Thr Leu Thr Val Asp Asn Pro Thr Asn
305                 310                 315                 320

Thr Ala Tyr Met Glu Leu Ser Ser Leu Arg Ser Glu Asp Thr Ala Phe
                325                 330                 335

Tyr Tyr Cys Val Asn Gly Asn Pro Trp Leu Ala Tyr Trp Gly Gln Gly
```

```
                340             345             350
Thr Leu Val Thr Val Ser Ser Gly Gln Pro Arg Glu Pro Gln Val Tyr
            355                 360                 365

Thr Leu Pro Pro Cys Arg Asp Glu Leu Thr Lys Asn Gln Val Ser Leu
        370                 375                 380

Trp Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 31
<211> LENGTH: 461
<212> TYPE: PRT
<213> ORGANISM: Artificial Sequence
<220> FEATURE:
<223> OTHER INFORMATION: polypeptide VH-CH1-linker-VL3-CH3 of BsAb
      Bio-CD33(SS)-Bio

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220
```

Gly Gly Gly Ser Gly Gly Gly Ser Gly Gly Gly Ser Gly Gly
225                 230                 235                 240

Gly Gly Ser Asp Ile Gln Leu Thr Gln Ser Pro Ser Thr Leu Ser Ala
            245                 250                 255

Ser Val Gly Asp Arg Val Thr Ile Thr Cys Arg Ala Ser Glu Ser Leu
        260                 265                 270

Asp Asn Tyr Gly Ile Arg Phe Leu Thr Trp Phe Gln Gln Lys Pro Gly
    275                 280                 285

Lys Ala Pro Lys Leu Leu Met Tyr Ala Ala Ser Asn Gln Gly Ser Gly
290                 295                 300

Val Pro Ser Arg Phe Ser Gly Ser Gly Ser Gly Thr Glu Phe Thr Leu
305                 310                 315                 320

Thr Ile Ser Ser Leu Gln Pro Asp Asp Phe Ala Thr Tyr Tyr Cys Gln
            325                 330                 335

Gln Thr Lys Glu Val Pro Trp Ser Phe Gly Cys Gly Thr Lys Val Glu
        340                 345                 350

Val Lys Gly Gln Pro Arg Glu Pro Gln Val Cys Thr Leu Pro Pro Ser
    355                 360                 365

Arg Asp Glu Leu Thr Lys Asn Gln Val Ser Leu Ser Cys Ala Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Val Ser Lys Leu Thr Val Asp Lys Ser Arg Trp Gln
        420                 425                 430

Gln Gly Asn Val Phe Ser Cys Ser Val Met His Glu Ala Leu His Asn
    435                 440                 445

His Tyr Thr Gln Lys Ser Leu Ser Leu Ser Pro Gly Lys
450                 455                 460

<210> SEQ ID NO 32
<211> LENGTH: 465
<212> TYPE: PRT
<213> ORGANISM: Artificial Sequence
<220> FEATURE:
<223> OTHER INFORMATION: polypeptide VH-CH1-linker-VH3-CH3 of BsAb
      Bio-GPC3(SS)-Bio

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Trp Asp Thr Tyr Gly Ala Ala Trp Phe Ala Tyr Trp Gly Gln
        100                 105                 110

Gly Thr Leu Val Thr Val Ser Ser Ala Ser Thr Lys Gly Pro Ser Val
    115                 120                 125

```
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Gly Gly Ser Gly Gly Gly Gly Ser Gly Gly Gly Gly Ser Gly Gly
225                 230                 235                 240

Gly Gly Ser Gln Val Gln Leu Val Gln Ser Gly Ala Glu Val Lys Lys
                245                 250                 255

Pro Gly Ala Ser Val Lys Val Ser Cys Lys Ala Ser Gly Tyr Thr Phe
            260                 265                 270

Thr Asp Tyr Glu Met His Trp Val Arg Gln Ala Pro Gly Gln Cys Leu
        275                 280                 285

Glu Trp Met Gly Ala Leu Asp Pro Lys Thr Gly Asp Thr Ala Tyr Ser
290                 295                 300

Gln Lys Phe Lys Gly Arg Val Thr Leu Thr Ala Asp Lys Ser Thr Ser
305                 310                 315                 320

Thr Ala Tyr Met Glu Leu Ser Ser Leu Thr Ser Glu Asp Thr Ala Val
                325                 330                 335

Tyr Tyr Cys Thr Arg Phe Tyr Ser Tyr Thr Tyr Trp Gly Gln Gly Thr
            340                 345                 350

Leu Val Thr Val Ser Ser Gly Gln Pro Arg Glu Pro Gln Val Tyr Thr
        355                 360                 365

Leu Pro Pro Cys Arg Asp Glu Leu Thr Lys Asn Gln Val Ser Leu Trp
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 33
<211> LENGTH: 462
<212> TYPE: PRT
<213> ORGANISM: Artificial Sequence
<220> FEATURE:
<223> OTHER INFORMATION: polypeptide VH-CH1-linker-VL3-CH3 of BsAb
      Bio-GPC3(SS)-Bio

<400> SEQUENCE: 33

Gln Val Gln Leu Val Gln Ser Gly Ala Glu Val Lys Lys Pro Gly Ser
```

-continued

```
1               5                   10                  15
Ser Val Lys Val Ser Cys Lys Ser Ser Gly Phe Asn Asn Lys Asp Thr
                20                  25                  30

Phe Phe Gln Trp Val Arg Gln Ala Pro Gly Gln Gly Leu Glu Trp Met
                35                  40                  45

Gly Arg Ile Asp Pro Ala Asn Gly Phe Thr Lys Tyr Ala Gln Lys Phe
                50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Gly
                210                 215                 220

Gly Gly Gly Ser Gly Gly Gly Ser Gly Gly Gly Ser Gly Gly Gly Gly
225                 230                 235                 240

Gly Gly Ser Asp Val Val Met Thr Gln Ser Pro Leu Ser Leu Pro Val
                245                 250                 255

Thr Pro Gly Glu Pro Ala Ser Ile Ser Cys Arg Ser Ser Gln Ser Leu
                260                 265                 270

Val His Ser Asn Arg Asn Thr Tyr Leu His Trp Tyr Leu Gln Lys Pro
                275                 280                 285

Gly Gln Ser Pro Gln Leu Leu Ile Tyr Lys Val Ser Asn Arg Phe Ser
                290                 295                 300

Gly Val Pro Asp Arg Phe Ser Gly Ser Gly Ser Gly Thr Asp Phe Thr
305                 310                 315                 320

Leu Lys Ile Ser Arg Val Glu Ala Glu Asp Val Gly Val Tyr Tyr Cys
                325                 330                 335

Ser Gln Asn Thr His Val Pro Pro Thr Phe Gly Cys Gly Thr Lys Leu
                340                 345                 350

Glu Ile Lys Gly Gln Pro Arg Glu Pro Gln Val Cys Thr Leu Pro Pro
                355                 360                 365

Ser Arg Asp Glu Leu Thr Lys Asn Gln Val Ser Leu Ser Cys Ala Val
                370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Val Ser Lys Leu Thr Val Asp Lys Ser Arg Trp
                420                 425                 430
```

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 34
<211> LENGTH: 474
<212> TYPE: PRT
<213> ORGANISM: Artificial Sequence
<220> FEATURE:
<223> OTHER INFORMATION: polypeptide VH-CH1-linker-VH3-CH3 of BsAb
      Dig-LeY(SS)-Dig

<400> SEQUENCE: 34

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Gly Gly Gly Ser Gly Gly Gly Ser Gly Gly Ser Gly
225                 230                 235                 240

Gly Gly Ser Gly Gly Gly Ser Asp Val Lys Leu Val Glu Ser Gly
                245                 250                 255

Gly Gly Leu Val Gln Pro Gly Gly Ser Leu Lys Leu Ser Cys Ala Thr
            260                 265                 270

Ser Gly Phe Thr Phe Ser Asp Tyr Tyr Met Tyr Trp Val Arg Gln Thr
        275                 280                 285

Pro Glu Lys Cys Leu Glu Trp Val Ala Tyr Ile Ser Asn Asp Asp Ser
    290                 295                 300

Ser Ala Ala Tyr Ser Asp Thr Val Lys Gly Arg Phe Thr Ile Ser Arg
305                 310                 315                 320

Asp Asn Ala Arg Asn Thr Leu Tyr Leu Gln Met Ser Arg Leu Lys Ser

```
                    325                 330                 335
Glu Asp Thr Ala Ile Tyr Tyr Cys Ala Arg Gly Leu Ala Trp Gly Ala
                340                 345                 350

Trp Phe Ala Tyr Trp Gly Gln Gly Thr Leu Val Thr Val Ser Ser Gly
                355                 360                 365

Gln Pro Arg Glu Pro Gln Val Tyr Thr Leu Pro Pro Cys Arg Asp Glu
                370                 375                 380

Leu Thr Lys Asn Gln Val Ser Leu Trp Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
                450                 455                 460

Gln Lys Ser Leu Ser Leu Ser Pro Gly Lys
465                 470

<210> SEQ ID NO 35
<211> LENGTH: 467
<212> TYPE: PRT
<213> ORGANISM: Artificial Sequence
<220> FEATURE:
<223> OTHER INFORMATION: polypeptide VH-CH1-linker-VL3-CH3 of BsAb
      Dig-LeY(SS)-Dig

<400> SEQUENCE: 35

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Ala Met Ser Trp Ile Arg Gln Ala Pro Gly Lys Gly Leu Glu Trp Val
                35                  40                  45

Ser Ser Ile Asn Ile Gly Ala Thr Tyr Ile Tyr Tyr Ala Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
                100                 105                 110

Ala Tyr Trp Gly Gln Gly Thr Thr Val Thr Val Ser Ser Ala Ser Thr
                115                 120                 125

Lys Gly Pro Ser Val Phe Pro Leu Ala Pro Ser Ser Lys Ser Thr Ser
                130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205
```

```
Asn Val Asn His Lys Pro Ser Asn Thr Lys Val Asp Lys Val Glu
    210                 215                 220
Pro Lys Ser Cys Gly Gly Gly Ser Gly Gly Gly Gly Ser Gly Gly
225                 230                 235                 240
Gly Gly Ser Gly Gly Gly Gly Ser Asp Val Leu Met Thr Gln Ser Pro
                245                 250                 255
Leu Ser Leu Pro Val Ser Leu Gly Asp Gln Ala Ser Ile Ser Cys Arg
        260                 265                 270
Ser Ser Gln Ile Ile Val His Ser Asn Gly Asn Thr Tyr Leu Glu Trp
    275                 280                 285
Tyr Leu Gln Lys Pro Gly Gln Ser Pro Lys Leu Leu Ile Tyr Lys Val
    290                 295                 300
Ser Asn Arg Phe Ser Gly Val Pro Asp Arg Phe Ser Gly Ser Gly Ser
305                 310                 315                 320
Gly Thr Asp Phe Thr Leu Lys Ile Ser Arg Val Glu Ala Glu Asp Leu
                325                 330                 335
Gly Val Tyr Tyr Cys Phe Gln Gly Ser His Val Pro Thr Phe Gly
        340                 345                 350
Cys Gly Thr Lys Leu Glu Ile Lys Gly Gln Pro Arg Glu Pro Gln Val
        355                 360                 365
Cys Thr Leu Pro Pro Ser Arg Asp Glu Leu Thr Lys Asn Gln Val Ser
370                 375                 380
Leu Ser Cys Ala Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Val Ser Lys Leu Thr Val
                420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 36
<211> LENGTH: 471
<212> TYPE: PRT
<213> ORGANISM: Artificial Sequence
<220> FEATURE:
<223> OTHER INFORMATION: polypeptide VH-CH1-linker-VH3-CH3 of BsAb
      Dig-CD33(SS)-Dig

<400> SEQUENCE: 36

Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Ala Met Ser Trp Ile Arg Gln Ala Pro Gly Lys Gly Leu Glu Trp Val
        35                  40                  45
Ser Ser Ile Asn Ile Gly Ala Thr Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
```

```
Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Gly Gly Gly Gly Ser Gly Gly Gly Ser Gly Gly Gly
225                 230                 235                 240

Gly Gly Ser Gly Gly Gly Ser Glu Val Gln Leu Val Gln Ser Gly
                245                 250                 255

Ala Glu Val Lys Lys Pro Gly Ser Ser Val Lys Val Ser Cys Lys Ala
            260                 265                 270

Ser Gly Tyr Thr Ile Thr Asp Ser Asn Ile His Trp Val Arg Gln Ala
        275                 280                 285

Pro Gly Gln Cys Leu Glu Trp Ile Gly Tyr Ile Tyr Pro Tyr Asn Gly
    290                 295                 300

Gly Thr Asp Tyr Asn Gln Lys Phe Lys Asn Arg Ala Thr Leu Thr Val
305                 310                 315                 320

Asp Asn Pro Thr Asn Thr Ala Tyr Met Glu Leu Ser Ser Leu Arg Ser
                325                 330                 335

Glu Asp Thr Ala Phe Tyr Tyr Cys Val Asn Gly Asn Pro Trp Leu Ala
            340                 345                 350

Tyr Trp Gly Gln Gly Thr Leu Val Thr Val Ser Ser Gly Gln Pro Arg
        355                 360                 365

Glu Pro Gln Val Tyr Thr Leu Pro Pro Cys Arg Asp Glu Leu Thr Lys
    370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 37
<211> LENGTH: 466
<212> TYPE: PRT
<213> ORGANISM: Artificial Sequence
<220> FEATURE:
```

<223> OTHER INFORMATION: polypeptide VH-CH1-linker-VL3-CH3 of BsAb
      Dig-CD33(SS)-Dig

<400> SEQUENCE: 37

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Leu Gly Thr Gln Thr Tyr Ile Cys
    195                 200                 205

Asn Val Asn His Lys Pro Ser Asn Thr Lys Val Asp Lys Lys Val Glu
210                 215                 220

Pro Lys Ser Cys Gly Gly Gly Ser Gly Gly Gly Ser Gly
225                 230                 235                 240

Gly Gly Ser Gly Gly Gly Ser Asp Ile Gln Leu Thr Gln Ser Pro
            245                 250                 255

Ser Thr Leu Ser Ala Ser Val Gly Asp Arg Val Thr Ile Thr Cys Arg
        260                 265                 270

Ala Ser Glu Ser Leu Asp Asn Tyr Gly Ile Arg Phe Leu Thr Trp Phe
    275                 280                 285

Gln Gln Lys Pro Gly Lys Ala Pro Lys Leu Leu Met Tyr Ala Ala Ser
290                 295                 300

Asn Gln Gly Ser Gly Val Pro Ser Arg Phe Ser Gly Ser Gly Ser Gly
305                 310                 315                 320

Thr Glu Phe Thr Leu Thr Ile Ser Ser Leu Gln Pro Asp Asp Phe Ala
            325                 330                 335

Thr Tyr Tyr Cys Gln Gln Thr Lys Glu Val Pro Trp Ser Phe Gly Cys
        340                 345                 350

Gly Thr Lys Val Glu Val Lys Gly Gln Pro Arg Glu Pro Gln Val Cys
    355                 360                 365

Thr Leu Pro Pro Ser Arg Asp Glu Leu Thr Lys Asn Gln Val Ser Leu
370                 375                 380

Ser Cys Ala Val Lys Gly Phe Tyr Pro Ser Asp Ile Ala Val Glu Trp
385                 390                 395                 400
```

-continued

```
Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 38
<211> LENGTH: 470
<212> TYPE: PRT
<213> ORGANISM: Artificial Sequence
<220> FEATURE:
<223> OTHER INFORMATION: polypeptide VH-CH1-linker-VH3-CH3 of BsAb
      Dig-GPC3(SS)-Dig

<400> SEQUENCE: 38

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Gly Gly Gly Ser Gly Gly Gly Ser Gly
225                 230                 235                 240

Gly Gly Ser Gly Gly Gly Ser Gln Val Gln Leu Val Gln Ser Gly
                245                 250                 255

Ala Glu Val Lys Lys Pro Gly Ala Ser Val Lys Val Ser Cys Lys Ala
            260                 265                 270

Ser Gly Tyr Thr Phe Thr Asp Tyr Glu Met His Trp Val Arg Gln Ala
```

```
                275                 280                 285
Pro Gly Gln Cys Leu Glu Trp Met Gly Ala Leu Asp Pro Lys Thr Gly
        290                 295                 300
Asp Thr Ala Tyr Ser Gln Lys Phe Lys Gly Arg Val Thr Leu Thr Ala
305                 310                 315                 320
Asp Lys Ser Thr Ser Thr Ala Tyr Met Glu Leu Ser Ser Leu Thr Ser
                325                 330                 335
Glu Asp Thr Ala Val Tyr Tyr Cys Thr Arg Phe Tyr Ser Tyr Thr Tyr
                340                 345                 350
Trp Gly Gln Gly Thr Leu Val Thr Val Ser Ser Gly Gln Pro Arg Glu
                355                 360                 365
Pro Gln Val Tyr Thr Leu Pro Pro Cys Arg Asp Glu Leu Thr Lys Asn
        370                 375                 380
Gln Val Ser Leu Trp Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
                420                 425                 430
Leu Thr Val Asp Lys Ser Arg Trp Gln Gln Gly Asn Val Phe Ser Cys
                435                 440                 445
Ser Val Met His Glu Ala Leu His Asn His Tyr Thr Gln Lys Ser Leu
        450                 455                 460
Ser Leu Ser Pro Gly Lys
465                 470

<210> SEQ ID NO 39
<211> LENGTH: 467
<212> TYPE: PRT
<213> ORGANISM: Artificial Sequence
<220> FEATURE:
<223> OTHER INFORMATION: polypeptide VH-CH1-linker-VL3-CH3 of BsAb
      Dig-GPC3(SS)-Dig

<400> SEQUENCE: 39

Gln Val Gln Leu Val Glu Ser Gly Gly Gly Leu Val Lys Pro Gly Gly
1               5                  10                  15
Ser Leu Arg Leu Ser Cys Ala Ala Ser Gly Phe Thr Phe Ser Asp Tyr
                20                  25                  30
Ala Met Ser Trp Ile Arg Gln Ala Pro Gly Lys Gly Leu Glu Trp Val
            35                  40                  45
Ser Ser Ile Asn Ile Gly Ala Thr Tyr Ile Tyr Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Pro Gly Ser Pro Tyr Glu Tyr Asp Lys Ala Tyr Tyr Ser Met
                100                 105                 110
Ala Tyr Trp Gly Gln Gly Thr Thr Val Thr Val Ser Ser Ala Ser Thr
            115                 120                 125
Lys Gly Pro Ser Val Phe Pro Leu Ala Pro Ser Ser Lys Ser Thr Ser
        130                 135                 140
Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
            165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
            195                 200                 205
Asn Val Asn His Lys Pro Ser Asn Thr Lys Val Asp Lys Lys Val Glu
            210                 215                 220
Pro Lys Ser Cys Gly Gly Gly Ser Gly Gly Gly Ser Gly Gly Gly Gly
225                 230                 235                 240
Gly Gly Ser Gly Gly Gly Ser Asp Val Val Met Thr Gln Ser Pro
            245                 250                 255
Leu Ser Leu Pro Val Thr Pro Gly Glu Pro Ala Ser Ile Ser Cys Arg
            260                 265                 270
Ser Ser Gln Ser Leu Val His Ser Asn Arg Asn Thr Tyr Leu His Trp
            275                 280                 285
Tyr Leu Gln Lys Pro Gly Gln Ser Pro Gln Leu Leu Ile Tyr Lys Val
            290                 295                 300
Ser Asn Arg Phe Ser Gly Val Pro Asp Arg Phe Ser Gly Ser Gly Ser
305                 310                 315                 320
Gly Thr Asp Phe Thr Leu Lys Ile Ser Arg Val Glu Ala Glu Asp Val
            325                 330                 335
Gly Val Tyr Tyr Cys Ser Gln Asn Thr His Val Pro Pro Thr Phe Gly
            340                 345                 350
Cys Gly Thr Lys Leu Glu Ile Lys Gly Gln Pro Arg Glu Pro Gln Val
            355                 360                 365
Cys Thr Leu Pro Pro Ser Arg Asp Glu Leu Thr Lys Asn Gln Val Ser
            370                 375                 380
Leu Ser Cys Ala Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
            405                 410                 415
Val Leu Asp Ser Asp Gly Ser Phe Phe Leu Val Ser Lys Leu Thr Val
            420                 425                 430
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
            450                 455                 460
Pro Gly Lys
465

<210> SEQ ID NO 40
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: Can be present in repeats of 2, 3, 4, 5 or 6,
      and Gly at position 4 can be present or absent

<400> SEQUENCE: 40

Gly Gly Gly Gly Ser
1               5
```

```
<210> SEQ ID NO 41
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: Can be present in repeats of 2, 3, 4, 5 or 6,
      and Gly at position 4 can be present or absent
<220> FEATURE:
<221> NAME/KEY: VARIANT
<222> LOCATION: 6, 7, 8
<223> OTHER INFORMATION: Can be present or absent

<400> SEQUENCE: 41

Gly Gly Gly Gly Ser Gly Gly Gly
1               5

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Gly Gly Gly Ser Gly Gly Gly Gly Ser
1               5                   10

<210> SEQ ID NO 43
<211> LENGTH: 4
<212> TYPE: PRT
<213> ORGANISM: Artificial Sequence
<220> FEATURE:
<223> OTHER INFORMATION: Synthetic Construct

<400> SEQUENCE: 43

Pro Lys Ser Cys
1

<210> SEQ ID NO 44
<211> LENGTH: 4
<212> TYPE: PRT
<213> ORGANISM: Artificial Sequence
<220> FEATURE:
<223> OTHER INFORMATION: Synthetic Construct

<400> SEQUENCE: 44

Leu Gly Gly Pro
1

<210> SEQ ID NO 45
<211> LENGTH: 12
<212> TYPE: PRT
<213> ORGANISM: Artificial Sequence
<220> FEATURE:
<223> OTHER INFORMATION: Synthetic Construct

<400> SEQUENCE: 45

Asp Lys Thr His Thr Cys Pro Pro Cys Pro Ala Pro
1               5                   10

<210> SEQ ID NO 46
<211> LENGTH: 4
<212> TYPE: PRT
<213> ORGANISM: Artificial Sequence
<220> FEATURE:
```

```
<223> OTHER INFORMATION: Synthetic Construct

<400> SEQUENCE: 46

Gln Val Gln Leu
1

<210> SEQ ID NO 47
<211> LENGTH: 20
<212> TYPE: PRT
<213> ORGANISM: Artificial Sequence
<220> FEATURE:
<223> OTHER INFORMATION: Synthetic Construct

<400> SEQUENCE: 47

Gly Gly Gly Gly Ser Gly Gly Gly Gly Ser Gly Gly Gly Gly Ser Gly
1               5                   10                  15

Gly Gly Gly Ser
            20
```

MULTISPECIFIC ANTIBODIES

CROSS REFERENCE TO RELATED APPLICATIONS

This application is a divisional of U.S. application Ser. No. 15/612,104, filed Jun. 2, 2017, which is a continuation of International Application No. PCT/EP2015/078155 having an international filing date of Dec. 1, 2015, and which claims benefit under 35 U.S.C. § 119 to European Patent Application No. 14196046.8 filed Dec. 3, 2014, the entire contents each of which are incorporated herein by reference in its entirety.

SEQUENCE LISTING

The content of the following submission on ASCII text file is incorporated herein by reference in its entirety: a computer readable form (CRF) of the Sequence Listing (file name: 146392041110SEQLIST.TXT, date recorded: Aug. 13, 2020, size: 134 KB).

FIELD OF THE INVENTION

The present invention relates to multispecific antibodies, methods for their production, pharmaceutical compositions containing said antibodies and uses thereof.

BACKGROUND OF THE INVENTION

Engineered proteins, such as bi- or multispecific antibodies capable of binding two or more antigens are known in the art. Such multispecific binding proteins can be generated using cell fusion, chemical conjugation, or recombinant DNA techniques.

A wide variety of recombinant multispecific antibody formats have been developed in the recent past, e.g. tetravalent bispecific antibodies by fusion of, e.g. an IgG antibody format and single chain domains (see e.g. Coloma, M. J., et. al., Nature Biotech. 15 (1997) 159-163; WO 2001/077342; and Morrison, S. L., Nature Biotech. 25 (2007) 1233-1234).

One drawback in multispecific antibody generation is the formation of mispaired byproducts, which have to be separated from the desired multispecific antibodies by sophisticated purification procedures, and reduce the production yield.

An approach to circumvent the problem of mispaired byproducts, which is known as "knobs-into-holes technology", aims at forcing the pairing of two different antibody heavy chains by introducing mutations into the CH3 domains to modify the contact interface. On one chain bulky amino acids were replaced by amino acids with short side chains to create a "hole". Conversely, amino acids with large side chains were introduced into the other CH3 domain, to create a "knob". By coexpressing these two heavy chains (and two identical light chains, which have to be appropriate for both heavy chains), high yields of heterodimer formation ("knob-hole") versus homodimer formation ("hole-hole" or "knob-knob") was observed (Ridgway, J. B., et al., Protein Eng. 9 (1996) 617-621; and WO 96/027011). The percentage of heterodimer could be further increased by remodeling the interaction surfaces of the two CH3 domains using a phage display approach and the introduction of a disulfide bridge to stabilize the heterodimers (Merchant, A. M., et al., Nature Biotech. 16 (1998) 677-681; Atwell, S., et al., J. Mol. Biol. 270 (1997) 26-35).

WO 2010/115598 A1 discloses trivalent bispecific antibodies based on a monospecific full length IgG molecule, wherein at the respective C-termini of each one of the heavy chains a variable heavy chain domain and a variable light chain domain is fused in order to form a third antigen binding site specifically binding to a second antigen. In order to promote heterodimerization of the two modified heavy chains, modification of the CH3 domains according to the knobs-into-holes technology is suggested.

Also several other antibody formats, wherein the antibody core structure (IgA, IgD, IgE, IgG or IgM) is no longer retained, have been developed; such as dia-, tria- or tetrabodies, minibodies and several single chain formats (scFv, Bis-scFv), which are capable of binding two or more antigens (Holliger, P., et. al, Nature Biotech. 23 (2005) 1126-1136; Fischer, N., and Léger, O., Pathobiology 74 (2007) 3-14; Shen, J., et. al., J. Immunol. Methods 318 (2007) 65-74; Wu, C., et al., Nature Biotech. 25 (2007) 1290-1297). All such formats use linkers either to fuse the antibody core (IgA, IgD, IgE, IgG or IgM) to a further binding protein (e.g. scFv) or to fuse e.g. two Fab fragments or scFv (Fischer, N., and Léger, O., Pathobiology 74 (2007) 3-14).

WO 94/09131 discloses multispecific antibodies, wherein a first and a second binding region formed by antibody fragments, e.g. Fab fragments, are associated with each other by associating domains that are capable of binding to each other. According to WO 94/09131 an associating domain (e.g. a VH and VL domain, respectively) is fused to each one of the Fab fragments, such that the first and second binding region are combined in order to provide a single protein including both binding specificities.

Antibody fragments have both pros and cons as therapeutics compared with full-size monoclonal antibodies: One advantage is that they are smaller and penetrate tissues and tumors more rapidly. In addition, the small size of fragments has been suggested to permit binding to epitopes not accessible to full-sized monoclonal antibodies. On the downside, fragments demonstrate short circulating half-lives in humans, likely due to kidney clearance. The shorter half-life may prevent sufficient accumulation of therapy at the targeted site. Production of antibody fragments is not trivial, as fragments are likely to form aggregates and can be less stable than full-size monoclonal antibodies. In addition, unwanted pairing of noncongnate heavy and light chains results in formation of inactive antigen-binding sites and/or other non-functional undesired side-products, which is a major problem in clinical-scale production and therapeutic application of antibody fragments.

These drawbacks are overcome with the antibody format of the invention.

SUMMARY OF THE INVENTION

The present invention relates to a multispecific antibody comprising at least three antigen binding sites, wherein two antigen binding sites are formed by a first antigen binding moiety and a second antigen binding moiety, wherein a) a third antigen binding site is formed by a variable heavy chain domain ($VH_3$) and a variable light chain domain ($VL_3$), wherein the N-terminus of the $VH_3$ domain is connected to the first antigen binding moiety via a first peptide connector, and the N-terminus of the $VL_3$ domain is connected to the second antigen binding moiety via a second peptide connector, b) the multispecific antibody comprises two constant heavy chain domains 3 (CH3), which are altered to promote heterodimerization by
  i) generation of a protuberance in one of the CH3 domains by substituting at least one original amino acid residue by an amino acid residue having a larger side chain volume than the original amino acid residue, and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains; or
  substituting at least one original amino acid residue in one of the CH3 domains by a positively charged amino acid, and substituting at least one original amino acid residue in the other one of the CH3 domains by a negatively charged amino acid;
  ii) introduction of at least one cysteine residue in each CH3 domain such that a disulfide bond is formed between the CH3 domains, or
  iii) both modifications of i) and ii);
c) the C-terminus of the $VH_3$ domain of the third antigen binding site is connected to one of the CH3 domains, and the C-terminus of the $VL_3$ domain of the third antigen binding site is connected to the other one of the CH3 domains, and
d) the multispecific antibody is devoid of constant heavy chain domains 2 (CH2).

In one embodiment of the invention the first antigen binding moiety is a first Fab fragment and the second antigen binding moiety is a second Fab fragment.

One embodiment of the invention relates to a multispecific antibody, wherein
  i) the CH3 domains are altered by generation of a protuberance in one of the CH3 domains by substituting at least one original amino acid residue by an amino acid residue having a larger side chain volume than the original amino acid residue, and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains; or
  substituting at least one original amino acid residue in one of the CH3 domains by a positively charged amino acid, and substituting at least one original amino acid residue in the other one of the CH3 domains by a negatively charged amino acid;
  ii) the CH3 domains are altered by introduction of at least one cysteine residue in each CH3 domain such that a disulfide bond is formed between the CH3 domains; and wherein the third binding site is disulfide stabilized by introduction of cysteine residues at the following positions to form a disulfide bond between the $VH_3$ and $VL_3$ domains (numbering according to EU index of Kabat):
    $VH_3$ at position 44, and $VL_3$ at position 100;
    $VH_3$ at position 105, and $VL_3$ at position 43; or
    $VH_3$ at position 101, and $VL_3$ at position 100.

One embodiment of the invention relates to a multispecific antibody, wherein
  i) the CH3 domains are altered by generation of a protuberance in one of the CH3 domains by substituting at least one original amino acid residue by an amino acid residue having a larger side chain volume than the original amino acid residue, and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains; or
  substituting at least one original amino acid residue in one of the CH3 domains by a positively charged amino acid, and substituting at least one original amino acid residue in the other one of the CH3 domains by a negatively charged amino acid;
  ii) the CH3 domains are altered by introduction of at least one cysteine residue in each CH3 domain such that a disulfide bond is formed between the CH3 domains; and wherein the third binding site is disulfide stabilized by introduction of cysteine residues in the $VH_3$ domain at position 44, and in the $VL_3$ domain at position 100.

One embodiment of the invention relates to a multispecific antibody, wherein the first and second peptide connector are peptides of at least 15 amino acids. One embodiment of the invention relates to a multispecific antibody, wherein the first and second peptide connector are peptides of 15-70 amino acids. One embodiment of the invention relates to a multispecific antibody, wherein the first and second peptide connector are peptides consisting of glycine and serine residues.

One embodiment of the invention relates to a multispecific antibody, wherein the C-terminus of the $VH_3$ domain is directly connected to one of the CH3 domains, and the C-terminus of the $VL_3$ domain is directly connected to the other one of the CH3 domains.

One embodiment of the invention relates to a trivalent multispecific antibody. One embodiment of the invention relates to a trivalent, bispecific multispecific antibody. One embodiment of the invention relates to a trivalent, bispecific multispecific antibody, wherein the first and the second antigen binding moiety specifically bind to a first antigen, and wherein the third binding site specifically binds to a second antigen, which is different from the first antigen.

One embodiment of the invention relates to a trivalent, trispecific multispecific antibody.

Another aspect of the invention is a complex comprising (i) a multispecific antibody according to the invention, wherein the antibody specifically binds at least to a hapten and a target protein, and (ii) the hapten, which is bound by the multispecific antibody, wherein the hapten is conjugated to a therapeutic or diagnostic agent.

Another aspect of the invention is a method for the preparation of the multispecific antibody according to the invention, comprising the steps of
  transforming a host cell with expression vectors comprising nucleic acids encoding the multispecific antibody,
  culturing said host cell under conditions that allow synthesis of said multispecific antibody, and
  recovering said multispecific antibody from said host cell culture.

Another aspect of the invention is a nucleic acid encoding the multispecific antibody according to the invention.

Another aspect of the invention is an expression vector comprising a nucleic acid according to the invention.

Another aspect of the invention is a host cell comprising the expression vector according to the invention.

Another aspect of the invention is a pharmaceutical composition comprising the multispecific antibody according to the invention in combination with at least one pharmaceutically acceptable carrier.

Another aspect of the invention is an immunoconjugate comprising the multispecific antibody according to the invention.

The multispecific antibodies according to the invention one the one hand show new properties due to their binding to different antigens, and on the other hand are suitable for production and pharmaceutical formulation due to their stability, low aggregation and pharmacokinetic and biological properties (e.g. low renal clearance due to having approximately the same molecular weight as a full length IgG; medium serum half-life due to avoided FcRn binding). Mispaired side products are avoided due to use of asymmetric heterodimerization strategies. Due to the distinctive arrangement of the at least three binding sites with respect to each other, the antibodies according to the invention are particularly suitable for binding to multiple antigens present on the surface of a single cell or for binding different epitopes on one antigen. As no CH2 domains are present in the antibodies according to the invention, mediation of effector functions by the antibodies is abolished.

DESCRIPTION OF THE FIGURES

FIG. 1A: Structure of a bispecific antibody according to the invention. The antibody comprising two binding arms forming a first and second binding site. A third antigen binding site formed by $VH_3$ and $VL_3$ domains which is fused to the N-terminus of respective CH3 domains. Peptide connectors link the N-terminus of the $VH_3$ and $VL_3$ domains with the first and second antigen binding moiety, respectively. Heterodimerization of the polypeptide chains including either the $VH_3$ or the $VL_3$ domain is promoted by alteration of the CH3 domains at least one of the approaches of disulfide stabilization and CH3 engineering by the knobs-into-holes technology (referred to in all figures as "KiH engineered") or by introduction of amino acids of opposite charge in corresponding positions of the CH3/CH3 interface (referred to in all figures as "(+/−)engineered"). In addition disulfide stabilization in the $VH_3/VL_3$ interface may be applied (not indicated).

FIG. 1B: Structure of a bispecific antibody according to the invention, wherein the first and second antigen binding moieties are Fv fragments. In this illustration, the Fv fragments bind to the same epitope. However, trispecific antibodies according to the invention may be generated by using two Fv fragments binding to different epitopes.

FIG. 1C: Structure of a bispecific antibody according to the invention, wherein the first and second antigen binding moieties are Fab fragments. In this illustration, the Fab fragments bind to the same epitope. However, trispecific antibodies according to the invention may be generated by using two Fab fragments binding to different epitopes.

FIG. 2A: Structure of a bispecific antibody according to the invention (right side) compared to full length IgG (left side). A third antigen binding site formed by $VH_3$ and $VL_3$ domains, which replace the CH2 domains of a full length IgG molecule. Hinge disulfides were removed to assure antigen access by connecting the Fab fragments with $VH_3$ and $VL_3$ via peptide connectors lacking an interchain disulfide bond. Heterodimerization of the polypeptide chains including either the $VH_3$ or the $VL_3$ domain is promoted by alteration of CH3 domains at least one of the approaches of disulfide stabilization and CH3 engineering by the knobs-into-holes technology or by introduction of amino acids of opposite charge in corresponding positions of the CH3/CH3 interface. In addition disulfide stabilization in the $VH_3/VL_3$ interface may be applied (not indicated).

FIG. 2B: Structure of the bispecific antibodies generated in example 1. $(Gly4Ser)_4$ peptide connectors were used to fuse the first and second Fab fragment with either $VH_3$ or $VL_3$. In addition heterodimerization of the different polypeptide chains was promoted by knobs-into-holes modifications and disulfide stabilization in the CH3-interface as well as disulfide stabilization of the $VH_3/VL_3$ binding site as outlined in detail in example 1.

FIG. 3A: Trispecific antibody, wherein the second Fab fragment includes a domain crossover of the $VH_2$ and $VL_2$ domains, resulting in a $VL_2$-CH1 (heavy chain), $VH_2$—CL (light chain) domain architecture. The first Fab fragment does not include a domain crossover, thus remaining in the wild type domain architecture of $VH_1$—CH1, $VL_1$-CL.

FIG. 3B: Trispecific antibody, wherein the second Fab fragment includes a domain crossover of the VH-CH1 and VL-CL domains, resulting in a $VL_2$-CL (heavy chain), $VH_2$—CH1 (light chain) domain architecture. The first Fab fragment does not include a domain crossover, thus remaining in the wild type domain architecture of $VH_1$—CH1, $VL_1$-CL.

FIG. 3C: Trispecific antibody, wherein the second Fab fragment includes a domain crossover of the CH1 and CL domains, resulting in a $VH_2$—CL (heavy chain), $VL_2$-CH1 (light chain) domain architecture. The first Fab fragment does not include a domain crossover, thus remaining in the wild type domain architecture of $VH_1$—CH1, $VL_1$-CL.

FIG. 3D: Trispecific antibody, wherein the second Fab fragment includes a domain crossover of the CH1 and CL domains, resulting in a $VH_2$—CL (heavy chain), $VL_2$-CH1 (light chain) domain architecture, and the first Fab fragment includes a domain crossover, of the $VH_1$ and $VL_1$ domains, resulting in a $VL_2$-CH1 (heavy chain), $VH_2$-CL (light chain) domain architecture.

FIG. 3E: Trispecific antibody, wherein the second Fab fragment is a single chain Fab fragment.

FIG. 3F: Trispecific antibody, wherein the first and the second Fab fragment are single chain Fv fragments, disulfide-stabilized Fv fragments or disulfide-stabilized single chain Fv fragments.

FIG. 3G: Trispecific antibody, wherein the first and the second Fab fragment are single domain binding sites or scaffold binding sites.

FIG. 3H: Multispecific antibody with five antigen binding sites, wherein the first and the second Fab fragment single domain binding sites or scaffold binding sites, and wherein further single domain binding sites or scaffold binding sites are fused to the N-terminus of the first and second binding site, respectively.

FIGS. 4A and 4B: Design of flexible connection between Fab fragments and third binding site that allows antigen access.

FIG. 4A: Removal of hinge region disulfides by sufficiently long peptide connectors without interchain disulfides allows antigen access for third antigen binding site. To stabilize the generated antibody format, at least one heterodimerization approach in addition to the natural VH$_3$/VL$_3$ interaction is required (indicated: disulfides in bold lines, knobs-into-holes modifications in CH3/CH3 interface).

FIG. 4B: Comparison of wild type IgG1 connection sites between CH1, hinge region and CH2 with the fusion sites of CH1, peptide connector, VH$_3$ domain of the generated antibody according to example 1. SEQ ID NOs are as follows: PKSC (SEQ ID NO: 43), LGGP (SEQ ID NO: 44), DKTHTCPPCPAP (SEQ ID NO: 45), QVQL (SEQ ID NO: 46), and GGGGSGGGGSGGGGSGGGGS (SEQ ID NO: 47).

FIGS. 5A and 5B: Design of stabilized interface between variable domains of the third binding site with their respective CH3 domains.

FIG. 5A: Disulfide stabilization of both, the Fv fragment comprising VH$_3$ and VL$_3$ as well as the CH3/CH3 interface leads to artificially introduced cysteine residues occurring in close proximity (a) to each other, and (b) to natural intrachain disulfide bond forming cysteines in the respective variable or constant domains. Due to close proximity of said cysteine residues potential mispairing in favor of desired disulfide bond formation can occur leading to protein misfolding and reduction of yield (as indicated in the table).

FIG. 5B: Exemplary fusion site of VL$_3$ with CH3 as used in a bispecific antibody according to the invention described in example 1, wherein the third binding site specifically binds to digoxigenin. Additionally introduced cysteine residues are indicated within the amino acid sequence in bold and underlined (SEQ ID NO: 01).

Alternative N-termini of CH3 domains applicable for fusion with a VH$_3$ or VL$_3$ domain are indicated below (SEQ ID NO: 02, SEQ ID NO: 03, SEQ ID NO: 04).

Figure 6A:
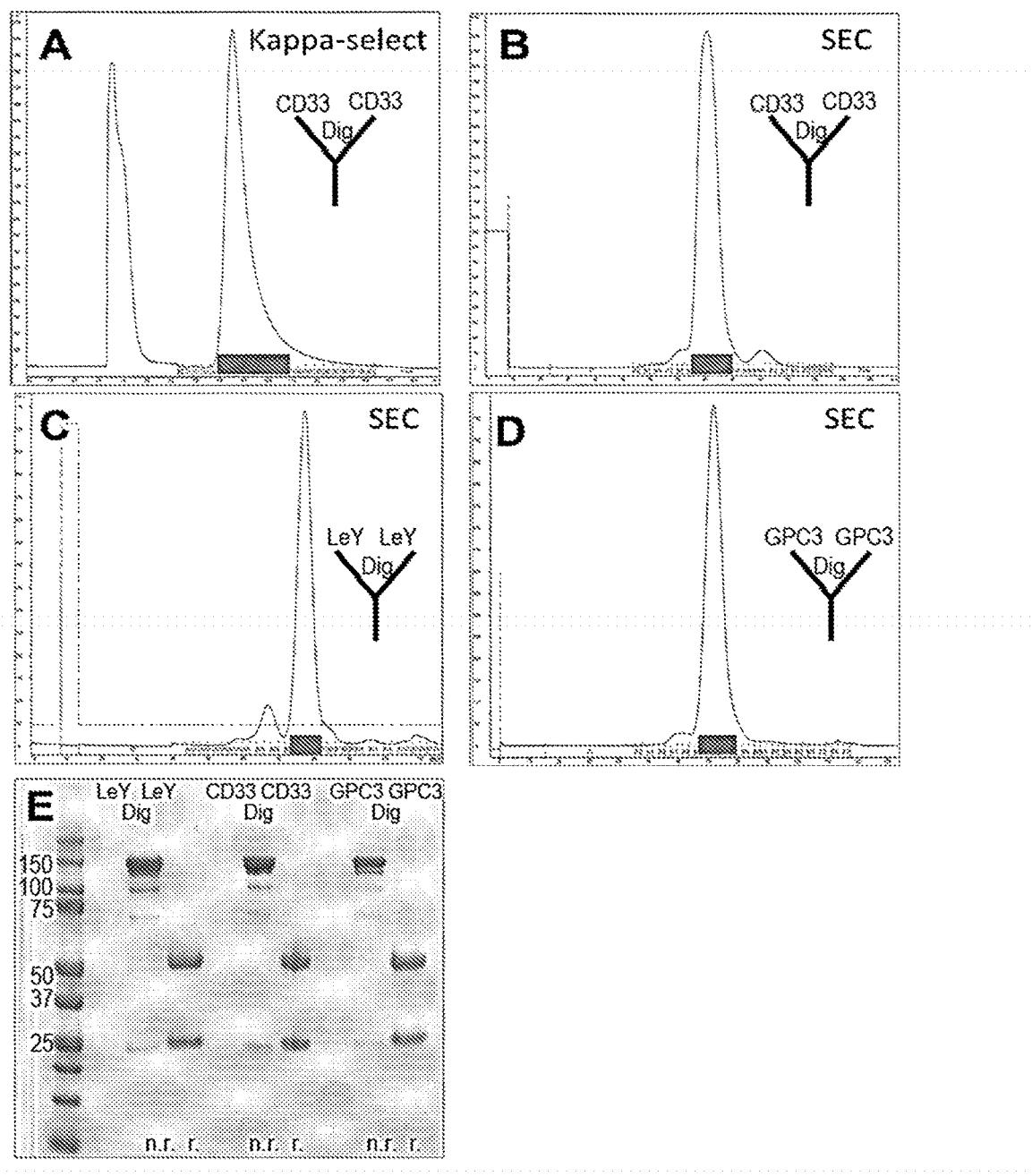
Figure 6B:
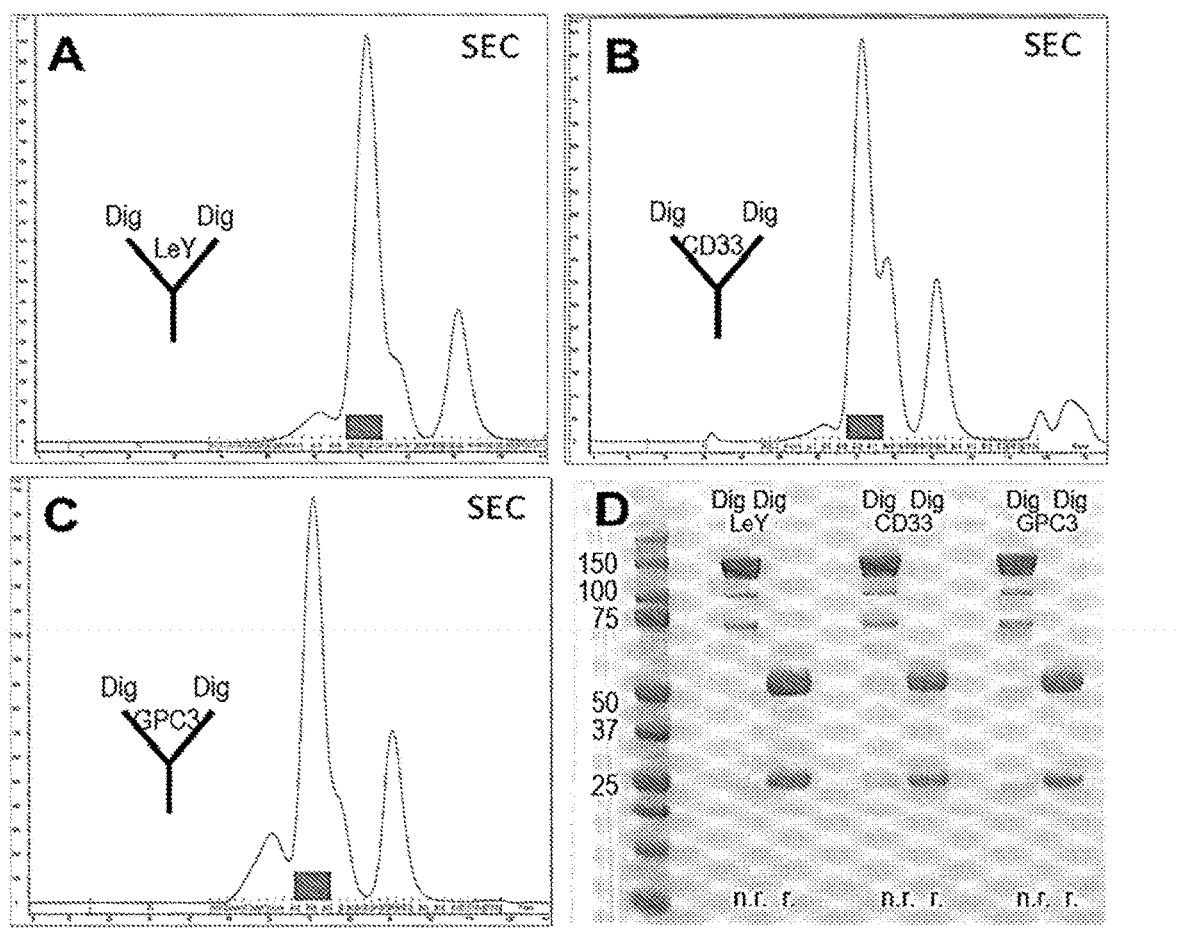

FIGS. 6A and 6B: Results of purification of bispecific antibodies of example 1.

FIG. 6A: (A) Representative chromatogram of the Kappa-select of an antibody, wherein the third binding site specifically binds to digoxigenin (BsAb CD33-Dig(SS)-CD33). (B)-(D) Size exclusion chromatography of the kappa-select binding fractions of BsAb CD33-Dig(SS)-CD33, LeY-Dig(SS)-LeY and GPC3-Dig(SS)-GPC3. Shaded boxes indicate fractions containing properly folded antibody. (E) SDS-PAGE of purified antibodies without (n.r.) and with (r.) sample reduction.

FIG. 6B: (A)-(C) Size exclusion chromatography of the kappa-select binding fractions of BsAb Dig-CD33-Dig, Dig-LeY-Dig and Dig-GPC3-Dig. Shaded boxes indicate fractions containing properly folded antibody. (D) SDS-PAGE of purified antibodies without (n.r.) and with (r.) sample reduction.

Figure 7:
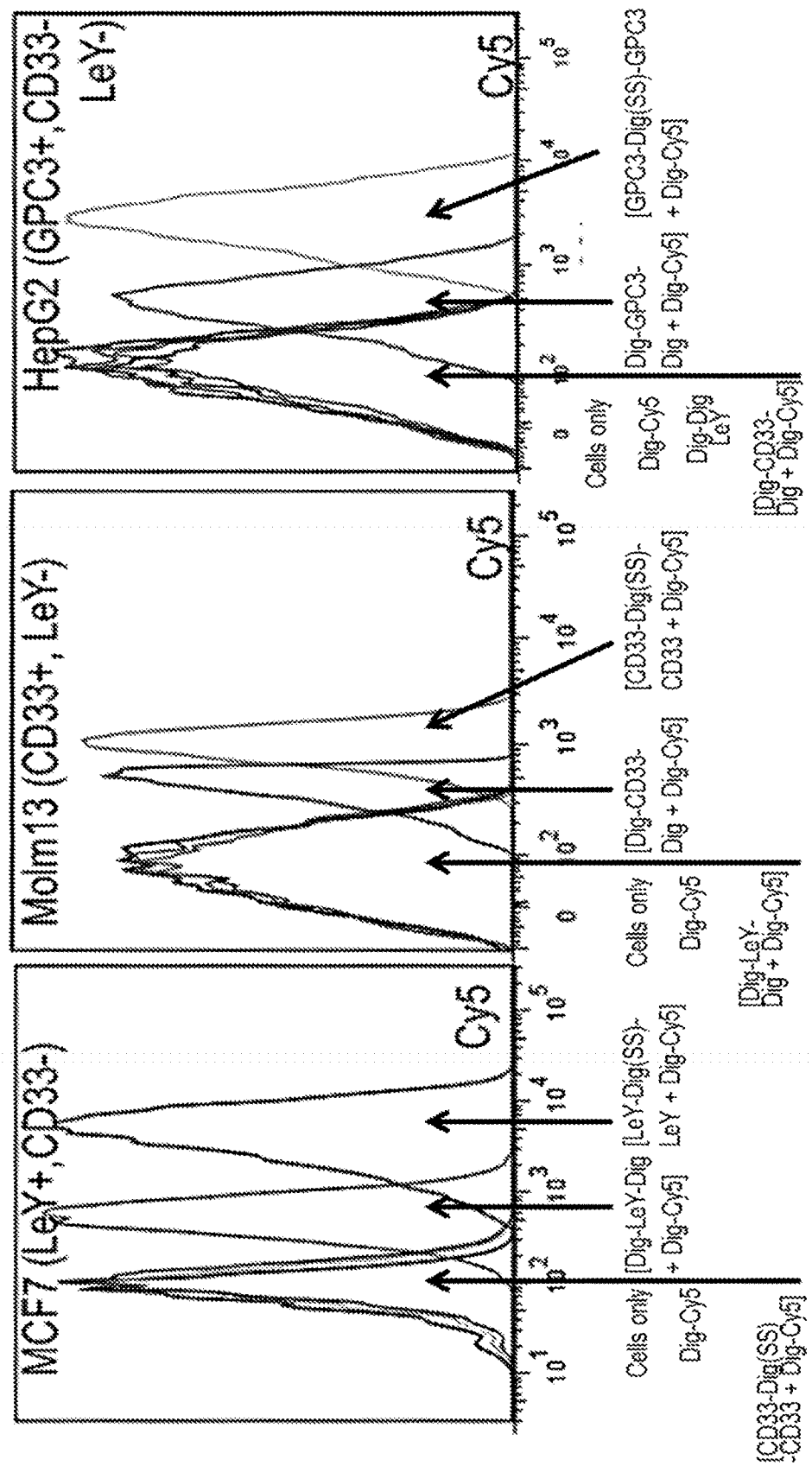

FIG. 7: Results of binding studies of bispecific antibodies of example 1. Simultaneous antigen binding of the antibodies generated in example 1 as analyzed by FACS analysis on LeY-expressing MCF7 cells, CD33-expressing Molm13 cells and GPC3-expressing HepG2 cells using Dig-Cy5 as payload to address hapten binding.

Figure 8:
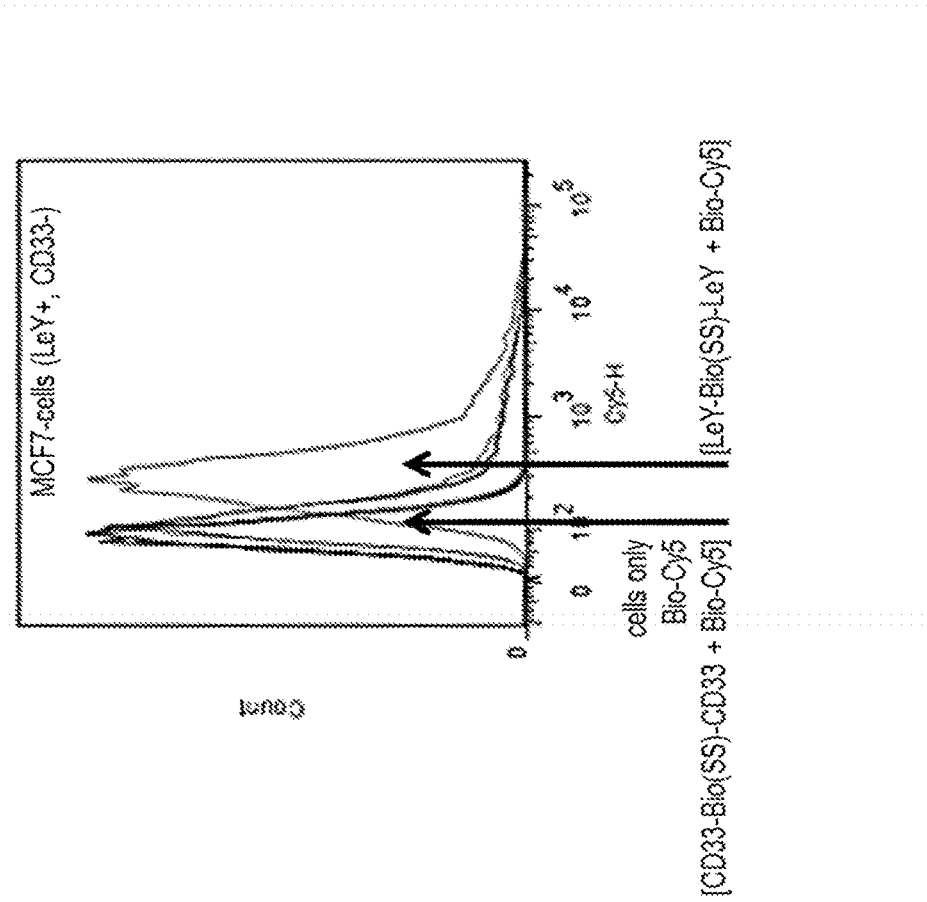

FIG. 8: Results of binding studies of bispecific antibodies of example 6. Simultaneous antigen binding of the BsAb BsAb LeY-Bio(SS)-LeY generated in example 6 as analyzed by FACS analysis on LeY-expressing and CD33 negative MCF7 cells using biotinylated Cy5 as payload to address hapten binding.

Figure 9:
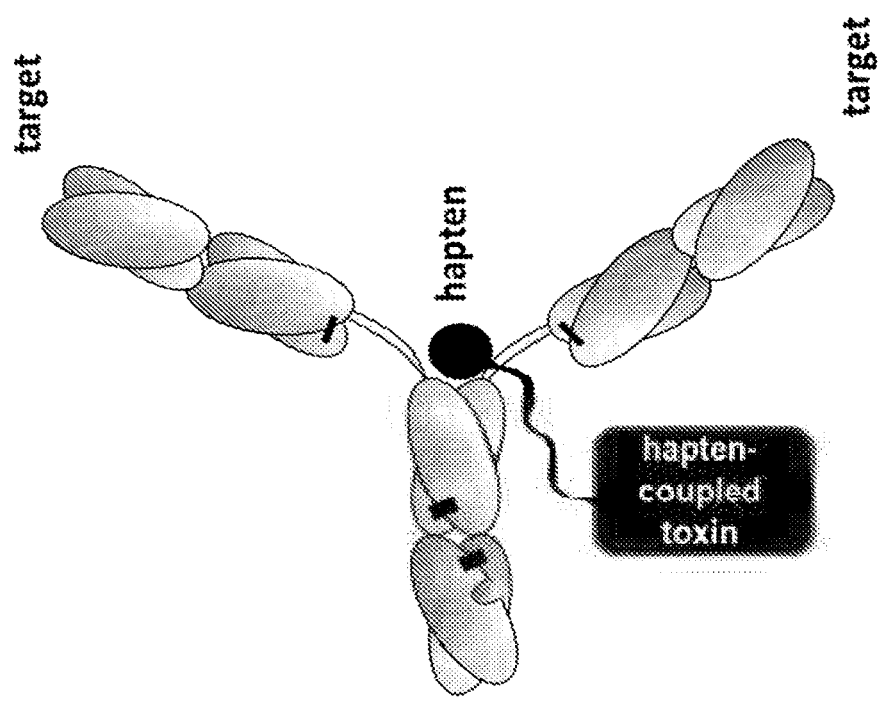

FIG. 9: Schematic illustration of bispecific antibody according to the invention complexed with a toxin as payload. Indicated is a complex formed between a bispecific antibody according to the invention (complexes of antibodies with multiple specificities may be formed accordingly) with a payload. The third binding site of a bispecific antibody according to the invention specifically binds to a hapten (e.g. digoxigenin, biotin) while the first and second binding site bind to target molecules (e.g. tumor associated antigens, like LeY, CD33, GPC3). The complex is formed by contacting a hapten-coupled payload (e.g. a toxin, like Pseudomonas Exotoxin, PE) with the bispecific antibody according to the invention. The complex may be used for targeted payload delivery to target-molecule expressing cells.

Figure 10:
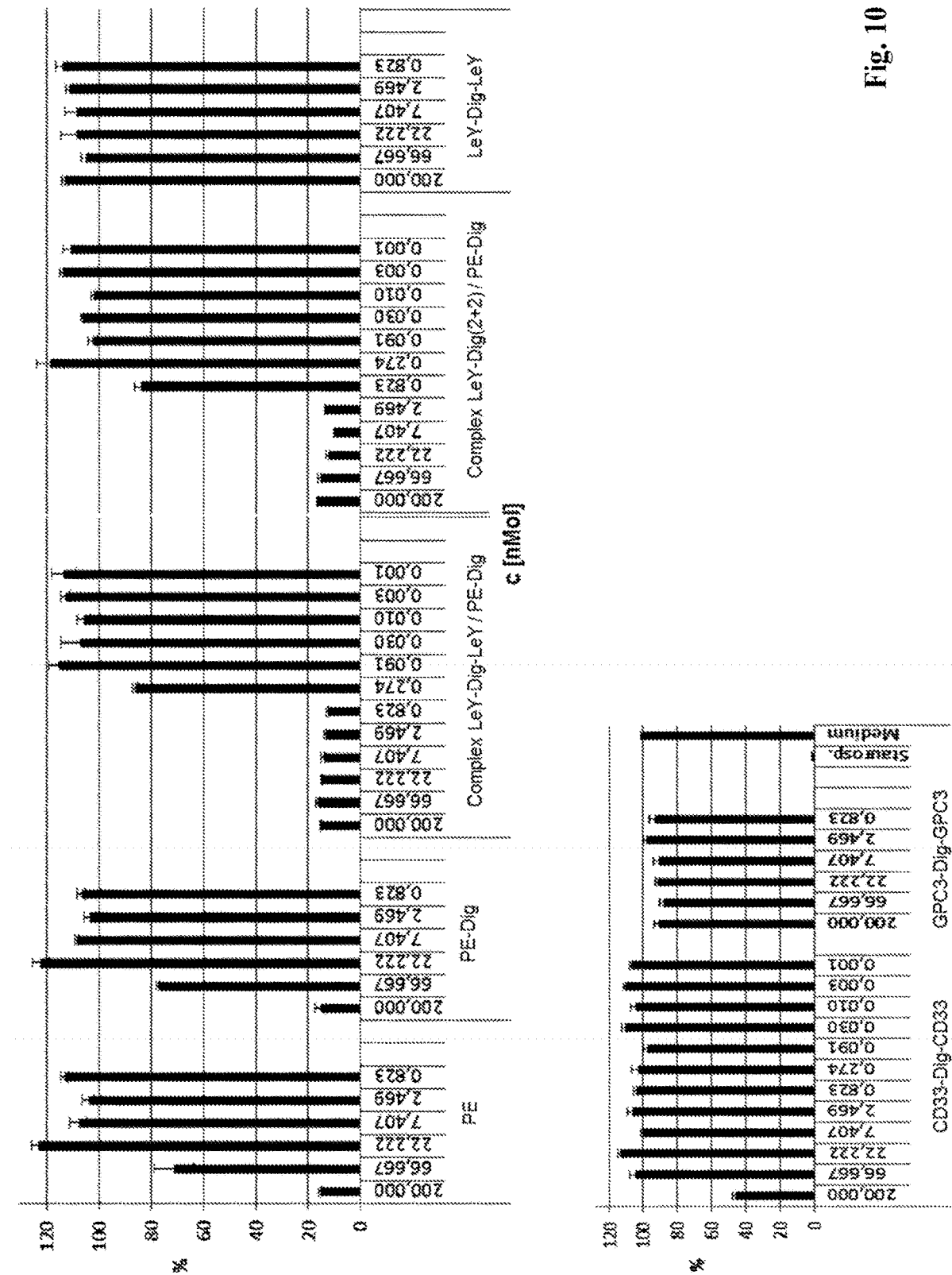

FIG. 10: Inhibition of MCF7 cell proliferation by a complex of BsAb LeY-Dig(SS)-LeY with digoxigenylated PE. Indicated are the results of a BrdU incorporation assay as described in detail in example 5. Y-axis indicates incorporation of BrdU into proliferating cells.

Figure 11:
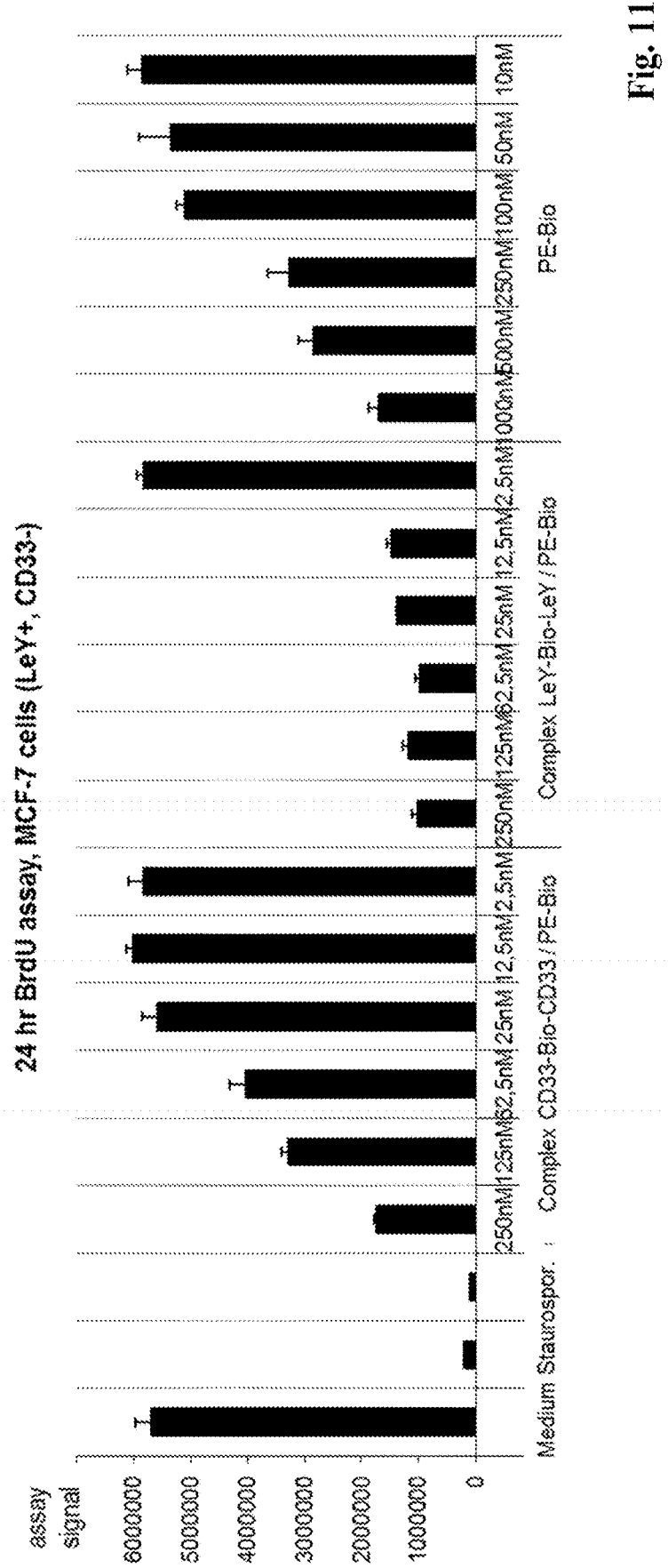

FIG. 11: Inhibition of MCF7 cell proliferation by a complex of BsAb LeY-Bio(SS)-LeY with biotinylated PE. Indicated are the results of a BrdU incorporation assay as described in detail in example 6. Y-axis indicates incorporation of BrdU into proliferating cells.

DETAILED DESCRIPTION OF THE INVENTION

1. Definitions

The terms "a", "an" and "the" generally include plural referents, unless the context clearly indicates otherwise.

The term "antigen binding moiety" as used herein refers to a moiety that specifically binds to a target antigen. The term includes antibodies as well as other natural (e.g. receptors, ligands) or synthetic (e.g. DARPins) molecules capable of specifically binding to a target antigen. In one preferred embodiment the antigen binding moiety of an antibody according to the invention is an antibody fragment.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv, scFab); and multispecific antibodies formed from antibody fragments.

As used herein, a "Fab fragment" refers to an antibody fragment comprising a light chain fragment comprising a VL domain and a constant domain of a light chain (CL), and a VH domain and a first constant domain (CH1) of a heavy chain. As such, in case the first and second binding moieties are a first and second Fab fragment, respectively, the first Fab fragment and the second Fab fragment of such an antibody according to the invention refer to two distinct Fab moieties, each one comprising a VL and CL domain as well as a VH and CH1 domain.

An "Fv fragment" is an antibody fragment which contains a complete antigen-binding site. This fragment consists of a dimer of one heavy- and one light-chain variable region domain, optionally in non-covalent association.

The terms "full length antibody", "intact antibody", and "whole antibody" are used herein interchangeably to refer to an antibody having a structure substantially similar to a native antibody structure or having heavy chains that contain an Fc region as defined herein.

The terms "monoclonal antibody" or "monoclonal antibody composition" as used herein refer to a preparation of antibody molecules of a single amino acid composition.

A "recombinant antibody" is an antibody which has been produced by a recombinantly engineered host cell. It is optionally isolated or purified.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially the entire FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

"Specificity" refers to selective recognition of a particular epitope of an antigen by the antigen binding moiety, e.g. an antibody. Natural antibodies, for example, are monospecific. The term "monospecific antibody" as used herein denotes an antibody that has one or more binding sites each of which bind to the same epitope of the same antigen. "Multispecific antibodies" bind two or more different epitopes (for example, two, three, four, or more different epitopes). The epitopes may be on the same or different antigens. An example of a multispecific antibody is a "bispecific antibody" which binds two different epitopes. When an antibody possesses more than one specificity, the recognized epitopes may be associated with a single antigen or with more than one antigen.

An epitope is a region of an antigen that is bound by an antibody or antigen binding moiety. The term "epitope" includes any polypeptide determinant capable of specific binding to an antibody or antigen binding moiety. In certain embodiments, epitope determinants include chemically active surface groupings of molecules such as amino acids, glycan side chains, phosphoryl, or sulfonyl, and, in certain embodiments, may have specific three dimensional structural characteristics, and/or specific charge characteristics.

As used herein, the terms "binding" and "specific binding" refer to the binding of the antibody or antigen binding moiety to an epitope of the antigen in an in vitro assay, preferably in a plasmon resonance assay (BIAcore®, GE-Healthcare Uppsala, Sweden) with purified wild-type antigen. In certain embodiments, an antibody or antigen binding moiety is said to specifically bind an antigen when it preferentially recognizes its target antigen in a complex mixture of proteins and/or macromolecules.

The affinity of the binding of an antibody to an antigen is defined by the terms $k_a$ (rate constant for the association of the antibody from the antibody/antigen complex), $k_D$ (dissociation constant), and $K_D$ ($k_D/k_a$). In one embodiment binding or that/which specifically binds to means a binding affinity ($K_D$) of $10^{-8}$ mol/l or less, in one embodiment $10^{-8}$ M to $10^{-13}$ mol/l. Thus, an multispecific antibody according to the invention specifically binds to each antigen for which it is specific with a binding affinity ($K_D$) of $10^{-8}$ mol/l or less, e.g. with a binding affinity ($K_D$) of $10^{-8}$ to $10^{-13}$ mol/l. in one embodiment with a binding affinity ($K_D$) of $10^{-9}$ to $10^{-13}$ mol/l.

The terms "binding site" or "antigen-binding site" as used herein denotes the region(s) of an antigen binding molecule (e.g. an antibody) to which a ligand (e.g. the antigen or antigen fragment of it) actually binds and which is, preferentially, derived from an antibody. In case of antibodies, the antigen-binding site includes antibody heavy chain variable domains (VH) and/or antibody light chain variable domains (VL), or pairs of VH/VL. The third antigen binding site in the antibody according the invention is formed by a pair of VH/VL.

Antigen-binding sites derived from antibodies that specifically bind to the desired antigen can be derived a) from known antibodies specifically binding to the antigen or b) from new antibodies or antibody fragments obtained by de novo immunization methods using inter alia either the antigen protein or nucleic acid or fragments thereof or by phage display.

When being derived from an antibody, an antigen-binding site of an antibody according to the invention can contain six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences. Also included within the scope of the invention are functional antigen binding sites comprised of fewer CDRs (i.e., where binding specificity is determined by three, four or five CDRs). For example, less than a complete set of 6 CDRs may be sufficient for binding.

The term "valent" as used herein denotes the presence of a specified number of binding sites in an antibody molecule. A natural antibody for example has two binding sites and is bivalent. As such, the term "trivalent" denotes the presence of three binding sites in an antibody molecule.

The "variable domains" or "variable region" as used herein denotes each of the pair of light and heavy chains which is involved directly in binding the antibody to the antigen.

The variable domain of a light chain is abbreviated as "VL" and the variable domain of a heavy chain is abbreviated as "VH". In accordance with the aforementioned, is referred herein to the variable domains of the third binding site by using "$VH_3$" and "$VL_3$", with the number three indicating the third binding site.

The variable domains of human light chains and heavy chains have the same general structure. Each variable domain comprises four framework (FR) regions, the sequences of which are widely conserved. The FR are connected by three "hypervariable regions" (or "complementarity determining regions", CDRs). CDRs on each chain are separated by such framework amino acids. Therefore, the light and heavy chains of an antibody comprise from N- to C-terminal direction the domains FR1, CDR1, FR2, CDR2, FR3, CDR3, and FR4. The FR adopt a beta-sheet conformation and the CDRs may form loops connecting the beta-sheet structure. The CDRs in each chain are held in their three-dimensional structure by the FR and form together with the CDRs from the other chain an "antigen binding site". Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, MD (1991).

In natural antibodies the VL and VH domains are arranged terminally at the light chains and heavy chains, respectively, which allows access of the antigen, thus assuring antigen binding. Within an antibody according to the invention the $VL_3$ and $VH_3$ domains of the third binding site may be arranged in between two constant domains when the antigen binding moieties are Fab fragments. Although being embedded by constant domains, specific binding of the third binding site was surprisingly observed.

The term "constant domains" or "constant region" as used within the current application denotes the sum of the domains of an antibody other than the variable region. The constant region is not directly involved in binding of an antigen, but exhibits various effector functions.

Depending on the amino acid sequence of the constant region of their heavy chains, antibodies are divided in the "classes": IgA, IgD, IgE, IgG and IgM, and several of these may are further divided into subclasses, such as IgG1, IgG2, IgG3, and IgG4, IgA1 and IgA2. The heavy chain constant regions that correspond to the different classes of antibodies are called α, δ, ε, γ and μ, respectively. The light chain constant regions (CL) which can be found in all five antibody classes are called κ (kappa) and λ (lambda).

The "constant domains" as used herein are from human origin, which is from a constant heavy chain region of a human antibody of the subclass IgG1, IgG2, IgG3, or IgG4 and/or a constant light chain region kappa or lambda region. Such constant domains and regions are well known in the state of the art and e.g. described by Kabat, et al., Sequences of Proteins of Immunological Interest, 5th ed., Public Health Service, National Institutes of Health, Bethesda, MD (1991).

The "Hinge region" is generally defined as stretching from about Glu216, or about Cys226, to about Pro230 of human IgG1 (Burton, Molec. Immunol. 22:161-206 (1985)). The antibody according to the invention is devoid of hinge region disulfides.

The "light chains" of antibodies from any vertebrate species can be assigned to one of two distinct types, called kappa (κ) and lambda (λ), based on the amino acid sequences of their constant domains. A wild type light chain typically contains two immunoglobulin domains, usually one variable domain (VL) that is important for binding to an antigen and a constant domain (CL).

Several different types of "heavy chains" exist that define the class or isotype of an antibody. A wild type heavy chain contains a series of immunoglobulin domains, usually with one variable domain (VH) that is important for binding antigen and several constant domains (CH1, CH2, CH3, etc.).

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. Due to the structure of the antibody according to the invention, in particular attributed to the lack of CH2 domains, Fc mediated effector functions by an antibody according to the invention are abolished.

"Antibody-dependent cell-mediated cytotoxicity" or "ADCC" refers to a form of cytotoxicity in which secreted immunoglobulins (Ig) bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express Fc-gammaRIII only, whereas monocytes express Fc-gammaRI, Fc-gammaRII, and Fc-gammaRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821, 337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. J. Immunol. 164: 4178-4184 (2000).

The "CH2 domain" of a human IgG Fc region usually extends from an amino acid residue at about position 231 to an amino acid residue at about position 340. The multispecific antibody is devoid of a CH2 domain. By "devoid of a CH2 domain" is meant that the antibodies according to the invention do not comprise a CH2 domain.

The "CH3 domain" comprises the stretch of residues C-terminal to a CH2 domain in an Fc region (i.e. from an amino acid residue at about position 341 to an amino acid residue at about position 447 of an IgG). Within an antibody according to the invention, one respective CH3 domain is arranged at the C-terminus of the $VH_3$ and $VL_3$ domain of the third binding site. The "CH3 domains" herein are variant CH3 domains, wherein the amino acid sequence of the natural CH3 domain was subjected to at least one distinct amino acid substitution (i.e. modification of the amino acid sequence of the CH3 domain) in order to promote dimerization of the two CH3 domains facing each other within the multispecific antibody.

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference.

Typically, in the heterodimerization approaches known in the art, the CH3 domain of one heavy chain and the CH3 domain of the other heavy chain are both engineered in a complementary manner so that the heavy chain comprising one engineered CH3 domain can no longer homodimerize with another heavy chain of the same structure. Thereby the heavy chain comprising one engineered CH3 domain is forced to heterodimerize with the other heavy chain comprising the CH3 domain, which is engineered in a complementary manner.

One heterodimerization approach known in the art is the so-called "knobs-into-holes" technology, which is described in detail providing several examples in e.g. WO 96/027011, Ridgway, J. B., et al., Protein Eng. 9 (1996) 617-621; Merchant, A. M., et al., Nat. Biotechnol. 16 (1998) 677-681; and WO 98/050431, which are herein included by reference. In the "knobs-into-holes" technology, within the interface formed between two CH3 domains in the tertiary structure of the antibody, particular amino acids on each CH3 domain are engineered to produce a protuberance ("knob") in one of the CH3 domains and a cavity ("hole") in the other one of the CH3 domains, respectively. In the tertiary structure of the multispecific antibody the introduced protuberance in the one CH3 domain is positionable in the introduced cavity in the other CH3 domain.

Further techniques for modifying the CH3 domains of the heavy chains of a multispecific antibody (apart from the "knobs-into-holes" technology) to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody according to the invention. The multispecific antibody including one of these modification in order to support heterodimerization is further referred to herein as "CH3-engineered" multispecific antibody.

According to the approach described in EP 1870459 heterodimerization of CH3 domains is based on the introduction of charged amino acids with opposite charges at specific amino acid positions in the CH3/CH3-domain-interface between both, the first and the second heavy chain (herein further referred to as a "CH3(+/−)-engineered multispecific antibody").

In one embodiment of a multispecific antibody according to the invention the approach described in WO2013/157953 is used to support heterodimerization of the first heavy chain and the second heavy chain of the multispecific antibody. In one embodiment of said CH3-engineered multispecific antibody according to the invention, in the CH3 domain of one heavy chain the amino acid T at position 366 (numbering according to EU index of Kabat) is substituted by K; and in the CH3 domain of the other heavy chain the amino acid L at position 351 (numbering according to EU index of Kabat) is substituted by D. In another embodiment of said CH3-engineered multispecific antibody according to the invention, in the CH3 domain of one heavy chain the amino acid T at position 366 (numbering according to EU index of Kabat) is substituted by K and the amino acid L at position 351 (numbering according to EU index of Kabat) is substituted by K; and in the CH3 domain of the other heavy chain the amino acid L at position 351 (numbering according to EU index of Kabat) is substituted by D.

In another embodiment of said CH3-engineered multispecific antibody according to the invention, in the CH3 domain of one heavy chain the amino acid T at position 366 (numbering according to EU index of Kabat) is substituted by K and the amino acid L at position 351 (numbering according to EU index of Kabat) is substituted by K; and in the CH3 domain of the other heavy chain the amino acid L at position 351 (numbering according to EU index of Kabat) is substituted by D. Additionally at least one of the following substitutions is comprised in the CH3 domain of the other heavy chain: the amino acid Y at position 349 (numbering according to EU index of Kabat) is substituted by E, the amino acid Y at position 349 (numbering according to EU index of Kabat) is substituted by D and the amino acid L at position 368 (numbering according to EU index of Kabat) is substituted by E. In one embodiment the amino acid L at position 368 (numbering according to EU index of Kabat) is substituted by E.

In one embodiment of a multispecific antibody according to the invention the approach described in WO2012/058768 is used to support heterodimerization of the first heavy chain and the second heavy chain of the multispecific antibody. In one embodiment of said CH3-engineered multispecific antibody according to the invention, in the CH3 domain of one heavy chain the amino acid L at position 351 (numbering according to EU index of Kabat) is substituted by Y and the amino acid Y at position 407 (numbering according to EU index of Kabat) is substituted by A; and in the CH3 domain of the other heavy chain the amino acid T at position 366 (numbering according to EU index of Kabat) is substituted by A and the amino acid K at position 409 (numbering according to EU index of Kabat) is substituted by F. In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted. Preferred substitutions are:

substituting the amino acid T at position 411 (numbering according to EU index of Kabat) by an amino acid selected from N, R, Q, K, D, E and W;
substituting the amino acid D at position 399 (numbering according to EU index of Kabat) by an amino acid selected from R, W, Y, and K;
substituting the amino acid S at position 400 (numbering according to EU index of Kabat) by an amino acid selected from E, D, R and K;
substituting the amino acid F at position 405 (numbering according to EU index of Kabat) by an amino acid selected from I, M, T, S, V and W;
substituting the amino acid N at position 390 (numbering according to EU index of Kabat) by an amino acid selected from R, K and D; and
substituting the amino acid K at position 392 (numbering according to EU index of Kabat) by an amino acid selected from V, M, R, L, F and E.

In another embodiment of said CH3-engineered multispecific antibody according to the invention (engineered according to WO2012/058768), in the CH3 domain of one heavy chain the amino acid L at position 351 (numbering according to EU index of Kabat) is substituted by Y and the amino acid Y at position 407 (numbering according to EU index of Kabat) is substituted by A; and in the CH3 domain of the other heavy chain the amino acid T at position 366 (numbering according to EU index of Kabat) is substituted by V and the amino acid K at position 409 (numbering according to EU index of Kabat) is substituted by F. In another embodiment of said CH3-engineered multispecific antibody according to the invention, in the CH3 domain of one heavy chain the amino acid Y at position 407 (numbering according to EU index of Kabat) is substituted by A; and in the CH3 domain of the other heavy chain the amino acid T at position 366 (numbering according to EU index of Kabat) is substituted by A and the amino acid K at position 409 (numbering according to EU index of Kabat) is substituted by F. In said last aforementioned embodiment, in the CH3 domain of said other heavy chain the amino acid K at position 392 (numbering according to EU index of Kabat) is substituted by E, the amino acid T at position 411 (numbering according to EU index of Kabat) is substituted by E, the amino acid D at position 399 (numbering according to EU index of Kabat) is substituted by R and the amino acid S at position 400 (numbering according to EU index of Kabat) is substituted by R.

In one embodiment of a multispecific antibody according to the invention the approach described in WO 2011/143545 is used to support heterodimerization of the first heavy chain and the second heavy chain of the multispecific antibody. In one embodiment of said CH3-engineered multispecific antibody according to the invention, amino acid modifications in the CH3 domains of both heavy chains are introduced at positions 368 and/or 409.

In one embodiment of a multispecific antibody according to the invention the approach described in WO 2011/090762 is used to support heterodimerization of the first heavy chain and the second heavy chain of the multispecific antibody. WO 2011/090762 relates to amino acid modifications according to the "knob-into-hole" technology. In one embodiment of said CH3(KiH)-engineered multispecific antibody according to the invention, in the CH3 domain of one heavy chain the amino acid T at position 366 (numbering according to EU index of Kabat) is substituted by W; and in the CH3 domain of the other heavy chain the amino acid Y at position 407 (numbering according to EU index of Kabat) is substituted by A. In another embodiment of said CH3(KiH)-engineered multispecific antibody according to the invention, in the CH3 domain of one heavy chain the amino acid T at position 366 (numbering according to EU index of Kabat) is substituted by Y; and in the CH3 domain of the other heavy chain the amino acid Y at position 407 (numbering according to EU index of Kabat) is substituted by T.

In one embodiment of a multispecific antibody according to the invention, which is of IgG2 isotype, the approach described in WO 2011/090762 is used to support heterodimerization of the first heavy chain and the second heavy chain of the multispecific antibody.

In one embodiment of a multispecific antibody according to the invention, the approach described in WO 2009/089004 is used to support heterodimerization of the first heavy chain and the second heavy chain of the multispecific antibody. In one embodiment of said CH3-engineered multispecific antibody according to the invention, in the CH3 domain of one heavy chain the amino acid K or N at position 392 (numbering according to EU index of Kabat) is substituted by a negatively charged amino acid (in one preferred embodiment by E or D, in one preferred embodiment by D); and in the CH3 domain of the other heavy chain the amino acid D at position 399 the amino acid E or D at position 356 or the amino acid E at position 357 (numberings according to EU index of Kabat) is substituted by a positively charged amino acid (in one preferred embodiment K or R, in one preferred embodiment by K, in one preferred embodiment the amino acids at positions 399 or 356 are substituted by K). In one further embodiment, in addition to the aforementioned substitutions, in the CH3 domain of the one heavy chain the amino acid K or R at position 409 (numbering according to EU index of Kabat) is substituted by a negatively charged amino acid (in one preferred embodiment by E or D, in one preferred embodiment by D). In one even further embodiment, in addition to or alternatively to the aforementioned substitutions, in the CH3 domain of the one heavy chain the amino acid K at position 439 and/or the amino acid K at position 370 (numbering according to EU index of Kabat) is substituted independently from each other by a negatively charged amino acid (in one preferred embodiment by E or D, in one preferred embodiment by D).

In one embodiment of a multispecific antibody according to the invention, the approach described in WO 2007/147901 is used to support heterodimerization of the first heavy chain and the second heavy chain of the multispecific antibody. In one embodiment of said CH3-engineered multispecific antibody according to the invention, in the CH3 domain of one heavy chain the amino acid K at position 253 (numbering according to EU index of Kabat) is substituted by E, the amino acid D at position 282 (numbering according to EU index of Kabat) is substituted by K and the amino acid K at position 322 (numbering according to EU index of Kabat) is substituted by D; and in the CH3 domain of the other heavy chain the amino acid D at position 239 (numbering according to EU index of Kabat) is substituted by K, the amino acid E at position 240 (numbering according to EU index of Kabat) is substituted by K and the amino acid K at position 292 (numbering according to EU index of Kabat) is substituted by D.

In one embodiment of a multispecific antibody according to the invention, the approach described in WO 2007/

110205 is used to support heterodimerization of the first heavy chain and the second heavy chain of the multispecific antibody.

In addition or alternatively to engineering the CH3 domains by above identified heterodimerization strategies, the introduction of an additional interchain disulfide bridge stabilizes the heterodimers (Atwell, S., et al., J. Mol. Biol. 270 (1997) 26-35; Merchant, A. M., et al., Nature Biotech. 16 (1998) 677-681). This is also referred to herein as "disulfide stabilization of the CH3 domains".

"Fused" and "connected" with respect to polypeptides refers to components that are linked by peptide bonds, either directly or via one or more peptide linkers ("peptide connector"). The term "peptide linker" or "peptide connector" as used herein interchangeably denotes a peptide of an amino acid sequence, which is preferably of synthetic origin. Typically the peptide connectors are composed of flexible residues like glycine and serine so that the adjacent protein domains are free to move relative to one another. Thus, typical peptide connectors used in accordance with the invention are glycine-serine linkers, i.e. peptide connectors consisting of a pattern of glycine and serine residues.

A first and a second peptide connector is used to fuse the first antigen binding moiety with the $VH_3$ domain and the second antigen binding moiety with the $VL_3$ domain. However the connection between the $VH_3$ domain and the $VL_3$ domain with their respective CH3 domain is realized directly, i.e. by direct connection of said domains, without including peptide linkers. Hence, the term "directly connected" as used herein with respect to the fusion/connection of polypeptides means that the connection site does not include a peptide linker, i.e. the amino acid sequence of the fusion polypeptide solely includes the amino acid sequences of the polypeptides that were fused to each other and is devoid of further amino acid residues of a peptide linker. This is conducted to achieve that the three-dimensional structure of
  (a) the fusion site of $VH_3$ and CH3 closely mimics both, the natural connection site of VH and CH1 as well as the natural connection site of CH2 and CH3 of the original "parent" antibody, of which the third binding site is derived; and
  (b) the fusion site of $VL_3$ and CH3 closely mimics both, the natural connection site of VH and CH1 as well as the natural connection site of CH2 and CH3 of the original "parent" antibody, of which the third binding site is derived.

The term antibodies with a "domain crossover" as referred to herein means antibodies, wherein in the antibody binding arm (e.g. within the Fab region) deviating from the natural domain architecture of antibodies at least one heavy chain domain was substituted by its corresponding light chain domain and vice versa. There are three general types of domain crossovers, (i) the crossover of the CH1 and the CL domain, which leads to crossover light chains of a VL-CH1 structure and crossover heavy chains including a VH-CL structure, (ii) the crossover of the VH and the VL domain, which leads to crossover light chains of a VH-CL structure and crossover heavy chains including a VL-CH1 structure, and (iii) the crossover of <VL-CL> and <VH-CH1> ("Fab crossover"), which leads to crossover light chains of a VH-CH1 structure and crossover heavy chains including a VL-CL structure (domain structures are indicated in N-terminal to C-terminal direction). Within the terms of the present invention "replaced by each other" with respect to corresponding heavy and light chains refers to the aforementioned domain crossover strategies. As such, when CH1 and CL domains are "replaced by each other" it is referred to the domain crossover mentioned under item (i) and the resulting heavy and light chain domain architecture. Accordingly, when VH1 and VL are "replaced by each other" it is referred to the domain crossover mentioned under item (ii); and when the CH1 and CL domains are "replaced by each other" and the VH1 and VL domains are "replaced by each other" it is referred to the domain crossover mentioned under item (iii). Bispecific antibodies including domain crossovers are disclosed, e.g. in WO 2009/080251, WO 2009/080252, WO 2009/080253, WO 2009/080254 and Schaefer, W. et al, PNAS, 108 (2011) 11187-1191. When antibodies according to the invention include a domain crossover, the domain crossover is "asymmetric", which indicates that either (a) only one of the first and the second Fab fragment includes a domain crossover, or (b) the first and the second Fab fragment include different domain crossovers indicated under items (i) to (iii) above, but not both of the first and the second Fab fragment include the same domain crossover.

The term "tertiary structure" of an antibody as used herein refers to the geometric shape of the antibody according to the invention. The tertiary structure comprises a polypeptide chain backbone comprising the antibody domains, while amino acid side chains interact and bond in a number of ways.

The term "amino acid" as used herein denotes an organic molecule possessing an amino moiety located at α-position to a carboxylic group. Examples of amino acids include: arginine, glycine, ornithine, lysine, histidine, glutamic acid, asparagic acid, isoleucine, leucine, alanine, phenylalanine, tyrosine, tryptophane, methionine, serine, proline. The amino acid employed is optionally in each case the L-form. The term "positively charged" or "negatively charged" amino acid refers to the amino acid side-chain charge at pH 7.4. Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

TABLE

Amino acids with specific properties

| Amino Acid | 3-Letter | 1-Letter | Side-chain polarity | Side-chain charge (pH 7.4) |
|---|---|---|---|---|
| Alanine | Ala | A | nonpolar | neutral |
| Arginine | Arg | R | basic polar | positive |
| Asparagine | Asn | N | polar | neutral |
| Aspartic acid | Asp | D | acidic polar | negative |
| Cysteine | Cys | C | nonpolar | neutral |
| Glutamic acid | Glu | E | acidic polar | negative |
| Glutamine | Gln | Q | polar | neutral |
| Glycine | Gly | G | nonpolar | neutral |
| Histidine | His | H | basic polar | positive (10%) neutral (90%) |
| Isoleucine | Ile | I | nonpolar | neutral |
| Leucine | Leu | L | nonpolar | neutral |
| Lysine | Lys | K | basic polar | positive |
| Methionine | Met | M | nonpolar | neutral |
| Phenylalanine | Phe | F | nonpolar | neutral |
| Proline | Pro | P | nonpolar | neutral |
| Serine | Ser | S | polar | neutral |
| Threonine | Thr | T | polar | neutral |
| Tryptophan | Trp | W | nonpolar | neutral |

TABLE-continued

Amino acids with specific properties

| Amino Acid | 3-Letter | 1-Letter | Side-chain polarity | Side-chain charge (pH 7.4) |
|---|---|---|---|---|
| Tyrosine | Tyr | Y | polar | neutral |
| Valine | Val | V | nonpolar | neutral |

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991). In particular, for variable domains and for the light chain constant domain CL of kappa and lambda isotype, the Kabat numbering system (see pages 647-660) of Kabat, et al., Sequences of Proteins of Immunological Interest, 5th ed., Public Health Service, National Institutes of Health, Bethesda, MD (1991) is used and is herein referred to as "numbering according to Kabat"; for the constant heavy chain domains (CH1, Hinge, CH2 and CH3) the Kabat EU index numbering system (see pages 661-723) is used and is herein referred to as "numbering according to EU index of Kabat".

Amino acid substitutions (or mutations) within the polypeptide chains of the multispecific antibody are prepared by introducing appropriate nucleotide changes into the antibody DNA, or by nucleotide synthesis. Such modifications can be performed, however, only in a very limited range. For example, the modifications do not alter the above mentioned antibody characteristics such as the IgG isotype and antigen binding, but may further improve the yield of the recombinant production, protein stability or facilitate the purification. In certain embodiments, antibody variants having one or more conservative amino acid substitutions are provided.

Antibodies according to the invention are produced by recombinant means. Methods for recombinant production of antibodies are widely known in the state of the art and comprise protein expression in prokaryotic and eukaryotic host cells with subsequent isolation of the antibody and usually purification to a pharmaceutically acceptable purity. For the expression of the antibodies as aforementioned in a host cell, nucleic acids encoding the respective antibody light and heavy chains are inserted into expression vectors by standard methods. Expression is performed in appropriate prokaryotic or eukaryotic host cells, like CHO cells, NS0 cells, SP2/0 cells, HEK293 cells, COS cells, PER.C6 cells, yeast, or E. coli cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

Antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a cleaved variant heavy chain). This may be the case where the final two C-terminal amino acids of the heavy chain are glycine (G446) and lysine (K447, numbering according to Kabat EU index).

Compositions of the invention, such as the pharmaceutical or diagnostic compositions described herein, comprise a population of antibodies of the invention. The population of antibodies may comprise antibodies having a full-length heavy chain and antibodies having a cleaved variant heavy chain.

The term "purified" as used herein refers to polypeptides, that are removed from their natural environment or from a source of recombinant production, or otherwise isolated or separated, and are at least 60%, e.g., at least 80%, free from other components, e.g. membranes and microsomes, with which they are naturally associated. Purification of antibodies (recovering the antibodies from the host cell culture) is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art.

See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. with affinity media for the purification of kappa or lambda-isotype constant light chain domains, e.g. KappaSelect or LambdaSelect), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with Phenyl-Sepharose™, aza-arenophilic resins, or m-aminophenylboronic acid), metal chelate affinity chromatography (e.g. with Ni(II)- and Cu(II)-affinity material), size exclusion chromatography, and electrophoretic methods (such as gel electrophoresis, capillary electrophoresis) (Vijayalakshmi, M. A., Appl. Biochem. Biotech. 75 (1998) 93-102).

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a vector are capable of directing the expression of nucleic acids to which they are operatively linked. When the expression vector is introduced into an appropriate host cell, it can be transcribed and translated into a polypeptide. When transforming host cells in methods according to the invention, "expression vectors" are used; thereby the term "vector" in connection with transformation of host cells as described herein means "expression vector". An "expression system" usually refers to a suitable host cell comprised of an expression vector that can function to yield a desired expression product.

As used herein, "expression" refers to the process by which a nucleic acid is transcribed into mRNA and/or to the process by which the transcribed mRNA (also referred to as a transcript) is subsequently translated into a peptide, polypeptide, or protein. The transcripts and the encoded polypeptides are individually or collectively referred to as gene products. If a nucleic acid is derived from genomic DNA, expression in a eukaryotic cell may include splicing of the corresponding mRNA.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546ff. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, F. N, et al., PNAS 69 (1972) 7110 et seq.

The term "host cell" as used in the current application denotes any kind of cellular system which can be engineered to generate the antibodies according to the current invention. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., J. Immunol. Methods 194 (1996) 191-199.

The term "pharmaceutical composition" refers to a preparation which is in such form as to permit the biological activity of an active ingredient contained therein to be effective, and which contains no additional components which are unacceptably toxic to a subject to which the composition would be administered. A pharmaceutical composition of the present invention can be administered by a variety of methods known in the art. As will be appreciated by the skilled artisan, the route and/or mode of administration will vary depending upon the desired results. To administer an antibody according to the invention by certain routes of administration, it may be necessary to coat the antibody with, or co-administer the antibody with, a material to prevent its inactivation. For example, the antibody may be administered to a subject in an appropriate carrier, for example, liposomes, or a diluent. Pharmaceutically acceptable diluents include saline and aqueous buffer solutions.

A pharmaceutical composition comprises an effective amount of the antibodies according to the invention. An "effective amount" of an agent, e.g., an antibody, refers to an amount effective, at dosages and for periods of time necessary, to achieve the desired therapeutic or prophylactic result. In particular, the "effective amount" denotes an amount of an antibody of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the antibody molecules used, disease state being treated, the severity or the disease treated, the age and relative health of the subject, the route and form of administration, the judgment of the attending medical or veterinary practitioner, and other factors.

A "pharmaceutically acceptable carrier" refers to an ingredient in a pharmaceutical formulation, other than an active ingredient, which is nontoxic to a subject. Pharmaceutically acceptable carriers includes any and all solvents, dispersion media, coatings, antibacterial and antifungal agents, isotonic and absorption delaying agents, and the like that are physiologically compatible. In one preferred embodiment, the carrier is suitable for intravenous, intramuscular, subcutaneous, parenteral, spinal or epidermal administration (e.g. by injection or infusion).

The pharmaceutical compositions according to the invention may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, in one embodiment the carrier is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "immunoconjugate" is an antibody conjugated to one or more heterologous molecule(s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

2. Detailed Description of the Embodiments of the Invention

I. Multispecific Antibody

The invention relates to a multispecific antibody comprising at least three antigen binding sites, wherein two antigen binding sites are formed by a first antigen binding moiety and a second antigen binding moiety, wherein
  a) a third antigen binding site is formed by a variable heavy chain domain ($VH_3$) and a variable light chain domain ($VL_3$), wherein
    the N-terminus of the $VH_3$ domain is connected to the first antigen binding moiety via a first peptide connector, and
    the N-terminus of the $VL_3$ domain is connected to the second antigen binding moiety via a second peptide connector,
  b) the multispecific antibody comprises two constant heavy chain domains 3 (CH3), which are altered to promote heterodimerization by
    i) generation of a protuberance in one of the CH3 domains by substituting at least one original amino acid residue by an amino acid residue having a larger side chain volume than the original amino acid residue, and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains (which corresponds to supporting heterodimerization by the knobs-into-holes technology); or substituting at least one original amino acid residue in one of the CH3 domains by a positively charged amino acid; and substituting at least one original amino acid residue in the other one of the CH3 domains by a negatively charged amino acid (which corresponds to supporting heterodimerization by introducing amino acids of opposite charges within the corresponding CH3 domains);
ii) introduction of at least one cysteine residue in each CH3 domain such that a disulfide bond is formed between the CH3 domains, or
iii) both modifications of i) and ii);
c) the C-terminus of the $VH_3$ domain of the third antigen binding site is connected to one of the CH3 domains mentioned under b), and the C-terminus of the $VL_3$ domain of the third antigen binding site is connected to the other one of the CH3 domains mentioned under b), and
d) the multispecific antibody is devoid of constant heavy chain domains 2 (CH2).

Figure 1A:
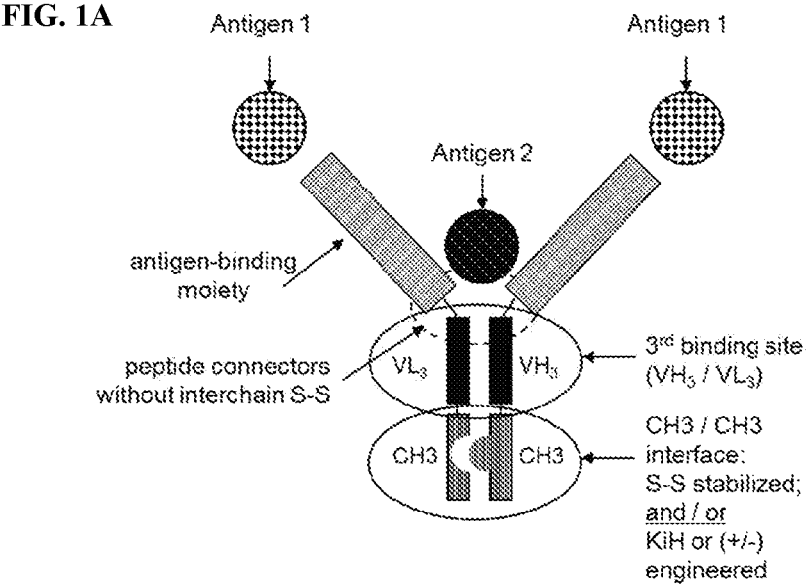
FIGS. 1A-1C: Design of multispecific antibodies according to the invention.
Figure 1B:
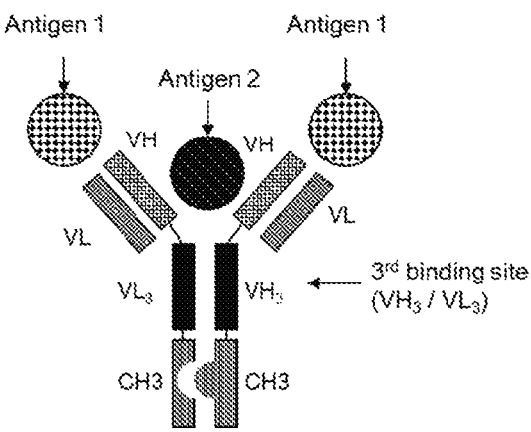
Figure 1C:
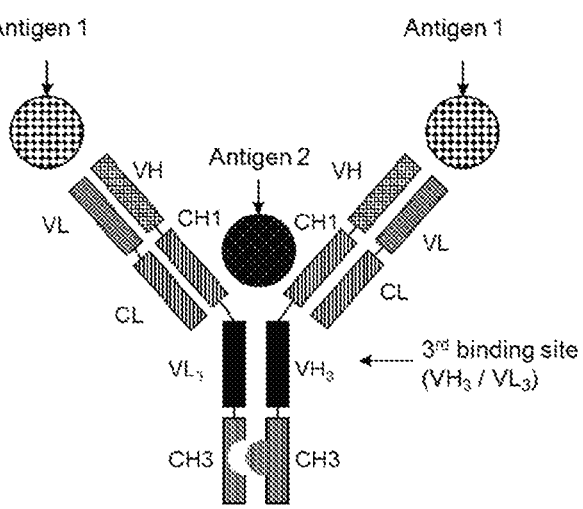

A scheme of the general structure of said multispecific antibody is depicted in FIGS. 1A-1C. The two binding arms of the multispecific antibody according to the invention formed by the first and second antigen binding moiety may bind to the same or different antigens. In contrast to a wild type IgG molecule, within the multispecific antibody according to the invention the CH2 domains were replaced by a third binding site, which is herein referred to $VH_3/VL_3$. As the multispecific antibody is devoid of CH2 domains, Fc mediated effector function is abolished, which is desired for several therapeutic applications. The multispecific antibodies are particularly suitable to bind different epitopes on the same target antigen (e.g. different epitopes on the same biomolecule) or different biomolecules on the same cell.

Heterodimerization

In one embodiment of the multispecific antibody, the CH3 domains are altered according to the knobs-into-holes technology. The multispecific antibody according to this embodiment is herein also referred to as "CH3(KiH)-engineered multispecific antibody" (wherein the abbreviation "KiH" stands for the "knob-into-hole technology"). Hence, according to this embodiment within a CH3(KiH)-engineered multispecific antibody the CH3 domains are altered to promote heterodimerization by generation of a protuberance in one of the CH3 domains by substituting at least one original amino acid residue by an amino acid residue having a larger side chain volume than the original amino acid residue; and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains.

In other words, this embodiment relates to a CH3(KiH)-engineered multispecific antibody according to the invention comprising a first heavy chain and a second heavy chain, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody,
wherein from the set of amino acids that is located in the interface in the CH3 domain of one heavy chain at least one amino acid residue is substituted by an amino acid residue having a larger side chain volume than the original amino acid residue, thereby generating a protuberance within the interface, wherein the protuberance is located in the CH3 domain of the one heavy chain, and wherein the protuberance is positionable in a cavity located in the CH3 domain of the other heavy chain within the interface; and
wherein from the set of amino acids that is located in the interface in the CH3 domain of the other heavy chain at least one amino acid residue is substituted by an amino acid residue having a smaller side chain volume than the original amino acid residue, thereby generating a cavity within the interface, wherein the cavity is located in the CH3 domain of the other heavy chain, and wherein in the cavity the protuberance within the interface located in the CH3 domain of the one heavy chain is positionable.

In one embodiment of said CH3(KiH)-engineered multispecific antibody according to the invention said amino acid residue having a larger side chain volume than the original amino acid residue is selected from R, F, Y and W.

In one embodiment of said CH3(KiH)-engineered multispecific antibody according to the invention said amino acid residue having a smaller side chain volume than the original amino acid residue is selected from A, S, T and V.

In one embodiment of said CH3(KiH)-engineered multispecific antibody according to the invention said amino acid residue having a larger side chain volume than the original amino acid residue is selected from R, F, Y and W; and said amino acid residue having a smaller side chain volume than the original amino acid residue is selected from A, S, T and V.

In one embodiment of said CH3(KiH)-engineered multispecific antibody according to the invention, the CH3 domain of the one heavy chain (the heavy chain comprising the "knob") comprises a T366W mutation, and the CH3 domain of the other heavy chain (the heavy chain comprising the "hole") comprises T366S, L368A and Y407V mutations (numberings according to EU index of Kabat).

In one embodiment of said CH3(KiH)-engineered multispecific antibody according to the invention, the CH3 domain of the one heavy chain (the heavy chain comprising the "knob") comprises T366W and G407Y mutations, and the CH3 domain of the other heavy chain (the heavy chain comprising the "hole") comprises T366S, L368A and Y407V mutations (numberings according to EU index of Kabat).

In another embodiment of said CH3(KiH)-engineered multispecific antibody according to the invention, the CH3 domain of the one heavy chain (the heavy chain comprising the "knob") comprises T366W, R409D and K370E mutations, and the CH3 domain of the other heavy chain (the heavy chain comprising the "hole") comprises T366S, L368A, Y407V, D399K and E357K mutations (numberings according to EU index of Kabat).

Alternatively to or in combination with the modifications according to the knobs-into-holes technology as defined above, the CH3 domains of the multispecific antibody according to the invention are altered to promote heterodimerization based on other heterodimerization approaches known in the art, preferably the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291.

In another embodiment of the multispecific antibody, alternatively to or in combination with the modifications according to the knobs-into-holes technology the CH3 domains are altered by the introduction of charged amino acids with opposite charges at specific amino acid positions in the CH3/CH3-domain-interface (e.g. as described in EP 1870459). The multispecific antibody according to this embodiment is herein also referred to as "CH3(+/−)-engineered multispecific antibody" (wherein the abbreviation "+/−" stands for the oppositely charged amino acids that were introduced in the respective CH3 domains). Hence, according to this embodiment within a CH3(+/−)-engineered multispecific antibody the CH3 domains are altered to promote heterodimerization by substituting at least one original amino acid residue in one of the CH3 domains by a positively charged amino acid; and substituting at least one original amino acid residue in the other one of the CH3 domains by a negatively charged amino acid.

In other words, this embodiment relates to a CH3(+/−)-engineered multispecific antibody according to the invention comprising a first heavy chain and a second heavy chain, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid.

In one embodiment of said CH3(+/−)-engineered multispecific antibody according to the invention the positively charged amino acid is selected from K, R and H; and the negatively charged amino acid is selected from E or D.

In one embodiment of said CH3(+/−)-engineered multispecific antibody according to the invention the positively charged amino acid is selected from K and R; and the negatively charged amino acid is selected from E or D.

In one embodiment of said CH3(+/−)-engineered multispecific antibody according to the invention the positively charged amino acid is K; and the negatively charged amino acid is E.

In one embodiment of said CH3(+/−)-engineered multispecific antibody according to the invention in the CH3 domain of one heavy chain the amino acid R at position 409 (numbering according to EU index of Kabat) is substituted by D and the amino acid K at position 370 (numbering according to EU index of Kabat) is substituted by E; and in the CH3 domain of the other heavy chain the amino acid D at position 399 (numbering according to EU index of Kabat) is substituted by K and the amino acid E at position 357 (numbering according to EU index of Kabat) is substituted by K.

In another embodiment of the multispecific antibody, the CH3 domains are disulfide stabilized. The multispecific antibody according to this embodiment is herein also referred to as "CH3(S-S)-engineered multispecific antibody" (wherein the abbreviation "S-S" stands for the disulfide stabilization). Hence, according to this embodiment within a CH3(S-S)-engineered multispecific antibody the CH3 domains are altered to promote heterodimerization by introduction of at least one cysteine residue in each CH3 domain such that a disulfide bond is formed between the CH3 domains.

In other words, this embodiment relates to a CH3(S-S)-engineered multispecific antibody according to the invention comprising a first heavy chain and a second heavy chain, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody, from the set of amino acids that is located in the interface in the CH3 domain of the one heavy chain a first amino acid is substituted by cysteine; and from the set of amino acids that is located in the interface in the CH3 domain of the other heavy chain a second amino acid is substituted by cysteine, wherein the second amino acid is facing the first amino acid within the interface; such that a disulfide bridge between the CH3 domain of the one heavy chain and the CH3 domain of the other heavy chain can be formed via the introduced cysteine residues.

In one embodiment of the CH3(S-S)-engineered multispecific antibody the CH3 domains are disulfide stabilized by a E356C or a S354C mutation in one of the CH3 domains and a Y349C mutation in the other CH3 domain (numberings according to EU index of Kabat). In one embodiment of the CH3(S-S)-engineered multispecific antibody the CH3 domains are disulfide stabilized by a S354C mutation in one of the CH3 domains and a Y349C mutation in the other CH3 domain (numberings according to EU index of Kabat).

In yet another preferred embodiment of the multispecific antibody, the CH3 domains are disulfide stabilized and altered according to the knobs-into-holes technology. The multispecific antibody according to this embodiment is herein also referred to as "CH3(KSS)-engineered multispecific antibody" (wherein the abbreviation "K" stands for the knobs-into-holes technology and the "SS" stands for the disulfide stabilization). Hence, according to this embodiment, within a CH3(KSS)-engineered multispecific antibody the CH3 domains are altered to promote heterodimerization by generation of a protuberance in one of the CH3 domains by substituting at least one original amino acid residue by an amino acid residue having a larger side chain volume than the original amino acid residue; and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains; and additional introduction of at least one cysteine residue in each CH3 domain such that a disulfide bond is formed between the CH3 domains.

In other words, this embodiment relates to a CH3(KSS)-engineered multispecific antibody according to the invention comprising a first heavy chain and a second heavy chain, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody, wherein from the set of amino acids that is located in the interface in the CH3 domain of one heavy chain at least one amino acid residue is substituted by an amino acid residue having a larger side chain volume than the original amino acid residue, thereby generating a protuberance within the interface, wherein the protuberance is located in the CH3 domain of the one heavy chain, and wherein the protuberance is positionable in a cavity located in the CH3 domain of the other heavy chain within the interface; and wherein from the set of amino acids that is located in the interface in the CH3 domain of the other heavy chain at least one amino acid residue is substituted by an amino acid residue having a smaller side chain volume than the original amino acid residue, thereby generating a cavity within the interface, wherein the cavity is located in the CH3 domain of the other heavy chain, and wherein in the cavity the protuberance within the interface located in the CH3 domain of the one heavy chain is positionable; and wherein from the set of amino acids that is located in the interface in the CH3 domain of the one heavy chain a first amino acid is substituted by cysteine; and from the set of amino acids that is located in the interface in the CH3 domain of the other heavy chain a second amino acid is substituted by cysteine, wherein the second amino acid is facing the first amino acid within the interface; such that a disulfide bridge between the CH3 domain of the one heavy chain and the CH3 domain of the other heavy chain can be formed via the introduced cysteine residues.

In one embodiment of said CH3(KSS)-engineered multispecific antibody according to the invention the E356C or S354C mutation is introduced in the CH3 domain of the "knob" chain and the Y349C mutations are introduced in the CH3 domain of the "hole" chain.

In one embodiment of said CH3(KSS)-engineered multispecific antibody according to the invention said amino acid residue having a larger side chain volume than the original amino acid residue is selected from R, F, Y and W.

In one embodiment of said CH3(KSS)-engineered multispecific antibody according to the invention said amino acid residue having a smaller side chain volume than the original amino acid residue is selected from A, S, T and V.

In one embodiment of said CH3(KSS)-engineered multispecific antibody according to the invention said amino acid residue having a larger side chain volume than the original amino acid residue is selected from R, F, Y and W; and said amino acid residue having a smaller side chain volume than the original amino acid residue is selected from A, S, T and V.

In one embodiment of said CH3(KSS)-engineered multispecific antibody according to the invention said amino acid residue having a larger side chain volume than the original amino acid residue is selected from R, F, Y and W; and said amino acid residue having a smaller side chain volume than the original amino acid residue is selected from A, S, T and V, and the CH3 domains are disulfide stabilized by a E356C or a S354C mutation in one of the CH3 domains (in one embodiment a S354C mutation) and a Y349C mutation in the other CH3 domain (numberings according to EU index of Kabat).

In one embodiment of said CH3(KSS)-engineered multispecific antibody according to the invention, the CH3 domain of the one heavy chain (the heavy chain comprising the "knob") comprises a T366W mutation, and the CH3 domain of the other heavy chain (the heavy chain comprising the "hole") comprises T366S, L368A and Y407V mutations (numberings according to EU index of Kabat), and the CH3 domains are disulfide stabilized by a E356C or a S354C mutation in one of the CH3 domains (in one embodiment a S354C mutation) and a Y349C mutation in the other CH3 domain (numberings according to EU index of Kabat).

In one embodiment of said CH3(KSS)-engineered multispecific antibody according to the invention, the CH3 domain of the one heavy chain (the heavy chain comprising the "knob") comprises T366W and G407Y mutations, and the CH3 domain of the other heavy chain (the heavy chain comprising the "hole") comprises T366S, L368A and Y407V mutations (numberings according to EU index of Kabat), and the CH3 domains are disulfide stabilized by a E356C or a S354C mutation in one of the CH3 domains (in one embodiment a S354C mutation) and a Y349C mutation in the other CH3 domain (numberings according to EU index of Kabat).

In another embodiment of said CH3(KSS)-engineered multispecific antibody according to the invention, the CH3 domain of the one heavy chain (the heavy chain comprising the "knob") comprises T366W, R409D and K370E mutations, and the CH3 domain of the other heavy chain (the heavy chain comprising the "hole") comprises T366S, L368A, Y407V, D399K and E357K mutations (numberings according to EU index of Kabat), the CH3 domains are disulfide stabilized by a E356C or a S354C mutation in one of the CH3 domains (in one embodiment a S354C mutation) and a Y349C mutation in the other CH3 domain (numberings according to EU index of Kabat).

In yet another preferred embodiment of the multispecific antibody, the CH3 domains are disulfide stabilized and altered by the introduction of charged amino acids with opposite charges at specific amino acid positions in the CH3/CH3-domain-interface.

The multispecific antibody according to this embodiment is herein also referred to as "CH3(+/−/SS)-engineered multispecific antibody" (wherein the abbreviation "+/−" stands for the amino acids of opposite charge and the "SS" stands for the disulfide stabilization). Hence, according to this embodiment, within a CH3((+/−/SS)-engineered multispecific antibody the CH3 domains are altered to promote heterodimerization by substituting at least one original amino acid residue in one of the CH3 domains by a positively charged amino acid; and substituting at least one original amino acid residue in the other one of the CH3 domains by a negatively charged amino acid; and additional introduction of at least one cysteine residue in each CH3 domain such that a disulfide bond is formed between the CH3 domains.

In other words, this embodiment relates to a CH3(+/−/SS)-engineered multispecific antibody according to the invention comprising a first heavy chain and a second heavy chain, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody,
   wherein from the set of amino acids that is located in the interface in the CH3 domain of one heavy chain a first amino acid is substituted by a positively charged amino acid; and
   wherein from the set of amino acids that is located in the interface in the CH3 domain of the other heavy chain a second amino acid is substituted by a negatively charged amino acid; and wherein
   from the set of amino acids that is located in the interface in the CH3 domain of the one heavy chain a first amino acid is substituted by cysteine; and from the set of amino acids that is located in the interface in the CH3 domain of the other heavy chain a second amino acid is substituted by cysteine, wherein the second amino acid is facing the first amino acid within the interface; such that a disulfide bridge between the CH3 domain of the one heavy chain and the CH3 domain of the other heavy chain can be formed via the introduced cysteine residues.

In one embodiment of the invention, the third binding site of the multispecific antibody is disulfide stabilized. Hence, the $VH_3$ and $VL_3$ domains are altered by introduction of at least one cysteine residue in the $VH_3$ domain and one cysteine residue in the $VL_3$ domain such that a disulfide bond is formed between the $VH_3$ and $VL_3$ domains. In one embodiment of the invention, the third binding site of the multispecific antibody is disulfide stabilized by introduction of cysteine residues at the following positions to form a disulfide bond between the $VH_3$ and $VL_3$ domains (numbering according to Kabat):
   $VH_3$ at position 44, and $VL_3$ at position 100;
   $VH_3$ at position 105, and $VL_3$ at position 43; or
   $VH_3$ at position 101, and $VL_3$ at position 100.

In one preferred embodiment the third binding site is disulfide stabilized by introduction of cysteine residues in the $VH_3$ domain at position 44, and in the $VL_3$ domain at position 100.

In one preferred embodiment of the invention, the third binding site of the multispecific antibody is disulfide stabilized and the CH3 domains are disulfide stabilized. Without being bound to this theory, the at least two disulfide bonds formed by this modification in different domains of the altered Fc domain of the multispecific antibody according to the invention replace the wild type IgG hinge disulfide interactions and thereby support heterodimerization while allowing antigen access to the third binding site. In one embodiment, the third binding site of a CH3(S-S)-engineered multispecific antibody according to the invention is disulfide stabilized by introduction of cysteine residues at the following positions to form a disulfide bond between the $VH_3$ and $VL_3$ domains (numbering according to Kabat):
   $VH_3$ at position 44, and $VL_3$ at position 100;
   $VH_3$ at position 105, and $VL_3$ at position 43; or
   $VH_3$ at position 101, and $VL_3$ at position 100.

In one preferred embodiment of the invention, the third binding site of a CH3(S-S)-engineered multispecific antibody according to the invention is disulfide stabilized by introduction of cysteine residues in the $VH_3$ domain at position 44, and in the $VL_3$ domain at position 100.

In another preferred embodiment of the invention, the third binding site of a CH3(S-S)-engineered multispecific antibody according to the invention is disulfide stabilized by introduction of cysteine residues in the $VH_3$ domain at position 44, and in the $VL_3$ domain at position 100; and the CH3 domains are disulfide stabilized by a E356C or a S354C mutation in one of the CH3 domains and a Y349C mutation in the other CH3 domain (numberings according to EU index of Kabat).

In another preferred embodiment of the invention, the heterodimerization is supported by knobs-into-holes modifications within the CH3 domains and, in addition, the third binding site of the multispecific antibody and the CH3 domains are disulfide stabilized, respectively. In a multispecific antibody according to this embodiment, the heterodimerization of the knobs-into-holes modified heavy chains is further supported by an artificial interchain disulfide bond, which is—in contrast to known knobs-into-holes approaches—not located within the CH3 domain, but in a different domain (i.e. between the $VH_3$ and $VL_3$ domains). Within the antibody according to this embodiment heterodimerization of the third binding module (comprising the $VH_3$—CH3 and $VL_3$-CH3 polypeptides) is promoted by four distinct interactions: (i) the natural interaction between $VH_3$ and $VL_3$, (ii) the disulfide stabilization in the $VH_3$/$VL_3$ interface, (iii) the disulfide stabilization in the CH3/CH3 interface; and (iv) the knobs-into-holes modifications in the CH3/CH3 interface. By this, formation of heterodimers rather than homodimer formation is promoted and stability of the antibody is improved.

In one embodiment, the third binding site of a CH3(KSS)-engineered multispecific antibody according to the invention is disulfide stabilized by introduction of cysteine residues at the following positions to form a disulfide bond between the $VH_3$ and $VL_3$ domains (numbering according to Kabat):
   $VH_3$ at position 44, and $VL_3$ at position 100;
   $VH_3$ at position 105, and $VL_3$ at position 43; or
   $VH_3$ at position 101, and $VL_3$ at position 100.

In one preferred embodiment of the invention, the third binding site of a CH3(KSS)-engineered multispecific antibody according to the invention is disulfide stabilized by introduction of cysteine residues in the $VH_3$ domain at position 44, and in the $VL_3$ domain at position 100.

In another preferred embodiment of the invention, the third binding site of a CH3(KSS)-engineered multispecific antibody according to the invention is disulfide stabilized by introduction of cysteine residues in the $VH_3$ domain at position 44, and in the $VL_3$ domain at position 100; and the amino acid residue having a larger side chain volume than the original amino acid residue is selected from R, F, Y and W; and the amino acid residue having a smaller side chain volume than the original amino acid residue is selected from A, S, T and V, and the CH3 domains are disulfide stabilized by a E356C or a S354C mutation in one of the CH3 domains (in one embodiment a S354C mutation) and a Y349C mutation in the other CH3 domain (numberings according to EU index of Kabat).

In another preferred embodiment of the invention, the third binding site of a CH3(KSS)-engineered multispecific antibody according to the invention is disulfide stabilized by introduction of cysteine residues in the $VH_3$ domain at position 44, and in the $VL_3$ domain at position 100; and the CH3 domain of one heavy chain (the heavy chain comprising the "knob") comprises a T366W mutation, and the CH3 domain of the other heavy chain (the heavy chain comprising the "hole") comprises T366S, L368A and Y407V mutations (numberings according to EU index of Kabat), and the CH3 domains are disulfide stabilized by a E356C or a S354C mutation in one of the CH3 domains (in one embodiment a S354C mutation) and a Y349C mutation in the other CH3 domain (numberings according to EU index of Kabat).

In another preferred embodiment of the invention, the third binding site of a CH3(KSS)-engineered multispecific antibody according to the invention is disulfide stabilized by introduction of cysteine residues in the $VH_3$ domain at position 44, and in the $VL_3$ domain at position 100; and the CH3 domain of the one heavy chain (the heavy chain comprising the "knob") comprises T366W and G407Y mutations, and the CH3 domain of the other heavy chain (the heavy chain comprising the "hole") comprises T366S, L368A and Y407V mutations (numberings according to EU index of Kabat), and the CH3 domains are disulfide stabilized by a E356C or a S354C mutation in one of the CH3 domains (in one embodiment a S354C mutation) and a Y349C mutation in the other CH3 domain (numberings according to EU index of Kabat).

In another preferred embodiment of the invention, the third binding site of a CH3(KSS)-engineered multispecific antibody according to the invention is disulfide stabilized by introduction of cysteine residues in the $VH_3$ domain at position 44, and in the $VL_3$ domain at position 100; and the CH3 domain of one heavy chain (the heavy chain comprising the "knob") comprises T366W, R409D and K370E mutations, and the CH3 domain of the other heavy chain (the heavy chain comprising the "hole") comprises T366S, L368A, Y407V, D399K and E357K mutations (numberings according to EU index of Kabat), the CH3 domains are disulfide stabilized by a E356C or a S354C mutation in one of the CH3 domains (in one embodiment a S354C mutation) and a Y349C mutation in the other CH3 domain (numberings according to EU index of Kabat).

In another preferred embodiment of the invention, the heterodimerization is supported by the introduction of charged amino acids with opposite charges at specific amino acid positions in the CH3/CH3-domain-interface and, in addition, the third binding site of the multispecific antibody and the CH3 domains are disulfide stabilized, respectively. In a multispecific antibody according to this embodiment, the heterodimerization of the modified heavy chains is further supported by an artificial interchain disulfide bond, which is not located within the CH3 domain, but in a different domain (i.e. between the $VH_3$ and $VL_3$ domains). In one embodiment, the third binding site of a CH3(+/-/SS)-engineered multispecific antibody according to the invention is disulfide stabilized by introduction of cysteine residues at the following positions to form a disulfide bond between the $VH_3$ and $VL_3$ domains (numbering according to Kabat):

$VH_3$ at position 44, and $VL_3$ at position 100;
$VH_3$ at position 105, and $VL_3$ at position 43; or
$VH_3$ at position 101, and $VL_3$ at position 100.

In one preferred embodiment of the invention, the third binding site of a CH3(+/-/SS)-engineered multispecific antibody according to the invention is disulfide stabilized by introduction of cysteine residues in the $VH_3$ domain at position 44, and in the $VL_3$ domain at position 100.

Peptide Connector

Within a multispecific antibody according to the invention, the N-terminus of the $VH_3$ and $VL_3$ domains of the third binding site are fused to the respective antigen binding moieties via a first and second peptide connector, respectively. In one embodiment of the invention, no interchain disulfide bond is formed between the first and the second peptide connector. In one embodiment of the invention, the first and second peptide connectors are identical to each other.

In one embodiment of the invention, the multispecific antibody is devoid of a hinge region. In another, alternative, embodiment of the invention, the multispecific antibody comprises a natural hinge region, which does not form interchain disulfides. One example is the hinge region peptide derived from an antibody of IgG4 isotype.

In one preferred embodiment of the invention, the first and second peptide connector are peptides of at least 15 amino acids. In another embodiment of the invention, the first and second peptide connector are peptides of 15-70 amino acids. In another embodiment of the invention, the first and second peptide connector are peptides of 20-50 amino acids. In another embodiment of the invention, the first and second peptide connector are peptides of 10-50 amino acids. Depending e.g. on the type of antigen to be bound by the third binding site, shorter (or even longer) peptide connectors may also be applicable in antibodies according to the invention.

In yet another embodiment of the invention, the first and second peptide connector are approximately of the length of the natural hinge region (which is for natural antibody molecules of IgG1 isotype about 15 amino acids, and for IgG3 isotype about 62 amino acids). Therefore in one embodiment, wherein the multispecific antibody is of IgG1 isotype, the peptide connectors are peptides of 10-20 amino acids, in one preferred embodiment of 12-17 amino acids. In another one embodiment, wherein the multispecific antibody is of IgG3 isotype, the peptide connectors are peptides of 55-70 amino acids, in one preferred embodiment of 60-65 amino acids.

In one embodiment of the invention, the first and second peptide connectors are glycine-serine linkers. In one embodiment of the invention, the first and second peptide connectors are peptides consisting of glycine and serine residues. In one embodiment of the invention, the glycine-serine linkers are of the structure (GxS)n (SEQ ID NO: 40) or (GxS)nGm (SEQ ID NO: 41)

with G=glycine, S=serine, x=3 or 4, n=2, 3, 4, 5 or 6, and m=0, 1, 2 or 3.

In one embodiment, of above defined glycine-serine linkers, x=3, n=3, 4, 5 or 6, and m=0, 1, 2 or 3; or x=4, n=2, 3, 4 or 5 and m=0, 1, 2 or 3. In one preferred embodiment, x=4 and n=2 or 3, and m=0. In yet another preferred embodiment, x=4 and n=2. In one embodiment said peptide connector is $(G_4S)_2$ (SEQ ID NO: 42).

In one preferred embodiment of the invention, the first and second peptide connectors are $(G_4S)_2$ (SEQ ID NO: 42) peptides, and the multispecific antibody is a CH3(KSS)-engineered multispecific antibody as defined above, wherein the third binding site is disulfide stabilized by introduction of cysteine residues in the $VH_3$ domain at position 44, and in the $VL_3$ domain at position 100; and wherein in the multispecific antibody the CH3 domain of the one heavy chain (the heavy chain comprising the "knob") comprises T366W and G407Y mutations, and the CH3 domain of the other heavy chain (the heavy chain comprising the "hole") comprises T366S, L368A and Y407V mutations (numberings according to EU index of Kabat), and the CH3 domains are disulfide stabilized by a E356C or a S354C mutation in one of the CH3 domains (in one embodiment a S354C mutation) and a Y349C mutation in the other CH3 domain (numberings according to EU index of Kabat).

In another preferred embodiment of the invention, the first and second peptide connectors are $(G_4S)_2$ (SEQ ID NO: 42) peptides, and the multispecific antibody is a CH3(KSS)-engineered multispecific antibody as defined above, wherein the third binding site is disulfide stabilized by introduction of cysteine residues in the $VH_3$ domain at position 44, and in the $VL_3$ domain at position 100; and wherein in the multispecific antibody the CH3 domain of the one heavy chain (the heavy chain comprising the "knob") comprises T366W, G407Y and S354C mutations, and the CH3 domain of the other heavy chain (the heavy chain comprising the "hole") comprises T366S, L368A, Y407V and Y349C mutations (numberings according to EU index of Kabat).

Fusion Site of the VH3 and VL3 Domains with Respective CH3 Domains

Within a multispecific antibody according to the invention, the respective C-terminus of the $VH_3$ and $VL_3$ domains of the third binding site is fused to CH3 domains. Obtaining a protein fold similar to a wild type IgG-Fc region can be achieved best, when the variable domains $VH_3$ and $VL_3$ are directly connected to the respective CH3 domains without the aid of a peptide connector. In addition, even in case the third binding site and the CH3/CH3 interface are both disulfide stabilized, the direct connection of the variable domains with the respective CH3 domain advantageously prevents mispairing of the cysteine residues, which are located in close proximity, when forming the desired interchain disulfide bonds.

Hence, in one embodiment of the invention the C-terminus of the $VH_3$ domain is directly connected to one of the CH3 domains, and the C-terminus of the $VL_3$ domain is directly connected to the other one of the CH3 domains. In one preferred embodiment of the invention the C-terminus of the $VH_3$ domain is directly connected to one of the CH3 domains, and the C-terminus of the $VL_3$ domain is directly connected to the other one of the CH3 domains, wherein the connection sites are devoid of an additional linker peptide.

In order to provide a fusion site that structurally closely mimics the natural transition sites between variable and constant domains of wild type antibody molecules, the C-terminus of the variable domains ($VH_3$ and $VL_3$, respectively) and/or the N-terminus of the CH3 domains (which are directly connected to the respective variable domains) may include mutations by substituting distinct amino acid residues.

Hence, in one embodiment of the invention, the N-terminus of the CH3 domain is modified by substituting at least one original amino acid residue. In one embodiment of the invention, the C-terminus of the $VH_3$ domain is modified by substituting at least one original amino acid residue. In one embodiment of the invention, the C-terminus of the $VL_3$ domain is modified by substituting at least one original amino acid residue.

In one preferred embodiment, the N-terminus of each one of the CH3 domains includes at least one amino acid mutation, the C-terminus of the $VH_3$ domain includes at least one amino acid mutation, and C-terminus of the $VL_3$ domain includes at least one amino acid mutation.

In one embodiment thereof, amino acid mutations in order to improve the tertiary structure of the fusion site to mimic the natural transition sites between variable and constant domains of wild type antibody molecules are performed by substituting at least one amino acid residue located at positions 341 to 350 of the CH3 domains (numbering according to EU index of Kabat). In one embodiment, at least one amino acid residue located at positions 341 to 345 of the CH3 domains is substituted (numbering according to EU index of Kabat). In one embodiment of the invention, the N-terminus of the CH3 domain consists of an amino acid sequence according to SEQ ID NO: 2. In one embodiment of the invention, the N-terminus of the CH3 domain consists of an amino acid sequence according to SEQ ID NO: 3 or SEQ ID NO: 4.

In another embodiment, amino acid mutations in order to improve the tertiary structure of the fusion site to mimic the natural transition sites between variable and constant domains of wild type antibody molecules are performed by substituting at least one amino acid residue of the ten C-terminal amino acid residues of the $VH_3$ domain, the $VL_3$ domain or both, the $VH_3$ domain and the $VL_3$ domain.

In one preferred embodiment, the N-terminus of each one of the CH3 domains includes at least one amino acid mutation located at positions 341 to 350 of the CH3 domains (numbering according to EU index of Kabat), and the ten C-terminal amino acid residues of the $VH_3$ domain include at least one amino acid mutation, and the ten C-terminal amino acid residues of the $VL_3$ domain include at least one amino acid mutation.

In another preferred embodiment, the N-terminus of each one of the CH3 domains includes at least one amino acid mutation located at positions 341 to 345 of the CH3 domains (numbering according to EU index of Kabat), and the five C-terminal amino acid residues of the $VH_3$ domain include at least one amino acid mutation, and the five C-terminal amino acid residues of the $VL_3$ domain include at least one amino acid mutation.

Antigen Binding Moieties

In one embodiment of the invention, the antigen binding moiety is a protein specifically binding to an antigen. In one embodiment the antigen binding moiety is selected from the group of antibodies, receptors, ligands, and DARPins capable of specifically binding to an antigen. In one embodiment the antigen binding moiety is an antibody fragment. In one preferred embodiment the antigen binding moiety is selected from the group consisting of Fv, Fab, Fab', Fab'-SH, $F(ab')_2$, and single-chain antibody molecules (e.g. scFv, scFab). In another preferred embodiment the antigen binding moiety an Fv or a Fab fragment.

In another preferred embodiment of the invention, the antigen binding moiety is a Fab fragment. In yet another particularly preferred embodiment of the invention, the first antigen binding moiety is a first Fab fragment and the second antigen binding moiety is a second Fab fragment.

In case the first and second binding moieties of a multispecific antibody according to the invention are Fab fragments, the multispecific antibody according to the invention has an IgG like shape and exhibits a comparable molecular weight as a wild type IgG molecule. Similar to a wild type IgG molecule, such multispecific antibody according to the invention comprises two binding arms based on Fab fragments. The binding arms may be of a wild type Fab structure or comprise further modifications as known in the art (e.g. the Fab fragments may be single chain Fabs, disulfide stabilized Fabs, disulfide stabilized single chain Fabs, or domain crossover Fabs). In order to assure antigen binding of the third binding site the hinge region of a wild type antibody, which naturally includes stabilizing disulfide bonds, is replaced by peptide connectors devoid of interchain disulfide bonds. Due to the lack of the stabilization arising from the removal of the natural hinge disulfides interaction, the altered Fc-like region of the multispecific antibody is stabilized by supporting CH3/CH3 heterodimerization by knobs-into-holes modifications or introduction of oppositely charged amino acids and/or additional interchain disulfides. In addition, correct assembly of the desired antibody molecule (e.g. avoid chain mispairing like the formation of heavy chain homodimers) is thereby supported.

Hence, in one particularly preferred embodiment the invention relates to a multispecific antibody comprising at least three antigen binding sites, wherein two antigen binding sites are formed by a first Fab fragment and a second Fab fragment, wherein
- a) a third antigen binding site is formed by a variable heavy chain domain (VH$_3$) and a variable light chain domain (VL$_3$), wherein
  the N-terminus of the VH$_3$ domain is connected to the first Fab fragment via a first peptide connector, and
  the N-terminus of the VL$_3$ domain is connected to the second Fab fragment via a second peptide connector,
- b) the multispecific antibody comprises two constant heavy chain domains 3 (CH3), which are altered to promote heterodimerization by
  - i) generation of a protuberance in one of the CH3 domains by substituting at least one original amino acid residue by an amino acid residue having a larger side chain volume than the original amino acid residue, and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains (which corresponds to supporting heterodimerization by the knobs-into-holes technology); or
    substituting at least one original amino acid residue in one of the CH3 domains by a positively charged amino acid; and substituting at least one original amino acid residue in the other one of the CH3 domains by a negatively charged amino acid (which corresponds to supporting heterodimerization by introducing amino acids of opposite charges within the corresponding CH3 domains);
  - ii) introduction of at least one cysteine residue in each CH3 domain such that a disulfide bond is formed between the CH3 domains; or
  - iii) both modifications of i) and ii);
- c) the C-terminus of the VH$_3$ domain of the third antigen binding site is connected to one of the CH3 domains, and the C-terminus of the VL$_3$ domain of the third antigen binding site is connected to the other one of the CH3 domains, and
- d) the multispecific antibody is devoid of constant heavy chain domains 2 (CH2).

In one aspect the invention relates to a multispecific antibody comprising at least three antigen binding sites, wherein two antigen binding sites are formed by a first Fab fragment and a second Fab fragment, wherein
- a) a third antigen binding site is formed by a variable heavy chain domain (VH$_3$) and a variable light chain domain (VL$_3$), wherein
  the N-terminus of the VH$_3$ domain is connected to the C-terminus of the constant heavy chain domain (CH1) or the constant light chain domain (CL) of the first Fab fragment via a first peptide connector, and
  the N-terminus of the VL$_3$ domain is connected to the C-terminus of the constant heavy chain domain (CH1) or the constant light chain domain (CL) of the second Fab fragment via a second peptide connector,
- b) the multispecific antibody comprises two constant heavy chain domains 3 (CH3), which are altered to promote heterodimerization by
  - i) generation of a protuberance in one of the CH3 domains by substituting at least one original amino acid residue by an amino acid residue having a larger side chain volume than the original amino acid residue, and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains (which corresponds to supporting heterodimerization by the knobs-into-holes technology); or
    substituting at least one original amino acid residue in one of the CH3 domains by a positively charged amino acid; and substituting at least one original amino acid residue in the other one of the CH3 domains by a negatively charged amino acid (which corresponds to supporting heterodimerization by introducing amino acids of opposite charges within the corresponding CH3 domains);
  - ii) introduction of at least one cysteine residue in each CH3 domain such that a disulfide bond is formed between the CH3 domains; or
  - iii) both modifications of i) and ii);
- c) the C-terminus of the VH$_3$ domain of the third antigen binding site is connected to one of the CH3 domains, and the C-terminus of the VL$_3$ domain of the third antigen binding site is connected to the other one of the CH3 domains, and
- d) the multispecific antibody is devoid of constant heavy chain domains 2 (CH2).

In one preferred embodiment, the first and the second binding site of the multispecific antibody according to the invention are formed by a first and second Fab fragment, respectively. In one embodiment the constant light chain domain of the first and/or the second Fab fragment is of kappa isotype. In one embodiment the constant light chain domain of the first and/or second Fab fragment is of lambda isotype. In one embodiment the constant light chain domain of the first Fab fragment is of kappa isotype and the constant light chain domain of the second Fab fragment is of lambda isotype.

In one embodiment of the invention, the first Fab fragment, the second Fab fragment or both, the first and the second Fab fragment are disulfide stabilized. In one embodiment, the first Fab fragment, the second Fab fragment or both, the first and the second Fab fragment are disulfide stabilized by introduction of cysteine residues at the following positions to form a disulfide bond between the corresponding VH and VL domains (numbering according to Kabat):

VH at position 44, and VL at position 100;
VH at position 105, and VL at position 43; or
VH at position 101, and VL at position 100.

In one preferred embodiment of the invention, the first Fab fragment, the second Fab fragment or both, the first and the second Fab fragment are disulfide stabilized, respectively, by introduction of cysteine residues in its VH domain at position 44, and in its VL domain at position 100.

In another embodiment of the invention, the first Fab fragment, the second Fab fragment or both, the first and the second Fab fragment are disulfide stabilized. In one embodiment, the first Fab fragment, the second Fab fragment or both, the first and the second Fab fragment are disulfide stabilized by introduction of cysteine residues at the following positions to form a disulfide bond between the corresponding VH and VL domains (numbering according to Kabat):

VH at position 44, and VL at position 100;
VH at position 105, and VL at position 43; or
VH at position 101, and VL at position 100, and and the natural disulfide bond between the polypeptide chains of the respective Fab fragment is abolished by substituting at least one of the interchain disulfide-bond-forming cysteine residues by another amino acid residue.

In yet another embodiment of the invention, the first Fab fragment, the second Fab fragment or both, the first and the second Fab fragment are disulfide stabilized, respectively, by introduction of cysteine residues in its VH domain at position 44, and in its VL domain at position 100; and the natural disulfide bond between the polypeptide chains of the respective Fab fragment is abolished by substituting at least one of the interchain disulfide-bond-forming cysteine residues by another amino acid residue.

According to this embodiment, the first Fab fragment, the second Fab fragment or both, the first and the second Fab fragment, are stabilized only by the artificial disulfide bond between VH at position 44 and VL at position 100.

In one embodiment of the invention, the first Fab fragment, the second Fab fragment or both, the first and the second Fab fragment are single chain Fab fragments (scFab), i.e. the domains of the Fab fragment are arranged on a single polypeptide chain. This embodiment is particularly useful, when the first and second Fab fragment bind to different epitopes (and hence, the multispecific antibody is at least trispecific). By this, side product formation and light chain mispairing (i.e. pairing of a light chain with the wrong heavy chain thereby forming non-functional binding sites) during recombinant expression may be reduced and the expression yield may be improved. In one preferred embodiment, exactly one of the Fab fragments (i.e. either the first Fab fragment or the second Fab fragment) is a single chain Fab fragment (while the other Fab fragment is not a single chain Fab fragment but rather built up of two polypeptide chains).

Therefore, in one preferred embodiment of a multispecific antibody including at least one single chain Fab fragment, the multispecific antibody is at least trispecific. In another preferred embodiment of a multispecific antibody including at least one single chain Fab fragment, the multispecific antibody is trispecific. In yet another preferred embodiment of a multispecific antibody including at least one single chain Fab fragment, the multispecific antibody is trivalent and trispecific.

In one embodiment of the invention, the first Fab fragment, the second Fab fragment or both, the first and the second Fab fragment are disulfide stabilized single chain Fab fragments (dsFab). In one embodiment, the first Fab fragment, the second Fab fragment or both, the first and the second Fab fragment are single chain Fab fragments, which are disulfide stabilized by introduction of cysteine residues at the following positions to form a disulfide bond between the corresponding VH and VL domains (numbering according to Kabat):

VH at position 44, and VL at position 100;
VH at position 105, and VL at position 43; or
VH at position 101, and VL at position 100.

In one preferred embodiment of the invention, the first Fab fragment, the second Fab fragment or both, the first and the second Fab fragment are single chain Fab fragments, which are disulfide stabilized, respectively, by introduction of cysteine residues in its VH domain at position 44, and in its VL domain at position 100. In one preferred embodiment, exactly one of the Fab fragments (i.e. either the first Fab fragment or the second Fab fragment) is a single chain Fab fragment, which is disulfide stabilized by introduction of cysteine residues in its VH domain at position 44, and in its VL domain at position 100.

In another preferred embodiment, the first Fab fragment, the second Fab fragment or both, the first and the second Fab fragment are single chain Fab fragments, which are disulfide stabilized by introduction of cysteine residues at the following positions to form a disulfide bond between the corresponding VH and VL domains (numbering according to Kabat):

VH at position 44, and VL at position 100;
VH at position 105, and VL at position 43; or
VH at position 101, and VL at position 100; and the natural disulfide bond between the polypeptide chains of the respective single chain Fab fragment is abolished by substituting at least one of the interchain disulfide-bond-forming cysteine residues by another amino acid residue. In yet another preferred embodiment of the invention, the first Fab fragment, the second Fab fragment or both, the first and the second Fab fragment are single chain Fab fragments, which are disulfide stabilized, respectively, by introduction of cysteine residues in its VH domain at position 44, and in its VL domain at position 100, and the natural disulfide bond between the polypeptide chains of the respective single chain Fab fragment is abolished by substituting at least one of the interchain disulfide-bond-forming cysteine residues by another amino acid residue.

In one embodiment of the invention, the first Fab fragment, the second Fab fragment or both, the first and the second Fab fragment are altered by a domain crossover, such that either:
a) only the CH1 and CL domains are replaced by each other;
b) only the VH and VL domains are replaced by each other; or
c) the CH1 and CL domains are replaced by each other and the VH and VL domains are replaced by each other, with the provision that in case both the first Fab fragment and the second Fab fragment are altered by a domain crossover, they are altered by different domain crossovers. This means for example that in case both Fab fragments comprise a domain crossover, when the first Fab fragment comprises the domain crossover defined under a), i.e. the CH1 and CL domains are replaced by each other, then the second Fab fragment comprises either the domain crossover defined under b) (i.e. replacement of corresponding VH and VL domains) or the domain crossover defined under c) (i.e. replacement of VH-CH1 with VL-CL), but the second Fab fragment does not comprise the domain crossover defined under a) (i.e. only the CH1 and CL domains are replaced by each other).

Hence, the multispecific antibody according to this embodiment comprises an asymmetric domain crossover with respect to the first and second Fab fragment, meaning that due to the domain crossover the light chains of the first Fab fragment and the second Fab fragment are no longer composed of the same domain architecture but are rather comprised of a different domain architecture. Thereby, pairing of the light chain of the first Fab fragment with the heavy chain of the second Fab fragment (and vice versa) is avoided. This embodiment is particularly useful, when the first and second Fab fragment bind to different epitopes (and hence, the multispecific antibody is at least trispecific). By this embodiment, side product formation and light chain mispairing (i.e. pairing of a light chain with the wrong heavy chain thereby forming non-functional binding sites) during recombinant expression may be reduced and the expression yield of the antibody may be improved.

Therefore, in one preferred embodiment of a multispecific antibody including a domain crossover in at least one of the Fab fragments, the multispecific antibody is at least trispecific. In another preferred embodiment of a multispecific antibody including a domain crossover in at least one of the Fab fragments, the multispecific antibody is trispecific. In yet another preferred embodiment of a multispecific antibody including a domain crossover in at least one of the Fab fragments, the multispecific antibody is trivalent and trispecific.

In one embodiment of the invention, only one of the Fab fragments (i.e. the first Fab fragment or the second Fab fragment but not both Fab fragments) is altered by a domain crossover such that only the CH1 and CL domains of the Fab fragment are replaced by each other.

In one embodiment of the invention, only one of the Fab fragments (i.e. the first Fab fragment or the second Fab fragment but not both Fab fragments) is altered by a domain crossover such that only the VH and VL domains of the Fab fragment are replaced by each other.

In case Fab fragments are used as binding arms of the multispecific antibody according to the invention, the antibody exhibits an IgG-like structure, however it comprises an additional binding site that replaces the original CH2/CH2 interface.

Further binding sites may be fused to the N-termini or C-termini of the heavy chains or light chains of the multispecific antibody in order to provide antibodies of higher valence. In one preferred embodiment the multispecific antibody is trivalent, thereby resembling the wild type three-dimensional structure of an IgG molecule.

Binding to Different Epitopes

In one embodiment of the invention the multispecific antibody comprises at least one polyepitopic binding site (i.e. is capable of binding to two different epitopes on one biological molecule or two different epitopes from different biological molecules, e.g. as disclosed in WO 2008/027236 A2). By this, multispecific antibodies of more than three specificities (e.g. tetraspecific antibodies) can be generated in a similar structure and molecular weight as wild type IgG molecules. In one embodiment of the invention, the first antigen binding moiety, the second antigen binding moiety or both, the first and the second antigen binding moiety comprise a polyepitopic binding site. In another embodiment of the invention, the third binding site comprises a polyepitopic binding site. In yet another embodiment, the first and the second antigen binding moiety and the third binding site of the multispecific antibody comprise a polyepitopic binding site.

The multispecific antibody according to the invention is capable of binding to different epitopes. This may be achieved by combining binding sites that specifically bind to a single antigen or, in addition, by including binding sites that are polyepitopic and hence, specifically bind to more than one epitope (in one preferred embodiment said polyepitopic binding site binds to two different epitopes). Thereby, trivalent multispecific antibodies may be produced that are capable of binding to a high number of different epitopes. In case the first and second antigen binding moieties are respective Fab fragments, the multispecific antibody advantageously maintains an IgG like shape and molecular weight. The multispecific antibodies are particularly suitable to bind different epitopes on the same target antigen (e.g. different epitopes on the same biomolecule) or different biomolecules on the same cell.

In one preferred embodiment, the multispecific antibody according to the invention includes three binding sites each one binding to a single epitope. Thereby, the multispecific antibody according to this embodiment may be bispecific or trispecific.

In another preferred embodiment, the multispecific antibody according to the invention includes at least one polyepitopic binding site (in one preferred embodiment said polyepitopic binding site binds to two different epitopes). In one embodiment, the multispecific antibody is a trispecific antibody, wherein the first and second antigen binding moieties include two identical polyepitopic binding sites (specifically binding each to two different epitopes) and the third binding site specifically binds to another (third) epitope. In another embodiment, the multispecific antibody is a trispecific antibody, wherein the first and second antigen binding moieties specifically bind to a first epitope and the third binding site is a polyepitopic binding site specifically binding to a second and a third epitope. Thereby, the multispecific antibody according to this embodiment is at least trispecific. When combing three different polyepitopic binding sites that each bind two different epitopes, in one embodiment of the multispecific antibody, the antibody may be up to hexaspecific.

In one embodiment of the invention the antibody is bispecific. In one embodiment of the invention the antibody is trivalent and bispecific. In one embodiment of the invention the antibody is bispecific and specifically binds two different antigens on one cell or two different epitopes of the same antigen. In one embodiment of the invention the antibody is trivalent and bispecific, and specifically binds two different antigens on one cell or two different epitopes of the same antigen.

In one preferred embodiment of the invention the antibody is bispecific, wherein the first antigen binding moiety and the second antigen binding moiety specifically bind to the same epitope, and wherein the third binding site specifically binds to a different epitope. In one preferred embodiment of the invention the antibody is trivalent and bispecific, wherein the first antigen binding moiety and the second antigen binding moiety specifically bind to the same epitope, and wherein the third binding site specifically binds to a different epitope.

Within a bispecific antibody according to these embodiments comprising a first and second antigen binding moiety in the form of Fab fragments, in one embodiment the first and second Fab fragment do not comprise a domain crossover. Hence, in one preferred embodiment, the light chains of the first and second Fab fragment are composed of VL and CL domains (from N-terminal to C-terminal direction).

In another embodiment of the invention the antibody is bispecific, wherein the first antigen binding moiety and the third binding site specifically bind to the same epitope, and wherein the second antigen binding moiety specifically binds to a different epitope. In another embodiment of the invention the antibody is trivalent and bispecific, wherein the first antigen binding moiety and the third binding site specifically bind to the same epitope, and wherein the second antigen binding moiety specifically binds to a different epitope.

Within a bispecific antibody according to these embodiments comprising a first and second antigen binding moiety in the form of Fab fragments, at least one of the Fab fragments either comprises a domain crossover or is provided in the form of a single chain Fab fragment. In one preferred embodiment, at least one of the Fab fragments comprises a domain crossover as defined above (optionally including further domain crossover embodiments such as introduction of charged amino acids into at least one of the Fab fragments). Thereby, chain mispairing is avoided and the expression yield of the multispecific antibody is improved.

In one embodiment of the invention the antibody is trispecific. In one embodiment of the invention the antibody is trivalent and trispecific.

In one preferred embodiment of a trispecific antibody according to the invention, each binding site binds to single epitope, wherein the first antigen binding moiety, the second antigen binding moiety and the third binding site specifically bind to a different epitope, respectively.

In another embodiment of a trispecific antibody according to the invention, the first and second antigen binding moiety bind to the same epitope and the third binding site binds to two different epitopes (and therefore is polyepitopic).

In yet another embodiment of a trispecific antibody according to the invention, the first and second antigen binding moiety are based on the same, polyepitopic binding sites (each one binding to two different epitopes), and the third binding site binds to a single epitope that is different from the epitopes bound by the first and second antigen binding moiety.

In all embodiments, wherein the antibody according to the invention comprises a first Fab fragment and a second Fab fragments as first and second antigen binding moiety and wherein said first Fab fragment and said second Fab fragment are based on different binding sites and hence, specifically bind to different epitopes, the Fab fragments are preferably specifically designed to avoid light chain mispairing between the light chains and heavy chains of the first Fab fragment and the second Fab fragment, respectively, by either using single chain Fab fragments (which may be further disulfide stabilized), or by using domain crossover strategies to achieve a different domain architecture in the light chains of the first Fab fragment and the second Fab fragment, thereby suppressing light chain mispairing.

In one embodiment of a multispecific antibody according to the invention, wherein the first Fab fragment and the second Fab fragment specifically bind to different epitopes, the first Fab fragment, the second Fab fragment or both, the first and the second Fab fragment are altered by a domain crossover, such that either:
a) only the CH1 and CL domains are replaced by each other;
b) only the VH and VL domains are replaced by each other; or
c) the CH1 and CL domains are replaced by each other and the VH and VL domains are replaced by each other,
with the provision that in case both the first Fab fragment and the second Fab fragment are altered by a domain crossover, they are altered by different domain crossovers.

In one embodiment of a multispecific antibody according to the invention, wherein the first Fab fragment and the second Fab fragment specifically bind to different epitopes, only one of the Fab fragments (i.e. the first Fab fragment or the second Fab fragment but not both Fab fragments) is altered by a domain crossover such that only the CH1 and CL domains of the Fab fragment are replaced by each other.

In one embodiment of a multispecific antibody according to the invention, wherein the first Fab fragment and the second Fab fragment specifically bind to different epitopes, only one of the Fab fragments (i.e. the first Fab fragment or the second Fab fragment but not both Fab fragments) is altered by a domain crossover such that only the VH and VL domains of the Fab fragment are replaced by each other.

In one embodiment of a multispecific antibody according to the invention, wherein the first Fab fragment and the second Fab fragment bind to different epitopes the first Fab fragment, the second Fab fragment or both, the first and the second Fab fragment are single chain Fab fragments (scFab).

In one embodiment of a multispecific antibody according to the invention, wherein the first Fab fragment and the second Fab fragment bind to different epitopes, the first Fab fragment, the second Fab fragment or both, the first and the second Fab fragment are disulfide stabilized single chain Fab fragments (dsFab). In one embodiment of a multispecific antibody according to the invention, wherein the first Fab fragment and the second Fab fragment bind to different epitopes, the first Fab fragment, the second Fab fragment or both, the first and the second Fab fragment are single chain Fab fragments, which are disulfide stabilized by introduction of cysteine residues at the following positions to form a disulfide bond between the corresponding VH and VL domains (numbering according to Kabat):

VH at position 44, and VL at position 100;
VH at position 105, and VL at position 43; or
VH at position 101, and VL at position 100.

In one embodiment of a multispecific antibody according to the invention, wherein the first Fab fragment and the second Fab fragment bind to different epitopes, the first Fab fragment, the second Fab fragment or both, the first and the second Fab fragment are single chain Fab fragments, which are disulfide stabilized, respectively, by introduction of cysteine residues in its VH domain at position 44, and in its VL domain at position 100. In one preferred embodiment, exactly one of the Fab fragments (i.e. either the first Fab fragment or the second Fab fragment) is a single chain Fab fragment, which is disulfide stabilized by introduction of cysteine residues in its VH domain at position 44, and in its VL domain at position 100.

In one embodiment of a multispecific antibody according to the invention, wherein the first Fab fragment and the second Fab fragment bind to different epitopes, the first Fab fragment is a single chain Fab fragment (in one embodiment a disulfide stabilized single chain Fab fragment) and the second Fab fragment comprises a domain crossover as defined above.

Antibody Isotypes

In one embodiment of the invention, the multispecific antibody comprises immunoglobulin constant regions of one or more immunoglobulin classes. Immunoglobulin classes include IgG, IgM, IgA, IgD, and IgE isotypes and, in the case of IgG and IgA, their subtypes. In one embodiment of the invention, the multispecific antibody has a constant domain structure of an IgG type antibody.

In one embodiment the constant domains of an antibody according to the invention are of human IgG1 or IgG4 subclass. In one embodiment, the CH3 domain is derived from a human IgG1 antibody. In one embodiment, the multispecific antibody is devoid of a CH4 domain.

In one embodiment of the invention the antibody is a monoclonal antibody. In one embodiment of the invention the antibody is a humanized monoclonal antibody. In one embodiment of the invention the antibody is a human monoclonal antibody.

In one embodiment of the invention the multispecific antibody is an isolated antibody.

In one embodiment, an antibody comprising a heavy chain including a CH3 domain as specified herein, comprises an additional C-terminal glycine-lysine dipeptide (G446 and K447, numbering according to EU index of Kabat). In one embodiment, an antibody comprising a heavy chain including a CH3 domain, as specified herein, comprises an additional C-terminal glycine residue (G446, numbering according to EU index of Kabat).

Complex Including Antibody and Hapten-Coupled Agent for Targeted Payload Delivery Another object of the invention is a complex comprising (i) a multispecific antibody according to the invention, wherein the antibody specifically binds at least to a hapten and a target protein (thereby including at least one binding site specifically binding to the hapten and at least one binding site specifically binding to the target protein), and (ii) the hapten, which is bound by the multispecific antibody, wherein the hapten is conjugated to a therapeutic or diagnostic agent. Within the complex, the hapten is bound to the binding site of the antibody, which specifically binds to the hapten. Thereby, the hapten conjugated to the therapeutic or diagnostic agent is non-covalently coupled to the antibody. Within the complex the antibody maintains its binding specificity and affinity while the therapeutic or diagnostic agent coupled to the hapten maintains its activity as well. Complexes of a hapten-binding bispecific antibody with haptenylated therapeutic or diagnostic agent in general are known in the art, e.g. from WO 2011/1003557 A1. The complexes according to the invention may be designed and applied as described in WO 2011/1003557 A1, the contents of which are fully incorporated herein by reference.

In one embodiment, the antibody present in the complex according to the invention is bispecific. In one embodiment, the hapten is selected from digoxigenin, biotin, theophylline, fluorescein, DOTA, and DOTAM. In one embodiment the target protein is a cell surface antigen or an intracellular antigen. In one embodiment the target protein is a cell surface or an intracellular tumor-associated antigen. In one embodiment the target protein is a cell surface tumor-associated antigen. In one embodiment the target protein is Lewis Y. In one embodiment the target protein is CD33. In one embodiment the target protein is Glypican 3.

In one embodiment of the invention said multispecific antibody is used as a payload delivery vehicle for the therapeutic or diagnostic agent. The therapeutic or diagnostic agent is conjugated with the hapten and thus coupled by the hapten-binding site of the multispecific antibody according to the invention to form the complex according to the invention. This complex is defined and stable and specifically delivers the payload to a target cell or tissue. Since the haptenylated therapeutic or diagnostic agent is coupled in a non-covalent manner to the multispecific antibody, the payload is stably bound to its delivery vehicle during circulation but also gets efficiently released after internalization. The conjugation with the hapten does not affect the activity of most therapeutic or diagnostic agents. The multispecific antibody thus does not contain an unusual covalently coupled payload and therefore exhibits low risk of immunogenicity. Therefore this simple conjugation procedure can be used for a great variety of payload molecules in combination with only one single multispecific antibody; the payload molecules being for example peptides, proteins, small molecules, imaging reagents and nucleic acids. Complexes of a haptenylated diagnostic or therapeutic agent with the multispecific antibody according to the invention containing at least one hapten binding site may confer benign biophysical behavior and improved PK parameters to the diagnostic or therapeutic agent, e.g. to diagnostic or therapeutic proteins, peptides or small molecules. Furthermore, such complexes are capable to target the delivery payload to cells which display the target protein antigen that is recognized by the at least one further binding site of the multispecific antibody.

In one embodiment the therapeutic or diagnostic agent coupled to the hapten is selected from the group consisting of a peptide, a protein, a small molecule, a radioactively labeled small molecule, a nucleic acid and an imaging agent.

In one embodiment the therapeutic or diagnostic agent is a peptide. Upon binding of a haptenylated peptide to a multispecific antibody according to the invention, the peptide retains its full biological activity. Non-limiting examples of peptides are Mellitin, Fam5B, INF7, FallV1 and FallV2. One aspect of the invention is the use of the multispecific antibodies according to the invention for delivery of toxin-derived peptides to target-antigen-expressing tumor cells.

In one embodiment the therapeutic or diagnostic agent is a protein. Upon binding of a haptenylated protein to a multispecific antibody according to the invention, the protein retains its full biological activity.

In one embodiment the therapeutic or diagnostic agent is a small molecule. In one embodiment the small molecule is a toxin or is a small molecule derived from a toxin. In one embodiment the small molecule is Pseudomonas Exotoxin.

In one embodiment the therapeutic or diagnostic agent is a radioactively labelled small molecule. The haptenylated radioisotope or the radioisotope attached to the haptenylated small molecule displays effective tissue penetration, fast clearance, and are retained only on cells covered by the complex according to the invention expressing the target protein antigen. This enables specific targeting and avoids systemic nonspecific release of therapeutic radioisotopes. One aspect of the invention is the use of the multispecific antibodies according to the invention for delivery of a haptenylated radioisotope or a radioisotope attached to a haptenylated small molecule to a diseased tissue. In one embodiment, said diseased tissue is a tumor and the target protein is a tumor associated antigen.

In one embodiment the therapeutic or diagnostic agent is a nucleic acid. In one embodiment the nucleic acid is double stranded RNA (dsRNA). Double-stranded ribonucleic acid (dsRNA) molecules have been shown to block gene expression in a highly conserved regulatory mechanism known as RNA interference (RNAi). Hence, one aspect of the invention is the of the multispecific antibodies according to the invention for targeted gene therapy of targeted dsRNA delivery.

In one embodiment the therapeutic or diagnostic agent is an imaging agent. In one embodiment, the imaging agent is a fluorophor. The imaging agent retains its properties despite being haptenylated and complexed to the antibody according to the invention. The haptenylated imaging agent displays effective tissue penetration, fast clearance, and are retained only on cells covered by the complex according to the invention expressing the target protein antigen. This enables effective time-resolved imaging, and assessment of tumor vascularization, or changes within tumor vascularization. One aspect of the invention is the use of the multispecific antibodies according to the invention for imaging of a diseased tissue. Another aspect of the invention is the use of the multispecific antibodies according to the invention of in vitro imaging, e.g. for FACS analyses. In one embodiment, said diseased tissue is a tumor and the target protein is a tumor associated antigen.

Another aspect is a method for the preparation of a complex according to the invention, the method including the steps of providing a multispecific antibody according to the invention, wherein the multispecific antibody specifically binds to a hapten and a target protein, providing a hapten, which is specifically bound by the multispecific antibody, wherein the hapten is conjugated to a therapeutic or diagnostic agent, and contacting the multispecific antibody with the hapten, which is conjugated to the therapeutic or diagnostic agent.

Another aspect of the invention is the use of the complex according to the invention as a medicament. Another aspect of the invention is the use of the complex according to the invention for diagnostic purposes.

Another aspect of the invention is the use of the complex according to the invention for delivery of a therapeutic or diagnostic agent to a target cell or tissue. Another aspect of the invention is the use of the complex according to the invention for targeted cancer therapy. Another aspect of the invention is the use of the complex according to the invention for targeted radiotherapy.

Another aspect of the invention is the use of the complex according to the invention for imaging of cells or tissues.

Another aspect of the invention is a composition comprising a complex according to the invention comprising the multispecific antibody according to the invention, which specifically binds to a hapten and a target protein, and a hapten that is conjugated to a therapeutic or diagnostic agent. In one embodiment, said composition is a diagnostic composition. In another embodiment the composition is a pharmaceutical composition.

II. Recombinant Method

The multispecific antibody is prepared by recombinant methods. Thus, the invention also relates to a method for the preparation of a multispecific antibody according to the invention, comprising the steps of transforming a host cell with expression vectors comprising nucleic acids encoding the multispecific antibody, culturing said host cell under conditions that allow synthesis of said multispecific antibody, and recovering said multispecific antibody from said host cell culture.

In one embodiment of the invention, the method includes the step of purification of the multispecific antibody via affinity chromatography. In one embodiment of the invention, the method includes the step of purification of the multispecific antibody via affinity chromatography on a kappa light chain or lambda light chain specific column.

Another object of the invention is a multispecific antibody produced by a method according to the invention.

Another object of the invention is a nucleic acid encoding the multispecific antibody according to the invention. In one embodiment, the nucleic acid according to the invention is an isolated nucleic acid.

Another object of the invention is an expression vector comprising a nucleic acid according to the invention. Another object of the invention is an expression vector comprising a nucleic acid according to the invention, wherein the expression vector is capable of expressing said nucleic acid in a host cell.

Another object of the invention is a host cell comprising a nucleic acid according to the invention. Another object of the invention is a host cell comprising an expression vector according to the invention. In one embodiment the host cell is a HEK293 cells or a CHO cell.

III. Pharmaceutical Composition

Another object of the invention is a pharmaceutical composition comprising a multispecific antibody according to the invention. One aspect of the invention is a pharmaceutical composition comprising a multispecific antibody according to the invention in combination with at least one pharmaceutically acceptable carrier.

In one embodiment, a composition (in one preferred embodiment a pharmaceutical composition) comprising a population of antibodies of the invention comprises an antibody comprising a heavy chain including a CH3 domain, as specified herein, with an additional C-terminal glycine-lysine dipeptide (G446 and K447, numbering according to EU index of Kabat). In one embodiment, a composition comprising a population of antibodies of the invention comprises an antibody comprising a heavy chain including a CH3 domain, as specified herein, with an additional C-terminal glycine residue (G446, numbering according to EU index of Kabat).

In one embodiment, such a composition comprises a population of antibodies comprised of antibodies comprising a heavy chain including a CH3 domain, as specified herein; antibodies comprising a heavy chain including a CH3 domain, as specified herein, with an additional C-terminal glycine residue (G446, numbering according to EU index of Kabat); and antibodies comprising a heavy chain including a CH3 domain, as specified herein, with an additional C-terminal glycine-lysine dipeptide (G446 and K447, numbering according to EU index of Kabat).

Another object of the invention is a pharmaceutical composition comprising a complex according to the invention comprising the multispecific antibody according to the invention, which specifically binds to a hapten and a target protein, and a hapten that is conjugated to a therapeutic or diagnostic agent. One aspect of the invention is a pharmaceutical composition comprising a complex according to the invention comprising the multispecific antibody according to the invention, which specifically binds to a hapten and a target protein, and a hapten that is conjugated to a therapeutic or diagnostic agent in combination with at least one pharmaceutically acceptable carrier.

Another object of the invention is an immunoconjugate comprising the multispecific antibody according to the invention coupled to a cytotoxic agent.

Another object of the invention is a pharmaceutical composition comprising an immunoconjugate comprising the multispecific antibody according to the invention coupled to a cytotoxic agent. One aspect of the invention is a pharmaceutical composition comprising an immunoconjugate comprising the multispecific antibody according to the invention coupled to a cytotoxic agent in combination with at least one pharmaceutically acceptable carrier.

Another object of the invention is the use of a multispecific antibody according to the invention for the manufacture of a pharmaceutical composition. Another object of the invention is a method for the manufacture of a pharmaceutical composition comprising a multispecific antibody according to the invention, including formulating the multispecific antibody according to the invention in combination with at least one pharmaceutically acceptable carrier.

Another object of the invention is the multispecific antibody according to the invention for use as a medicament. Another object of the invention is the multispecific antibody according to the invention for use in the treatment of cancer. Another object of the invention is the multispecific antibody according to the invention for use in the treatment of inflammatory diseases, autoimmune diseases, rheumatoid arthritis, psoriatic arthritis, muscle diseases (e.g. muscular dystrophy), multiple sclerosis, chronic kidney diseases, bone diseases (e.g. bone degeneration in multiple myeloma), systemic lupus erythematosus, lupus nephritis, and/or vascular injury.

Another object of the invention is a pharmaceutical composition comprising a multispecific antibody according to the invention in combination with at least one pharmaceutically acceptable carrier for use as a medicament. Another object of the invention is a pharmaceutical composition comprising a multispecific antibody according to the invention in combination with at least one pharmaceutically acceptable carrier for use in the treatment of cancer. Another object of the invention is a pharmaceutical composition comprising a multispecific antibody according to the invention in combination with at least one pharmaceutically acceptable carrier for use in the treatment of inflammatory diseases, autoimmune diseases, rheumatoid arthritis, psoriatic arthritis, muscle diseases (e.g. muscular dystrophy), multiple sclerosis, chronic kidney diseases, bone diseases (e.g. bone degeneration in multiple myeloma), systemic lupus erythematosus, lupus nephritis, and/or vascular injury.

Another object of the invention is a complex according to the invention comprising the multispecific antibody according to the invention, which specifically binds to a hapten and a target protein, and a hapten that is conjugated to a therapeutic or diagnostic agent for use as a medicament. Another object of the invention is a complex according to the invention comprising the multispecific antibody according to the invention, which specifically binds to a hapten and a target protein, and a hapten that is conjugated to a therapeutic or diagnostic agent for use in the treatment of cancer. Another object of the invention is a complex according to the invention comprising the multispecific antibody according to the invention, which specifically binds to a hapten and a target protein, and a hapten that is conjugated to a therapeutic or diagnostic agent for use in the treatment of inflammatory diseases, autoimmune diseases, rheumatoid arthritis, psoriatic arthritis, muscle diseases (e.g. muscular dystrophy), multiple sclerosis, chronic kidney diseases, bone diseases (e.g. bone degeneration in multiple myeloma), systemic lupus erythematosus, lupus nephritis, and/or vascular injury.

Another object of the invention is an immunoconjugate comprising the multispecific antibody according to the invention coupled to a cytotoxic agent for use as a medicament. Another object of the invention is an immunoconjugate comprising the multispecific antibody according to the invention coupled to a cytotoxic agent for use in the treatment of cancer. Another object of the invention is an immunoconjugate comprising the multispecific antibody according to the invention coupled to a cytotoxic agent for use in the treatment of inflammatory diseases, autoimmune diseases, rheumatoid arthritis, psoriatic arthritis, muscle diseases (e.g. muscular dystrophy), multiple sclerosis, chronic kidney diseases, bone diseases (e.g. bone degeneration in multiple myeloma), systemic lupus erythematosus, lupus nephritis, and/or vascular injury.

Another object of the invention is the use of a multispecific antibody according to the invention for the manufacture of a medicament. Another object of the invention is the use of a multispecific antibody according to the invention for the manufacture of a medicament for the treatment of cancer. Another object of the invention is the use of a multispecific antibody according to the invention for the manufacture of a medicament for the treatment of inflammatory diseases, autoimmune diseases, rheumatoid arthritis, psoriatic arthritis, muscle diseases (e.g. muscular dystrophy), multiple sclerosis, chronic kidney diseases, bone diseases (e.g. bone degeneration in multiple myeloma), systemic lupus erythematosus, lupus nephritis, and/or vascular injury.

Another object of the invention is a method of treatment of a patient suffering from a disease by administering a multispecific antibody according to the invention to the patient in the need of such treatment. Another object of the invention is a method of treatment of a patient suffering from cancer by administering a multispecific antibody according to the invention to the patient in the need of such treatment. Another object of the invention is a method of treatment of a patient suffering from at least one of the following diseases including inflammatory diseases, autoimmune diseases, rheumatoid arthritis, psoriatic arthritis, muscle diseases (e.g. muscular dystrophy), multiple sclerosis, chronic kidney diseases, bone diseases (e.g. bone degeneration in multiple myeloma), systemic lupus erythematosus, lupus nephritis, and vascular injury; by administering a multispecific antibody according to the invention to the patient in the need of such treatment.

3. Specific Embodiments of the Invention

In the following specific embodiments of the invention are listed.
1. A multispecific antibody comprising at least three antigen binding sites, wherein two antigen binding sites are formed by a first antigen binding moiety and a second antigen binding moiety, wherein
    a) a third antigen binding site is formed by a variable heavy chain domain ($VH_3$) and a variable light chain domain ($VL_3$), wherein
        the N-terminus of the $VH_3$ domain is connected to the first antigen binding moiety via a first peptide connector, and
        the N-terminus of the $VL_3$ domain is connected to the second antigen binding moiety via a second peptide connector,
    b) the multispecific antibody comprises two constant heavy chain domains 3 (CH3), which are altered to promote heterodimerization by
        i) generation of a protuberance in one of the CH3 domains by substituting at least one original amino acid residue by an amino acid residue having a larger side chain volume than the original amino acid residue, and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains; or
            substituting at least one original amino acid residue in one of the CH3 domains by a positively charged amino acid, and substituting at least one original amino acid residue in the other one of the CH3 domains by a negatively charged amino acid;
        ii) introduction of at least one cysteine residue in each CH3 domain such that a disulfide bond is formed between the CH3 domains, or
        iii) both modifications of i) and ii);
    c) the C-terminus of the $VH_3$ domain of the third antigen binding site is connected to one of the CH3 domains, and the C-terminus of the $VL_3$ domain of the third antigen binding site is connected to the other one of the CH3 domains, and
    d) the multispecific antibody is devoid of constant heavy chain domains 2 (CH2).

2. The multispecific antibody according to embodiment 1, wherein the multispecific antibody comprises two constant heavy chain domains 3 (CH3), which are altered to promote heterodimerization by generation of a protuberance in one of the CH3 domains by substituting at least one original amino acid residue by an amino acid residue having a larger side chain volume than the original amino acid residue, and generation of a cavity in the other one of the CH3 domains by substituting at least one original amino acid residue by an amino acid residue having a smaller side chain volume than the original amino acid residue, such that the protuberance generated in one of the CH3 domains is positionable in the cavity generated in the other one of the CH3 domains.
3. The multispecific antibody according to embodiment 2, wherein said amino acid residue having a larger side chain volume than the original amino acid residue is selected from R, F, Y and W.
4. The multispecific antibody according to embodiment 2 or 3, wherein said amino acid residue having a smaller side chain volume than the original amino acid residue is selected from A, S, T and V.
5. The multispecific antibody according to any one of embodiments 2 to 4, wherein the CH3 domain of the one heavy chain comprises a T366W mutation, and the CH3 domain of the other heavy chain (the heavy chain comprising the "hole") comprises T366S, L368A and 407V mutations (numberings according to EU index of Kabat).
6. The multispecific antibody according to any one of embodiments 2 to 5, wherein the CH3 domain of the one heavy chain comprises T366W and G407Y mutations, and the CH3 domain of the other heavy chain comprises T366S, L368A and Y407V mutations (numberings according to EU index of Kabat).
7. The multispecific antibody according to embodiment 1, wherein the multispecific antibody comprises two constant heavy chain domains 3 (CH3), which are altered to promote heterodimerization by substituting at least one original amino acid residue in one of the CH3 domains by a positively charged amino acid, and substituting at least one original amino acid residue in the other one of the CH3 domains by a negatively charged amino acid.
8. The multispecific antibody according to any one of embodiments 2 to 6, wherein the multispecific antibody comprises two constant heavy chain domains 3 (CH3), which are altered to promote heterodimerization by substituting at least one original amino acid residue in one of the CH3 domains by a positively charged amino acid, and substituting at least one original amino acid residue in the other one of the CH3 domains by a negatively charged amino acid.
9. The multispecific antibody according to embodiment 7 or 8, wherein said positively charged amino acid is selected from K, R and H.
10. The multispecific antibody according to any one of embodiments 7 to 9, wherein said negatively charged amino acid is selected from E or D.
11. The multispecific antibody according to any one of embodiments 7 to 10, wherein in the CH3 domain of one heavy chain the amino acid R at position 409 (numbering according to EU index of Kabat) is substituted by D and the amino acid K at position 370 (numbering according to EU index of Kabat) is substituted by E; and in the CH3 domain of the other heavy chain the amino acid D at position 399 (numbering according to EU index of Kabat) is substituted by K and the amino acid E at position 357 (numbering according to EU index of Kabat) is substituted by K.
12. The multispecific antibody according to embodiment 2, wherein the multispecific antibody comprises two constant heavy chain domains 3 (CH3), which are altered to promote heterodimerization by introduction of at least one cysteine residue in each CH3 domain such that a disulfide bond is formed between the CH3 domains.
13. The multispecific antibody according to any one of embodiments 3 to 6, wherein the multispecific antibody comprises two constant heavy chain domains 3 (CH3), which are altered to promote heterodimerization by introduction of at least one cysteine residue in each CH3 domain such that a disulfide bond is formed between the CH3 domains.
14. The multispecific antibody according to embodiment 7, wherein the multispecific antibody comprises two constant heavy chain domains 3 (CH3), which are altered to promote heterodimerization by introduction of at least one cysteine residue in each CH3 domain such that a disulfide bond is formed between the CH3 domains.
15. The multispecific antibody according to embodiment 8, wherein the multispecific antibody comprises two constant heavy chain domains 3 (CH3), which are altered to promote heterodimerization by introduction of at least one cysteine residue in each CH3 domain such that a disulfide bond is formed between the CH3 domains.
16. The multispecific antibody according to embodiment 9 or 10, wherein the multispecific antibody comprises two constant heavy chain domains 3 (CH3), which are altered to promote heterodimerization by introduction of at least one cysteine residue in each CH3 domain such that a disulfide bond is formed between the CH3 domains.
17. The multispecific antibody according to any one of embodiments 12 to 16, wherein the CH3 domains are disulfide stabilized by a E356C or a S354C mutation in one of the CH3 domains and a Y349C mutation in the other CH3 domain (numberings according to EU index of Kabat.
18. The multispecific antibody according to any one of embodiments 12 to 16, wherein the CH3 domains are disulfide stabilized by a S354C mutation in one of the CH3 domains and a Y349C mutation in the other CH3 domain (numberings according to EU index of Kabat).
19. The multispecific antibody according to embodiment 1, wherein the third binding site is disulfide stabilized by introduction of cysteine residues at the following positions to form a disulfide bond between the $VH_3$ and $VL_3$ domains (numbering according to Kabat):
$VH_3$ at position 44, and $VL_3$ at position 100;
$VH_3$ at position 105, and $VL_3$ at position 43; or
$VH_3$ at position 101, and $VL_3$ at position 100.
20. The multispecific antibody according to embodiment 2, wherein the third binding site is disulfide stabilized by introduction of cysteine residues at the following positions to form a disulfide bond between the $VH_3$ and $VL_3$ domains (numbering according to Kabat):
$VH_3$ at position 44, and $VL_3$ at position 100;
$VH_3$ at position 105, and $VL_3$ at position 43; or
$VH_3$ at position 101, and $VL_3$ at position 100.

21. The multispecific antibody according to embodiment 7 or 8, wherein the third binding site is disulfide stabilized by introduction of cysteine residues at the following positions to form a disulfide bond between the $VH_3$ and $VL_3$ domains (numbering according to Kabat):
VH$_3$ at position 44, and VL$_3$ at position 100;
VH$_3$ at position 105, and VL$_3$ at position 43; or
VH$_3$ at position 101, and VL$_3$ at position 100.
22. The multispecific antibody according to any one of the preceding embodiments, wherein the third binding site is disulfide stabilized by introduction of cysteine residues at the following positions to form a disulfide bond between the VH$_3$ and VL$_3$ domains (numbering according to Kabat):
VH$_3$ at position 44, and VL$_3$ at position 100;
VH$_3$ at position 105, and VL$_3$ at position 43; or
VH$_3$ at position 101, and VL$_3$ at position 100.
23. The multispecific antibody according to any one of embodiments 19 to 22, wherein the third binding site is disulfide stabilized by introduction of cysteine residues in the VH$_3$ domain at position 44, and in the VL$_3$ domain at position 100.
24. The multispecific antibody according to any one of the preceding embodiments, wherein no interchain disulfide bond is formed between the first and the second peptide connector.
25. The multispecific antibody according to any one of the preceding embodiments, wherein the first and second peptide connectors are identical to each other.
26. The multispecific antibody according to any one of the preceding embodiments, wherein the first and second peptide connector are peptides of at least 15 amino acids.
27. The multispecific antibody according to any one of the preceding embodiments, wherein the first and second peptide connector are peptides of 15-70 amino acids.
28. The multispecific antibody according to any one of embodiments 1 to 25, wherein the first and second peptide connector are peptides of 10-20 amino acids.
29. The multispecific antibody according to any one embodiments 1 to 27, wherein the first and second peptide connector are peptides of 55-70 amino acids.
30. The multispecific antibody according to any one of the preceding embodiments, wherein the peptide connectors are glycine-serine linkers.
31. The multispecific antibody according to embodiment 30, wherein the glycine-serine linkers are of the structure (GxS)n or (GxS)nGm with G=glycine, S=serine, x=3 or 4, n=2, 3, 4, 5 or 6, and m=0, 1, 2 or 3.
32. The multispecific antibody according to any one of the preceding embodiments, wherein the variable domains VH$_3$ and VL$_3$ are directly connected to the respective CH3 domains without the aid of a peptide connector.
33. The multispecific antibody according to any one of the preceding embodiments, wherein the C-terminus of the VH$_3$ domain is directly connected to one of the CH3 domains, and the C-terminus of the VL$_3$ domain is directly connected to the other one of the CH3 domains, wherein the connection sites are devoid of an additional linker peptide.
34. The multispecific antibody according to any one of the preceding embodiments, wherein the N-terminus of the CH3 domain is modified by substituting at least one original amino acid residue.
35. The multispecific antibody according to embodiment 34, wherein at least one amino acid residue located at positions 341 to 350 of the CH3 domains (numbering according to EU index of Kabat) is substituted.
36. The multispecific antibody according to embodiment 34 or 35, wherein the N-terminus of the CH3 domain consists of an amino acid sequence according to SEQ ID NO: 2, SEQ ID NO: 3 or SEQ ID NO: 4.
37. The multispecific antibody according to any one of the preceding embodiments, wherein the C-terminus of the VH$_3$ domain is modified by substituting at least one original amino acid residue.
38. The multispecific antibody according to any one of the preceding embodiments, wherein the C-terminus of the VL$_3$ domain is modified by substituting at least one original amino acid residue.
39. The multispecific antibody according to any one of the preceding embodiments, wherein the N-terminus of each one of the CH3 domains includes at least one amino acid mutation, the C-terminus of the VH$_3$ domain includes at least one amino acid mutation, and C-terminus of the VL$_3$ domain includes at least one amino acid mutation.
40. The multispecific antibody according to any one of the preceding embodiments, wherein the antigen binding moiety is a protein specifically binding to an antigen.
41. The multispecific antibody according to embodiment 40, wherein the antigen binding moiety is selected from the group of antibodies, receptors, ligands, and DARPins capable of specifically binding to an antigen.
42. The multispecific antibody according to embodiment 40, wherein the antigen binding moiety is an antibody or an antibody fragment.
43. The multispecific antibody according to embodiment 42, wherein at least one of the first and the second antigen binding moiety is a Fab fragment.
44. The multispecific antibody according to embodiment 42, wherein the first and the second antigen binding moiety are Fab fragments.
45. The multispecific antibody according to embodiment 44, wherein the constant light chain domain of the first and/or the second Fab fragment is of kappa isotype.
46. The multispecific antibody according to embodiment 44, wherein the constant light chain domain of the first and/or the second Fab fragment is of lambda isotype.
47. The multispecific antibody according to embodiment 44, wherein the constant light chain domain of the first Fab fragment is of kappa isotype and the constant light chain domain of the second Fab fragment is of lambda isotype.
48. The multispecific antibody according to embodiment 43 or 44, wherein at least one Fab fragment is disulfide-stabilized.
49. The multispecific antibody according to embodiment 44, wherein the Fab fragments are disulfide-stabilized.
50. The multispecific antibody according to embodiment 43 or 44, wherein the Fab fragments are disulfide stabilized by introduction of cysteine residues at the following positions to form a disulfide bond between the corresponding VH and VL domains (numbering according to Kabat):
VH at position 44, and VL at position 100;
VH at position 105, and VL at position 43; or
VH at position 101, and VL at position 100.

51. The multispecific antibody according to any one of embodiments 48 to 50, wherein the natural disulfide bond between the polypeptide chains of the respective Fab fragment is abolished by substituting at least one of the interchain disulfide-bond-forming cysteine residues by another amino acid residue.

52. The multispecific antibody according to embodiment 43, 44 or 48, wherein at least one Fab fragment is a single chain Fab fragment.

53. The multispecific antibody according to embodiment 43, 44 or 48, wherein at least one Fab fragment is altered by a domain crossover, such that either:
   a) only the CH1 and CL domains are replaced by each other;
   b) only the VH and VL domains are replaced by each other; or
   c) the CH1 and CL domains are replaced by each other and the VH and VL domains are replaced by each other,
   with the provision that in case both the first Fab fragment and the second Fab fragment are altered by a domain crossover, they are altered by different domain crossovers.

54. The multispecific antibody according to any one of the preceding embodiments, wherein the antibody is trivalent.

55. The multispecific antibody according to any one of the preceding embodiments, wherein the antibody comprises at least one polyepitopic binding site.

56. The multispecific antibody according to any one of the preceding embodiments, wherein the antibody is trivalent.

57. The multispecific antibody according to any one of the preceding embodiments, wherein the antibody comprises three binding sites each one binding to a single epitope.

58. The multispecific antibody according to any one of the preceding embodiments, wherein the antibody is bispecific or trispecific.

59. The multispecific antibody according to any one of the preceding embodiments, wherein the antibody comprises at least one binding site specifically binding to a hapten.

60. The multispecific antibody according to any one of the preceding embodiments, wherein the antibody comprises exactly one binding site specifically binding to a hapten.

61. The multispecific antibody according to any one of the preceding embodiments, wherein the antibody comprises at least one binding site specifically binding to a target protein.

62. The multispecific antibody according to embodiment 61, wherein the target protein is a cell surface or an intracellular tumor-associated antigen.

63. The multispecific antibody according to any one of the preceding embodiments, wherein the antibody comprises at least one binding site specifically binding to a hapten and at least one binding site specifically binding to a target protein.

64. A complex comprising
   (i) the multispecific antibody according to embodiment 63, wherein the multispecific antibody specifically binds to a hapten and a target protein,
   (ii) the hapten, which is specifically bound by the multispecific antibody, wherein the hapten is conjugated to a therapeutic or diagnostic agent.

65. The complex according to embodiment 64, wherein the hapten is selected from digoxigenin, biotin, theophylline, fluorescein, DOTA, and DOTAM.

66. The complex according to embodiment 64 or 65, wherein the target protein is a cell surface antigen or an intracellular antigen.

67. The complex according to embodiment 66, wherein the target protein is a cell surface or an intracellular tumor-associated antigen.

68. The complex according to any one of embodiments 64 to 67, wherein the therapeutic or diagnostic agent coupled to the hapten is selected from the group consisting of a peptide, a protein, a small molecule, a radioactively labeled small molecule, a nucleic acid and an imaging agent.

69. A method for the preparation of the multispecific antibody according to any one of embodiments 1 to 63, comprising the steps of
   transforming a host cell with expression vectors comprising nucleic acids encoding the multispecific antibody,
   culturing said host cell under conditions that allow synthesis of said multispecific antibody, and
   recovering said multispecific antibody from said host cell culture.

70. The method according to claim 69, further including the step of purification of the multispecific antibody via affinity chromatography on a kappa light chain or lambda light chain specific column.

71. A multispecific antibody produced by the method according to embodiment 69 or 70.

72. A method for the preparation of a complex, including the steps of
   providing a multispecific antibody according to embodiments 63, wherein the multispecific antibody specifically binds to a hapten and a target protein,
   providing a hapten, which is specifically bound by the multispecific antibody, wherein the hapten is conjugated to a therapeutic or diagnostic agent, and
   contacting the multispecific antibody with the hapten, which is conjugated to the therapeutic or diagnostic agent.

73. A complex produced by the method according to embodiment 72.

74. A nucleic acid encoding the multispecific antibody according to any one of embodiments 1 to 63.

75. An expression vector comprising a nucleic acid according to embodiment 73.

76. A host cell comprising a nucleic acid according to embodiment 74.

77. A host cell comprising an expression vector according to embodiment 75.

78. A composition comprising the multispecific antibody according to any one of embodiments 1 to 63.

79. A pharmaceutical or diagnostic composition comprising the multispecific antibody according to any one of embodiments 1 to 63.

80. A pharmaceutical composition comprising the multispecific antibody according to any one of embodiments 1 to 63 in combination with at least one pharmaceutically acceptable carrier.

81. A composition comprising the complex according to any one of embodiments 64 to 68.

82. A pharmaceutical or diagnostic composition comprising the complex according to any one of embodiments 64 to 68.

83. A pharmaceutical composition comprising the complex according to any one of embodiments 64 to 68 in combination with at least one pharmaceutically acceptable carrier.
84. A diagnostic composition comprising the complex according to any one of embodiments 64 to 68.
85. An immunoconjugate comprising the multispecific antibody according to any one of embodiments 1 to 63 coupled to a cytotoxic agent.
86. The immunoconjugate according to embodiment 85, wherein the multispecific antibody specifically binds to a cell surface tumor-associated antigen or an intracellular tumor-associated antigen.
87. A composition comprising the immunoconjugate according to embodiment 85 or 86.
88. A pharmaceutical or diagnostic composition comprising the immunoconjugate according to embodiment 85 or 86.
89. A pharmaceutical composition comprising the immunoconjugate according to embodiment 85 or 86 in combination with at least one pharmaceutically acceptable carrier.
90. A pharmaceutical composition comprising the multispecific antibody according to embodiment 62, or a complex according to any one of embodiments 64 to 68, or an immunoconjugate according to embodiment 86, in combination with at least one pharmaceutically acceptable carrier
91. The multispecific antibody according to any one of embodiments 1 to 63 for use as a medicament.
92. The multispecific antibody according to embodiment 62 for use as a medicament.
93. The multispecific antibody according to embodiment 62 for use as in the treatment of cancer.
94. The complex according to any one of embodiments 64 to 68 for use as a medicament.
95. The complex according to any one of embodiments 64 to 68 for use in the treatment of cancer.
96. The immunoconjugate according to embodiment 85 or 86 for use as a medicament.
97. The immunoconjugate according to embodiment 86 for use as a medicament.
98. The immunoconjugate according to embodiment 85 or 86 for the treatment of cancer.
99. Use of the multispecific antibody according to any one of embodiments 1 to 63 for diagnostic purposes.
100. Use according to embodiment 99 for imaging.
101. A method of treatment of a patient suffering from a disease by administering a multispecific antibody according to any one of embodiments 1 to 63 to the patient in the need of such treatment.
102. A method of treatment of a patient suffering from a disease by administering a multispecific antibody according to any one of embodiments 62 or 63 to the patient in the need of such treatment.
103. The method according to embodiment 102, wherein the disease is cancer.
104. A method of treatment of a patient suffering from a disease by administering a complex according to any one of embodiments 64 to 68 to the patient in the need of such treatment.
105. The method according to embodiment 104, wherein the disease is cancer.
106. A method of treatment of a patient suffering from a disease by administering an immunoconjugate according to embodiment 85 or 86 to the patient in the need of such treatment.
107. A method of treatment of a patient suffering from a disease by administering an immunoconjugate according to embodiment 86 to the patient in the need of such treatment.
108. The method according to embodiment 106 or 107, wherein the disease is cancer.
109. The method according to any one of embodiments 101, 104 and 106, wherein the disease is selected from inflammatory diseases, autoimmune diseases, rheumatoid arthritis, psoriatic arthritis, muscle diseases, multiple sclerosis, chronic kidney diseases, bone diseases, systemic lupus erythematosus, lupus nephritis, and/or vascular injury.

DESCRIPTION OF THE AMINO ACID SEQUENCES

SEQ ID NO: 1 exemplary fusion site of <anti-DIG> $VL_3$—CH3 fusion site of an antibody according to example 1
SEQ ID NO: 2 N-terminus of CH3 domains (alternative 1)
SEQ ID NO: 3 N-terminus of CH3 domains (alternative 2)
SEQ ID NO: 4 N-terminus of CH3 domains (alternative 3)
SEQ ID NO: 5 light chain polypeptide with digoxigenin binding site
SEQ ID NO: 6 polypeptide VH—CH1-linker-$VH_3$—CH3 of BsAb Dig-LeY-Dig
SEQ ID NO: 7 polypeptide VH—CH1-linker-$VL_3$—CH3 of BsAb Dig-LeY-Dig
SEQ ID NO: 8 light chain polypeptide with Lewis Y binding site
SEQ ID NO: 9 polypeptide VH—CH1-linker-$VH_3$—CH3 of BsAb LeY-Dig(SS)-LeY
SEQ ID NO: 10 polypeptide VH—CH1-linker-$VL_3$—CH3 of BsAb LeY-Dig(SS)-LeY
SEQ ID NO: 11 polypeptide VH—CH1-linker-$VH_3$—CH3 of BsAb Dig-CD33-Dig
SEQ ID NO: 12 polypeptide VH—CH1-linker-$VL_3$—CH3 of BsAb Dig-CD33-Dig
SEQ ID NO: 13 light chain polypeptide with CD33 binding site
SEQ ID NO: 14 polypeptide VH—CH1-linker-$VH_3$—CH3 of BsAb CD33-Dig(SS)-CD33
SEQ ID NO: 15 polypeptide VH—CH1-linker-$VL_3$—CH3 of BsAb CD33-Dig(SS)-CD33
SEQ ID NO: 16 polypeptide VH—CH1-linker-$VH_3$—CH3 of BsAb Dig-GPC3-Dig
SEQ ID NO: 17 polypeptide VH—CH1-linker-$VL_3$—CH3 of BsAb Dig-GPC3-Dig
SEQ ID NO: 18 light chain polypeptide with Glypican 3 binding site
SEQ ID NO: 19 polypeptide VH—CH1-linker-$VH_3$—CH3 of BsAb GPC3-Dig(SS)-GPC3
SEQ ID NO: 20 polypeptide VH—CH1-linker-$VL_3$—CH3 of BsAb GPC3-Dig(SS)-GPC3
SEQ ID NO: 21 polypeptide VH—CH1-linker-$VH_3$—CH3 of BsAb LeY-Bio(SS)-LeY
SEQ ID NO: 22 polypeptide VH—CH1-linker-$VL_3$—CH3 of BsAb LeY-Bio(SS)-LeY
SEQ ID NO: 23 polypeptide VH—CH1-linker-$VH_3$—CH3 of BsAb CD33-Bio(SS)-CD33
SEQ ID NO: 24 polypeptide VH—CH1-linker-$VL_3$—CH3 of BsAb CD33-Bio(SS)-CD33
SEQ ID NO: 25 polypeptide VH—CH1-linker-$VH_3$—CH3 of BsAb GPC3-Bio(SS)-GPC3
SEQ ID NO: 26 polypeptide VH—CH1-linker-$VL_3$—CH3 of BsAb GPC3-Bio(SS)-GPC3
SEQ ID NO: 27 light chain polypeptide with Biotin binding site
SEQ ID NO: 28 polypeptide VH—CH1-linker-$VH_3$—CH3 of BsAb Bio-LeY(SS)-Bio
SEQ ID NO: 29 polypeptide VH—CH1-linker-$VL_3$—CH3 of BsAb Bio-LeY(SS)-Bio
SEQ ID NO: 30 polypeptide VH—CH1-linker-$VH_3$—CH3 of BsAb Bio-CD33(SS)-Bio
SEQ ID NO: 31 polypeptide VH—CH1-linker-$VL_3$—CH3 of BsAb Bio-CD33(SS)-Bio
SEQ ID NO: 32 polypeptide VH—CH1-linker-$VH_3$—CH3 of BsAb Bio-GPC3(SS)-Bio
SEQ ID NO: 33 polypeptide VH—CH1-linker-$VL_3$—CH3 of BsAb Bio-GPC3(SS)-Bio -continued SEQ ID NO: 34 polypeptide VH—CH1-linker-VH$_3$—CH3 of BsAb Dig-LeY(SS)-Dig
SEQ ID NO: 35 polypeptide VH—CH1-linker-VL$_3$—CH3 of BsAb Dig-LeY(SS)-Dig
SEQ ID NO: 36 polypeptide VH—CH1-linker-VH$_3$—CH3 of BsAb Dig-CD33(SS)-Dig
SEQ ID NO: 37 polypeptide VH—CH1-linker-VL$_3$—CH3 of BsAb Dig-CD33(SS)-Dig
SEQ ID NO: 38 polypeptide VH—CH1-linker-VH$_3$—CH3 of BsAb Dig-GPC3(SS)-Dig
SEQ ID NO: 39 polypeptide VH—CH1-linker-VL$_3$—CH3 of BsAb Dig-GPC3(SS)-Dig

EXAMPLES

The following examples are provided to aid the understanding of the present invention, the true scope of which is set forth in the appended claims. It is understood that modifications can be made in the procedures set forth without departing from the spirit of the invention.

Example 1

Production and expression of trivalent, bispecific antibodies according to the invention specifically binding to digoxigenin (Dig) and one of the cell surface antigens Lewis-Y (LeY), CD33 and glypican3 (GPC3)

Figure 2A:
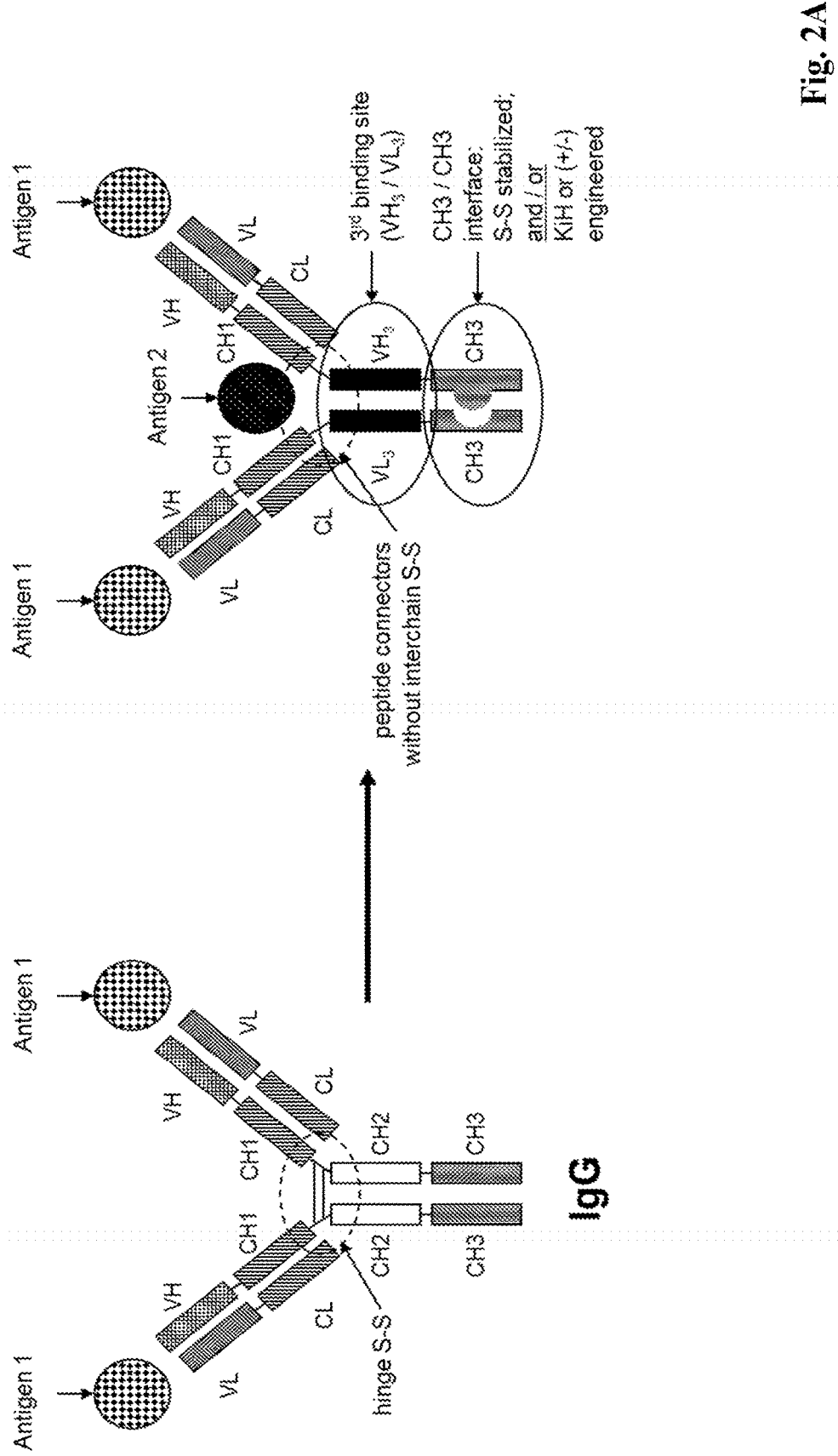
FIGS. 2A and 2B: Design of multispecific antibodies according to the invention comprising a first Fab fragment and a second Fab fragment.

Bispecific antibodies comprising three antigen binding sites were designed in an IgG-like structure being composed of two regular Fab arms as first and second binding moieties, which were fused via flexible glycine-serine peptide linkers to a third approximately Fab-sized binding module. This third binding module replaces the original IgG Fc region of a full length antibody and is composed of a variable heavy chain domain VH$_3$ fused to a first CH3 domain, and a variable light chain domain VL$_3$ fused to a second CH3 domain (FIG. 2A). The domain architecture of the bispecific antibodies is indicated in FIGS. 2A and 2B (illustrating antibodies with and without an additional disulfide bond present within the third binding site).

The amino acid sequences of the third binding module, in particular the fusion site of the CH3 domains with either VH$_3$ or VL$_3$ were designed in a manner that possesses no strain or sterical disturbance on the overall IgG like structure, and retains IgG like properties.

The Fab fragments are fused to third binding module via peptide connectors that are designed to replace the original hinge region of a full length IgG (FIGS. 4A and 4B). The peptide connectors do not contain interchain disulfide bridges, which facilitates antigen access to the third binding site. Loss of hinge disulfide bridges however also destabilizes the antibody derivative as it removes the covalent interchain connection. To compensate the loss of hinge-disulfides, and to regain stability, heterodimerization strategies to promote heterodimerization of the domains of the third binding module were applied (see FIG. 2A).

Figure 2B:
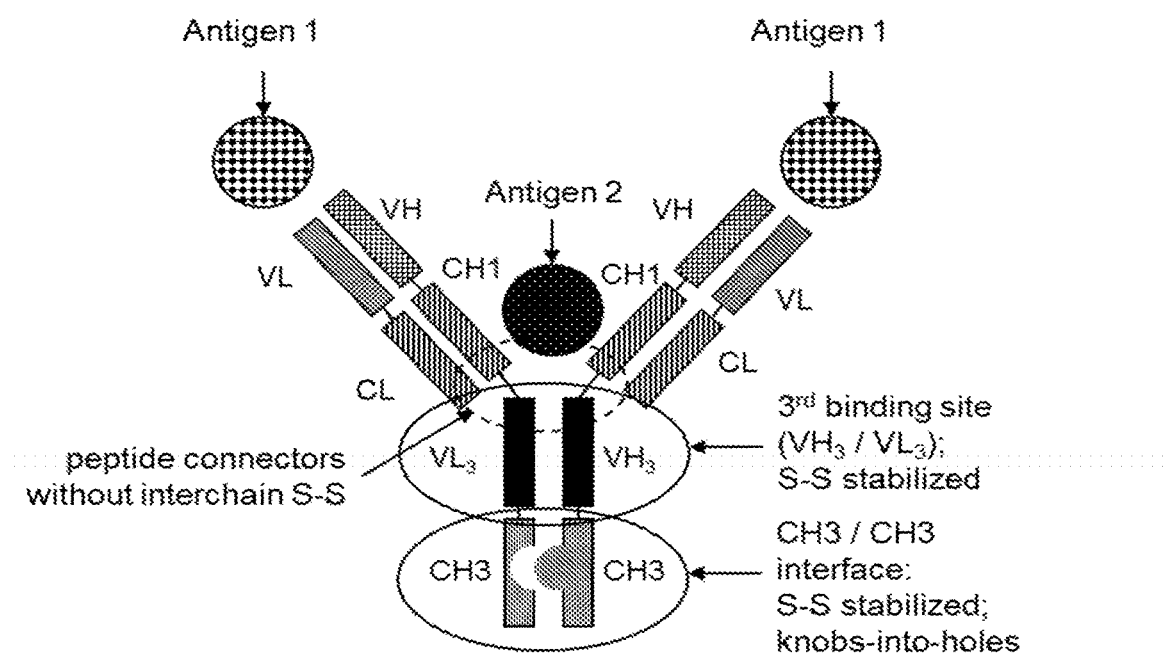
Figure 3A:
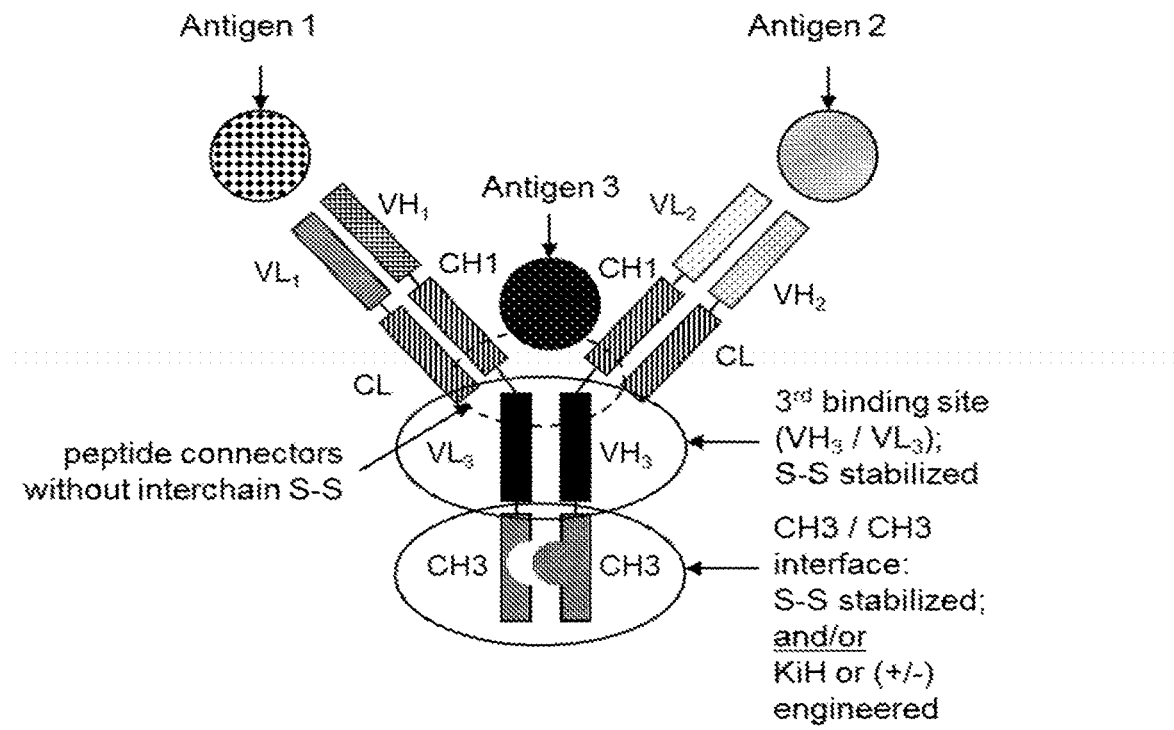
FIGS. 3A-3H: Exemplary multispecific antibodies according to the invention.
Figure 3B:
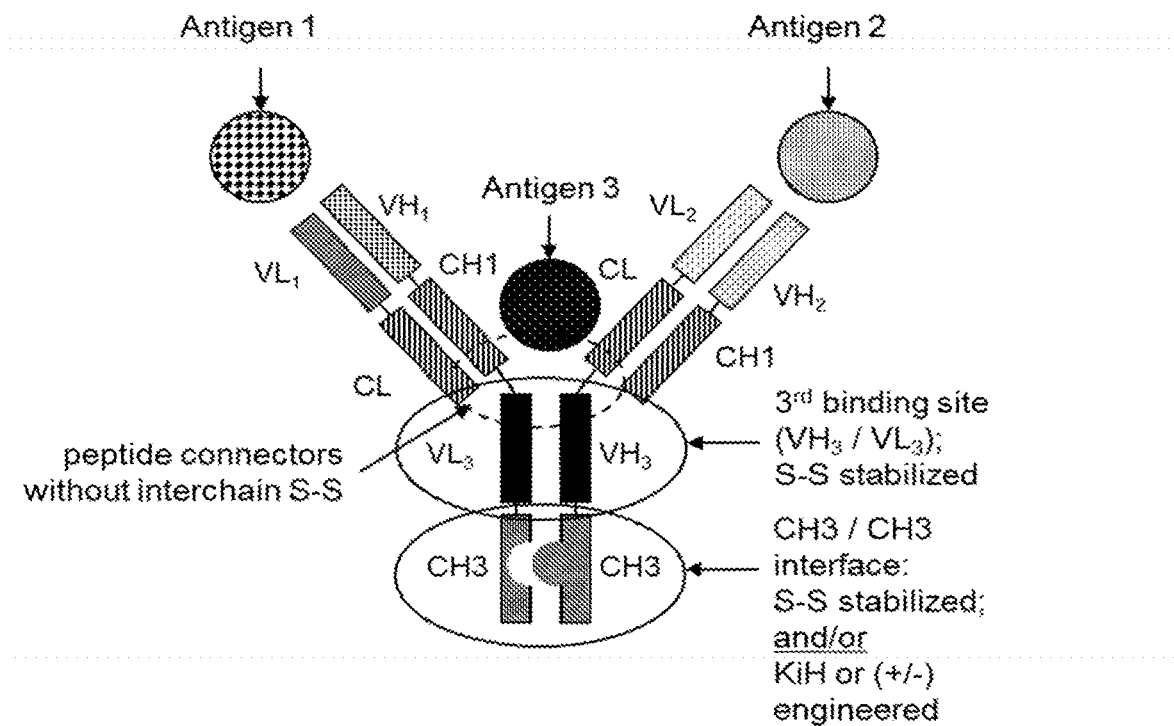
Figure 3C:
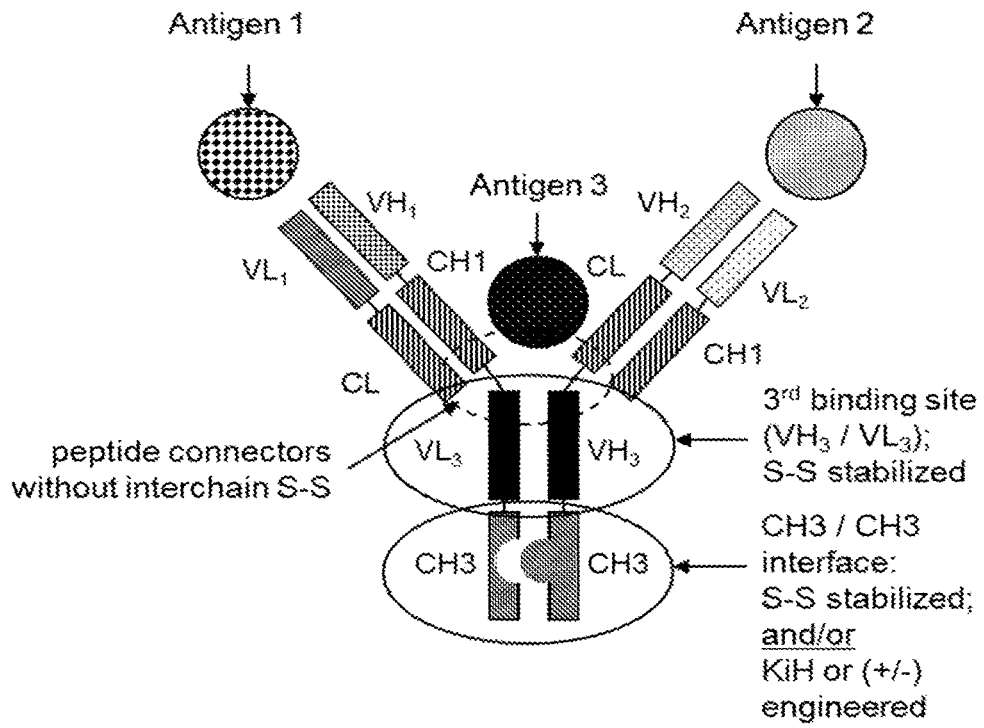
Figure 3D:
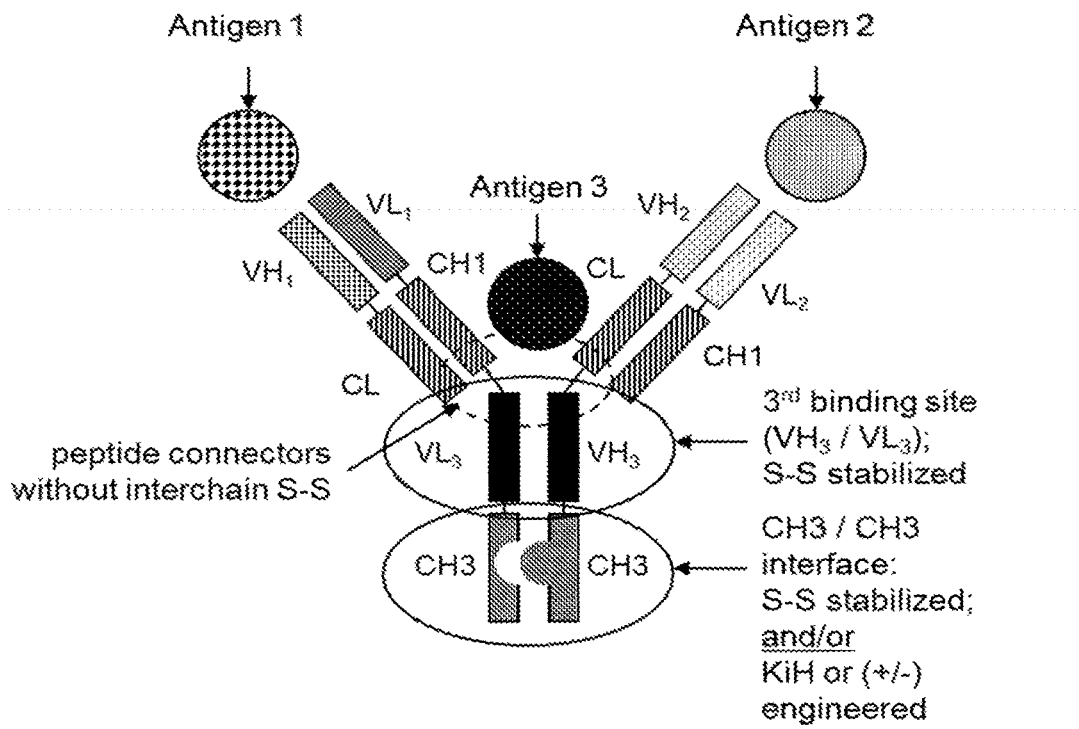
Figure 3E:
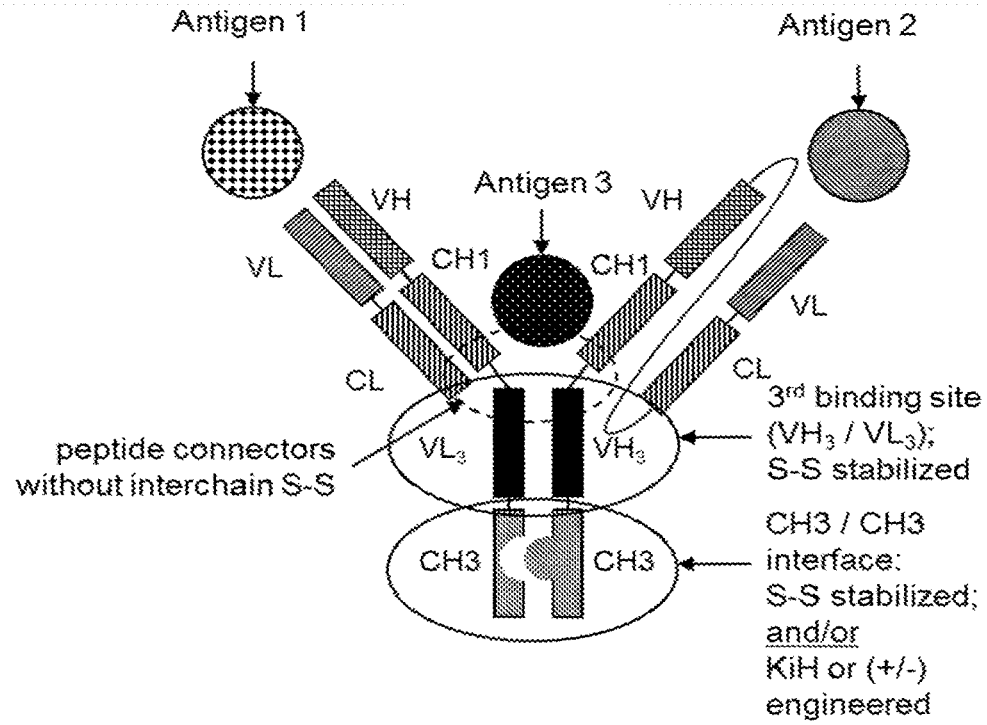
Figure 3F:
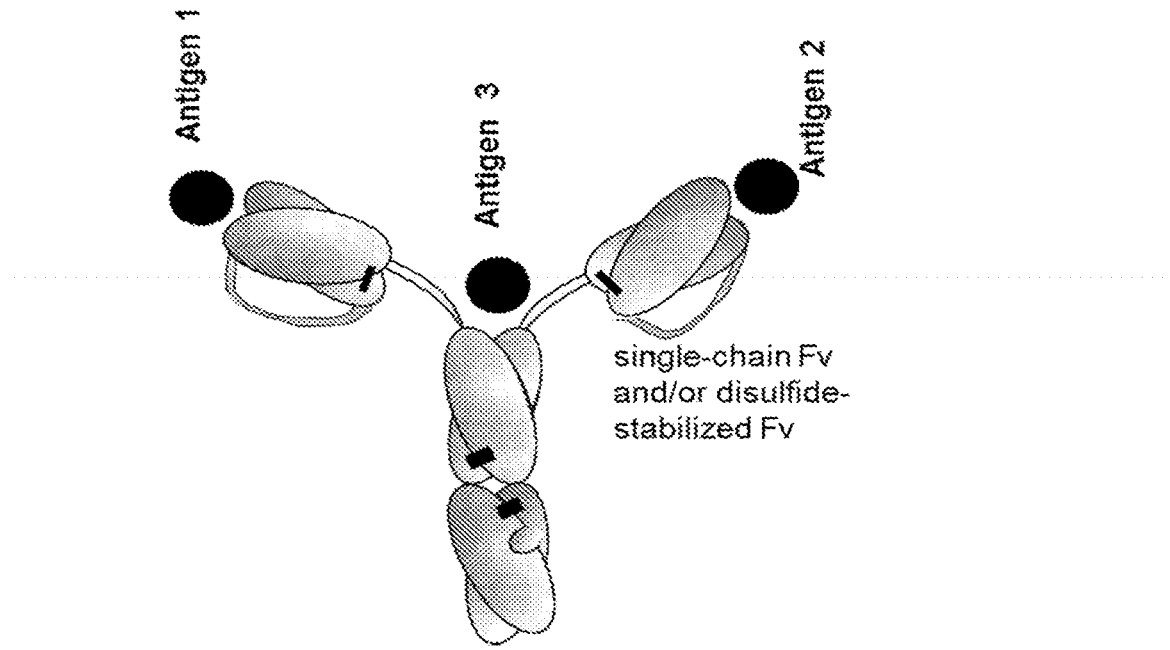
Figure 3G:
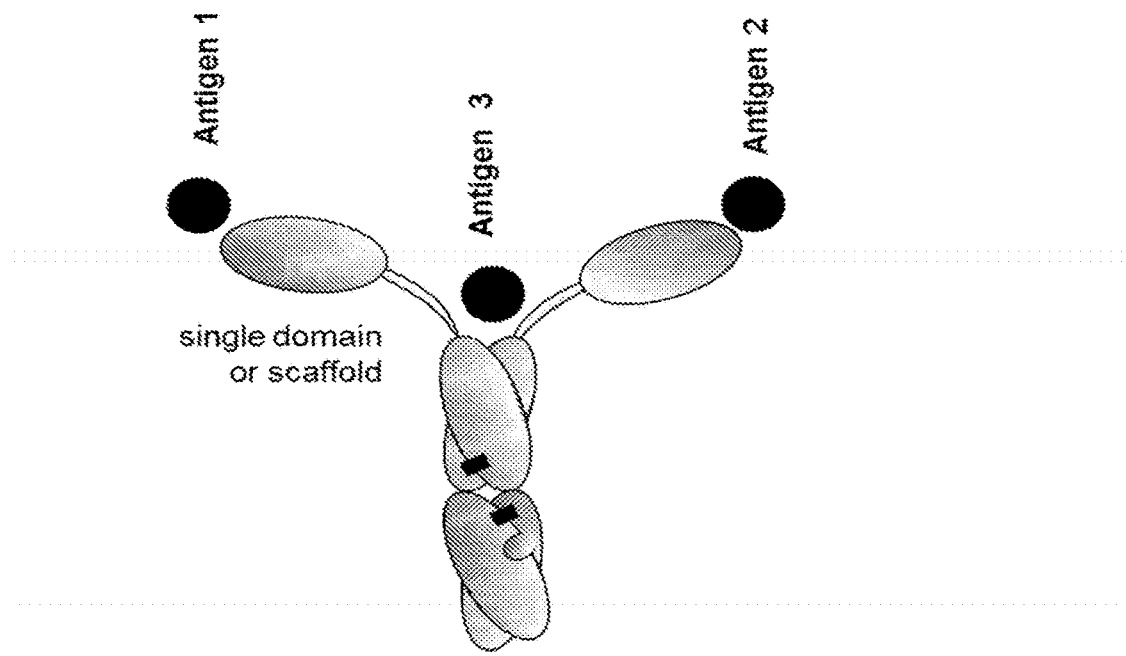
Figure 3H:
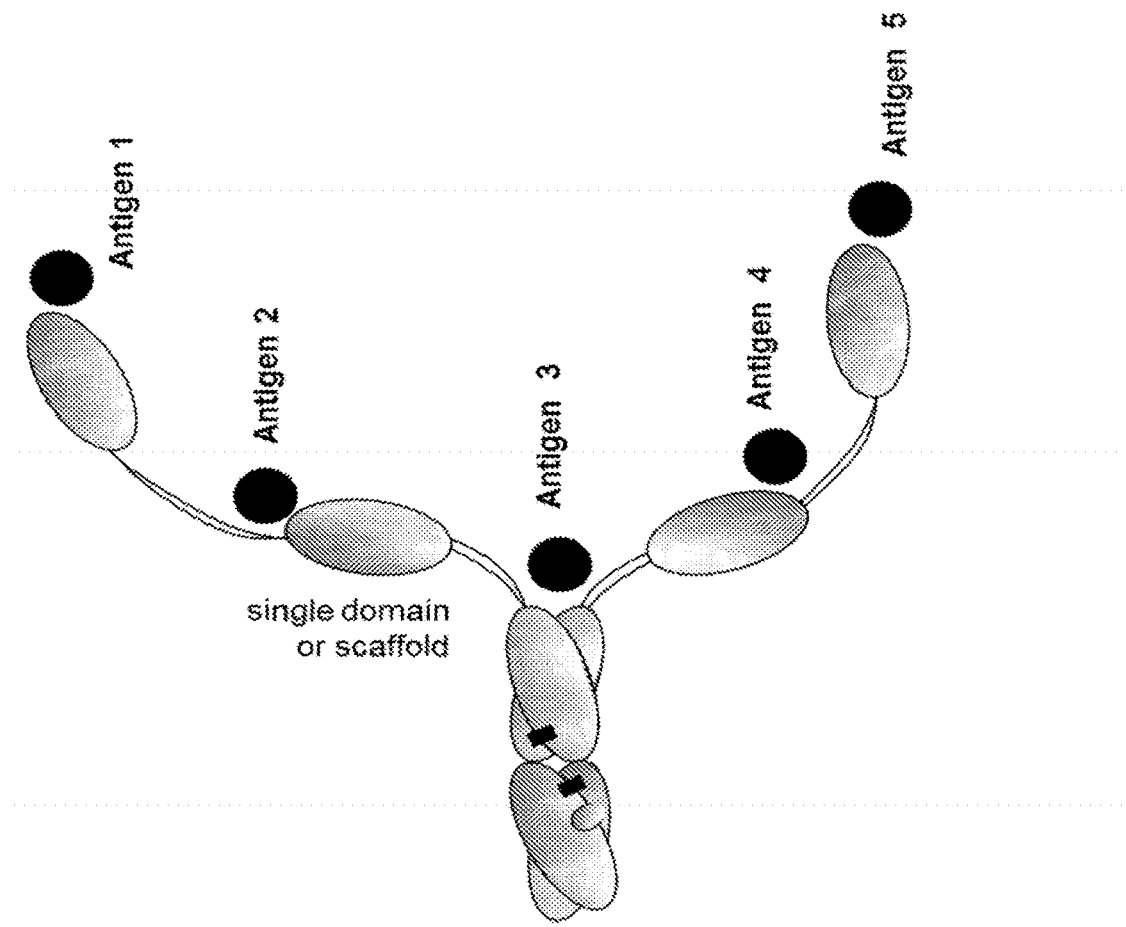

The bispecific antibody molecules generated in this example comprise disulfide-stabilized CH3-domains with either a "knob" (protuberance) or a "hole" (cavity) modification (FIGS. 2A and 2B). Within this examples, antibodies with and without disulfide-stabilization in the VH$_3$ and VL$_3$ domains were provided (see Table 4).

The bispecific antibodies according to Table 3 were generated by classical molecular biology techniques and expressed transiently in HEK293 suspension cells.

Briefly, the antibodies were produced by co-transfection of expression vectors that encode the light chains of the desired antibodies with expression vectors encoding the two corresponding "heavy chains" (i.e. the polypeptides of the domain structures VH-CH1-linker-VH$_3$-CH3 and VH-CH1-linker-VL3-CH3, respectively). The expression cassettes, plasmid properties and conditions for transient expression were the same as described by Metz et al. Protein Engineering Design and Selection 09/2012; 25(10):571-8 and in WO 2012025525 A1, both documents are herein included by reference. The polypeptide components of the antibodies were expressed by CMV promoter driven transcription in HEK293 suspension cells that were grown at 37° C. in a humidified 8% $CO_2$ environment. 7 days after transfection, culture supernatants that contained the secreted bispecific antibodies were sterile filtered.

TABLE 1

Domain architecture of indicated bispecific antibodies

| molecule name | Fab fragments derived from | 3$^{rd}$ binding site derived from |
|---|---|---|
| BsAb Dig-LeY-Dig | <Dig> | <LeY> |
| BsAb LeY-Dig(SS)-LeY | <LeY> | <Dig> |
| BsAb Dig-CD33-Dig | <Dig> | <CD33> |
| BsAb CD33-Dig(SS)-CD33 | <CD33> | <Dig> |
| BsAb Dig-GPC3-Dig | <Dig> | <GPC3> |
| BsAb GPC3-Dig(SS)-GPC3 | <GPC3> | <Dig> |

The bispecific antibodies included the characteristics indicated in Table 4. All constructs comprised constant light chain domains of kappa isotype. In addition, in all constructs, the "knobs" substitutions were introduced in the CH3 domain fused to VH$_3$ and the "hole" substitutions were introduced in the CH3 domain fused to VL$_3$. However with the same effect, the "knob" may be introduced into the CH3 domain fused to VL$_3$ and the "hole" may be introduced into the CH3 domain fused to VH$_3$.

TABLE 2

Characteristics of indicated bispecific antibodies

| molecule name | 1$^{st}$ and 2$^{nd}$ peptide connector | S—S bond between VH$_3$ and VL$_3$ | knobs-into-holes substitutions in CH3/CH3 interface | S—S between CH3 and CH3 |
|---|---|---|---|---|
| BsAb Dig-LeY-Dig | (Gly$_4$Ser)$_4$ | — | Trp366, Tyr407 (knob); Ser366, Ala368, Val407 (hole) | Cys354 (knob); Cys349 (hole) |
| BsAb LeY-Dig(SS)-LeY | (Gly$_4$Ser)$_4$ | VH$_3$ Cys44 VL$_3$ Cys100 | Trp366, Tyr407 (knob); Ser366, Ala368, Val407 (hole) | Cys354 (knob); Cys349 (hole) |
| BsAb Dig-CD33-Dig | (Gly$_4$Ser)$_4$ | — | Trp366, Tyr407 (knob); Ser366, Ala368, Val407 (hole) | Cys354 (knob); Cys349 (hole) |
| BsAb CD33-Dig(SS)-CD33 | (Gly$_4$Ser)$_4$ | VH$_3$ Cys44 VL$_3$ Cys100 | Trp366, Tyr407 (knob); Ser366, Ala368, Val407 (hole) | Cys354 (knob); Cys349 (hole) |
| BsAb Dig-GPC3-Dig | (Gly$_4$Ser)$_4$ | — | Trp366, Tyr407 (knob); Ser366, Ala368, Val407 (hole) | Cys354 (knob); Cys349 (hole) |

TABLE 2-continued

Characteristics of indicated bispecific antibodies

| molecule name | 1st and 2nd peptide connector | S—S bond between VH₃ and VL₃ | knobs-into-holes substitutions in CH3/CH3 interface | S—S between CH3 and CH3 |
|---|---|---|---|---|
| BsAb GPC3-Dig(SS)-GPC3 | (Gly₄Ser)₄ | VH₃ Cys44 VL₃ Cys100 | Trp366, Tyr407 (knob); Ser366, Ala368, Val407 (hole) | Cys354 (knob); Cys349 (hole) |

The amino acid sequences of the polypeptide chains of the tested bispecific antibodies are indicated in Table 5.

TABLE 3

Amino acid sequences of polypeptide chains of indicated bispecific antibodies

| molecule name | light chains SEQ ID NO: | polypeptide VH—CH1-linker-VH₃—CH3 SEQ ID NO: | polypeptide VH—CH1-linker-VL₃—CH3 SEQ ID NO: |
|---|---|---|---|
| BsAb Dig-LeY-Dig | 5 | 6 | 7 |
| BsAb LeY-Dig(SS)-LeY | 8 | 9 | 10 |
| BsAb Dig-CD33-Dig | 5 | 11 | 12 |
| BsAb CD33-Dig(SS)-CD33 | 13 | 14 | 15 |
| BsAb Dig-GPC3-Dig | 5 | 16 | 17 |
| BsAb GPC3-Dig(SS)-GPC3 | 18 | 19 | 20 |

Example 2

Purification and Characterization of Trivalent, Bispecific Antibodies According to the Invention The bispecific antibodies expressed above in example 1 were purified from the supernatant by affinity chromatography via a HITRAP® KappaSelect column (GE Healthcare), as due to the lack of CH2 domains the bispecific antibodies do not bind to protein A. In a second purification step, homogeneous bispecific antibodies were obtained by applying size exclusion chromatography equilibrated with 20 mM histidin, 140 mM NaCl, at pH 6.0 as previously described for IgG-derived bispecific antibodies (S. Metz et al., Proc. Natl. Acad. Sci. U.S.A 108 (2011) 8194-8199).

Exemplary results of these purification steps for bispecific antibodies with different specificities as indicated in Table 3 are shown in FIGS. 6A and 6B. SDS PAGE analyses that demonstrate identity and purity of the generated multispecific antibodies are also shown in FIGS. 6A and 6B.

The bispecific antibodies could be generated by the described production and purification method with yields between 3-20 mg/L, as indicated in detail in Table 6.

TABLE 4

Yield of indicated bispecific antibodies

| molecule name | Yield [mg/L] |
|---|---|
| BsAb Dig-LeY-Dig | 5.7 |
| BsAb LeY-Dig(SS)-LeY | 3.0 |
| BsAb Dig-CD33-Dig | 6.9 |
| BsAb CD33-Dig(SS)-CD33 | 20.3 |
| BsAb Dig-GPC3-Dig | 8.3 |
| BsAb GPC3-Dig(SS)-GPC3 | 3.5 |

Example 3

Design of Complex Disulfide Pattern to Promote Heterodimerization

Within the bispecific antibodies generated in example 1, heterodimerization of the third binding module is promoted by four distinct interactions: (i) the interaction between VH₃ and VL₃, (ii) the disulfide stabilization in the VH₃/VL₃ interface, (iii) the disulfide stabilization in the CH3/CH3 interface; and (iv) the knobs-into-holes modifications in the CH3/CH3 interface (which may be alternatively replaced by other comparable heterodimerization strategies known to support interaction of CH3 domains, like e.g. the introduction of oppositely charged amino acids within the CH3/CH3 interface). By this, formation of heterodimers rather than homodimer formation is promoted.

As the disulfide stabilizations of the VH₃/VL₃ as well as the CH3/CH3 interface required introduction of additional disulfides in close proximity, it was necessary to avoid the formation of mispaired disulfides during the production process leading to misfolded and non-functional molecules (FIG. 5A).

As it is well-known, wild type full length IgG possess one intrachain disulfide bond within each of its domains as well as interchain disulfide bonds to connect the heavy chains via the hinge regions of the antibody. The hinge region cysteines do not interfere with folding of the individual antibody domains and do not interact in intradomain disulfide formation.

However, within antibodies according to the invention comprising disulfide stabilizations within the VH₃/VL₃ interface as well as in the CH3/CH3 interface, additional unpaired cysteines are introduced, which in order to assure correct folding must not pair with intrachain disulfide bond forming cysteines but instead must form defined separate interdomain bonds. Within the antibodies according to the invention, the variable domains are directly connected to their respective CH3 domains (i.e. by peptide bond formation between amino acids of a variable domain with an amino acid of a CH3 domain, without including a peptide linker). It was expected that such a sequence composition and close proximity of cysteine residues (including the natural and the additionally introduced cysteine residues) would favor to a large degree the formation of mispaired disulfides (FIG. 5A).

Therefore, a fusion site between the variable domains (VH₃ and VL₃) and their respective CH3 domains was created (FIG. 5B), which allows correct disulfide bond formation and avoids disulfide mispairing. In each polypeptide chain of the third binding module, the cysteine residues necessary for the additional disulfide stabilization are in close proximity to cysteine residues required for intrachain disulfide bond formation, but nevertheless surprisingly do not interfere with the intrachain disulfides and pair with the correct corresponding cysteine residue in the other polypeptide chain.

Figure 5B:
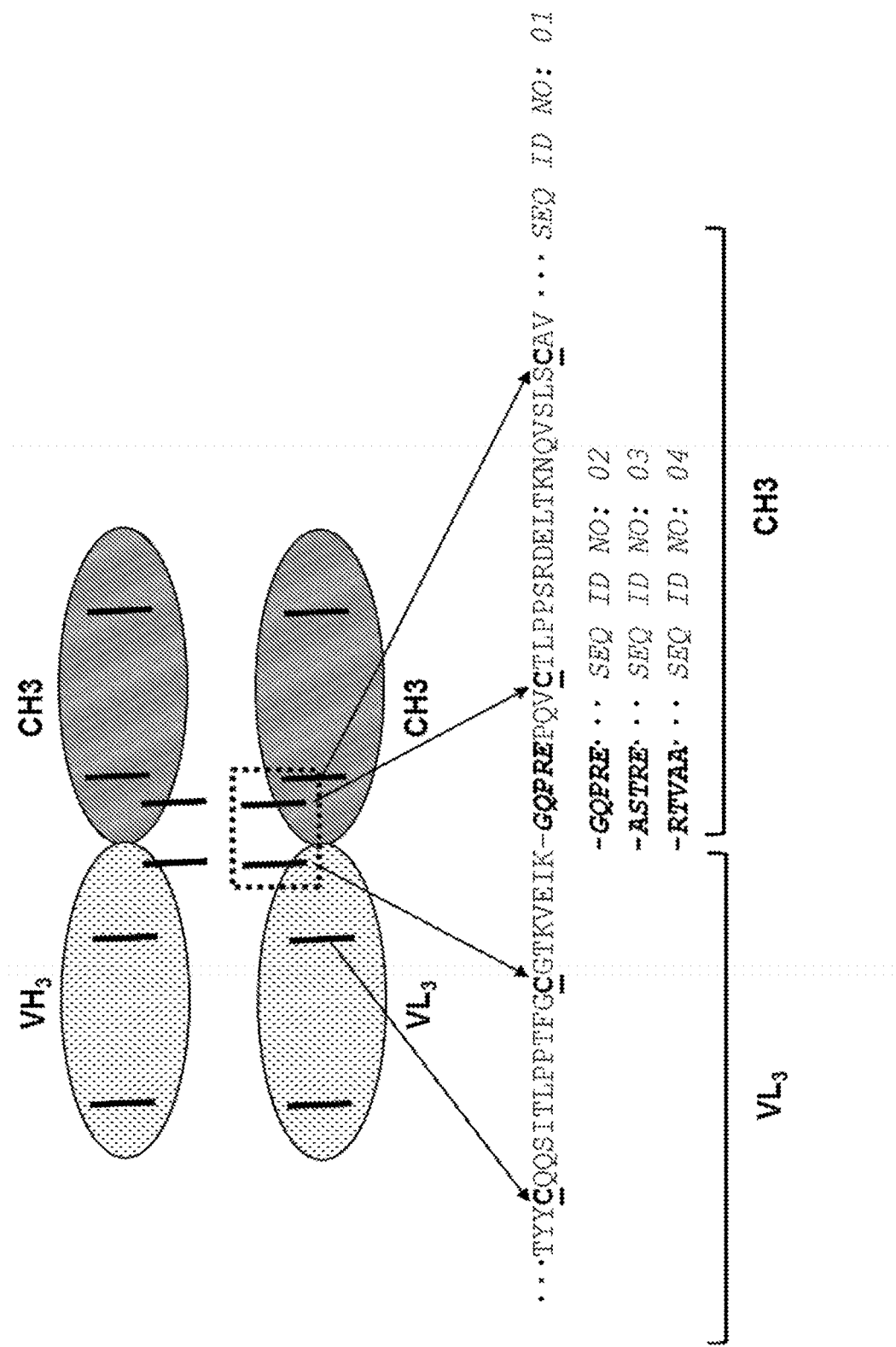

FIG. 5B depict fusion sites including such a complex cysteine pattern in the third binding module, which allow correct protein folding.

Another goal of the design of the fusion site between the variable domains and the CH3 domains was to closely mimic the natural transition sites present in the original parent antibody between (i) the VH and CH1 domains as well as the CH2 and CH3 domains for the fusion site between VH₃ and CH3; and (ii) the VL and CL domains as well as the CH2 and CH3 domains for the fusion site between VL₃ and CH3. Therefore, distinct amino acid residues at the C-terminus of the variable domains and the N-terminus of the CH3 domains may be substituted by another amino acid residue in order to provide a fusion site of a tertiary structure of a distinct homology to the natural transition site between variable and constant regions. Exemplary alternative amino acid sequences of the N-terminus of the CH3 domains are indicated in FIG. 5B.

Example 4

Binding Studies of Trivalent, Bispecific Antibodies According to the Invention

Simultaneous antigen binding of the antibodies generated in example 1 was analyzed by FACS analysis on LeY-expressing MCF7 cells, CD33-expressing Molm13 cells and GPC3-expressing HepG2 cells using Dig-Cy5 as payload to address hapten binding. Results are shown in FIG. 7.

Simultaneous hapten binding and cell surface binding was observed for all bispecific antibodies with the Dig-specific binding site in the third binding module and the antigen binding sites specific for the respective cell surface marker within the Fab fragments. Simultaneous hapten binding and cell surface binding was also observed for the antibodies with the Dig-specific binding sites in the Fab fragments and the antigen binding sites specific for the respective cell surface marker in the third binding module.

The data indicate that the third binding site is easily accessible for small antigens, e.g. haptens (like digoxigenin). The third binding site is also accessible for binding larger antigens such as proteins, e.g. cell surface proteins. For those antigens, binding efficacy may depend on epitope accessibility and potential steric hindrance. As demonstrated, cell surface antigens CD33, GPC3 or LeY are accessible to the third binding site of an antibody according to the invention.

Due to these characteristics, the antibodies according to the invention may can be applied to simultaneously address or crosslink two targets, e.g. for imaging, or for targeted payload delivery.

Example 5

Application of Trivalent, Bispecific Antibodies According to the Invention for Targeted Payload Delivery Antibodies according to the invention (BsAb LeY-Dig (SS)-LeY) provided in example 1 and 2 were complexed with a digoxigeninylated truncated Pseudomonas Exotoxin (PE) derivative as toxic payload. A schematic illustration of such complex is indicated in FIG. 9. In order to assess whether the complexes including the antibodies according to the invention are capable of targeting cancer cells thereby inducing cell death, cells of a LeY-expressing MCF7 breast cancer cell line were contacted in vitro with the complexes. Induction of cell death was assessed by a commercial BrdU assay (Cell Proliferation ELISA, BrdU (chemoluminescence), Cat. No. 11 669 915 001, Roche) according to the manufacturer's instructions.

The following controls were analysed in parallel:
staurosporin (positive control),
no additives (medium only, negative control)
free PE,
free digoxigeninylated PE (PE-Dig),
free antibody BsAb LeY-Dig(SS)-LeY that was not complexed with PE-Dig,
free antibody BsAb GPC3-Dig(SS)-GPC3 (which does not bind to MCF7 breast cancer cells),
complex of BsAb CD33-Dig(SS)-CD33 (provided in examples 1 and 2) with digoxigeninylated PE (negative control to assess the unspecific activity of a complex including an antibody according to the invention and a toxin as CD33 does not bind to MCF7 breast cancer cells; demonstrated in FIG. 7).

The following comparative example was analysed in parallel:

As complexes of bispecific antibodies specifically binding to digoxigenin and a target antigen with digoxigenin-coupled small molecules are known in the art (disclosed in WO 2011/1003557 A1, domain architecture as indicated in FIG. 17a), such antibody complex was used as a comparative example. In brief, the bispecific antibody was composed of a full length antibody specifically binding to LeY with an Fv fragment specifically binding to Dig fused to the C-terminus of each heavy chain (referred to as "BsAb LeY-Dig (2+2)"). Variable domains of this antibody were the same as the BsAb LeY-Dig(SS)-LeY antibody according to the invention.

The results (FIG. 10) demonstrate that only the complex of the BsAb LeY-Dig(SS)-LeY antibody according to the invention and the digoxigeninylated PE are capable of effectively targeting MCF7 breast cancer cells in low nanomolar concentrations indicating specific targeting of the cancer cells. To the contrary, complexes that address the CD33 antigen which is not present on MCF7 breast cancer cells show barely any toxicity. In addition, toxin without targeting vehicles or the control-antibodies without a toxic payload did not show noticeable activity.

Example 6

Production and Analysis of Trivalent, Bispecific Antibodies According to the Invention Specifically Binding to Biotin (Bio) and One of the Cell Surface Antigens Lewis-Y (LeY), CD33 and Glypican3 (GPC3)

Bispecific antibodies comprising three antigen binding sites with the same domain architecture specifically binding to biotin and LeY, or biotin and CD33, or biotin and GPC3 were designed as described for the antibodies according to example 1. The domain architecture of the bispecific antibodies is indicated in FIGS. 2A and 2B indicating that Fab fragments were used as first and second antigen binding site.

TABLE 5

Domain architecture of indicated bispecific antibodies

| molecule name | Fab fragments derived from | 3$^{rd}$ binding site derived from |
| --- | --- | --- |
| BsAb LeY-Bio(SS)-LeY | <LeY> | <Bio> |
| BsAb CD33-Bio(SS)-CD33 | <CD33> | <Bio> |
| BsAb GPC3-Bio(SS)-GPC3 | <GPC3> | <Bio> |

The bispecific antibodies included the characteristics indicated in Tables 7 and 8. All constructs comprised constant light chain domains of kappa isotype. In addition, in all constructs, the "knobs" substitutions were introduced in the CH3 domain fused to VH$_3$ and the "hole" substitutions were introduced in the CH3 domain fused to VL$_3$.

TABLE 6

Characteristics of indicated bispecific antibodies

| molecule name | 1st and 2nd peptide connector | S—S bond between VH3 and VL3 | knobs-into-holes substitutions in CH3/CH3 interface | S—S between CH3 and CH3 |
|---|---|---|---|---|
| BsAb LeY-Bio(SS)-LeY | (Gly4Ser)4 | VH3 Cys44 VL3 Cys100 | Trp366, Tyr407 (knob); Ser366, Ala368, Val407 (hole) | Cys354 (knob); Cys349 (hole) |
| BsAb CD33-Bio(SS)-CD33 | (Gly4Ser)4 | VH3 Cys44 VL3 Cys100 | Trp366, Tyr407 (knob); Ser366, Ala368, Val407 (hole) | Cys354 (knob); Cys349 (hole) |
| BsAb GPC3-Bio(SS)-GPC3 | (Gly4Ser)4 | VH3 Cys44 VL3 Cys100 | Trp366, Tyr407 (knob); Ser366, Ala368, Val407 (hole) | Cys354 (knob); Cys349 (hole) |

The amino acid sequences of the polypeptide chains of the tested bispecific antibodies are indicated in Table 9.

TABLE 7

Amino acid sequences of polypeptide chains of indicated bispecific antibodies

| molecule name | light chains SEQ ID NO: | polypeptide VH—CH1-linker-VH3—CH3 SEQ ID NO: | polypeptide VH—CH1-linker-VL3—CH3 SEQ ID NO: |
|---|---|---|---|
| BsAb LeY-Bio(SS)-LeY | 8 | 21 | 22 |
| BsAb CD33-Bio(SS)-CD33 | 13 | 23 | 24 |
| BsAb GPC3-Bio(SS)-GPC3 | 18 | 25 | 26 |

The three antibodies were transiently expressed in HEK293 cells and purified as described in examples 1 and 2.

TABLE 8

Yield of indicated bispecific antibodies

| molecule name | Yield [mg/L] |
|---|---|
| BsAb LeY-Bio(SS)-LeY | 3.8 |
| BsAb CD33-Bio(SS)-CD33 | 8.3 |
| BsAb GPC3-Bio(SS)-GPC3 | 3.8 |

In order to test simultaneous antigen binding of the BsAb LeY-Bio(SS)-LeY, the antibody was analyzed by FACS analysis on LeY-expressing MCF7 cells using biotinylated Cy5 as payload. The results of the FACS analysis are shown in FIG. 8.

Simultaneous binding to biotin and the MCF7 cell surface was observed for the BsAb LeY-Bio(SS)-LeY antibody. As a control, a complex of the BsAb CD33-Bio(SS)-CD33 with biotinylated Cy5 as payload was run in parallel, demonstrating that no unspecific binding of the complex to cancer cells was identified. The results that the third binding site of the antibody according to the invention is easily accessible for hapten binding, specifically for binding to biotin and biotin-coupled payloads.

Example 7

Application of Trivalent, Bispecific Antibodies According to the Invention for Targeted Payload Delivery Using the same approach as described in example 5, the antibodies according to the invention prepared in example 6 were assessed for their applicability in targeted payload delivery. For this, the antibodies were complexed with a biotinylated truncated Pseudomonas Exotoxin (PE) derivative as toxic payload. A schematic illustration of such complex is indicated in FIG. 9.

In order to assess whether the complexes of BsAb LeY-Bio(SS)-LeY with biotinylated PC are capable of targeting cancer cells thereby inducing cell death, the cells of a LeY-expressing MCF7 breast cancer cell line were contacted in vitro with the complexes. Induction of cell death was assessed by a commercial BrdU assay (Cell Proliferation ELISA, BrdU (chemoluminescence), Cat. No. 11 669 915 001, Roche) according to the manufacturer's instructions.

The following controls were analysed in parallel:
staurosporin (positive control),
no additives (medium only, negative control)
free biotinylated PE (PE-Bio),
complex of BsAb CD33-Bio(SS)-CD33 (provided in examples 1 and 2) with biotinylated PE (negative control to assess the unspecific activity of a complex including an antibody according to the invention and a toxin as CD33 does not bind to MCF7 breast cancer cells; demonstrated in FIG. 7).

The results (FIG. 11) demonstrate that only the complex of the BsAb LeY-Bio(SS)-LeY antibody according to the invention and the biotinylated PE are capable of effectively targeting MCF7 breast cancer cells in low nanomolar concentrations indicating specific targeting of the cancer cells. To the contrary, complexes that address the CD33 antigen which is not present on MCF7 breast cancer cells show barely any toxicity. In addition, toxin without targeting vehicles or the control-antibodies without a toxic payload did not show noticeable activity.

Example 8

Production Trivalent, Bispecific Antibodies According to the Invention Specifically Binding to Either Biotin (Bio) or Digoxigenin (Dig) in Combination with One of the Cell Surface Antigens Lewis-Y (LeY), CD33 and GPC3

Bispecific antibodies comprising three antigen binding sites with the same domain architecture specifically binding to either biotin (Bio) or digoxigenin (Dig) in combination with one of the cell surface antigens Lewis-Y (LeY), CD33 and GPC3 were designed as described for the antibodies according to example 1. The domain architecture of the bispecific antibodies is indicated in FIGS. 2A and 2B indicating that Fab fragments are used as first and second antigen binding site.

The bispecific antibodies include the characteristics indicated in Tables 11 and 12. All constructs comprise constant light chain domains of kappa isotype. In addition, in all constructs, the "knobs" substitutions are introduced in the CH3 domain fused to VH3 and the "hole" substitutions are introduced in the CH3 domain fused to VL3.

TABLE 9

Domain architecture of indicated bispecific antibodies

| molecule name | Fab fragments derived from | 3rd binding site derived from |
|---|---|---|
| BsAb Bio-LeY(SS)-Bio | <Bio> | <LeY> |
| BsAb Bio-CD33(SS)-Bio | <Bio> | <CD33> |
| BsAb Bio-GPC3(SS)-Bio | <Bio> | <GPC3> |
| BsAb Dig-LeY(SS)-Dig | <Dig> | <LeY> |
| BsAb Dig-CD33(SS)-Dig | <Dig> | <CD33> |
| BsAb Dig-GPC3(SS)-Dig | <Dig> | <GPC3> |

TABLE 10

Characteristics of indicated bispecific antibodies

| molecule name | 1st and 2nd peptide connector | S—S bond between $VH_3$ and $VL_3$ | knobs-into-holes substitutions in CH3/CH3 interface | S—S between CH3 and CH3 |
|---|---|---|---|---|
| BsAb Bio-LeY(SS)-Bio | $(Gly_4Ser)_4$ | $VH_3$ Cys44 $VL_3$ Cys100 | Trp366, Tyr407 (knob); Ser366, Ala368, Val407 (hole) | Cys354 (knob); Cys349 (hole) |
| BsAb Bio-CD33(SS)-Bio | $(Gly_4Ser)_4$ | $VH_3$ Cys44 $VL_3$ Cys100 | Trp366, Tyr407 (knob); Ser366, Ala368, Val407 (hole) | Cys354 (knob); Cys349 (hole) |
| BsAb Bio-GPC3(SS)-Bio | $(Gly_4Ser)_4$ | $VH_3$ Cys44 $VL_3$ Cys100 | Trp366, Tyr407 (knob); Ser366, Ala368, Val407 (hole) | Cys354 (knob); Cys349 (hole) |
| BsAb Dig-LeY(SS)-Dig | $(Gly_4Ser)_4$ | $VH_3$ Cys44 $VL_3$ Cys100 | Trp366, Tyr407 (knob); Ser366, Ala368, Val407 (hole) | Cys354 (knob); Cys349 (hole) |
| BsAb Dig-CD33(SS)-Dig | $(Gly_4Ser)_4$ | $VH_3$ Cys44 $VL_3$ Cys100 | Trp366, Tyr407 (knob); Ser366, Ala368, Val407 (hole) | Cys354 (knob); Cys349 (hole) |
| BsAb Dig-GPC3(SS)-Dig | $(Gly_4Ser)_4$ | $VH_3$ Cys44 $VL_3$ Cys100 | Trp366, Tyr407 (knob); Ser366, Ala368, Val407 (hole) | Cys354 (knob); Cys349 (hole) |

The amino acid sequences of the polypeptide chains of the tested bispecific antibodies are indicated in Table 13.

TABLE 11

Amino acid sequences of polypeptide chains of indicated bispecific antibodies

| molecule name | light chains SEQ ID NO: | polypeptide VH—CH1-linker-$VH_3$—CH3 SEQ ID NO: | polypeptide VH—CH1-linker-$VL_3$—CH3 SEQ ID NO: |
|---|---|---|---|
| BsAb Bio-LeY(SS)-Bio | 27 | 28 | 29 |
| BsAb Bio-CD33(SS)-Bio | 27 | 30 | 31 |
| BsAb Bio-GPC3(SS)-Bio | 27 | 32 | 33 |
| BsAb Dig-LeY(SS)-Dig | 5 | 34 | 35 |
| BsAb Dig-CD33(SS)-Dig | 5 | 36 | 37 |
| BsAb Dig-GPC3(SS)-Dig | 5 | 38 | 39 |

The antibodies are expressed and purified as described in examples 1 and 2.

What is claimed is:

1. A multispecific antibody comprising at least three antigen binding sites, wherein two antigen binding sites are formed by a first Fab fragment comprising a constant heavy chain domain (CH1) and a constant light chain domain (CL) and a second Fab fragment comprising a constant heavy chain domain (CH1) and a constant light chain domain (CL), wherein a) a third antigen binding site is formed by a variable heavy chain domain ($VH_3$) and a variable light chain domain ($VL_3$), wherein the N-terminus of the $VH_3$ domain is connected to the C-terminus of the CH1 or CL of the first Fab fragment via a first peptide connector, and the N-terminus of the $VL_3$ domain is connected to the C-terminus of the CH1 or CL of the second Fab fragment via a second peptide connector, wherein the third binding site is disulfide stabilized by introduction of cysteine residues at the following positions to form a disulfide bond between the $VH_3$ and $VL_3$ domains, according to Kabat numbering:

(i) $VH_3$ at position 44, and $VL_3$ at position 100;
(ii) $VH_3$ at position 105, and $VL_3$ at position 43; or
(iii) $VH_3$ at position 101, and $VL_3$ at position 100;

b) the multispecific antibody comprises a first and a second constant heavy chain domains 3 (CH3), which are altered to promote heterodimerization by i) generation of a protuberance in the first $CH_3$ domain by substituting at least one original amino acid residue with an amino acid residue having a larger side chain volume than the original amino acid residue, and generation of a cavity in the second $CH_3$ domain by substituting at least one original amino acid residue with an amino acid residue having a smaller side chain volume than the original amino acid residue, such that the protuberance generated in the first $CH_3$ domain is positionable in the cavity generated in the second $CH_3$ domain; or substituting at least one original amino acid residue in the first $CH_3$ domain with a positively charged amino acid, and substituting at least one original amino acid residue in the second $CH_3$ domain with a negatively charged amino acid;

ii) introduction of at least one cysteine residue in each $CH_3$ domain such that a disulfide bond is formed between the $CH_3$ domains, or iii) both modifications of i) and ii);

c) the C-terminus of the $VH_3$ domain of the third antigen binding site is connected to the N-terminus of one of the $CH_3$ domains, wherein the N-terminus of the $CH_3$ domain comprises the amino acid sequence set forth in SEQ ID NO:2, and the C-terminus of the $VL_3$ domain of the third antigen binding site is connected to the N-terminus of the other one of the $CH_3$ domains, wherein the N-terminus of the other $CH_3$ domain comprises the amino acid sequence set forth in SEQ ID NO:2, and d) the multispecific antibody is devoid of constant heavy chain domains 2 ($CH_2$).

2. The multispecific antibody according to claim 1, wherein the first peptide connector and the second peptide connector are peptides of at least 15 amino acids.

3. The multispecific antibody according to claim 1, wherein no interchain disulfide bond is formed between the first peptide connector and the second peptide connector.

4. The multispecific antibody according to claim 1, wherein the C-terminus of the $VH_3$ domain is directly connected to one of the $CH_3$ domains, and the C-terminus of the $VL_3$ domain is directly connected to the other $CH_3$ domain.

5. The multispecific antibody according to claim 1, wherein the antibody is trivalent.

6. A pharmaceutical composition comprising the multispecific antibody according to claim 1, in combination with at least one pharmaceutically acceptable carrier.

7. An immunoconjugate comprising the multispecific antibody according to claim 1 coupled to a cytotoxic agent.

8. The multispecific antibody according to claim 1, wherein the antibody is bispecific.

* * * * *